(12) United States Patent
Kysil et al.

(10) Patent No.: US 11,834,450 B2
(45) Date of Patent: Dec. 5, 2023

(54) COMPOUNDS HAVING ((3-NITROPHENYL)SULFONYL)ACETAMIDE AS BCL-2 INHIBITORS

(71) Applicant: Eil Therapeutics, Inc., San Diego, CA (US)

(72) Inventors: Volodymyr Kysil, San Diego, CA (US); Vladislav Zenonovich Parchinsky, Moscow (RU); Alexei Pushechnikov, San Diego, CA (US); Alexandre Vasilievich Ivachtchenko, Hallandale Beach, FL (US); Ruben Abagyan, La Jolla, CA (US); Andrew Orry, San Diego, CA (US); Polo Chun-Hung Lam, San Diego, CA (US); Nikolay Savchuk, San Diego, CA (US)

(73) Assignee: EIL THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 17/698,956

(22) Filed: Mar. 18, 2022

(65) Prior Publication Data

US 2022/0306625 A1      Sep. 29, 2022

Related U.S. Application Data

(60) Provisional application No. 63/163,326, filed on Mar. 19, 2021.

(51) Int. Cl.
| | | |
|---|---|---|
| C07D 471/04 | (2006.01) | |
| C07D 405/14 | (2006.01) | |
| A61K 45/06 | (2006.01) | |
| C07D 519/00 | (2006.01) | |
| C07D 405/12 | (2006.01) | |

(52) U.S. Cl.
CPC ............ *C07D 471/04* (2013.01); *A61K 45/06* (2013.01); *C07D 405/12* (2013.01); *C07D 405/14* (2013.01); *C07D 519/00* (2013.01)

(58) Field of Classification Search
CPC .................................................. C07D 405/14
See application file for complete search history.

(56) References Cited

U.S. PATENT DOCUMENTS

| | | | | |
|---|---|---|---|---|
| 8,580,794 B2 * | 11/2013 | Doherty | ................... | A61P 31/18 544/364 |
| 2002/0055631 A1 | 5/2002 | Augeri et al. | | |
| 2002/0086887 A1 | 7/2002 | Augeri et al. | | |
| 2004/0192681 A1 | 9/2004 | Augeri et al. | | |
| 2005/0159427 A1 | 4/2005 | Bruncko et al. | | |
| 2006/0128706 A1 | 6/2006 | Bruncko et al. | | |
| 2006/0258657 A1 | 11/2006 | Bruncko et al. | | |
| 2007/0015787 A1 | 1/2007 | Bruncko et al. | | |
| 2008/0182845 A1 | 7/2008 | Bardwell et al. | | |
| 2009/0137585 A1 | 5/2009 | Augeri et al. | | |
| 2010/0022773 A1 | 1/2010 | Bruncko et al. | | |
| 2010/0152183 A1 | 6/2010 | Bruncko et al. | | |
| 2010/0298321 A1 | 11/2010 | Bruncko et al. | | |
| 2010/0305122 A1 * | 12/2010 | Bruncko | ................. | A61P 35/00 544/230 |
| 2011/0124628 A1 | 5/2011 | Bruncko et al. | | |
| 2011/0144112 A9 | 6/2011 | Bruncko et al. | | |
| 2011/0237553 A1 | 9/2011 | Ding et al. | | |
| 2011/0256129 A1 | 10/2011 | Bruncko et al. | | |
| 2012/0035134 A1 | 2/2012 | Diebold et al. | | |
| 2012/0190688 A1 | 7/2012 | Bruncko et al. | | |
| 2012/0214796 A1 | 8/2012 | Ding et al. | | |
| 2013/0190488 A1 | 7/2013 | Bruncko et al. | | |
| 2013/0267514 A1 | 10/2013 | Bruncko et al. | | |
| 2013/0267534 A1 | 10/2013 | Bruncko et al. | | |
| 2013/0296295 A1 | 11/2013 | Bruncko et al. | | |
| 2014/0057889 A1 | 2/2014 | Bruncko et al. | | |
| 2014/0057890 A1 | 2/2014 | Bruncko et al. | | |
| 2014/0094471 A1 | 4/2014 | Bruncko et al. | | |
| 2014/0107119 A1 | 4/2014 | Bruncko et al. | | |
| 2014/0113910 A1 | 4/2014 | Bruncko et al. | | |
| 2014/0187531 A1 | 7/2014 | Bruncko et al. | | |
| 2015/0328239 A1 | 11/2015 | Diebold et al. | | |
| 2016/0009687 A1 | 1/2016 | Ding et al. | | |
| 2016/0176906 A1 | 6/2016 | Diebold et al. | | |
| 2017/0158666 A1 | 6/2017 | Bruncko et al. | | |
| 2019/0119247 A1 | 4/2019 | Bruncko et al. | | |
| 2020/0231566 A1 | 7/2020 | Bruncko et al. | | |
| 2021/0221789 A1 | 7/2021 | Bruncko et al. | | |
| 2021/0269433 A1 * | 9/2021 | Guo | ..................... | C07D 207/09 |

OTHER PUBLICATIONS venclexta.com, Abbvie/Genentech, 2019.*

* cited by examiner

*Primary Examiner* — Jeffrey S Lundgren
*Assistant Examiner* — Eric Tran
(74) *Attorney, Agent, or Firm* — Snell & Wilmer L.L.P.

(57) ABSTRACT

The present invention is generally directed to inhibitors of BCL-2 proteins useful in the treatment of diseases and disorders modulated by said enzyme and having the Formula (I):

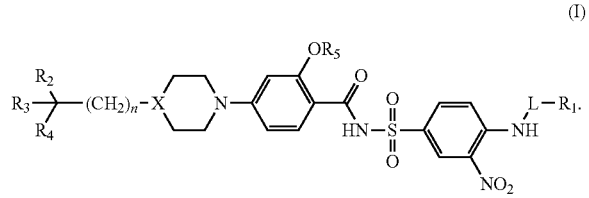

9 Claims, No Drawings

COMPOUNDS HAVING ((3-NITROPHENYL)SULFONYL)ACETAMIDE AS BCL-2 INHIBITORS

CROSS-REFERENCE TO RELATED INVENTIONS

This application claims priority to, and the benefit of, U.S. Provisional Application No. 63/163,326, filed Mar. 19, 2021, the contents of which are incorporated by reference in their entirety.

FIELD OF INVENTION

The present invention is directed to inhibitors of B-cell lymphoma 2 (BCL-2) proteins. The inhibitors described herein can be useful in the treatment of diseases or disorders associated with BCL-2. In particular, the invention is concerned with compounds and pharmaceutical compositions inhibiting BCL-2, methods of treating diseases or disorders associated with BCL-2, and methods of synthesizing these compounds.

BACKGROUND OF THE INVENTION

Apoptosis, or programmed cell death, is a physiological process that is crucial for embryonic development and maintenance of tissue homeostasis.

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in autoimmune diseases, inflammatory diseases and viral infections. Accordingly, absence of apoptosis is one of the phenotypic signatures of cancer (Hanahan, D. et al., Cell, 2000, 100, 57-70).

The BCL-2 family of proteins plays a major role in tumorogenesis. BCL-2 proteins are characterized based on the presence of BCL-2 homology (BH) domains. The anti-apoptotic proteins contain all the BH1-4 domains; the pro-apoptotic proteins contain either the BH3 domain only or multiple BH domains. The BH3 domain is necessary in executing the pro apoptotic function of these proteins. In anti-apoptotic proteins, the BH3 domain remains hidden or buried inside other BH domains and hence they exclusively function as protectors of cell survival. The BCL-2 proteins use BH domains to interact with each other. The anti-apoptotic BCL-2 proteins interact with pro-apoptotic members and inhibit their function to maintain cellular homeostasis. It is the shift in balance between anti-apoptotic and pro-apoptotic BCL-2 proteins that may decide the fate of cancer cells.

Cancer therapeutics targeting the BCL-2 family mainly have focused on neutralizing one or more anti-apoptotic members by inhibiting their function using small molecule inhibitors or by suppressing their expression utilizing anti-sense oligonucleotides. The concept was to inhibit the anti-apoptotic BCL-2 members' function and thus allowing pro-apoptotic members to induce cell death in cancer cells. However, cancer cells treated with BCL-2 inhibitors were found to upregulate other anti-apoptotic BCL-2 or non-BCL-2 family proteins involved in cell survival, resulting in therapeutic resistance.

There is a need for therapeutic agents that can induce cell death in tumors or cancers with increased expression of BCL-2. This invention is intended to fill this unmet needs associated with current BCL-2 inhibition therapy.

SUMMARY OF THE INVENTION

A first aspect of the invention relates to compounds of Formula (I):

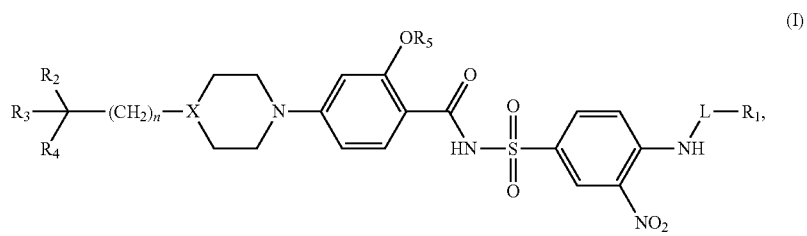

and pharmaceutically acceptable salts, isomers, solvates, prodrugs, or tautomers thereof, wherein:

X is selected from N and CH;

L is selected from bond, $C_1$-$C_6$ alkylenyl, $C_2$-$C_6$ alkenylenyl, $C_2$-$C_6$ alkynylenyl, —C(O)—, —C(O)O—, —C(O)NR$_L$—, —NR$_L$—, and —O—;

$R_L$ is selected from H and $C_1$-$C_3$ alkyl;

$R_1$ is selected from $C_1$-$C_6$ alkyl, —N($R_6$)$_2$, $C_3$-$C_{10}$ cycloalkyl, aryl, 3- to 10-membered heterocyclyl, and heteroaryl, wherein the alkyl, cycloalkyl, aryl, heterocyclyl, and heteroaryl are optionally substituted with one or more $R_6$, wherein when $R_1$ is —N($R_6$)$_2$, then L is not —NR$_L$— or —O—; $R_2$ is selected from $C_3$-$C_{10}$ cycloalkyl, $C_3$-$C_{10}$ cycloalkenyl, aryl, 3- to 15-membered heterocyclyl, and heteroaryl, wherein the cycloalkyl, cycloalkenyl, aryl, heterocyclyl, and heteroaryl are optionally substituted with one or more $R_7$;

$R_3$ is selected from H, $C_1$-$C_6$ alkyl, and aryl, wherein the aryl is optionally substituted with one or more $R_8$;

or $R_2$ and $R_3$, together with the atom to which they are attached, come together to form $C_6$-$C_{16}$ aryl optionally substituted with one or more $R_7$;

$R_4$ is selected from H and —OH;

$R_5$ is selected from aryl and 5- to 10-membered heteroaryl, wherein the aryl or heteroaryl is optionally substituted with one or more $R_9$;

each $R_6$ is independently selected from halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, —OR$_{15}$, oxo, —CN, —C(O)R$_{12}$, —C(O)N(R$_{12}$)$_2$, —(CH$_2$)$_o$OR$_{12}$, —N(R$_{12}$)$_2$, —NHC(O)R$_{12}$, —NHS(O)$_2$R$_{12}$, —S(O)$_2$N(R$_{12}$)$_2$, —S(O)$_2$R$_{12}$, $C_3$-$C_{10}$ cycloalkyl, aryl, 3- to 10-membered heterocyclyl, and heteroaryl, wherein the alkyl, alkoxy, alkenyl, alkynyl, aryl, cycloalkyl, heteroaryl, and heterocyclyl is optionally substituted with one or more halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, amino, alkylamino, dialkylamino, —OH, oxo, —CN, $C_3$-$C_{10}$ cycloalkyl, aryl, 3- to 10-membered heterocyclyl, and heteroaryl;

each $R_7$ is independently selected from halogen, $C_1$-$C_6$ alkyl, $C_1$-$C_6$ haloalkyl, —OH, oxo, —C(O)$R_{10}$, aryl, and heteroaryl, wherein the aryl and heteroaryl are optionally substituted with one or more $R_{11}$;

each $R_8$ is independently selected from halogen, $C_1$-$C_6$ alkyl, and —OH;

each $R_9$ is independently selected from halogen, $C_1$-$C_6$ alkyl, $C_2$-$C_6$ alkenyl, $C_2$-$C_6$ alkynyl, $C_1$-$C_6$ haloalkyl, —CN, —C(O)N($R_{12}$)$_2$, —C(O)O$R_{12}$, —(CH$_2$)$_o$O$R_{12}$, —OH, oxo, —N($R_{12}$)$_2$, —NHC(O)$R_{12}$, —NHS(O)$_2$$R_{12}$, and —S(O)$_2$N($R_{12}$)$_2$;

each $R_{10}$ is independently selected from $C_1$-$C_6$ alkyl, $C_1$-$C_6$ haloalkyl, —(CH$_2$)$_p$—N($R_{13}$)$_2$, $C_3$-$C_{10}$ cycloalkyl, aryl, 3- to 10-membered heterocyclyl, and heteroaryl, wherein the cycloalkyl, aryl, heterocyclyl, and heteroaryl are optionally substituted with one or more $R_{14}$;

each $R_{11}$ is independently selected from halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_3$-$C_{10}$ cycloalkyl, —O$R_{15}$, aryl, 3- to 10-membered heterocyclyl, and heteroaryl;

each $R_{12}$ is independently selected from H, halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_3$-$C_{10}$ cycloalkyl, aryl, 3- to 10-membered heterocyclyl, and heteroaryl;

each $R_{13}$ is selected from H, halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_3$-$C_{10}$ cycloalkyl, aryl, 3- to 10-membered heterocyclyl, and heteroaryl;

each $R_{14}$ is selected from halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_3$-$C_{10}$ cycloalkyl, aryl, 3- to 10-membered heterocyclyl, and heteroaryl;

each $R_{15}$ is independently selected from halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_3$-$C_{10}$ cycloalkyl, —(CH$_2$)$_q$-aryl, 3- to 10-membered heterocyclyl, and heteroaryl; and each n, o, p, and q is an integer independently selected from 0, 1, and 2.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the invention relates to a method of treating a disease or disorder associated with modulation of BCL-2 proteins, such as Isoform 1 and Isoform 2. The method comprises administering to a patient in need of a treatment for diseases or disorders associated with modulation of BCL-2 proteins an effective amount of a compound of Formula (I), or a pharmaceutically acceptable salt, hydrate, solvate, prodrug, stereoisomer, tautomer, or pharmaceutical composition thereof.

Another aspect of the invention is directed to a method of inhibiting BCL-2 proteins including, but not limited to Isoform 1 and Isoform 2. The method involves administering to a patient in need thereof an effective amount of a compound of Formula (I), or a pharmaceutically acceptable salt, hydrate, solvate, prodrug, stereoisomer, tautomer, or pharmaceutical composition thereof.

Another aspect of the invention is directed to a method of treating or preventing a disease or disorder disclosed herein in a subject in need thereof. The method involves administering to a patient in need thereof an effective amount of a compound of Formula (I), or a pharmaceutically acceptable salt, hydrate, solvate, prodrug, stereoisomer, tautomer, or pharmaceutical composition thereof.

Another aspect of the present invention relates to compounds of Formula (I), and pharmaceutically acceptable salts, hydrates, solvates, prodrugs, stereoisomers, tautomers, or pharmaceutical compositions thereof, for use in the manufacture of a medicament for inhibiting BCL-2 proteins, such as Isoform 1 and Isoform 2.

Another aspect of the present invention relates to compounds of Formula (I), and pharmaceutically acceptable salts, hydrates, solvates, prodrugs, stereoisomers, tautomers, or pharmaceutical compositions thereof, for use in the manufacture of a medicament for treating or preventing a disease or disorder disclosed herein.

Another aspect of the present invention relates to the use of a compound of Formula (I), or a pharmaceutically acceptable salt, hydrate, solvate, prodrug, stereoisomer, tautomer, or pharmaceutical composition thereof, in the treatment of a disease associated with inhibiting BCL-2 proteins, such as Isoform 1 and Isoform 2.

Another aspect of the present invention relates to the use of a compound of Formula (I), or a pharmaceutically acceptable salt, hydrate, solvate, prodrug, stereoisomer, tautomer, or pharmaceutical composition thereof, in the treatment of a disease or disorder disclosed herein.

The present invention further provides methods of treating a disease or disorder associated with modulation of BCL-2 proteins including, cancer and metastasis, comprising administering to a patient suffering from at least one of said diseases or disorders a compound of Formula (I), or a pharmaceutically acceptable salt, hydrate, solvate, prodrug, stereoisomer, tautomer, or pharmaceutical composition thereof.

The present invention provides inhibitors of BCL-2 proteins that are therapeutic agents in the treatment of diseases such as cancer and metastasis.

The present invention further provides compounds and compositions with an improved efficacy and safety profile relative to known BCL-2 protein inhibitors. The present disclosure also provides agents with novel mechanisms of action toward BCL-2 protein in the treatment of various types of diseases including cancer and metastasis.

In some aspects, the present disclosure provides a compound obtainable by, or obtained by, a method for preparing compounds described herein (e.g., a method comprising one or more steps described in General Schemes A-F).

In some aspects, the present disclosure provides an intermediate as described herein, being suitable for use in a method for preparing a compound as described herein (e.g., the intermediate is selected from the intermediates described in Examples 1-15).

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims

DETAILED DESCRIPTION OF THE INVENTION

The present disclosure relates to compounds and compositions that are capable of inhibiting the activity BCL-2 proteins including, but not limited to Isoform 1 and Isoform 2. The disclosure features methods of treating, preventing or ameliorating a disease or disorder in which BCL-2 plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of BCL-2 mediated diseases and disorders by inhibiting the activity of BCL-2 proteins. Inhibition of BCL-2 can be an effective approach to the treatment, prevention, or amelioration of diseases including, but not limited to, cancer and metastasis. Decreasing BCL-2 activity can suppress cancer mutagenesis, dampen tumor evolution, and/or decrease the probability of adverse outcomes, such as drug resistance and/or metastases.

In a first aspect of the invention, the compounds of Formula (I) are described:

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—(C$_1$-C$_6$) alkyl, (C$_1$-C$_6$) alkyl, (C$_1$-C$_6$) alkoxy, (C$_1$-C$_6$) haloalkyl, (C$_1$-C$_6$) haloalkoxy, —O—(C$_2$-C$_6$) alkenyl, —O—(C$_2$-C$_6$) alkynyl, (C$_2$-C$_6$) alkenyl, (C$_2$-C$_6$) alkynyl, —OH, —OP(O)(OH)$_2$, —OC(O)(C$_1$-C$_6$) alkyl, —C(O)(C$_1$-C$_6$) alkyl, —OC(O)O(C$_1$-C$_6$) alkyl, —NH$_2$, —NH((C$_1$-C$_6$) alkyl), —N((C$_1$-C$_6$) alkyl)$_2$, —NHC(O)(C$_1$-C$_6$) alkyl, —C(O)NH(C$_1$-C$_6$) alkyl, —S(O)$_2$(C$_1$-C$_6$) alkyl, —S(O)NH(C$_1$-C$_6$) alkyl, and S(O)N((C$_1$-C$_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable sub-

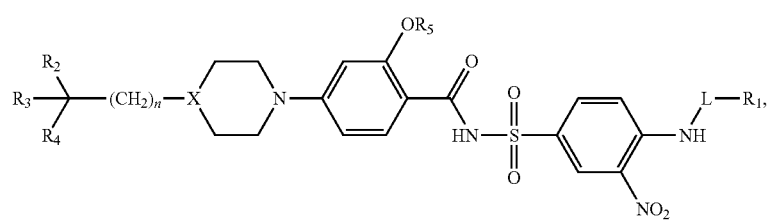

(I)

and pharmaceutically acceptable salts, hydrates, solvates, prodrugs, stereoisomers, and tautomers thereof, wherein X, L, R$^1$, R$^2$, R$^3$, R$^4$, R$^5$, and n are described herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

stituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—(C$_1$-C$_6$)

alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$. The substituents can themselves be optionally substituted. Furthermore, when containing two or more fused rings, the aryl groups herein defined may have a saturated or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, 10,11-dihydro-5H-dibenzo[a,d][7]annulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, Se, or B, the remaining ring atoms being C. Heteroaryl as herein defined also means a bicyclic heteroaromatic group wherein the heteroatom is selected from N, O, S, P, Se, or B. Heteroaryl as herein defined also means a tricyclic heteroaromatic group containing one or more ring heteroatoms selected from N, O, S, P, Se, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4] thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated aromatic ring, e.g., a 5-membered heteroaromatic ring containing 1 to 3 heteroatoms selected from N, O, S, P, Se, or B, or a 6-membered heteroaromatic ring containing 1 to 3 nitrogens, wherein the saturated or partially unsaturated ring includes 0 to 4 heteroatoms selected from N, O, S, P, Se, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, or benzo[c][1,2]oxaborol-1(3H)-olyl.

"Halogen" or "halo" refers to fluorine, chlorine, bromine, or iodine.

"Alkyl" refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above-mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

The term "alkenylene" or "alkenylenyl" refers to a divalent alkenyl radical. Any of the above-mentioned monovalent alkenyl groups may be an alkylene by abstraction of a second hydrogen atom from the alkenyl. As herein defined, alkenylene may also be a $C_2$-$C_6$ alkenylene. An alkenylene may further be a $C_2$-$C_4$ alkenylene. Typical alkenylene groups include, but are not limited to, —CH=CH—, —C(CH$_3$)=CH—, —C(CH$_3$)=C(CH$_3$)—, —CH$_2$CH=CH—, —CH$_2$CH=C(CH$_3$)—, —CH$_2$CH=CHCH$_2$—, and the like.

The term "alkynylene" or "alkynylenyl" refers to a divalent alkynyl radical. Any of the above-mentioned monovalent alkynyl groups may be an alkylene by abstraction of a second hydrogen atom from the alkynyl. As herein defined, alkynylene may also be a $C_2$-$C_6$ alkynylene. An alkynylene may further be a $C_2$-$C_4$ alkynylene. Typical alkenylene groups include, but are not limited to, —C≡C—, —CH$_2$C≡C—, —C≡C—CH(CH$_3$)—, —CH$_2$—CH$_2$—C≡C—, and the like "Cycloalkyl" means a saturated or partially unsaturated hydrocarbon monocyclic or polycyclic (e.g., fused, bridged, or spiro rings) system having 3 to 30 carbon atoms (e.g., C$_3$-C$_{12}$, C$_3$-C$_{10}$, or C$_3$-C$_5$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methyl-bicyclo[3.1.1]heptanyl, 2,6,6-trimethylbicyclo[3.1.1]heptanyl, adamantyl, and derivatives thereof. In the case of polycyclic cycloalkyl, only one of the rings in the cycloalkyl needs to be non-aromatic.

"Heterocyclyl", "heterocycle" or "heterocycloalkyl" refers to a saturated or partially unsaturated 3-10 membered monocyclic, 7-12 membered bicyclic (fused, bridged, or spiro rings), or 11-14 membered tricyclic ring system (fused, bridged, or spiro rings) having one or more heteroatoms (such as O, N, S, P, Se, or B), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 2-azaspiro[3.4]octan-1-onyl, 2-azaspiro[3.4]octanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 1,2,3,4-tetrahydroisoquinolinyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—NH$_2$, R≠H), secondary (R$_2$—NH, R$_2$≠H) and tertiary (R$_3$—N, R≠H) amines. A substituted amine is intended to mean an amine where at least one of the hydrogen atoms has been replaced by the substituent.

The term "amino" as used herein means a substituent containing at least one nitrogen atom. Specifically, —NH$_2$, —NH(alkyl) or alkylamino, —N(alkyl)$_2$ or dialkylamino, amide-, carbamide-, urea, and sulfamide substituents are included in the term "amino".

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2$H and $^{14}$C). Deuterated (i.e., $^2$H or D) and carbon-14 (i.e., $^{14}$C) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease or disorder in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting BCL-2 proteins, such as Isoform 1 and Isoform 2, which are useful for the treatment of diseases and disorders associated with modulation of an BCL-2 protein. The invention further relates to compounds, or pharmaceutically acceptable salts, hydrates, solvates, prodrugs, stereoisomers, or tautomers thereof, which can be useful for inhibiting BCL-2.

In some embodiments, the compounds of Formula (I) have the structure of Formula (I'):

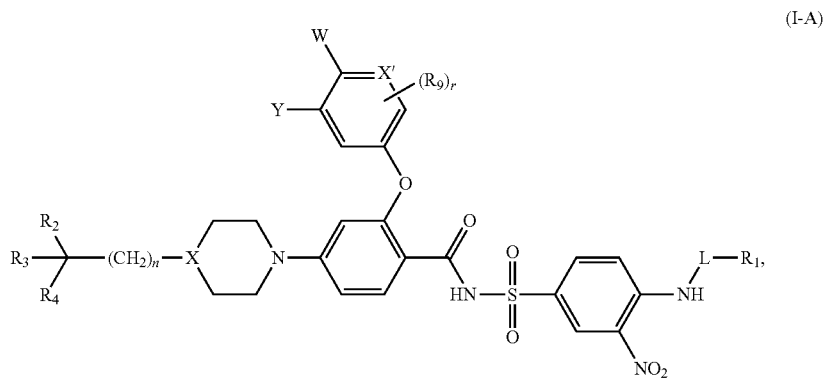

(I-A)

and pharmaceutically acceptable salts, isomers, solvates, prodrugs, or tautomers thereof, wherein X' is selected from N and CH;

W is selected from H, —OH, —N($R_{12}$)$_2$, and —NHC(O)$R_{12}$;

Y is selected from H, halogen, $C_1$-$C_6$ alkyl, $C_2$-$C_6$ alkenyl, $C_2$-$C_6$ alkynyl, $C_1$-$C_6$ haloalkyl, and —CN;

or W and Y, together with the atoms to which they are attached, come together to form 5- or 6-membered heteroaryl; and r is an integer selected from 0, 1, 2, 3, 4, and 5.

In some embodiments, X' is N. In some embodiments, X' is CH.

In some embodiments, W is H. In some embodiments, W is —OH. In some embodiments, W is —NH$R_{16}$.

In some embodiments, Y is H. In some embodiments, Y is halogen. In some embodiments, Y is $C_1$-$C_6$ alkyl. In some embodiments, Y is $C_2$-$C_6$ alkenyl. In some embodiments, Y is $C_2$-$C_6$ alkynyl. In some embodiments, Y is $C_1$-$C_6$ haloalkyl. In some embodiments, Y is —CN.

In some embodiments, W and Y, together with the atoms to which they are attached, come together to form 5-membered heteroaryl.

In some embodiments, W and Y, together with the atoms to which they are attached, come together to form 6-membered heteroaryl.

In some embodiments, r is 0. In some embodiments, r is 1. In some embodiments, r is 2. In some embodiments, r is 3. In some embodiments, r is 4. In some embodiments, r is 5.

In some embodiments, the compounds of Formula (I) have the structure of Formula (I-A-1), (I-A-2), or (I-A-3):

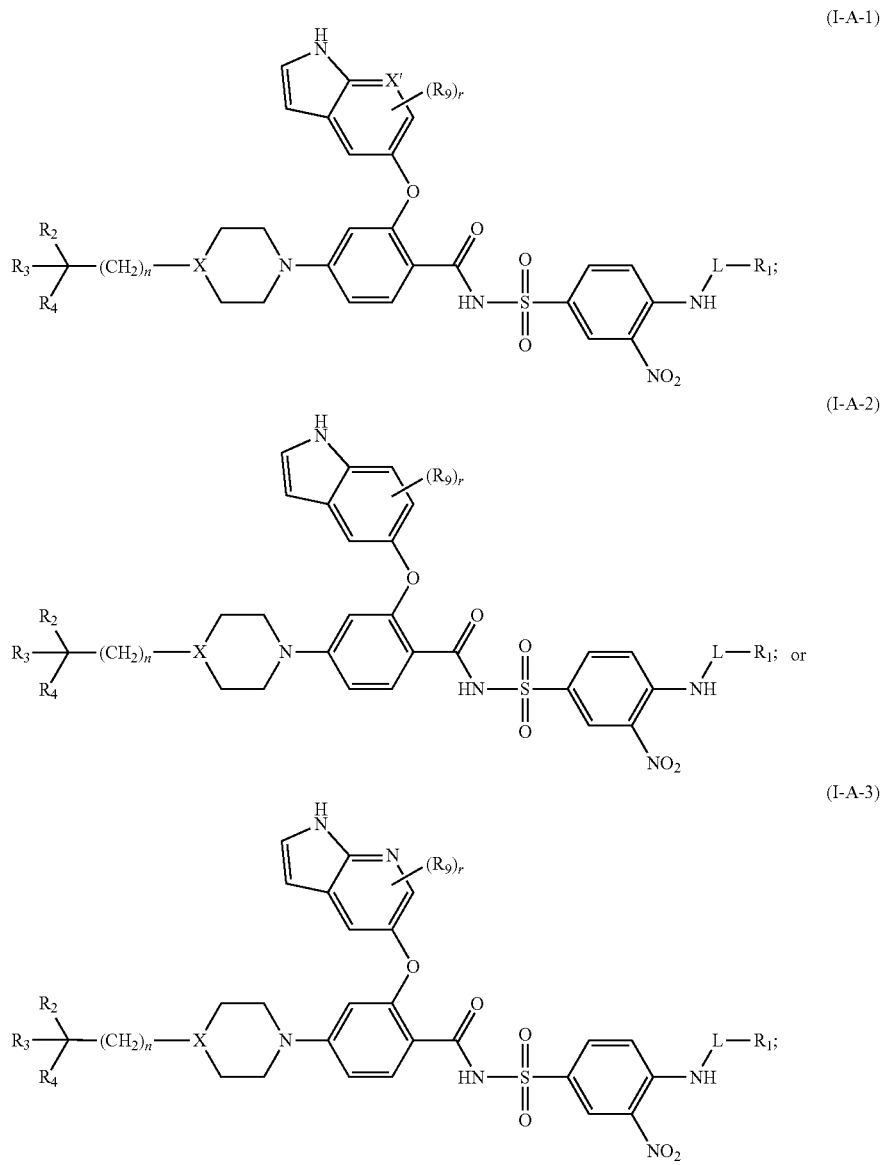

(I-A-1)

(I-A-2)

(I-A-3)

and pharmaceutically acceptable salts, isomers, solvates, prodrugs, or tautomers thereof.

In some embodiments, the compounds of Formula (I) have the structure of Formula (I-A-1).

In some embodiments, the compounds of Formula (I) have the structure of Formula (I-A-2).

In some embodiments, the compounds of Formula (I) have the structure of Formula (I-A-3).

In some embodiments, the compounds of Formula (I) have the structure of Formula (I-B-1) or (I-B-2):

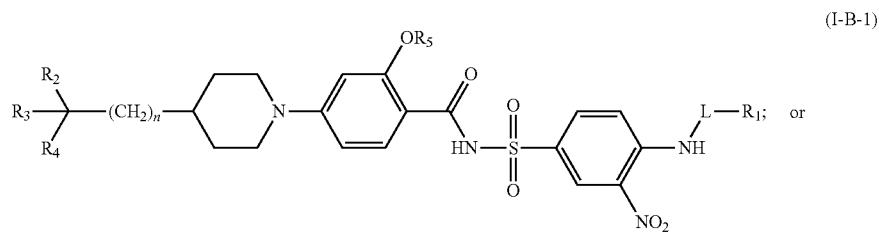

(I-B-1)

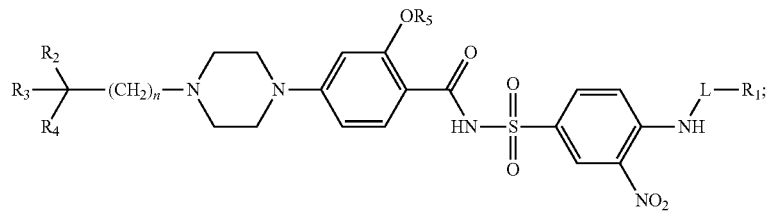

(I-B-2)

and pharmaceutically acceptable salts, isomers, solvates, prodrugs, or tautomers thereof.

In some embodiments, the compounds of Formula (I) have the structure of Formula (I-B-1).

In some embodiments, the compounds of Formula (I) have the structure of Formula (I-B-2).

In some embodiments, the compounds of Formula (I) have the structure of Formula (I-C-1) or (I-C-2):

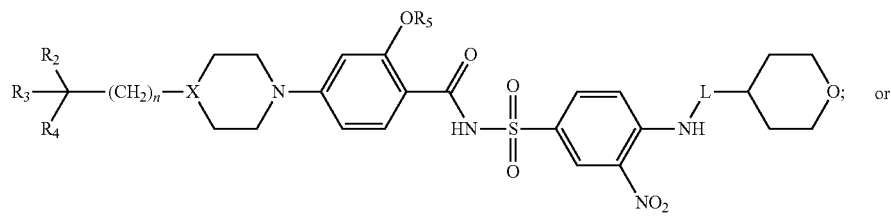

(I-C-1)

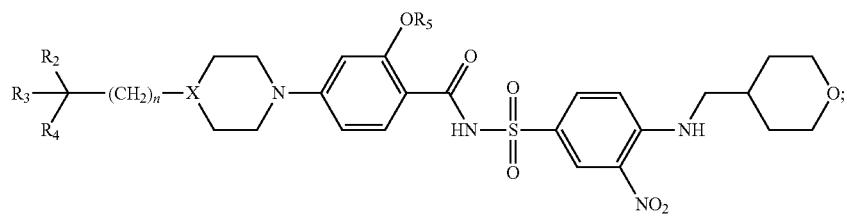

(I-C-2)

and pharmaceutically acceptable salts, isomers, solvates, prodrugs, or tautomers thereof.

In some embodiments, the compounds of Formula (I) have the structure of Formula (I-C-1).

In some embodiments, the compounds of Formula (I) have the structure of Formula (I-C-2).

In some embodiments, the compounds of Formula (I) have the structure of Formula (I-D-1), (I-D-2), (I-D-3), (I-D-4), (I-D-5), (I-D-6), or (I-D-7):

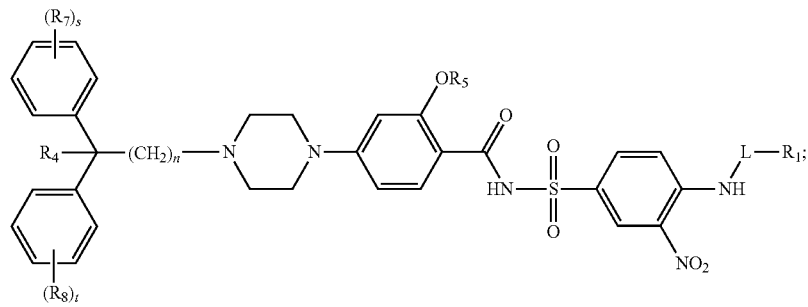

(I-D-1)

-continued
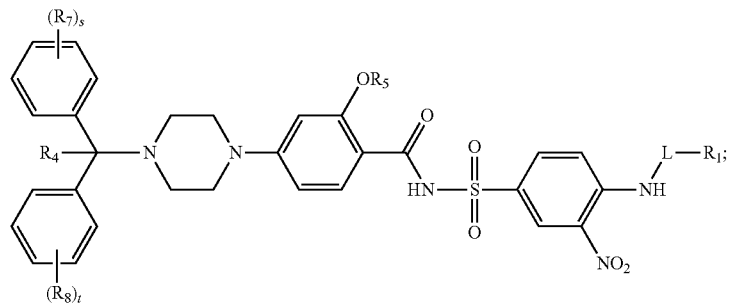
(I-D-2)
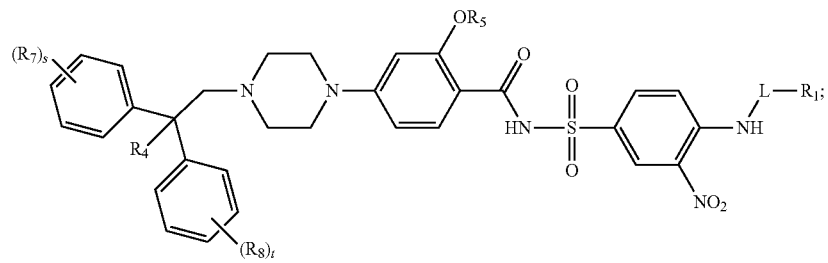
(I-D-3)
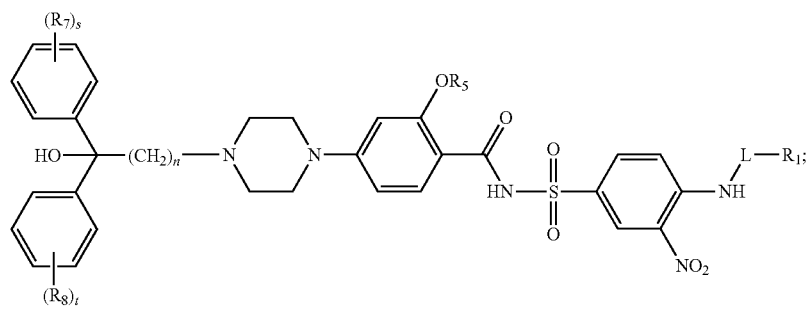
(I-D-4)
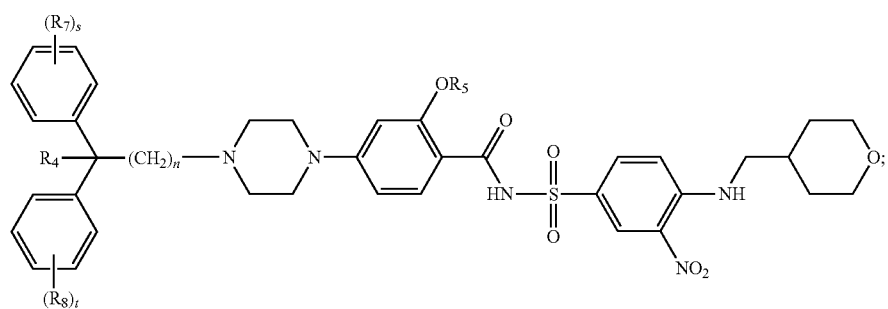
(I-D-5)
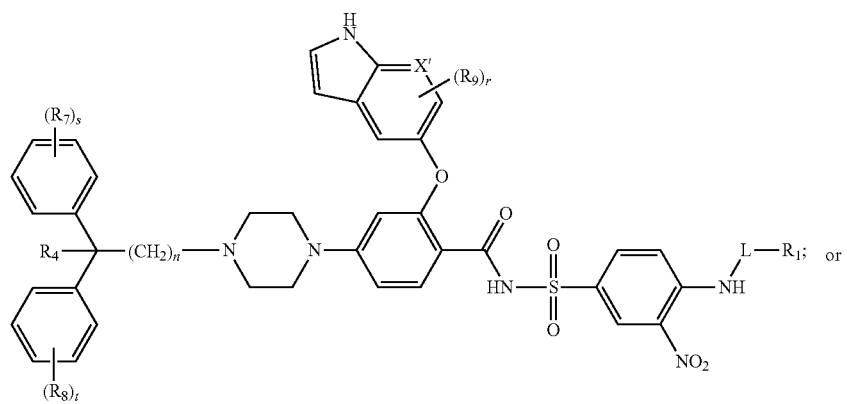
(I-D-6)

-continued

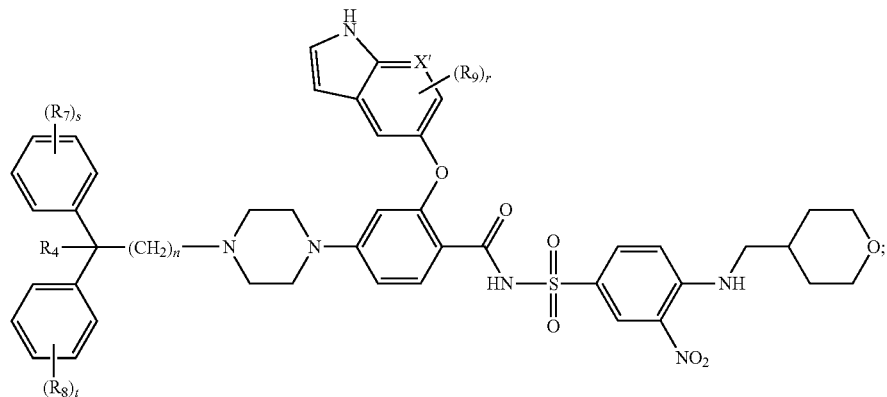

(I-D-7)

and pharmaceutically acceptable salts, isomers, solvates, prodrugs, or tautomers thereof, wherein X' is selected from N and CH, and r, s, and t are integers each independently, at each occurrence, selected from 0, 1, 2, 3, 4, and 5.

In some embodiments, the compounds of Formula (I) have the structure of Formula (I-D-1).

In some embodiments, the compounds of Formula (I) have the structure of Formula (I-D-2).

In some embodiments, the compounds of Formula (I) have the structure of Formula (I-D-3).

In some embodiments, the compounds of Formula (I) have the structure of Formula (I-D-4).

In some embodiments, the compounds of Formula (I) have the structure of Formula (I-D-5).

In some embodiments, the compounds of Formula (I) have the structure of Formula (I-D-6).

In some embodiments, the compounds of Formula (I) have the structure of Formula (I-D-7).

In some embodiments, X' is N. In some embodiments, X' is CH.

In some embodiments, r is 0. In some embodiments, r is 1. In some embodiments, r is 2. In some embodiments, r is 3. In some embodiments, r is 4. In some embodiments, r is 5.

In some embodiments, s is 0. In some embodiments, s is 1. In some embodiments, s is 2. In some embodiments, s is 3. In some embodiments, s is 4. In some embodiments, s is 5.

In some embodiments, t is 0. In some embodiments, t is 1. In some embodiments, t is 2. In some embodiments, t is 3. In some embodiments, t is 4. In some embodiments, t is 5.

In some embodiments, the compounds of Formula (I) have the structure of Formula (I-E-1), (I-E-2), (I-E-3), (I-E-4), (I-E-5), (I-E-6), (I-E-7), (I-E-8), (I-E-9), or (I-E-10):

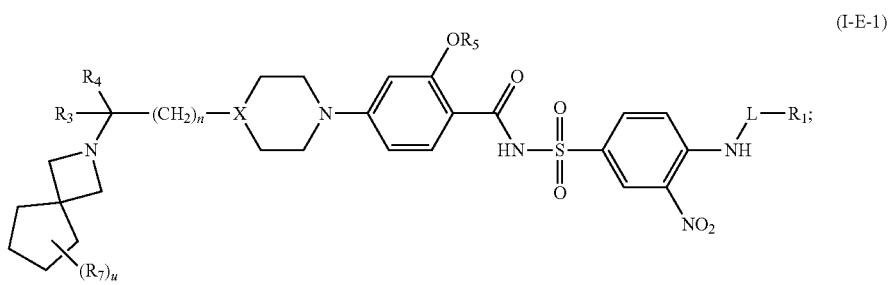

(I-E-1)

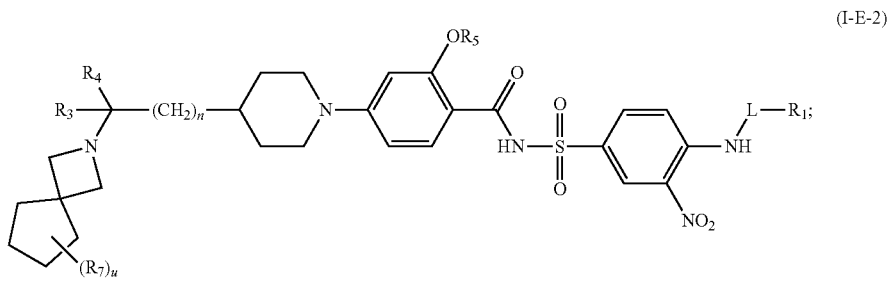

(I-E-2)

-continued
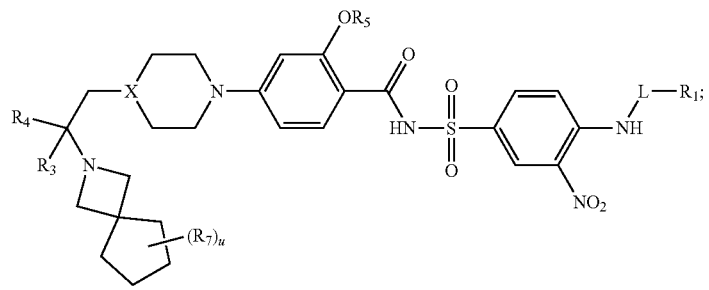
(I-E-3)
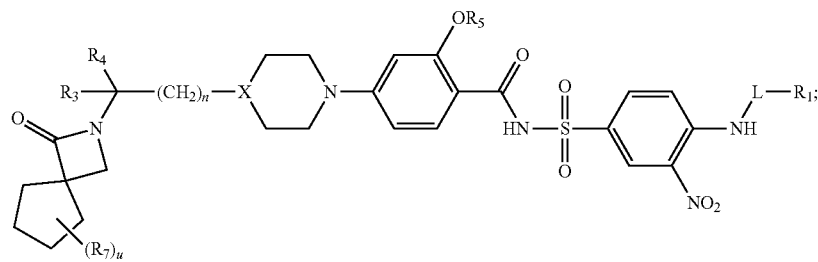
(I-E-4)
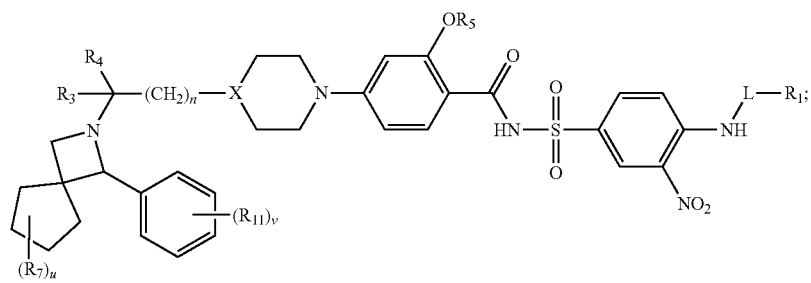
(I-E-5)
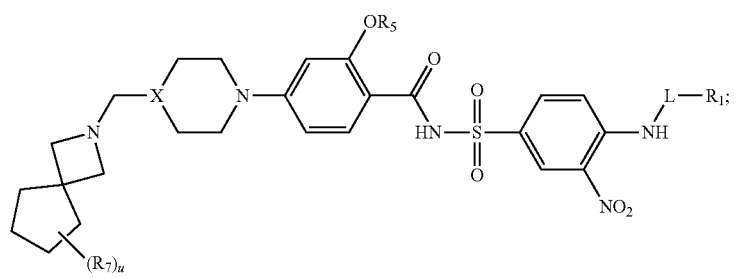
(I-E-6)
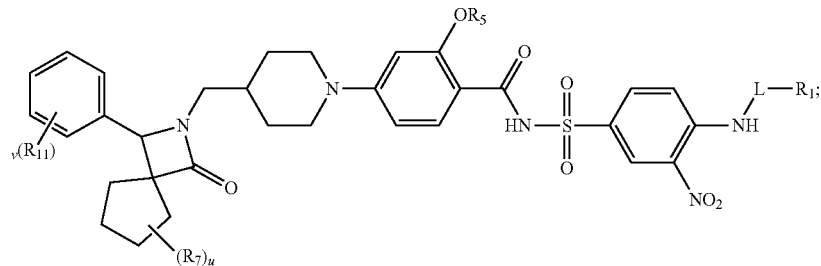
(I-E-7)

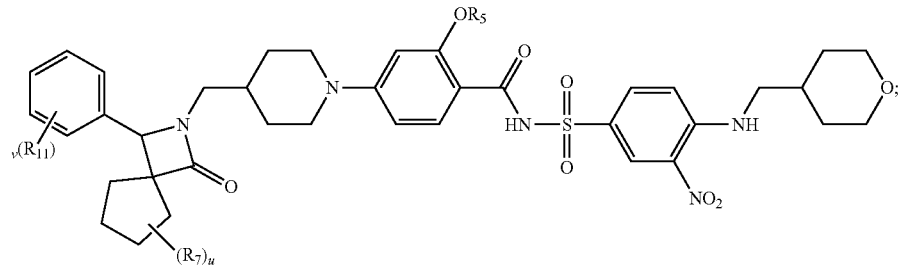
(I-E-8)

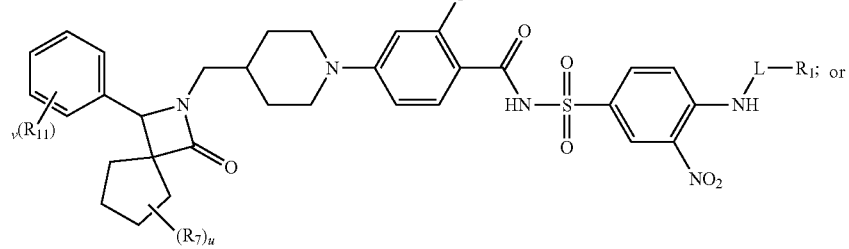
(I-E-9)

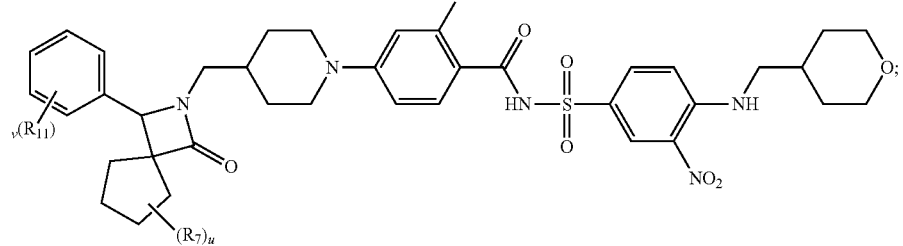
(I-E-10)

and pharmaceutically acceptable salts, isomers, solvates, prodrugs, or tautomers thereof, wherein X' is selected from N and CH, and r, u, and v are integers, at each occurrence, each independently selected from 0, 1, 2, 3, 4, and 5.

In some embodiments, the compounds of Formula (I) have the structure of Formula (I-E-1).

In some embodiments, the compounds of Formula (I) have the structure of Formula (I-E-2).

In some embodiments, the compounds of Formula (I) have the structure of Formula (I-E-3).

In some embodiments, the compounds of Formula (I) have the structure of Formula (I-E-4).

In some embodiments, the compounds of Formula (I) have the structure of Formula (I-E-5).

In some embodiments, the compounds of Formula (I) have the structure of Formula (I-E-6).

In some embodiments, the compounds of Formula (I) have the structure of Formula (I-E-7).

In some embodiments, the compounds of Formula (I) have the structure of Formula (I-E-8).

In some embodiments, the compounds of Formula (I) have the structure of Formula (I-E-9).

In some embodiments, the compounds of Formula (I) have the structure of Formula (I-E-10).

In some embodiments, X' is N. In some embodiments, X' is CH.

In some embodiments, r is 0. In some embodiments, r is 1. In some embodiments, r is 2. In some embodiments, r is 3. In some embodiments, r is 4. In some embodiments, r is 5.

In some embodiments, u is 0. In some embodiments, u is 1. In some embodiments, u is 2. In some embodiments, u is 3. In some embodiments, u is 4. In some embodiments, u is 5.

In some embodiments, v is 0. In some embodiments, v is 1. In some embodiments, v is 2. In some embodiments, v is 3. In some embodiments, v is 4. In some embodiments, v is 5.

In some embodiments, the compounds of Formula (I) have the structure of Formula (I-F-1), (I-F-2), (I-F-3), (I-F-4), (I-F-5), (I-F-6), (I-F-7), (I-F-8), or (I-F-9):
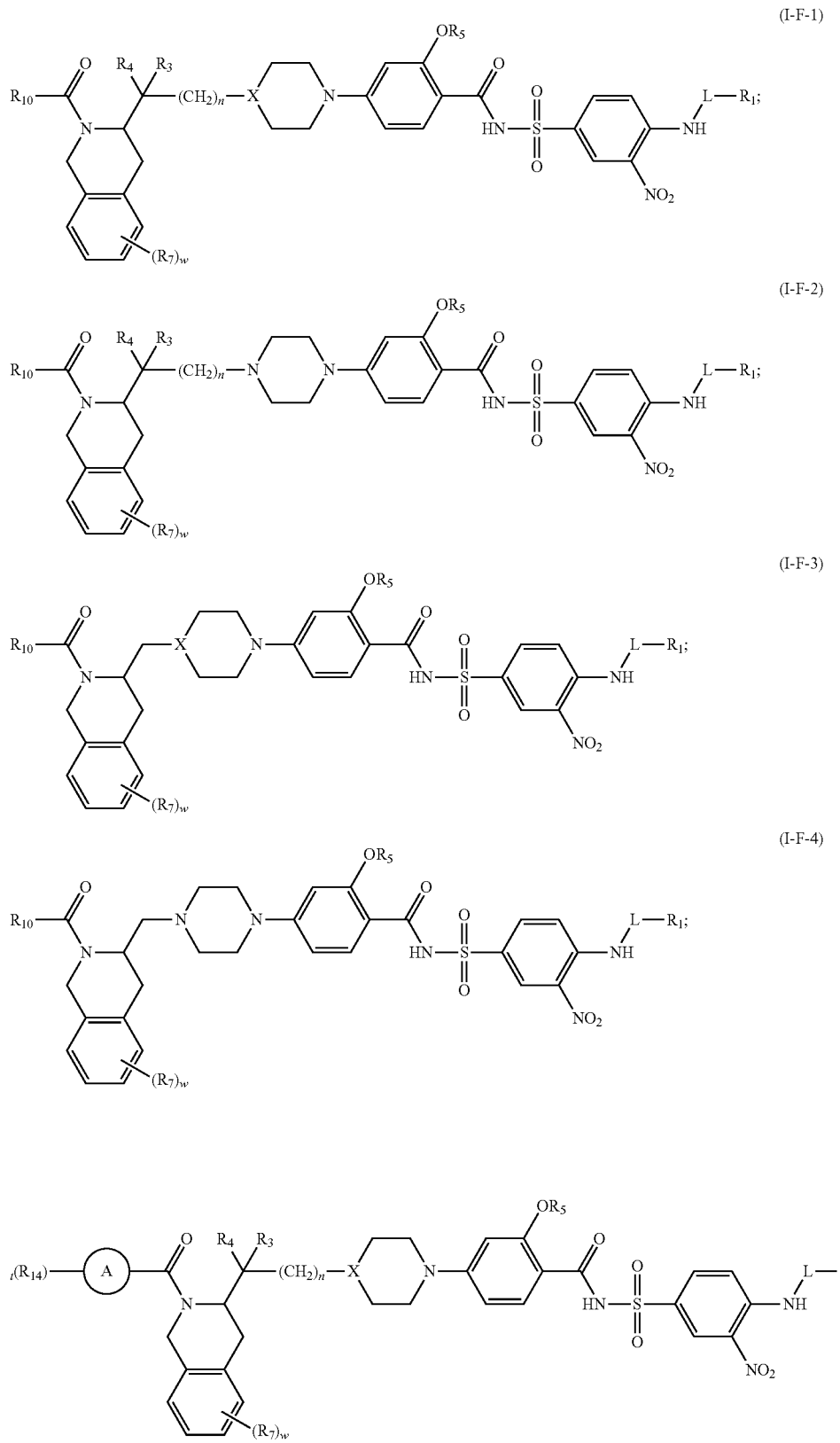

(I-F-6)
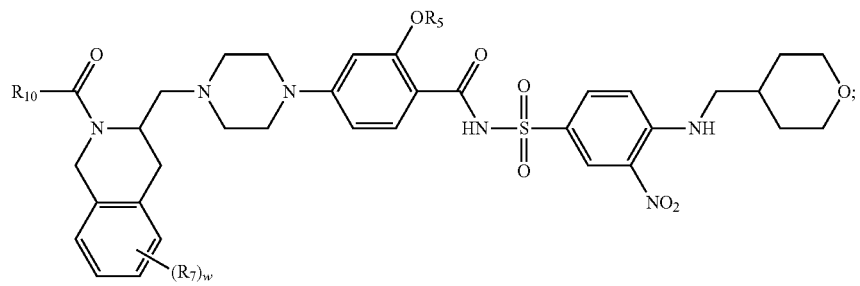
(I-F-7)
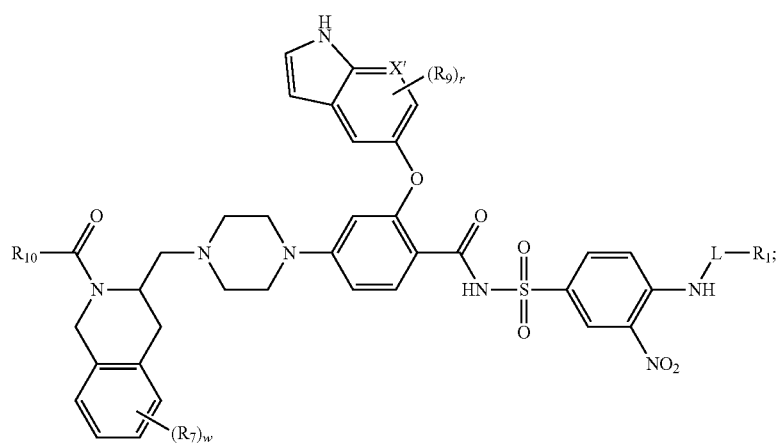
(I-F-8)
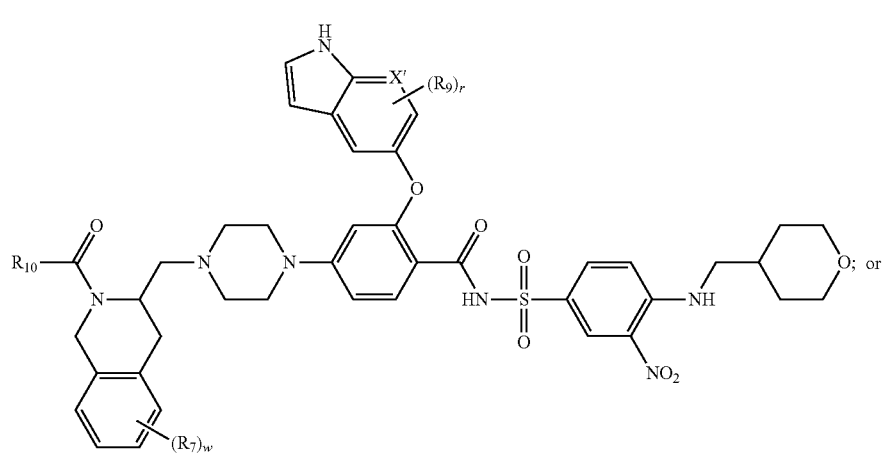
(I-F-9)
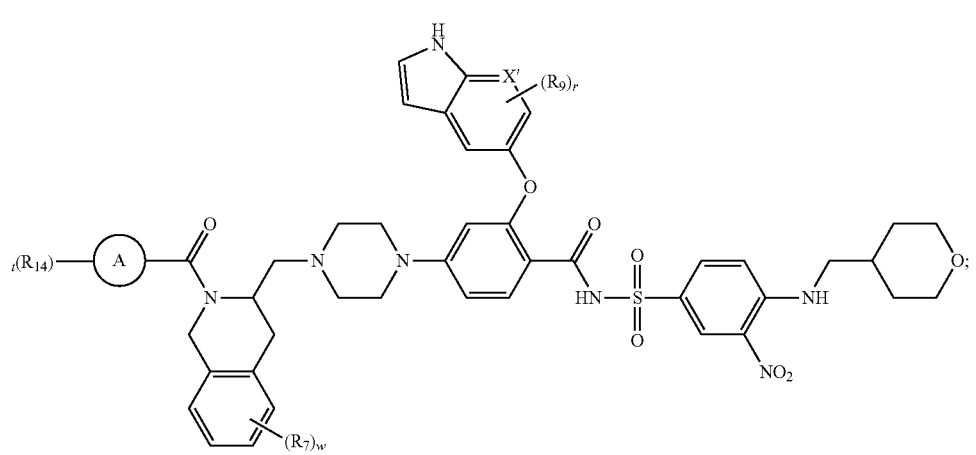

and pharmaceutically acceptable salts, isomers, solvates, prodrugs, or tautomers thereof, wherein X' is selected from N and CH, r, w, and t are integers, at each occurrence, each independently selected from 0, 1, 2, 3, 4, and 5, and Ring A is selected from $C_3$-$C_{10}$ cycloalkyl, aryl, 3- to 10-membered heterocyclyl, and heteroaryl.

In some embodiments, the compounds of Formula (I) have the structure of Formula (I-F-1).

In some embodiments, the compounds of Formula (I) have the structure of Formula (I-F-2).

In some embodiments, the compounds of Formula (I) have the structure of Formula (I-F-3).

In some embodiments, the compounds of Formula (I) have the structure of Formula (I-F-4).

In some embodiments, the compounds of Formula (I) have the structure of Formula (I-F-5).

In some embodiments, the compounds of Formula (I) have the structure of Formula (I-F-6).

In some embodiments, the compounds of Formula (I) have the structure of Formula (I-F-7).

In some embodiments, the compounds of Formula (I) have the structure of Formula (I-F-8).

In some embodiments, the compounds of Formula (I) have the structure of Formula (I-F-9).

In some embodiments, X' is N. In some embodiments, X' is CH.

In some embodiments, r is 0. In some embodiments, r is 1. In some embodiments, r is 2. In some embodiments, r is 3. In some embodiments, r is 4. In some embodiments, r is 5.

In some embodiments, w is 0. In some embodiments, w is 1. In some embodiments, w is 2. In some embodiments, w is 3. In some embodiments, w is 4. In some embodiments, w is 5.

In some embodiments, x is 0. In some embodiments, x is 1. In some embodiments, x is 2. In some embodiments, x is 3. In some embodiments, x is 4. In some embodiments, x is 5.

In some embodiments, the compounds of Formula (I) have the structure of Formula (I-G-1), (I-G-2), (I-G-3), or (I-G-4):

and pharmaceutically acceptable salts, isomers, solvates, prodrugs, or tautomers thereof.

In some embodiments, the compounds of Formula (I) have the structure of Formula (I-G-1).

In some embodiments, the compounds of Formula (I) have the structure of Formula (I-G-2).

In some embodiments, the compounds of Formula (I) have the structure of Formula (I-G-3).

In some embodiments, the compounds of Formula (I) have the structure of Formula (I-G-4).

In some embodiments, X is N. In some embodiments, X is CH.

In some embodiments, L is bond. In some embodiments, L is $C_1$-$C_6$ alkylenyl. In some embodiments, L is methylenyl. In some embodiments, L is ethylenyl. In some embodiments, L is propylenyl. In some embodiments, L is —$CH_2C(CH_3)_2CH_2$—. In some embodiments, L is $C_2$-$C_6$ alkenylenyl. In some embodiments, L is $C_2$-$C_6$ alkynylenyl. In some embodiments, L is —C(O)—. In some embodiments, L is —C(O)O—. In some embodiments, L is —C(O)$NR_L$—. In some embodiments, L is —$NR_L$—. In some embodiments, L is —O—.

In some embodiments, $R_L$ is H. In some embodiments, $R_L$ is $C_1$-$C_3$ alkyl. In some embodiments, $R_L$ is methyl. In some embodiments, $R_L$ is ethyl. In some embodiments, $R_L$ is propyl.

In some embodiments, $R_1$ is $C_1$-$C_6$ alkyl. In some embodiments, $R_1$ is methyl. In some embodiments, $R_1$ is ethyl. In some embodiments, $R_1$ is propyl. In some embodiments, $R_1$ is butyl. In some embodiments, $R_1$ is pentyl. In some embodiments, $R_1$ is hexyl. In some embodiments, $R_1$ is isopropyl. In some embodiments, $R_1$ is isobutyl. In some embodiments, $R_1$ is tert-butyl. In some embodiments, $R_1$ is —$N(R_6)_2$ and L is not —$NR_L$— or —O—. In some embodiments, $R_1$ is $C_3$-$C_{10}$ cycloalkyl. In some embodiments, $R_1$ is $C_3$-$C_{10}$ cycloalkyl substituted with one or more $R_6$. In some embodiments, $R_1$ is aryl. In some embodiments, $R_1$ is aryl substituted with one or more $R_6$. In some embodiments, $R_1$ is 3- to 10-membered heterocyclyl. In some embodiments, $R_1$ is 3- to 10-membered heterocyclyl substituted with one or more $R_6$. In some embodiments, $R_1$ is 6-membered heterocyclyl. In some embodiments, $R_1$ is 6-membered heterocyclyl substituted with one or more $R_6$. In some embodiments, $R_1$ is 6-membered heterocyclyl comprising at least one O atom. In some embodiments, $R_1$ is 6-membered heterocyclyl comprising at least one O atom substituted with one or more $R_6$. In some embodiments, $R_1$ is pyranyl. In some embodiments, $R_1$ is pyranyl substituted with one or more $R_6$. In some embodiments, $R_1$ is dioxanyl. In some embodiments, $R_1$ is dioxanyl substituted with one or more $R_6$. In some embodiments, $R_1$ is piperidinyl. In some embodiments, $R_1$ is piperidinyl substituted with one or more $R_6$. In some embodiments, $R_1$ is pyrrolidinyl. In some embodiments, $R_1$ is pyrrolidinyl substituted with one or more $R_6$. In some embodiments, $R_1$ is piperazinyl. In some embodiments, $R_1$ is piperazinyl substituted with one or more $R_6$. In some embodiments, $R_1$ is morpholinyl. In some embodiments, $R_1$ is morpholinyl substituted with one or more $R_6$. In some embodiments, $R_1$ is heteroaryl. In some embodiments, $R_1$ is heteroaryl substituted with one or more $R_6$.

In some embodiments, $R_1$ is selected from —$CF_3$, —$N(CH_3)_2$,

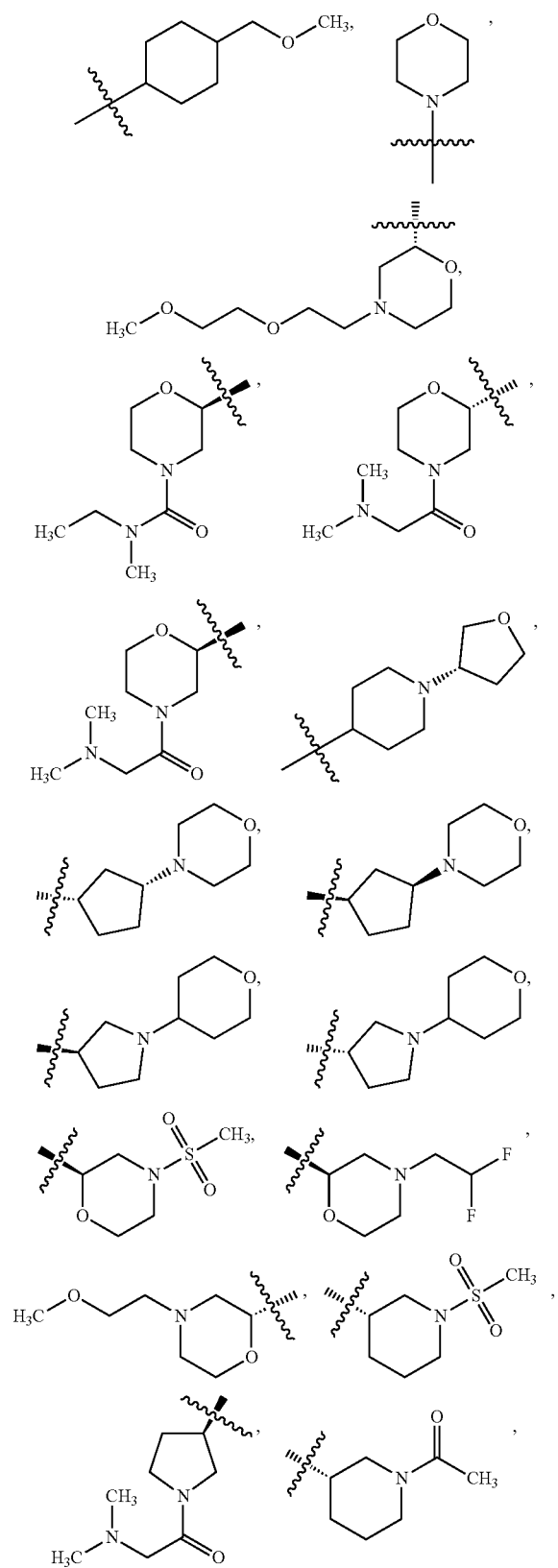

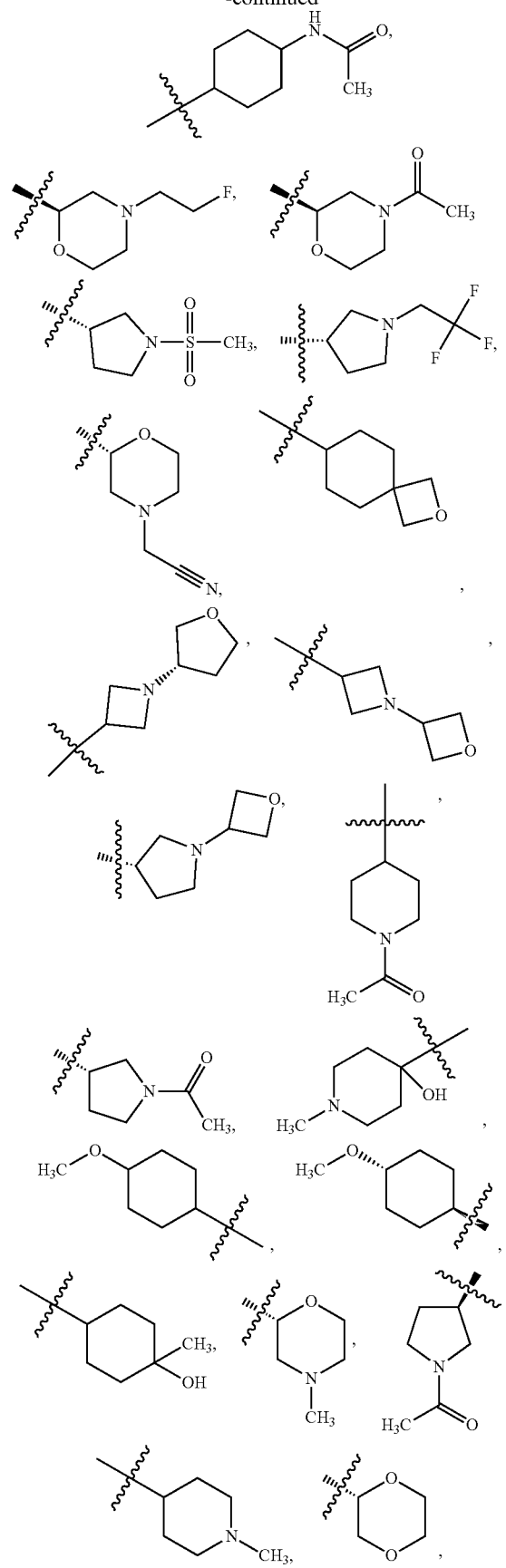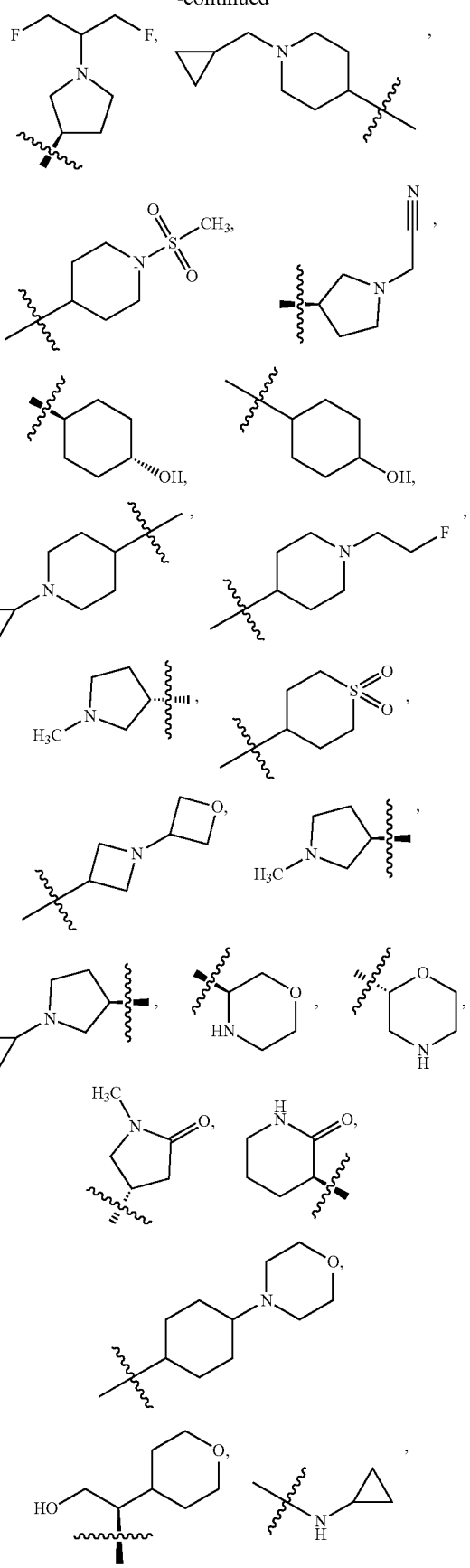

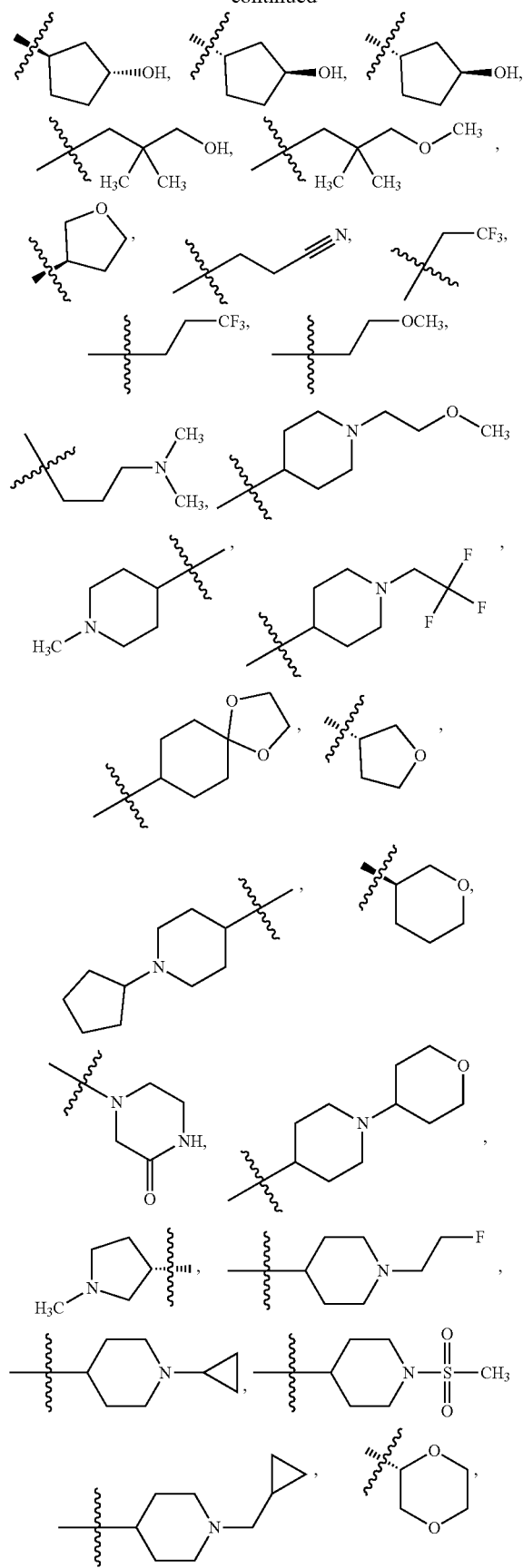
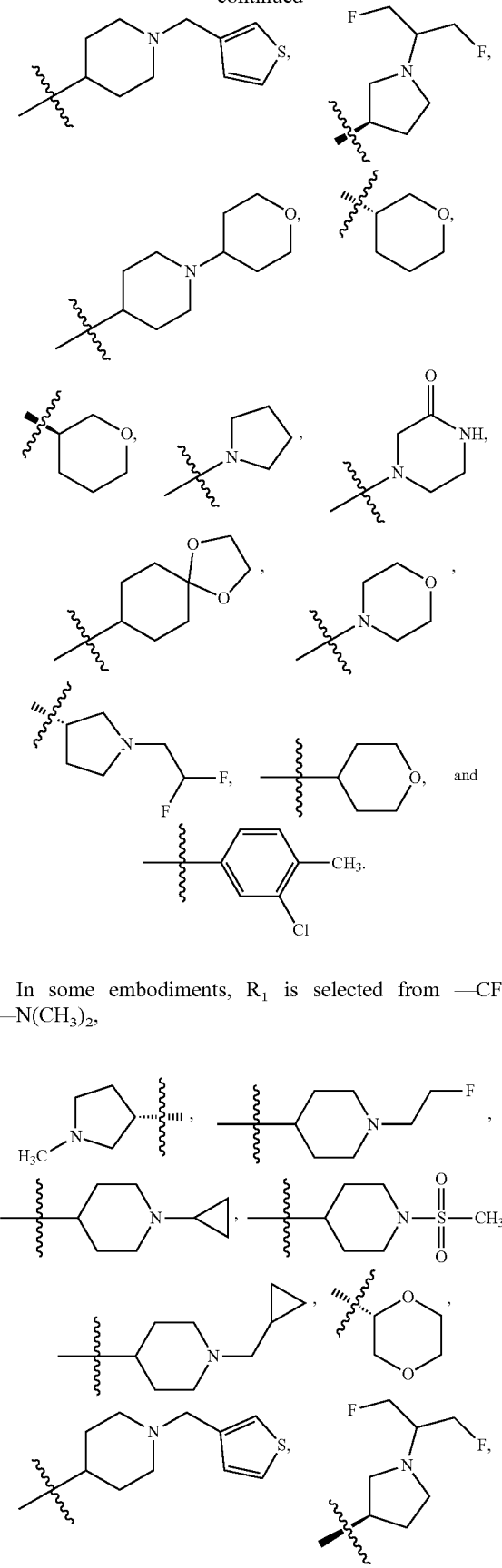
In some embodiments, $R_1$ is selected from —$CF_3$, —$N(CH_3)_2$,

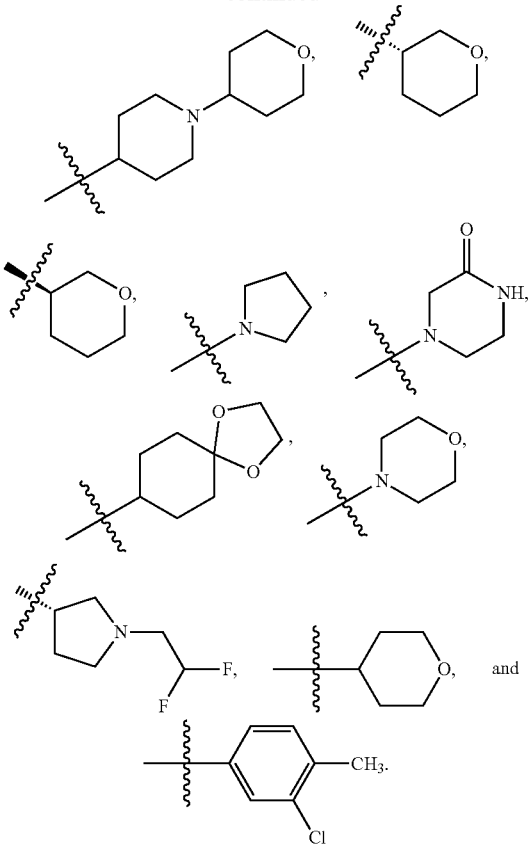

In some embodiments, $R_1$ is selected from and
In some embodiments, $R_1$ is

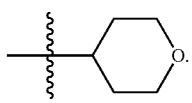

In some embodiments, $R_1$ is

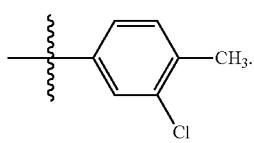 [SMILES: *c1ccc(C)c(Cl)c1]

In some embodiments, $R_2$ is $C_3$-$C_{10}$ cycloalkyl. In some embodiments, $R_2$ is $C_3$-$C_{10}$ cycloalkyl substituted with one or more $R_7$. In some embodiments, $R_2$ is $C_6$ cycloalkyl. In some embodiments, $R_2$ is $C_6$ cycloalkyl substituted with one or more $R_7$. In some embodiments, $R_2$ is $C_3$-$C_{10}$ cycloalkenyl. In some embodiments, $R_2$ is $C_3$-$C_{10}$ cycloalkenyl substituted with one or more $R_7$. In some embodiments, $R_2$ is $C_6$ cycloalkenyl. In some embodiments, $R_2$ is $C_6$ cycloalkenyl substituted with one or more $R_7$. In some embodiments, $R_2$ is aryl. In some embodiments, $R_2$ is aryl substituted with one or more $R_7$. In some embodiments, $R_2$ is phenyl. In some embodiments, $R_2$ is phenyl substituted with one or more $R_7$. In some embodiments, $R_2$ is 3- to 10-membered heterocyclyl. In some embodiments, $R_2$ is 3- to 15-membered heterocyclyl substituted with one or more $R_7$. In some embodiments, $R_2$ is 3- to 15-membered heterocyclyl, wherein the heterocyclyl is bicyclic. In some embodiments, $R_2$ is 3- to 15-membered heterocyclyl, wherein the heterocyclyl is spirocyclic. In some embodiments, $R_2$ is 8-membered heterocyclyl. In some embodiments, $R_2$ is 8-membered heterocyclyl substituted with one or more $R_7$. In some embodiments, $R_2$ is 8-membered heterocyclyl, wherein the heterocyclyl is bicyclic and spirocyclic. In some embodiments, $R_2$ is 13-membered heterocyclyl. In some embodiments, $R_2$ is 13-membered heterocyclyl substituted with one or more $R_7$. In some embodiments, $R_2$ is 13-membered heterocyclyl, wherein the heterocyclyl is tricyclic and spirocyclic. In some embodiments, $R_2$ is 3- to 15-membered heterocyclyl and least one $R_7$ is oxo. In some embodiments, $R_2$ is 3- to 15-membered heterocyclyl and at least one $R_7$ is aryl. In some embodiments, $R_2$ is 3- to 15-membered heterocyclyl and at least two $R_7$ are aryl. In some embodiments, $R_2$ is heteroaryl. In some embodiments, $R_2$ is heteroaryl substituted with one or more $R_7$. In some embodiments, $R_2$ is 10-membered heteroaryl. In some embodiments, $R_2$ is bicyclic heteroaryl. In some embodiments, $R_2$ is 13-membered heteroaryl. In some embodiments, $R_2$ is tricyclic heteroaryl.

In some embodiments, $R_2$ is selected from

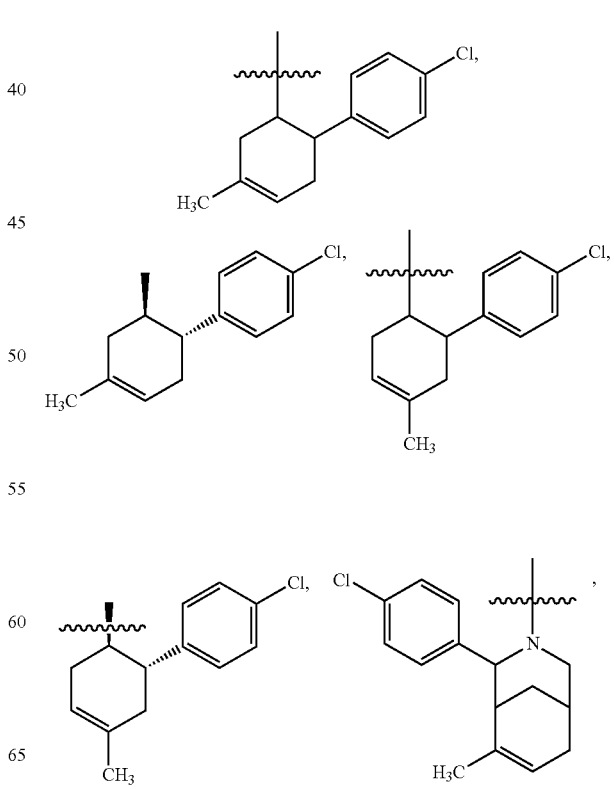

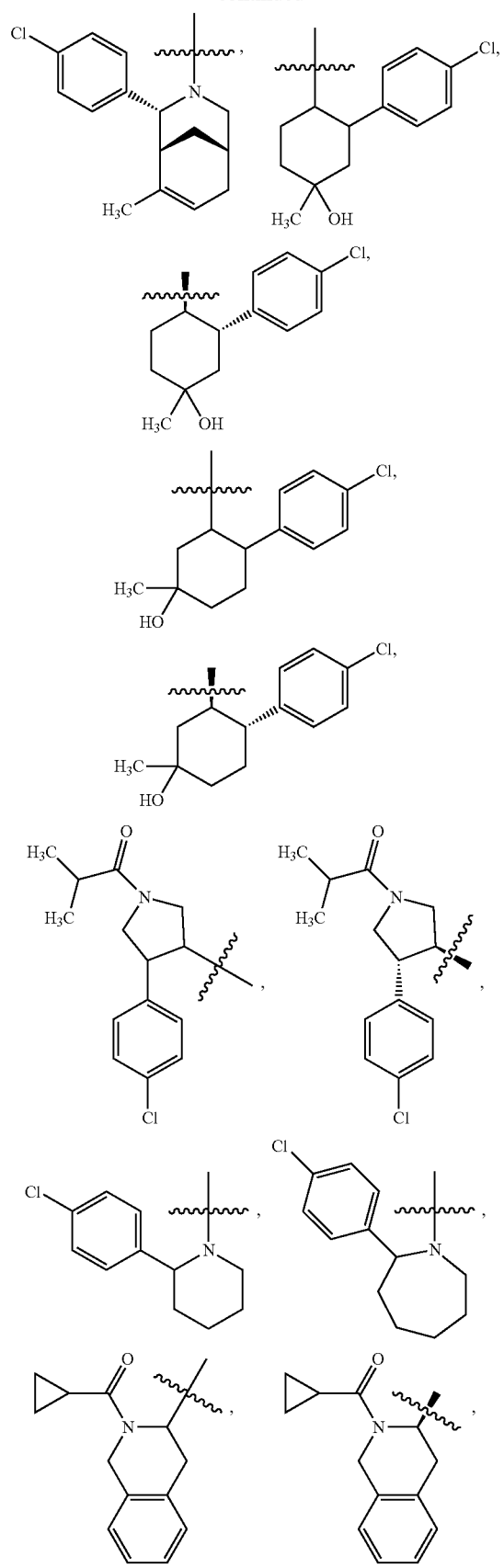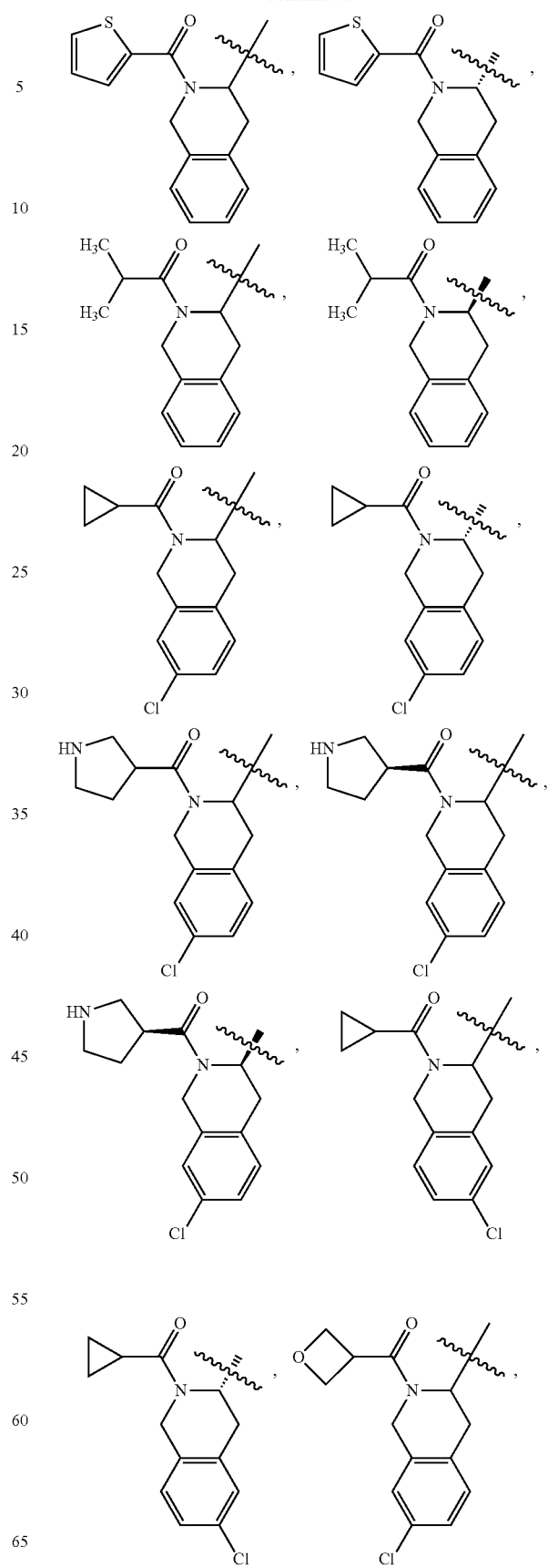

-continued
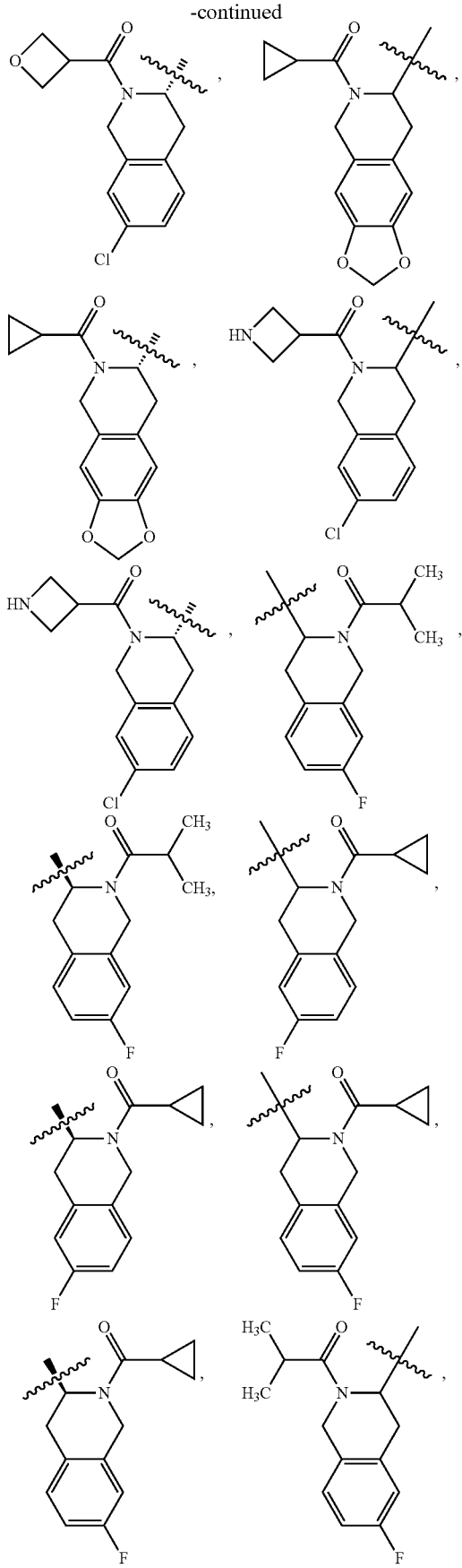
-continued
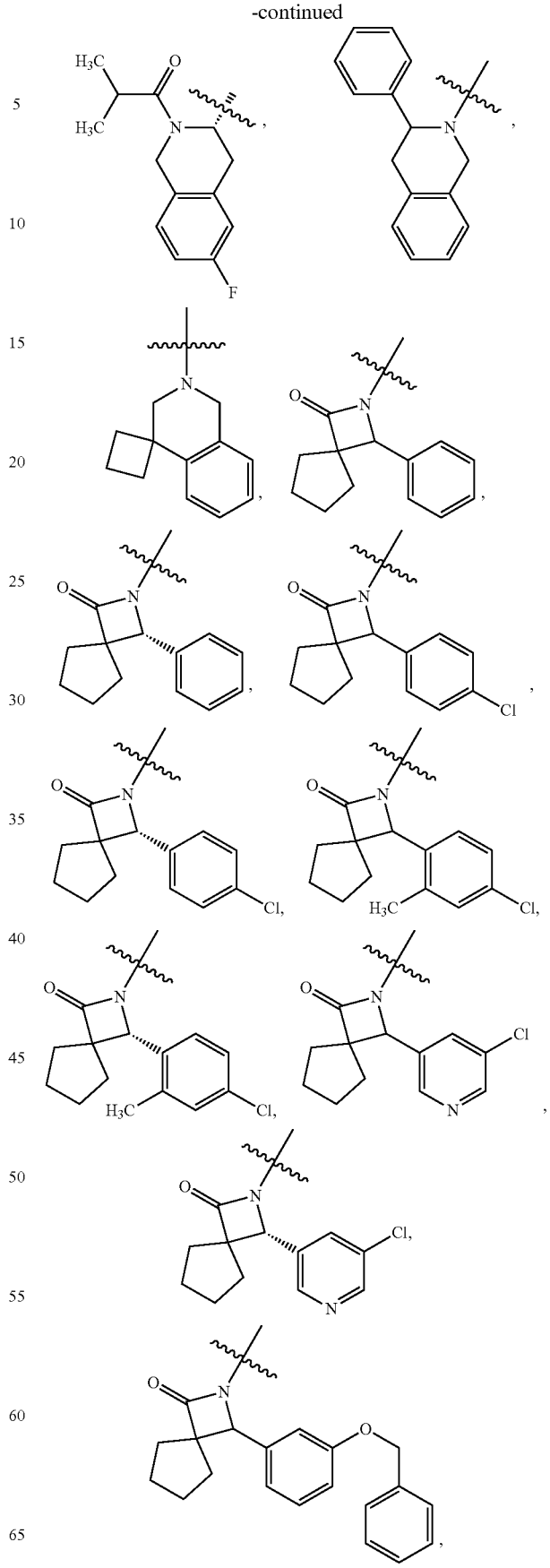

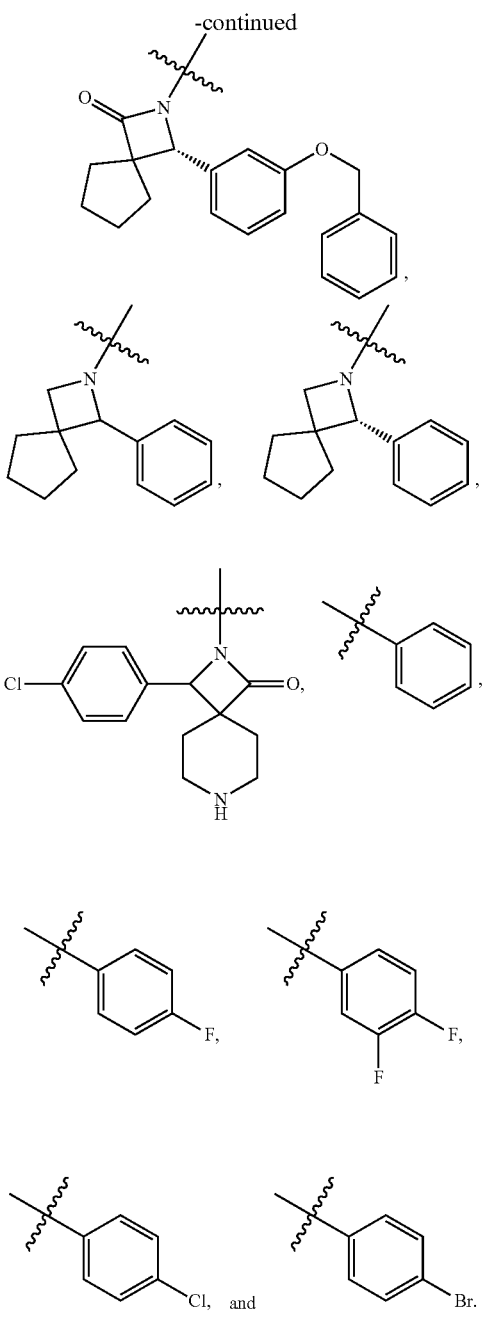

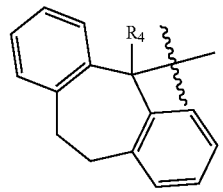

In some embodiments, $R_3$ is H. In some embodiments, $R_3$ is $C_1$-$C_6$ alkyl. In some embodiments, $R_3$ is methyl. In some embodiments, $R_3$ is ethyl. In some embodiments, $R_3$ is propyl. In some embodiments, $R_3$ is butyl. In some embodiments, $R_3$ is pentyl. In some embodiments, $R_3$ is hexyl. In some embodiments, $R_3$ is isopropyl. In some embodiments, $R_3$ is isobutyl. In some embodiments, $R_3$ is tert-butyl. In some embodiments, $R_3$ is aryl. In some embodiments, $R_3$ is aryl substituted with one or more $R_8$. In some embodiments, $R_3$ is phenyl. In some embodiments, $R_3$ is phenyl substituted with one or more $R_8$.

In some embodiments, $R_2$ and $R_3$, together with the atom to which they are attached, come together to form $C_6$-$C_{16}$ aryl optionally substituted with one or more $R_7$;

In some embodiments, $R_2$ and $R_3$, together with the atom to which they are attached, come together to form $C_{15}$ aryl.

In some embodiments, $R_2$ and $R_3$ together with the atom to which they are attached, come together to form

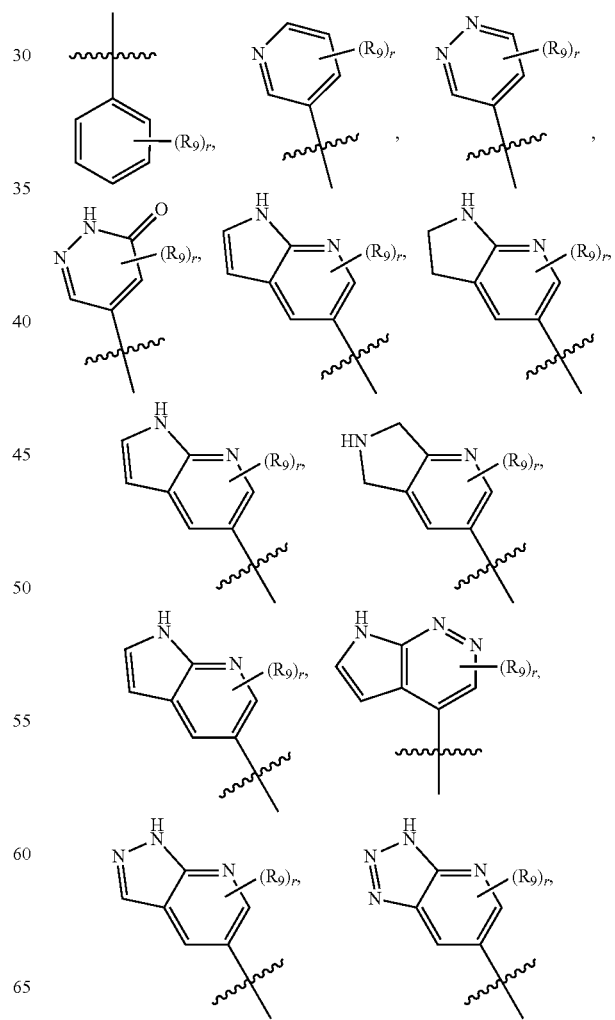

In some embodiments, $R_2$ and $R_3$ are each aryl.
In some embodiments, $R_4$ is H. In some embodiments, $R_4$ is —OH.
In some embodiments, $R_3$ and $R_4$ are H.
In some embodiments, $R_5$ is aryl. In some embodiments, $R_5$ is aryl substituted with one or more $R_9$. In some embodiments, $R_5$ is phenyl. In some embodiments, $R_5$ is phenyl substituted with one or more $R_9$. In some embodiments, $R_5$ is 5- to 10-membered heteroaryl. In some embodiments, $R_5$ is 5- to 10-membered heteroaryl substituted with one or more $R_9$. In some embodiments, $R_5$ is 6-membered heteroaryl. In some embodiments, $R_5$ is 9-membered heteroaryl. In some embodiments, $R_5$ is bicyclic heteroaryl.

In some embodiments, $R_5$ is selected from

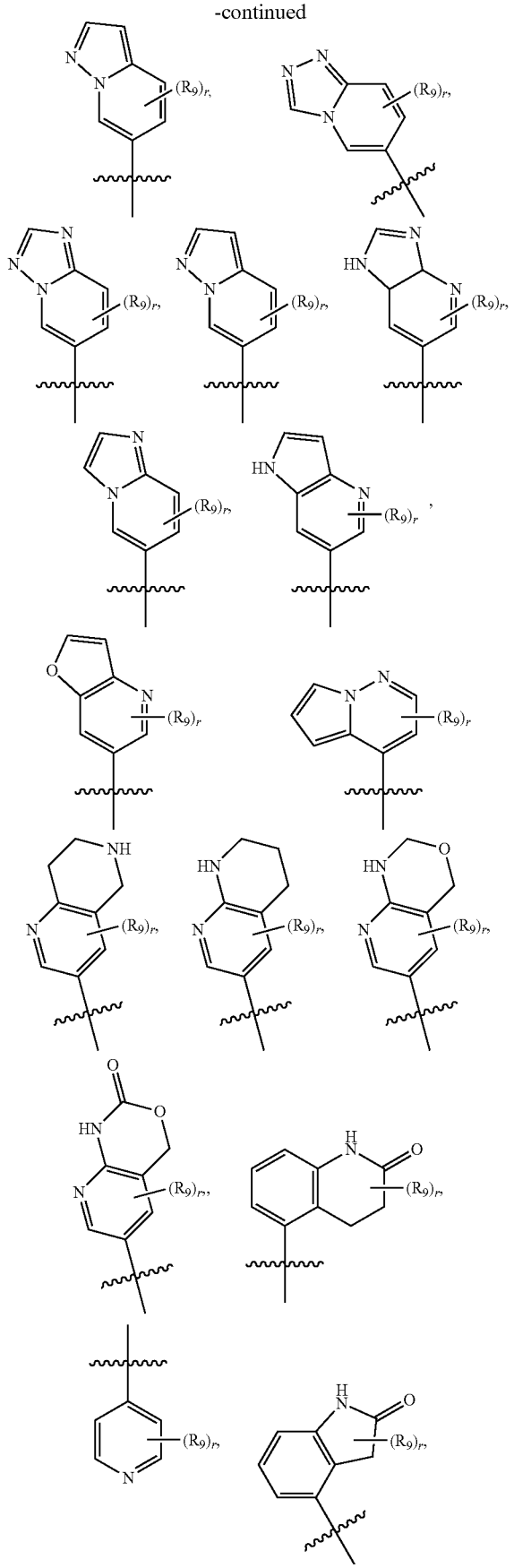
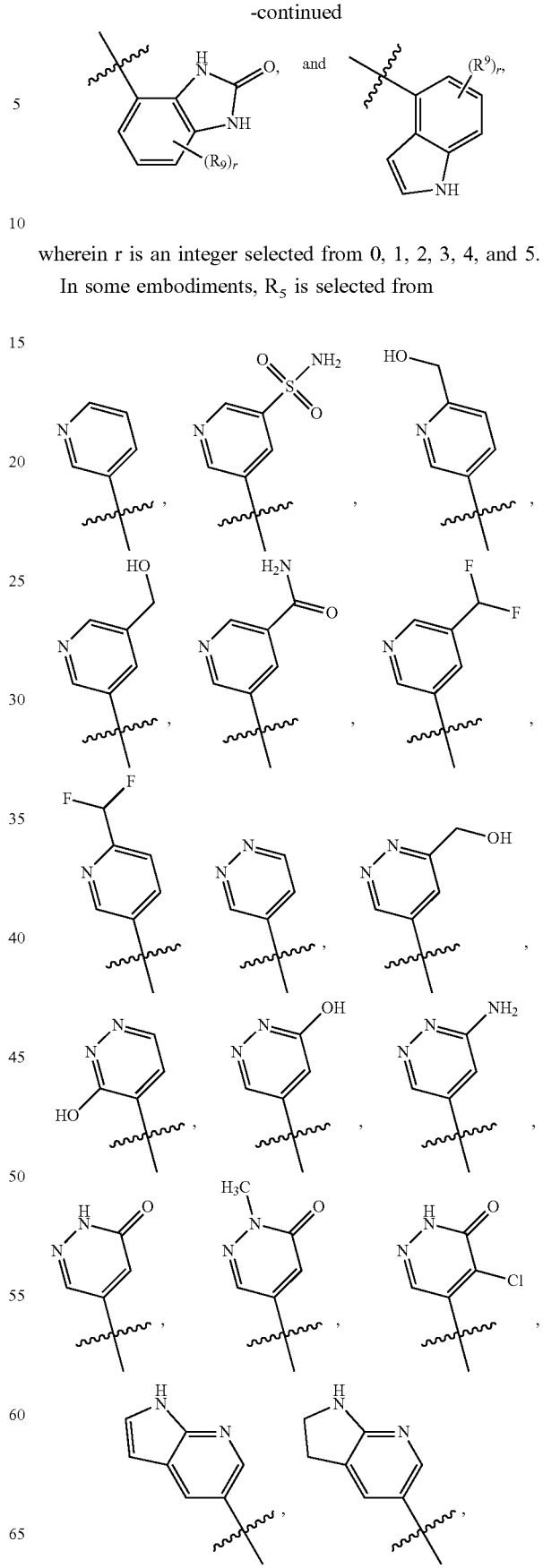
wherein r is an integer selected from 0, 1, 2, 3, 4, and 5.
In some embodiments, $R_5$ is selected from

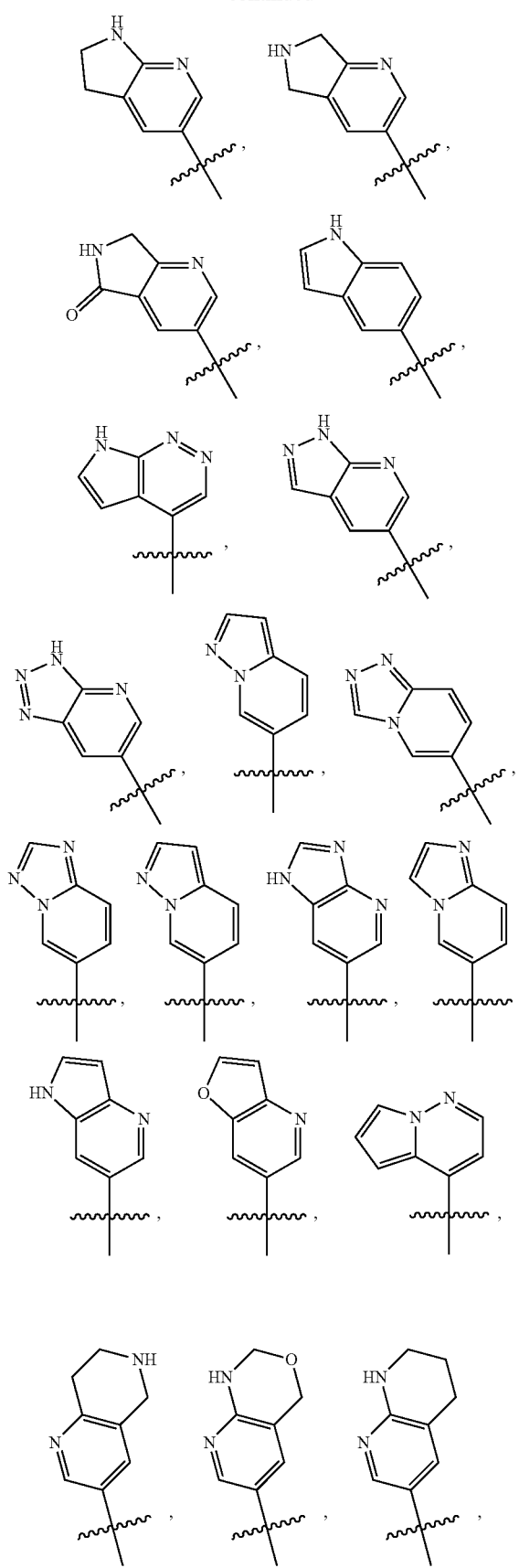
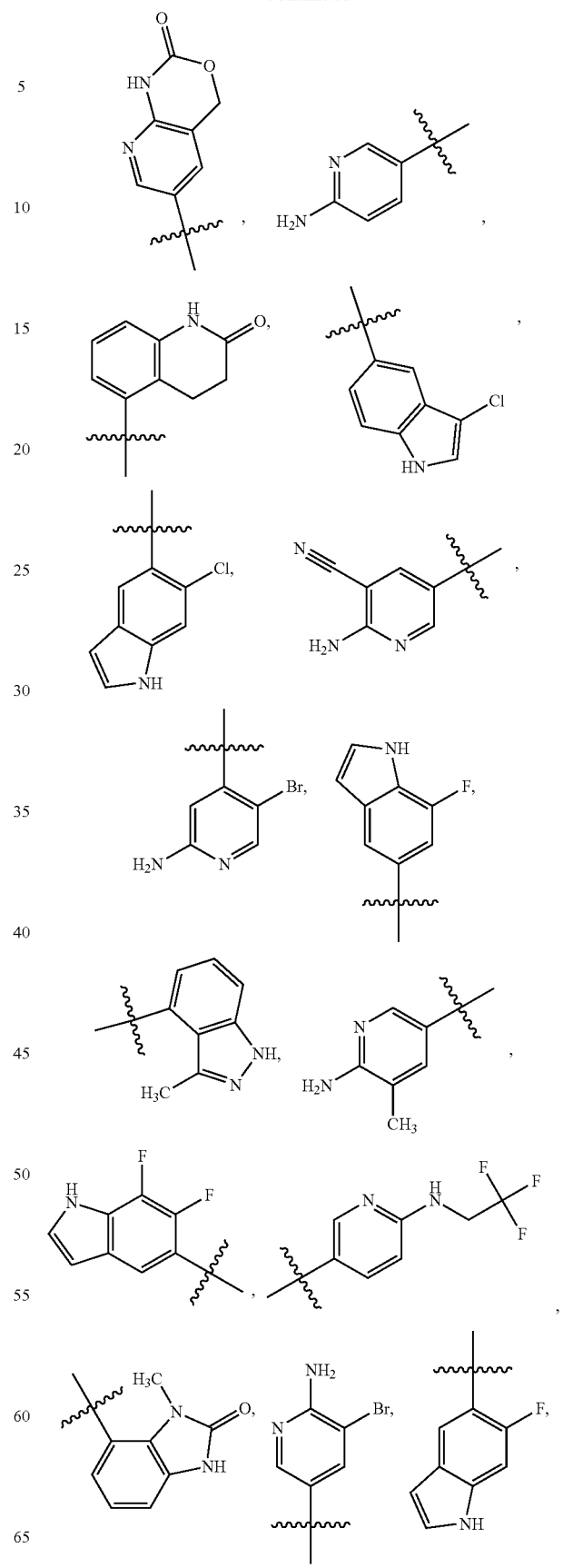

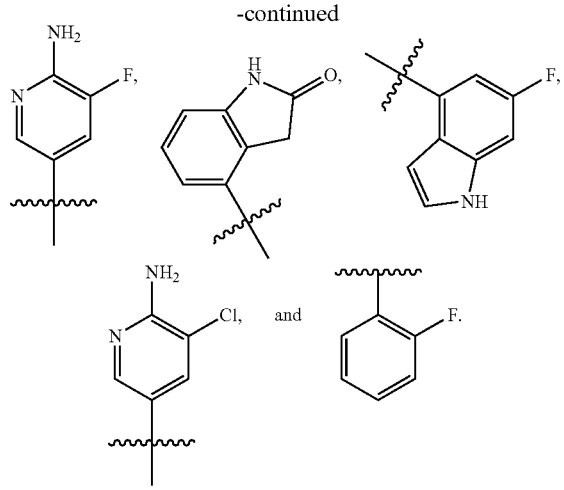
In some embodiments, R$_5$ is selected from
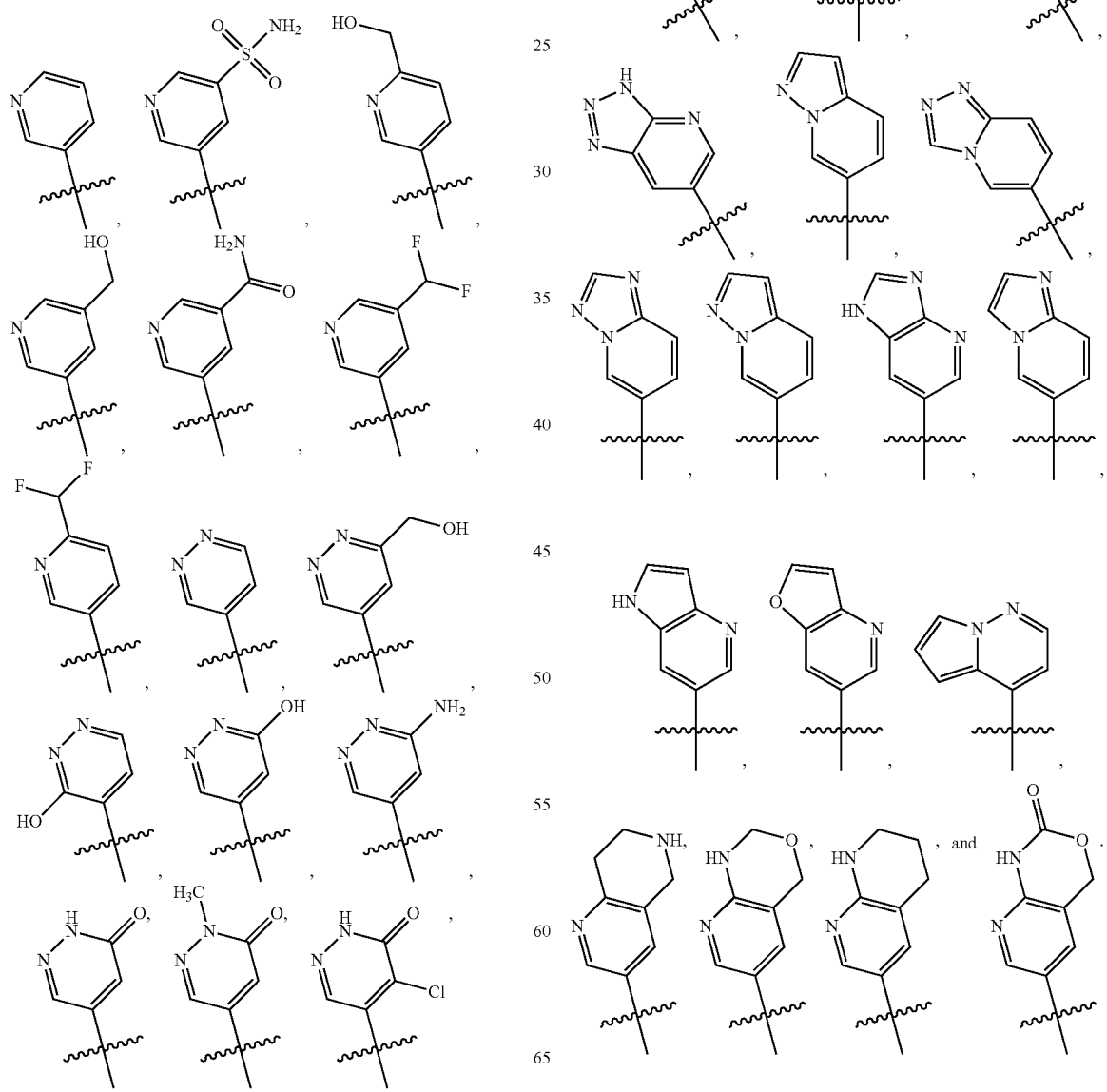
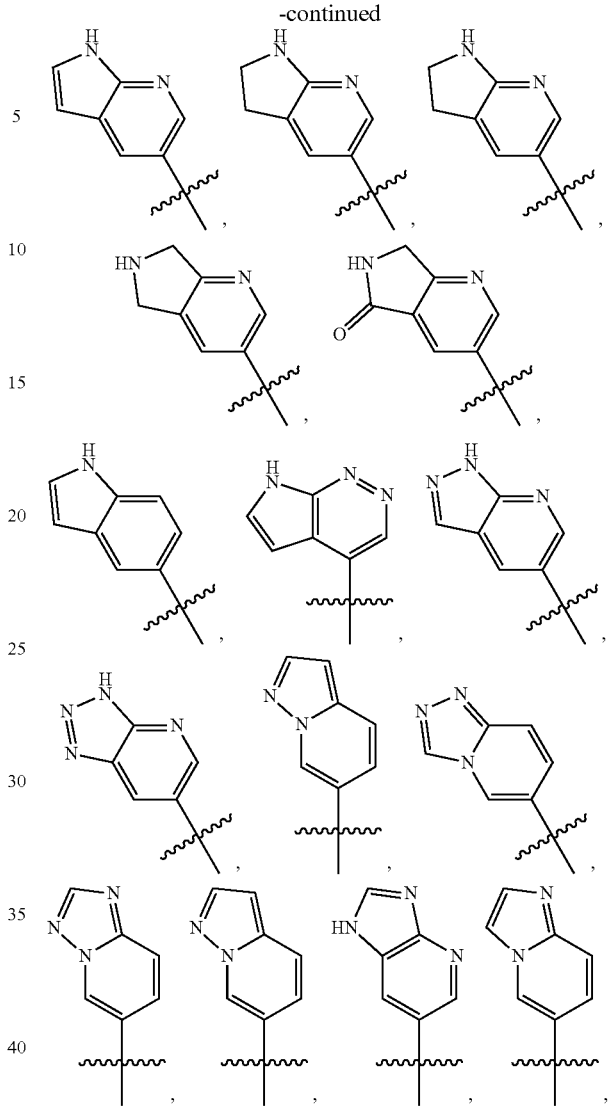

In some embodiments, $R_5$ is

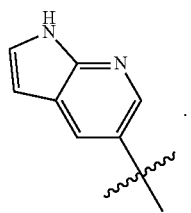 [SMILES: *c1cnc2[nH]ccc2c1]

In some embodiments, $R_5$ is

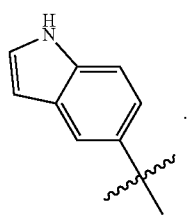 [SMILES: *c1ccc2[nH]ccc2c1]

In some embodiments, at least one $R_6$ is halogen. In some embodiments, at least one $R_6$ is fluoro. In some embodiments, at least one $R_6$ is chloro. In some embodiments, at least one $R_6$ is bromo. In some embodiments, at least one $R_6$ is iodo. In some embodiments, at least one $R_6$ is $C_1$-$C_6$ alkyl. In some embodiments, at least one $R_6$ is methyl. In some embodiments, at least one $R_6$ is ethyl. In some embodiments, at least one $R_6$ is propyl. In some embodiments, at least one $R_6$ is butyl. In some embodiments, at least one $R_6$ is pentyl. In some embodiments, at least one $R_6$ is hexyl. In some embodiments, at least one $R_6$ is isopropyl. In some embodiments, at least one $R_6$ is isobutyl. In some embodiments, at least one $R_6$ is tert-butyl. In some embodiments, at least one $R_6$ is $C_2$-$C_6$ alkenyl. In some embodiments, at least one $R_6$ is $C_2$-$C_6$ alkynyl. In some embodiments, at least one $R_6$ is $C_1$-$C_6$ alkoxy. In some embodiments, at least one $R_6$ is $C_1$-$C_6$ haloalkyl. In some embodiments, at least one $R_6$ is —$CF_3$. In some embodiments, at least one $R_6$ is —$CH_2CH_2F$. In some embodiments, at least one $R_6$ is —$CH_2CHF_2$. In some embodiments, at least one $R_6$ is —$CH(CH_2F)_2$. In some embodiments, at least one $R_6$ is $C_1$-$C_6$ haloalkoxyl. In some embodiments, at least one $R_6$ is —$OR_{15}$. In some embodiments, at least one $R_6$ is oxo. In some embodiments, at least one $R_6$ is —CN. In some embodiments, at least one $R_6$ is —$C(O)R_{12}$. In some embodiments, at least one $R_6$ is —$C(O)N(R_{12})_2$. In some embodiments, at least one $R_6$ is —$(CH_2)_oOR_{12}$. In some embodiments, at least one $R_6$ is —$N(R_{12})_2$. In some embodiments, at least one $R_6$ is —$NHC(O)R_{12}$. In some embodiments, at least one $R_6$ is —$NHS(O)_2R_{12}$. In some embodiments, at least one $R_6$ is —$S(O)_2N(R_{12})_2$. In some embodiments, at least one $R_6$ is —$S(O)_2R_{12}$. In some embodiments, at least one $R_6$ is $C_3$-$C_{10}$ cycloalkyl. In some embodiments, at least one $R_6$ is cyclopropyl. In some embodiments, at least one $R_6$ is aryl. In some embodiments, at least one $R_6$ is 3- to 10-membered heterocyclyl. In some embodiments, at least one $R_6$ is pyranyl. In some embodiments, at least one $R_6$ is heteroaryl. In some embodiments, at least one $R_6$ is $C_1$-$C_6$ alkyl substituted with one or more $C_3$-$C_{10}$ cycloalkyl. In some embodiments, at least one $R_6$ is $C_1$-$C_6$ alkyl substituted with cyclopropyl. In some embodiments, at least one $R_6$ is $C_1$-$C_6$ alkyl substituted with one or more aryl. In some embodiments, at least one $R_6$ is $C_1$-$C_6$ alkyl substituted with one or more 3- to 10-membered heterocyclyl. In some embodiments, at least one $R_6$ is $C_1$-$C_6$ alkyl substituted with one or more heteroaryl. In some embodiments, at least one $R_6$ is $C_1$-$C_6$ alkyl substituted with one or more thiophenyl.

In some embodiments, at least one $R_7$ is halogen. In some embodiments, at least one $R_7$ is fluoro. In some embodiments, at least one $R_7$ is chloro. In some embodiments, at least one $R_7$ is bromo. In some embodiments, at least one $R_7$ is iodo. In some embodiments, at least one $R_7$ is $C_1$-$C_6$ alkyl. In some embodiments, at least one $R_7$ is methyl. In some embodiments, at least one $R_7$ is ethyl. In some embodiments, at least one $R_7$ is propyl. In some embodiments, at least one $R_7$ is butyl. In some embodiments, at least one $R_7$ is pentyl. In some embodiments, at least one $R_7$ is hexyl. In some embodiments, at least one $R_7$ is isopropyl. In some embodiments, at least one $R_7$ is isobutyl. In some embodiments, at least one $R_7$ is tert-butyl. In some embodiments, at least one $R_7$ is $C_1$-$C_6$ haloalkyl. In some embodiments, at least one $R_7$ is —OH. In some embodiments, at least one $R_7$ is oxo. In some embodiments, at least one $R_7$ is —$C(O)R_{10}$. In some embodiments, at least one $R_7$ is aryl. In some embodiments, at least one $R_7$ is aryl substituted with one or more $R_{11}$. In some embodiments, at least one $R_7$ is heteroaryl. In some embodiments, at least one $R_7$ is heteroaryl substituted with one or more $R_{11}$.

In some embodiments, at least one $R_7$ is selected from —F, —Cl, —Br, oxo,

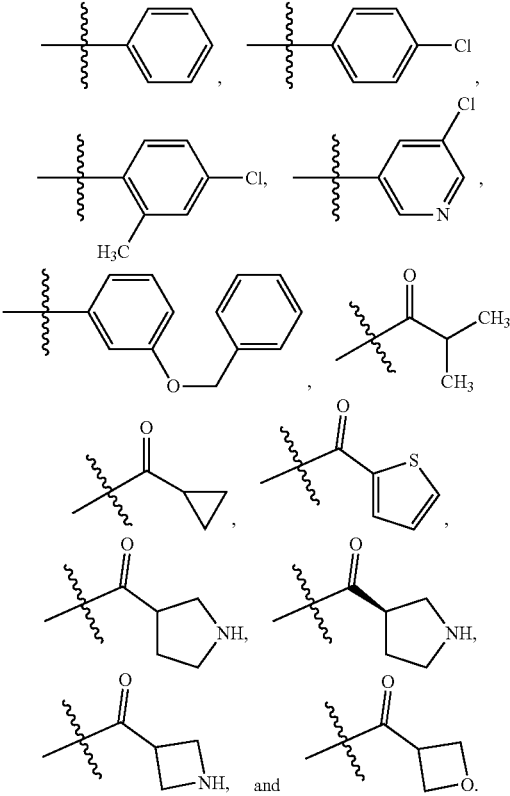

In some embodiments, at least one $R_8$ is halogen. In some embodiments, at least one $R_8$ is fluoro. In some embodiments, at least one $R_8$ is chloro. In some embodiments, at least one $R_8$ is bromo. In some embodiments, at least one $R_8$ is iodo. In some embodiments, at least one $R_8$ is $C_1$-$C_6$ alkyl. In some embodiments, at least one $R_8$ is methyl. In some embodiments, at least one $R_8$ is ethyl. In some embodiments, at least one $R_8$ is propyl. In some embodiments, at least one $R_8$ is butyl. In some embodiments, at least one $R_8$ is pentyl. In some embodiments, at least one $R_8$ is hexyl. In some embodiments, at least one $R_8$ is isopropyl. In some embodiments, at least one $R_8$ is isobutyl. In some embodiments, at least one $R_8$ is tert-butyl. In some embodiments, at least one $R_8$ is —OH.

In some embodiments, at least one $R_9$ is halogen. In some embodiments, at least one $R_9$ is fluoro. In some embodiments, at least one $R_9$ is chloro. In some embodiments, at least one $R_9$ is bromo. In some embodiments, at least one $R_9$ is iodo. In some embodiments, at least one $R_9$ is $C_1$-$C_6$ alkyl. In some embodiments, at least one $R_9$ is methyl. In some embodiments, at least one $R_9$ is ethyl. In some embodiments, at least one $R_9$ is propyl. In some embodiments, at least one $R_9$ is butyl. In some embodiments, at least one $R_9$ is pentyl. In some embodiments, at least one $R_9$ is hexyl. In some embodiments, at least one $R_9$ is isopropyl. In some embodiments, at least one $R_9$ is isobutyl. In some embodiments, at least one $R_9$ is tert-butyl. In some embodiments, at least one $R_9$ is $C_2$-$C_6$ alkenyl. In some embodiments, at least one $R_9$ is $C_2$-$C_6$ alkynyl. In some embodiments, at least one $R_9$ is $C_1$-$C_6$ haloalkyl. In some embodiments, at least one $R_9$ is —CN. In some embodiments, at least one $R_9$ is —C(O)N($R_{12}$)$_2$. In some embodiments, at least one $R_9$ is —C(O)O$R_{12}$. In some embodiments, at least one $R_9$ is —(CH$_2$)$_o$O$R_{12}$. In some embodiments, at least one $R_9$ is —OH. In some embodiments, at least one $R_9$ is oxo. In some embodiments, at least one $R_9$ is —N($R_{12}$)$_2$. In some embodiments, at least one $R_9$ is —NHC(O)$R_{12}$. In some embodiments, at least one $R_9$ is —NHS(O)$_2$$R_{12}$. In some embodiments, at least one $R_9$ is —S(O)$_2$N($R_{12}$)$_2$.

In some embodiments, at least one $R_{10}$ is $C_1$-$C_6$ alkyl. In some embodiments, at least one $R_{10}$ is methyl. In some embodiments, at least one $R_{10}$ is ethyl. In some embodiments, at least one $R_{10}$ is propyl. In some embodiments, at least one $R_{10}$ is butyl. In some embodiments, at least one $R_{10}$ is pentyl. In some embodiments, at least one $R_{10}$ is hexyl. In some embodiments, at least one $R_{10}$ is isopropyl. In some embodiments, at least one $R_{10}$ is isobutyl. In some embodiments, at least one $R_{10}$ is tert-butyl. In some embodiments, at least one $R_{10}$ is $C_1$-$C_6$ haloalkyl. In some embodiments, at least one $R_{10}$ is —(CH$_2$)$_p$—N($R_{13}$)$_2$. In some embodiments, at least one $R_{10}$ is $C_3$-$C_{10}$ cycloalkyl. In some embodiments, at least one $R_{10}$ is $C_3$-$C_{10}$ cycloalkyl substituted with one or more $R_{14}$. In some embodiments, at least one $R_{10}$ is aryl. In some embodiments, at least one $R_{10}$ is aryl substituted with one or more $R_{14}$. In some embodiments, at least one $R_{10}$ is 3- to 10-membered heterocyclyl. In some embodiments, at least one $R_{10}$ is 3- to 10-membered heterocyclyl substituted with one or more $R_{14}$. In some embodiments, at least one $R_{10}$ is heteroaryl. In some embodiments, at least one $R_{10}$ is heteroaryl substituted with one or more $R_{14}$.

In some embodiments, at least one $R_{11}$ is halogen. In some embodiments, at least one $R_{11}$ is fluoro. In some embodiments, at least one $R_{11}$ is chloro. In some embodiments, at least one $R_{11}$ is bromo. In some embodiments, at least one Ru is iodo. In some embodiments, at least one Ru is $C_1$-$C_6$ alkyl. In some embodiments, at least one Ru is methyl. In some embodiments, at least one Ru is ethyl. In some embodiments, at least one Ru is propyl. In some embodiments, at least one Ru is butyl. In some embodiments, at least one Ru is pentyl. In some embodiments, at least one Ru is hexyl. In some embodiments, at least one Ru is isopropyl. In some embodiments, at least one Ru is isobutyl. In some embodiments, at least one Ru is tert-butyl. In some embodiments, at least one Ru is $C_1$-$C_6$ alkenyl. In some embodiments, at least one Ru is $C_1$-$C_6$ alkynyl. In some embodiments, at least one Ru is $C_1$-$C_6$ alkoxy. In some embodiments, at least one Ru is $C_1$-$C_6$ haloalkyl. In some embodiments, at least one Ru is $C_1$-$C_6$ haloalkoxy. In some embodiments, at least one Ru is —O$R_{15}$. In some embodiments, at least one Ru is $C_3$-$C_{10}$ cycloalkyl. In some embodiments, at least one Ru is aryl. In some embodiments, at least one Ru is 3- to 10-membered heterocyclyl. In some embodiments, at least one Ru is heteroaryl.

In some embodiments, at least one $R_{12}$ is H. In some embodiments, at least one $R_{12}$ is halogen. In some embodiments, at least one $R_{12}$ is fluoro. In some embodiments, at least one $R_{12}$ is chloro. In some embodiments, at least one $R_{12}$ is bromo. In some embodiments, at least one $R_{12}$ is iodo. In some embodiments, at least one $R_{12}$ is $C_1$-$C_6$ alkyl. In some embodiments, at least one $R_{12}$ is methyl. In some embodiments, at least one $R_{12}$ is ethyl. In some embodiments, at least one $R_{12}$ is propyl. In some embodiments, at least one $R_{12}$ is butyl. In some embodiments, at least one $R_{12}$ is pentyl. In some embodiments, at least one $R_{12}$ is hexyl. In some embodiments, at least one $R_{12}$ is isopropyl. In some embodiments, at least one $R_{12}$ is isobutyl. In some embodiments, at least one $R_{12}$ is tert-butyl. In some embodiments, at least one $R_{12}$ is $C_1$-$C_6$ alkenyl. In some embodiments, at least one $R_{12}$ is $C_1$-$C_6$ alkynyl. In some embodiments, at least one $R_{12}$ is $C_1$-$C_6$ alkoxy. In some embodiments, at least one $R_{12}$ is $C_1$-$C_6$ haloalkyl. In some embodiments, at least one $R_{12}$ is —CH$_2$CF$_3$. In some embodiments, at least one $R_{12}$ is $C_1$-$C_6$ haloalkoxy. In some embodiments, at least one $R_{12}$ is $C_3$-$C_{10}$ cycloalkyl. In some embodiments, at least one $R_{12}$ is aryl. In some embodiments, at least one $R_{12}$ is 3- to 10-membered heterocyclyl. In some embodiments, at least one $R_{12}$ is heteroaryl.

In some embodiments, at least one $R_{13}$ is H. In some embodiments, at least one $R_{13}$ is halogen. In some embodiments, at least one $R_{13}$ is fluoro. In some embodiments, at least one $R_{13}$ is chloro. In some embodiments, at least one $R_{13}$ is bromo. In some embodiments, at least one $R_{13}$ is iodo. In some embodiments, at least one $R_{13}$ is $C_1$-$C_6$ alkyl. In some embodiments, at least one $R_{13}$ is methyl. In some embodiments, at least one $R_{13}$ is ethyl. In some embodiments, at least one $R_{13}$ is propyl. In some embodiments, at least one $R_{13}$ is butyl. In some embodiments, at least one $R_{13}$ is pentyl. In some embodiments, at least one $R_{13}$ is hexyl. In some embodiments, at least one $R_{13}$ is isopropyl. In some embodiments, at least one $R_{13}$ is isobutyl. In some embodiments, at least one $R_{13}$ is tert-butyl. In some embodiments, at least one $R_{13}$ is $C_1$-$C_6$ alkenyl. In some embodiments, at least one $R_{13}$ is $C_1$-$C_6$ alkynyl. In some embodiments, at least one $R_{13}$ is $C_1$-$C_6$ alkoxy. In some embodiments, at least one $R_{13}$ is $C_1$-$C_6$ haloalkyl. In some embodiments, at least one $R_{13}$ is $C_1$-$C_6$ haloalkoxy. In some embodiments, at least one $R_{13}$ is $C_3$-$C_{10}$ cycloalkyl. In some embodiments, at least one $R_{13}$ is aryl. In some embodiments, at least one $R_{13}$ is 3- to 10-membered heterocyclyl. In some embodiments, at least one $R_{13}$ is heteroaryl.

In some embodiments, at least one $R_{14}$ is halogen. In some embodiments, at least one $R_{14}$ is fluoro. In some embodiments, at least one $R_{14}$ is chloro. In some embodiments, at least one $R_{14}$ is bromo. In some embodiments, at least one $R_{14}$ is iodo. In some embodiments, at least one $R_{14}$ is $C_1$-$C_6$ alkyl. In some embodiments, at least one $R_{14}$ is methyl. In some embodiments, at least one $R_{14}$ is ethyl. In some embodiments, at least one $R_{14}$ is propyl. In some embodiments, at least one $R_{14}$ is butyl. In some embodiments, at least one $R_{14}$ is pentyl. In some embodiments, at least one $R_{14}$ is hexyl. In some embodiments, at least one $R_{14}$ is isopropyl. In some embodiments, at least one $R_{14}$ is isobutyl. In some embodiments, at least one $R_{14}$ is tert-butyl. In some embodiments, at least one $R_{14}$ is $C_1$-$C_6$ alkenyl. In some embodiments, at least one $R_{14}$ is $C_1$-$C_6$ alkynyl. In some embodiments, at least one $R_{14}$ is $C_1$-$C_6$ alkoxy. In some embodiments, at least one $R_{14}$ is $C_1$-$C_6$ haloalkyl. In some embodiments, at least one $R_{14}$ is $C_1$-$C_6$ haloalkoxy. In some embodiments, at least one $R_{14}$ is $C_3$-$C_{10}$ cycloalkyl. In some embodiments, at least one $R_{14}$ is aryl. In some embodiments, at least one $R_{14}$ is 3- to 10-membered heterocyclyl. In some embodiments, at least one $R_{14}$ is heteroaryl.

In some embodiments, at least one $R_{15}$ is H. In some embodiments, at least one $R_{15}$ is halogen. In some embodiments, at least one $R_{15}$ is fluoro. In some embodiments, at least one $R_{15}$ is chloro. In some embodiments, at least one $R_{15}$ is bromo. In some embodiments, at least one $R_{15}$ is iodo. In some embodiments, at least one $R_{15}$ is $C_1$-$C_6$ alkyl. In some embodiments, at least one $R_{15}$ is methyl. In some embodiments, at least one $R_{15}$ is ethyl. In some embodiments, at least one $R_{15}$ is propyl. In some embodiments, at least one $R_{15}$ is butyl. In some embodiments, at least one $R_{15}$ is pentyl. In some embodiments, at least one $R_{15}$ is hexyl. In some embodiments, at least one $R_{15}$ is isopropyl. In some embodiments, at least one $R_{15}$ is isobutyl. In some embodiments, at least one $R_{15}$ is tert-butyl. In some embodiments, at least one $R_{15}$ is $C_1$-$C_6$ alkenyl. In some embodiments, at least one $R_{15}$ is $C_1$-$C_6$ alkynyl. In some embodiments, at least one $R_{15}$ is $C_1$-$C_6$ alkoxy. In some embodiments, at least one $R_{15}$ is $C_1$-$C_6$ haloalkyl. In some embodiments, at least one $R_{15}$ is $C_1$-$C_6$ haloalkoxy. In some embodiments, at least one $R_{15}$ is $C_3$-$C_{10}$ cycloalkyl. In some embodiments, at least one $R_{15}$ is —$(CH_2)_q$-aryl. In some embodiments, at least one $R_{15}$ is 3- to 10-membered heterocyclyl. In some embodiments, at least one $R_{15}$ is heteroaryl.

In some embodiments, n is 0. In some embodiments, n is 1. In some embodiments, n is 2.

In some embodiments, o is 0. In some embodiments, o is 1. In some embodiments, o is 2.

In some embodiments, p is 0. In some embodiments, p is 1. In some embodiments, p is 2.

In some embodiments, q is 0. In some embodiments, q is 1. In some embodiments, q is 2.

Non-limiting illustrative compounds of the present disclosure include:

| Compound No | Structure | Name |
|---|---|---|
| 1 | 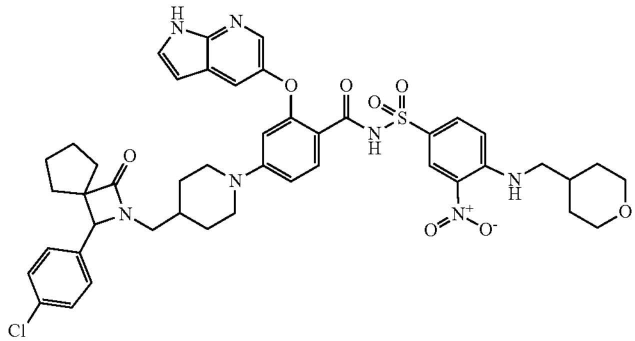 [SMILES: O=C(NS(=O)(=O)c1ccc(NCC2CCOCC2)c([N+](=O)[O-])c1)c1ccc(N2CCC(CN3C(=O)C4(CCCC4)C3c3ccc(Cl)cc3)CC2)cc1Oc1cnc2[nH]ccc2c1] | 4-[4-[[1-(4-chlorophenyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 2 | 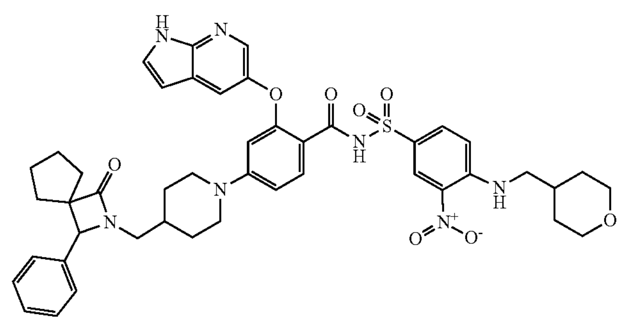 [SMILES: O=C(NS(=O)(=O)c1ccc(NCC2CCOCC2)c([N+](=O)[O-])c1)c1ccc(N2CCC(CN3C(=O)C4(CCCC4)C3c3ccccc3)CC2)cc1Oc1cnc2[nH]ccc2c1] | N-[3-nitro-4-(tetrahydropyran-4-ylmethylamino)phenyl]sulfonyl-4-[4-[(3-oxo-1-phenyl-2-azaspiro[3.4]octan-2-yl)methyl]-1-piperidyl]-2-(1H-pyrrolo[2,3-b]pyridin-5-yloxy)benzamide |

| Compound No | Structure | Name |
|---|---|---|
| 3 | 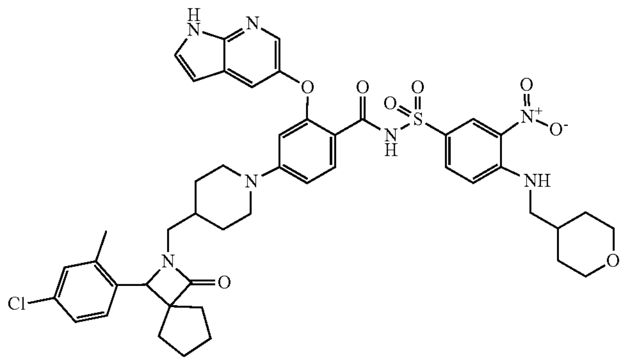 [SMILES: Cc1cc(Cl)ccc1C1N(CC2CCN(c3ccc(C(=O)NS(=O)(=O)c4ccc(NCC5CCOCC5)c([N+](=O)[O-])c4)c(Oc4cnc5[nH]ccc5c4)c3)CC2)C(=O)C12CCCC2] | 4-[4-[[1-(4-chloro-2-methyl-phenyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 4 | 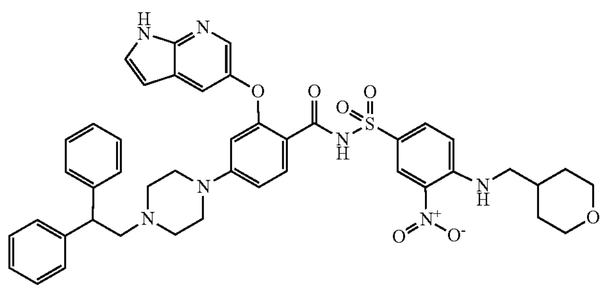 [SMILES: O=C(NS(=O)(=O)c1ccc(NCC2CCOCC2)c([N+](=O)[O-])c1)c1ccc(N2CCN(CC(c3ccccc3)c3ccccc3)CC2)cc1Oc1cnc2[nH]ccc2c1] | 4-[4-(2,2-diphenylethyl)piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 5 | 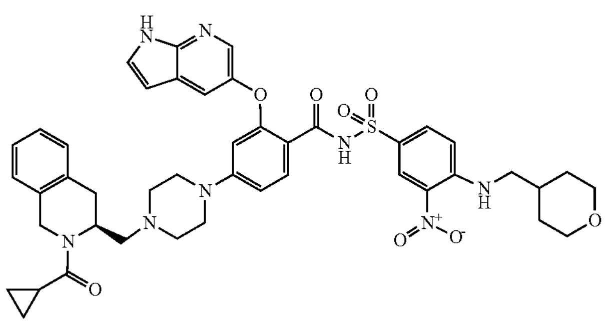 | 4-[4-[[(3S)-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 6 | 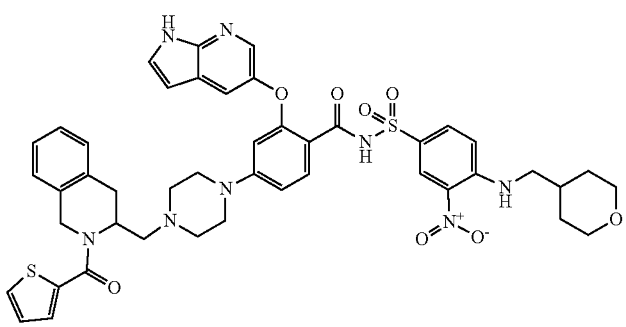 [SMILES: O=C(NS(=O)(=O)c1ccc(NCC2CCOCC2)c([N+](=O)[O-])c1)c1ccc(N2CCN(CC3Cc4ccccc4CN3C(=O)c3cccs3)CC2)cc1Oc1cnc2[nH]ccc2c1] | N-[3-nitro-4-(tetrahydropyran-4-ylmethylamino)phenyl]sulfonyl-2-(1H-pyrrolo[2,3-b]pyridin-5-yloxy)-4-[4-[[2-(thiophene-2-carbonyl)-3,4-dihydro-1H-isoquinolin-3-yl]methyl]piperazin-1-yl]benzamide |
| 7 | 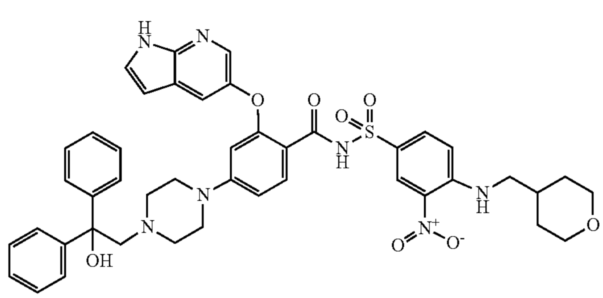 [SMILES: O=C(NS(=O)(=O)c1ccc(NCC2CCOCC2)c([N+](=O)[O-])c1)c1ccc(N2CCN(CC(O)(c3ccccc3)c3ccccc3)CC2)cc1Oc1cnc2[nH]ccc2c1] | 4-[4-(2-hydroxy-2,2-diphenyl-ethyl)piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 8 | 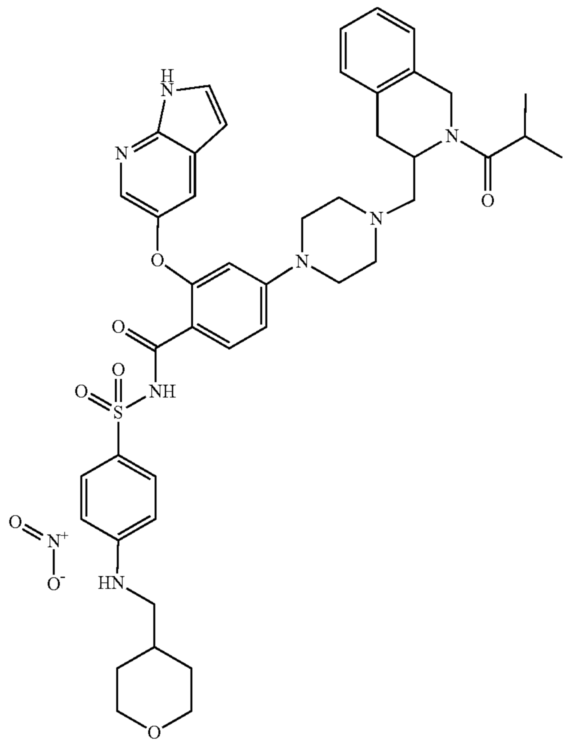 | 4-[4-[[2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 9 | 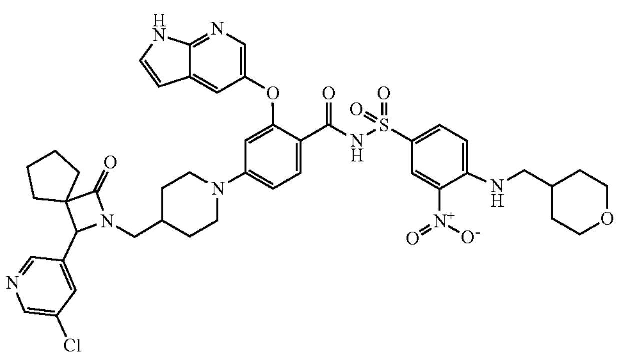 | 4-[4-[[1-(5-chloro-3-pyridyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 10 | 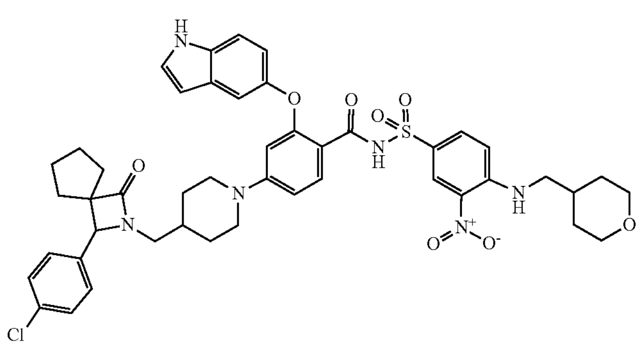 [SMILES: O=C(NS(=O)(=O)c1ccc(NCC2CCOCC2)c([N+](=O)[O-])c1)c1ccc(N2CCC(CN3C(=O)C4(CCCC4)C3c3ccc(Cl)cc3)CC2)cc1Oc1ccc2[nH]ccc2c1] | 4-[4-[[1-(4-chlorophenyl)-3-oxo-2-azaspiro[3.4]octan-2-yl]methyl]-1-piperidyl]-2-(1H-indol-5-yloxy)-N-[3-nitro-4-(tetrahydropyran-4-ylmethylamino)phenyl]sulfonyl-benzamide |

| Compound No | Structure | Name |
|---|---|---|
| 11 | 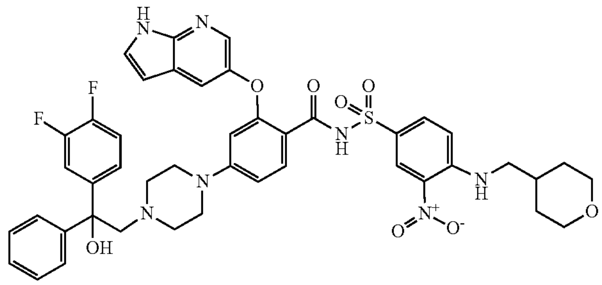 [SMILES: O=C(NS(=O)(=O)c1ccc(NCC2CCOCC2)c([N+](=O)[O-])c1)c1ccc(N2CCN(CC(O)(c3ccccc3)c3ccc(F)c(F)c3)CC2)cc1Oc1cnc2[nH]ccc2c1] | 4-[4-[2-(3,4-difluorophenyl)-2-hydroxy-2-phenyl-ethyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 12 | 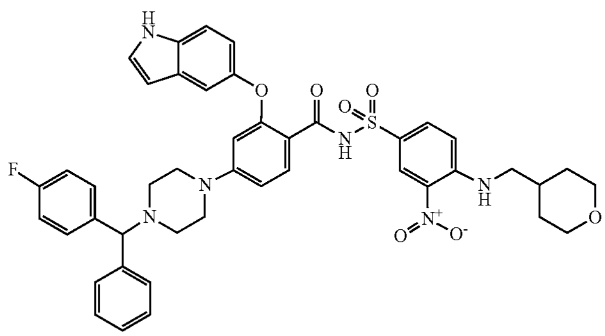 [SMILES: O=C(NS(=O)(=O)c1ccc(NCC2CCOCC2)c([N+](=O)[O-])c1)c1ccc(N2CCN(C(c3ccccc3)c3ccc(F)cc3)CC2)cc1Oc1ccc2[nH]ccc2c1] | 4-[4-[(4-fluorophenyl)-phenyl-methyl]piperazin-1-yl]-2-(1H-indol-5-yloxy)-N-[3-nitro-4-(tetrahydropyran-4-ylmethylamino)phenyl]sulfonyl-benzamide |
| 13 | 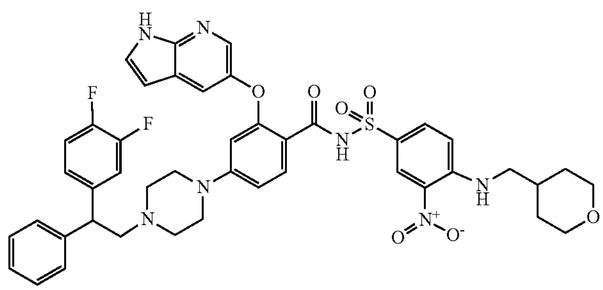 [SMILES: O=C(NS(=O)(=O)c1ccc(NCC2CCOCC2)c([N+](=O)[O-])c1)c1ccc(N2CCN(CC(c3ccccc3)c3ccc(F)c(F)c3)CC2)cc1Oc1cnc2[nH]ccc2c1] | 4-[4-[2-(3,4-difluorophenyl)-2-phenyl-ethyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 14 | 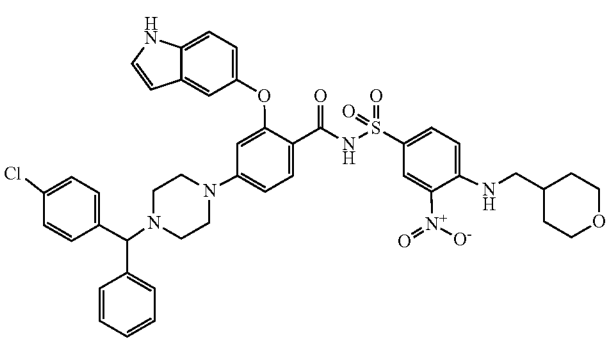 [SMILES: O=C(NS(=O)(=O)c1ccc(NCC2CCOCC2)c([N+](=O)[O-])c1)c1ccc(N2CCN(C(c3ccccc3)c3ccc(Cl)cc3)CC2)cc1Oc1ccc2[nH]ccc2c1] | 4-[4-[(4-chlorophenyl)-phenyl-methyl]piperazin-1-yl]-2-(1H-indol-5-yloxy)-N-[3-nitro-4-(tetrahydropyran-4-ylmethylamino)phenyl]sulfonyl-benzamide |
| 15 | 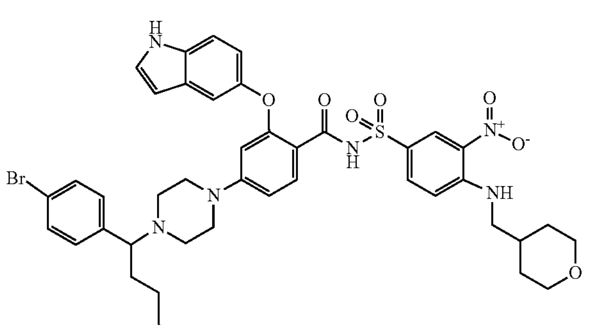 [SMILES: CCCC(c1ccc(Br)cc1)N1CCN(c2ccc(C(=O)NS(=O)(=O)c3ccc(NCC4CCOCC4)c([N+](=O)[O-])c3)c(Oc3ccc4[nH]ccc4c3)c2)CC1] | 4-[4-[1-(4-bromophenyl)butyl]piperazin-1-yl]-2-(1H-indol-5-yloxy)-N-[3-nitro-4-(tetrahydropyran-4-ylmethylamino)phenyl]sulfonyl-benzamide |

| Compound No | Structure | Name |
|---|---|---|
| 16 | 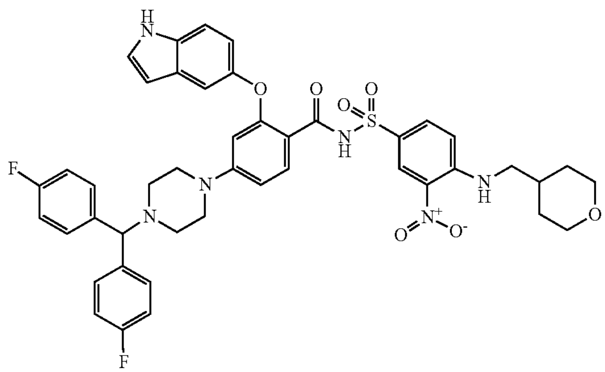 [SMILES: O=C(NS(=O)(=O)c1ccc(NCC2CCOCC2)c([N+](=O)[O-])c1)c1ccc(N2CCN(C(c3ccc(F)cc3)c3ccc(F)cc3)CC2)cc1Oc1ccc2[nH]ccc2c1] | 4-[4-[bis(4-fluorophenyl)methyl]piperazin-1-yl]-2-(1H-indol-5-yloxy)-N-[3-nitro-4-(tetrahydropyran-4-ylmethylamino)phenyl]sulfonyl-benzamide |
| 17 | 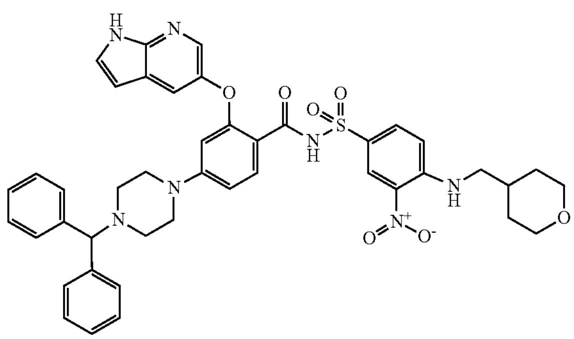 [SMILES: O=C(NS(=O)(=O)c1ccc(NCC2CCOCC2)c([N+](=O)[O-])c1)c1ccc(N2CCN(C(c3ccccc3)c3ccccc3)CC2)cc1Oc1cnc2[nH]ccc2c1] | 4-(4-benzhydrylpiperazin-1-yl)-N-[3-nitro-4-(tetrahydropyran-4-ylmethylamino)phenyl]sulfonyl-2-(1H-pyrrolo[2,3-b]pyridin-5-yloxy)benzamide |
| 18 | 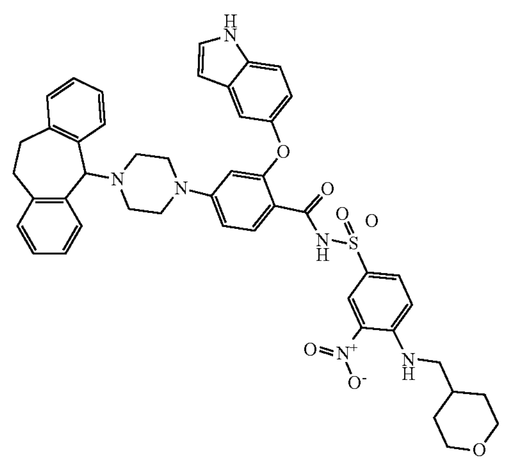 | 2-(1H-indol-5-yloxy)-N-[3-nitro-4-(tetrahydropyran-4-ylmethylamino)phenyl]sulfonyl-4-[4-(2-tricyclo[9.4.0.0.3,8]pentadeca-1(11),3(8),4,6,12,14-hexaenyl)piperazin-1-yl]benzamide |
| 19 | 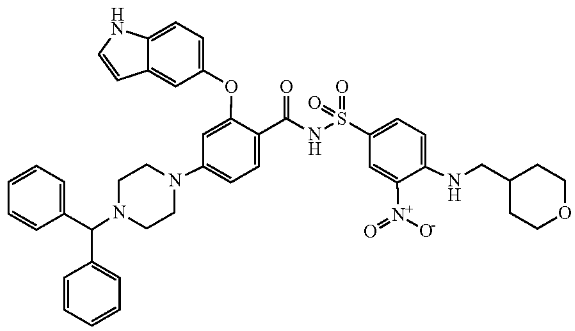 | 4-(4-benzhydrylpiperazin-1-yl)-2-(1H-indol-5-yloxy)-N-[3-nitro-4-(tetrahydropyran-4-ylmethylamino)phenyl]sulfonyl-benzamide |

-continued

| Compound No | Structure | Name |
|---|---|---|
| 20 | 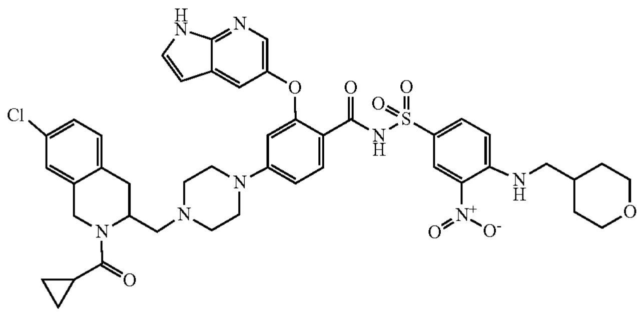 [SMILES: O=C(NS(=O)(=O)c1ccc(NCC2CCOCC2)c([N+](=O)[O-])c1)c1ccc(N2CCN(CC3Cc4ccc(Cl)cc4CN3C(=O)C3CC3)CC2)cc1Oc1cnc2[nH]ccc2c1] | 4-[4-[[7-chloro-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 21 | 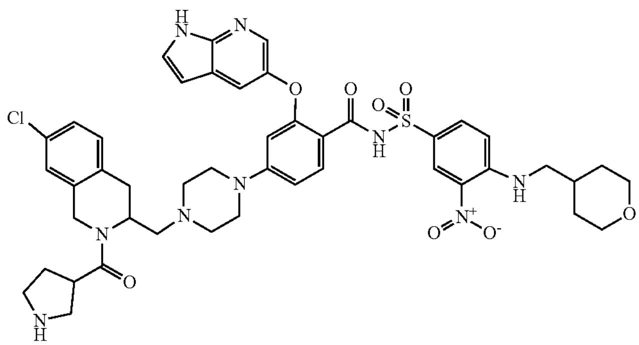 [SMILES: O=C(NS(=O)(=O)c1ccc(NCC2CCOCC2)c([N+](=O)[O-])c1)c1ccc(N2CCN(CC3Cc4ccc(Cl)cc4CN3C(=O)C3CCNC3)CC2)cc1Oc1cnc2[nH]ccc2c1] | 4-[4-[[7-chloro-2-(pyrrolidine-3-carbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 22 | 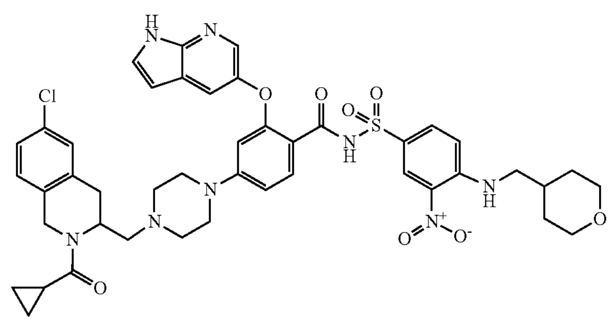 [SMILES: O=C(NS(=O)(=O)c1ccc(NCC2CCOCC2)c([N+](=O)[O-])c1)c1ccc(N2CCN(CC3Cc4cc(Cl)ccc4CN3C(=O)C3CC3)CC2)cc1Oc1cnc2[nH]ccc2c1] | 4-[4-[[6-chloro-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 23 | 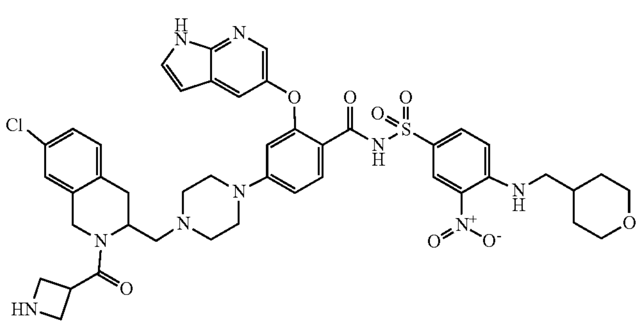 [SMILES: O=C(NS(=O)(=O)c1ccc(NCC2CCOCC2)c([N+](=O)[O-])c1)c1ccc(N2CCN(CC3Cc4ccc(Cl)cc4CN3C(=O)C3CNC3)CC2)cc1Oc1cnc2[nH]ccc2c1] | 4-[4-[[2-(azetidine-3-carbonyl)-7-chloro-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 24 | 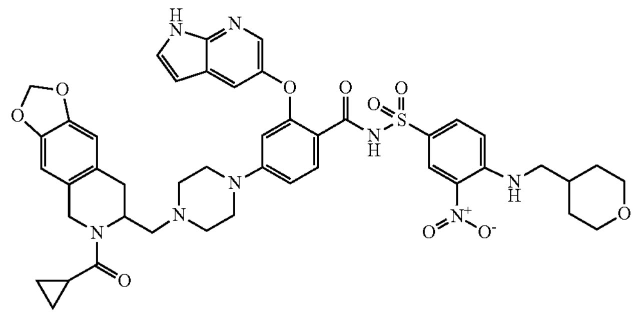 [SMILES: O=C(NS(=O)(=O)c1ccc(NCC2CCOCC2)c([N+](=O)[O-])c1)c1ccc(N2CCN(CC3Cc4cc5c(cc4CN3C(=O)C3CC3)OCO5)CC2)cc1Oc1cnc2[nH]ccc2c1] | 4-[4-[[6-(cyclopropanecarbonyl)-7,8-dihydro-5H-[1,3]dioxolo[4,5-g]isoquinolin-7-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 25 | 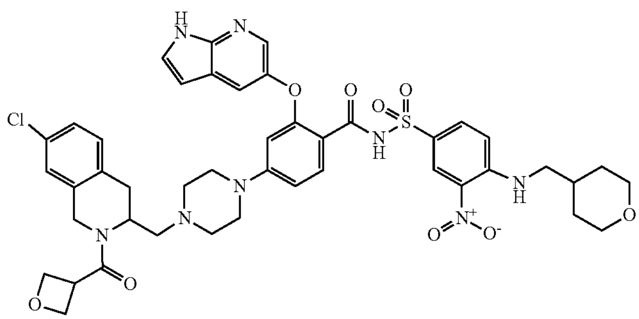 [SMILES: O=C(NS(=O)(=O)c1ccc(NCC2CCOCC2)c([N+](=O)[O-])c1)c1ccc(N2CCN(CC3Cc4ccc(Cl)cc4CN3C(=O)C3COC3)CC2)cc1Oc1cnc2[nH]ccc2c1] | 4-[4-[[7-chloro-2-(oxetane-3-carbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 26 | 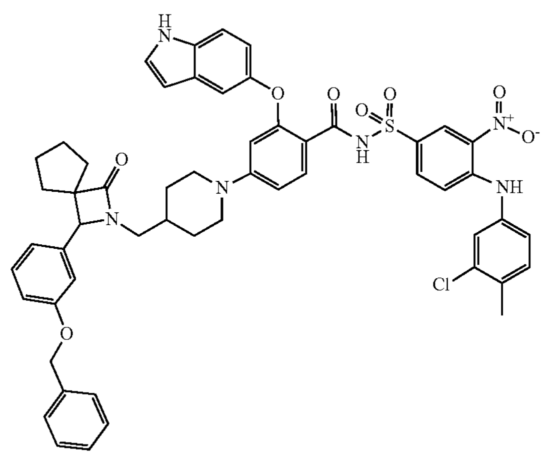 [SMILES: Cc1ccc(Nc2ccc(S(=O)(=O)NC(=O)c3ccc(N4CCC(CN5C(=O)C6(CCCC6)C5c5cccc(OCc6ccccc6)c5)CC4)cc3Oc3ccc4[nH]ccc4c3)cc2[N+](=O)[O-])cc1Cl] | 4-[4-[[1-(3-benzyloxyphenyl)-3-oxo-2-azaspiro[3,4]octan-2-yl]methyl]-1-piperidyl]-N-[4-(3-chloro-4-methyl-anilino)-3-nitro-phenyl]sulfonyl-2-(1H-indol-5-yloxy)benzamide |
| 27 | 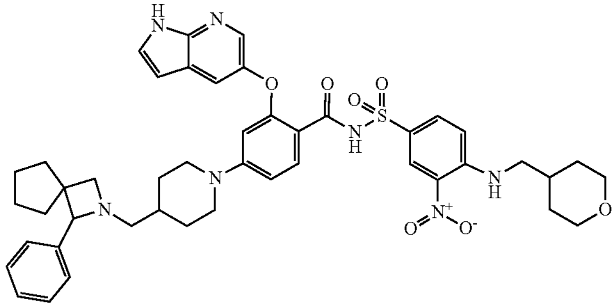 [SMILES: O=C(NS(=O)(=O)c1ccc(NCC2CCOCC2)c([N+](=O)[O-])c1)c1ccc(N2CCC(CN3CC4(CCCC4)C3c3ccccc3)CC2)cc1Oc1cnc2[nH]ccc2c1] | N-[3-nitro-4-(tetrahydropyran-4-ylmethylamino)phenyl]sulfonyl-4-[4-[(3-phenyl-2-azaspiro[3.4]octan-2-yl)methyl]-1-piperidyl]-2-(1H-pyrrolo[2,3-b]pyridin-5-yloxy)benzamide |

-continued

| Compound No | Structure | Name |
|---|---|---|
| 28 | 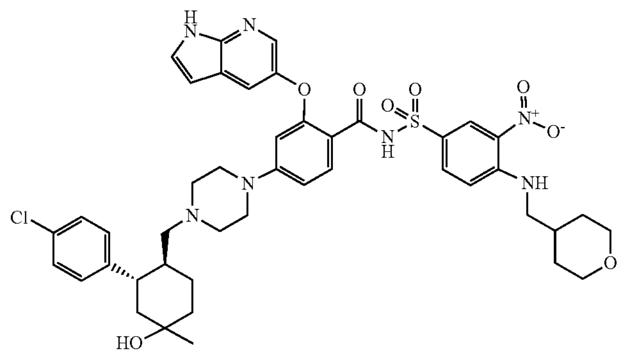 [SMILES: CC1(O)CC[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(1S,2S)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 29 | 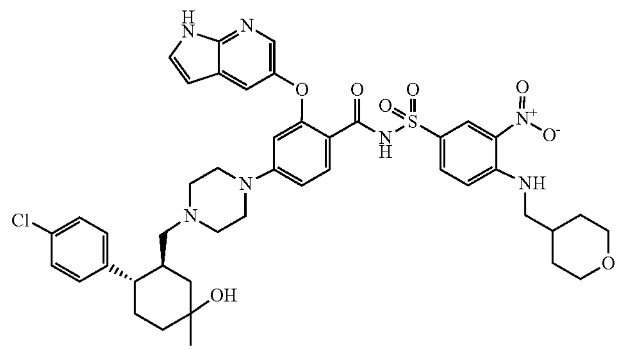 | 4-[4-[[(1S,2S)-2-(4-chlorophenyl)-5-hydroxy-5-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 30 | 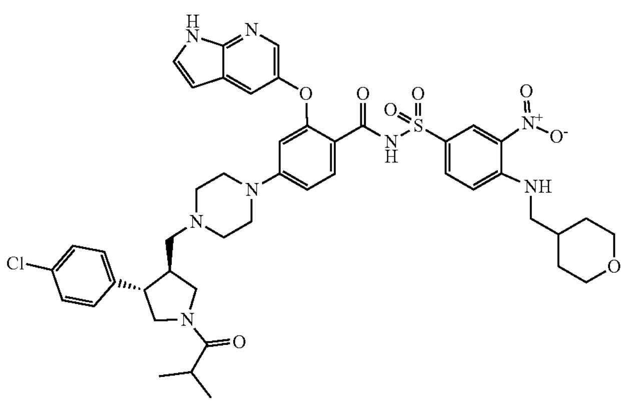 [SMILES: CC(C)C(=O)N1C[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(3S,4S)-4-(4-chlorophenyl)-1-(2-methylpropanoyl)pyrrolidin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 31 | 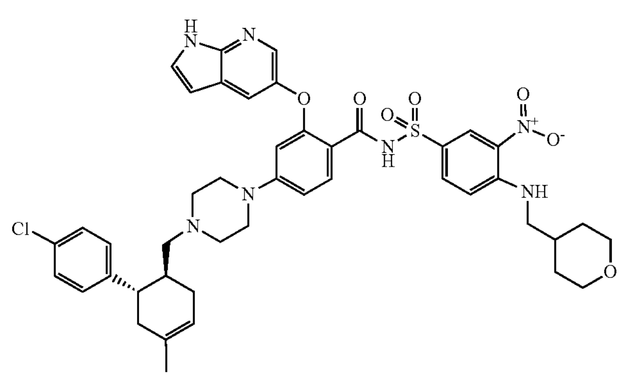 [SMILES: CC1=CC[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(1S,6S)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 32 | 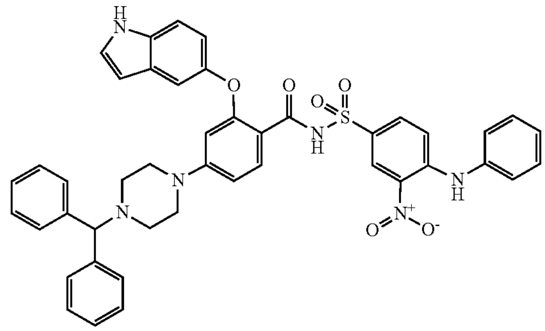 [SMILES: O=C(NS(=O)(=O)c1ccc(Nc2ccccc2)c([N+](=O)[O-])c1)c1ccc(N2CCN(C(c3ccccc3)c3ccccc3)CC2)cc1Oc1ccc2[nH]ccc2c1] | N-(4-anilino-3-nitro-phenyl)sulfonyl-4-(4-benzhydrylpiperazin-1-yl)-2-(1H-indol-5-yloxy)benzamide |
| 33 | 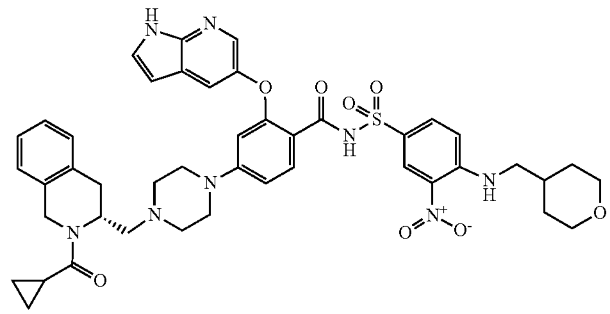 [SMILES: O=C(NS(=O)(=O)c1ccc(NCC2CCOCC2)c([N+](=O)[O-])c1)c1ccc(N2CCN(C[C@H]3Cc4ccccc4CN3C(=O)C3CC3)CC2)cc1Oc1cnc2[nH]ccc2c1] | 4-[4-[[(3R)-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 34 | 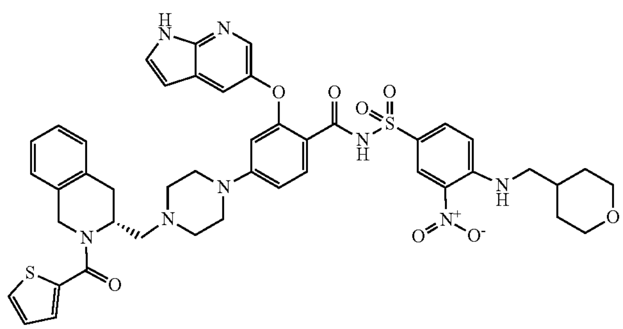 [SMILES: O=C(NS(=O)(=O)c1ccc(NCC2CCOCC2)c([N+](=O)[O-])c1)c1ccc(N2CCN(C[C@H]3Cc4ccccc4CN3C(=O)c3cccs3)CC2)cc1Oc1cnc2[nH]ccc2c1] | N-[3-nitro-4-(tetrahydropyran-4-ylmethylamino)phenyl]sulfonyl-2-(1H-pyrrolo[2,3-b]pyridin-5-yloxy)-4-[4-[[(3R)-2-(thiophene-2-carbonyl)-3,4-dihydro-1H-isoquinolin-3-yl]methyl]piperazin-1-yl]benzamide |
| 35 | 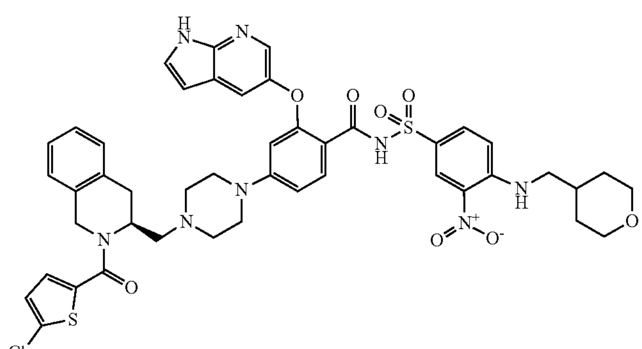 | 4-[4-[[(3S)-2-(5-chlorothiophene-2-carbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 36 | 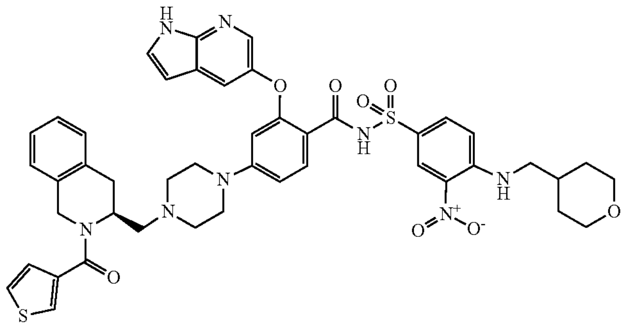 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)c3ccsc3)CC2)cc1Oc1cnc2[nH]ccc2c1] | N-[3-nitro-4-(tetrahydropyran-4-ylmethylamino)phenyl]sulfonyl-2-(1H-pyrrolo[2,3-b]pyridin-5-yloxy)-4-[4-[[(3S)-2-(thiophene-3-carbonyl)-3,4-dihydro-1H-isoquinolin-3-yl]methyl]piperazin-1-yl]benzamide |
| 37 | 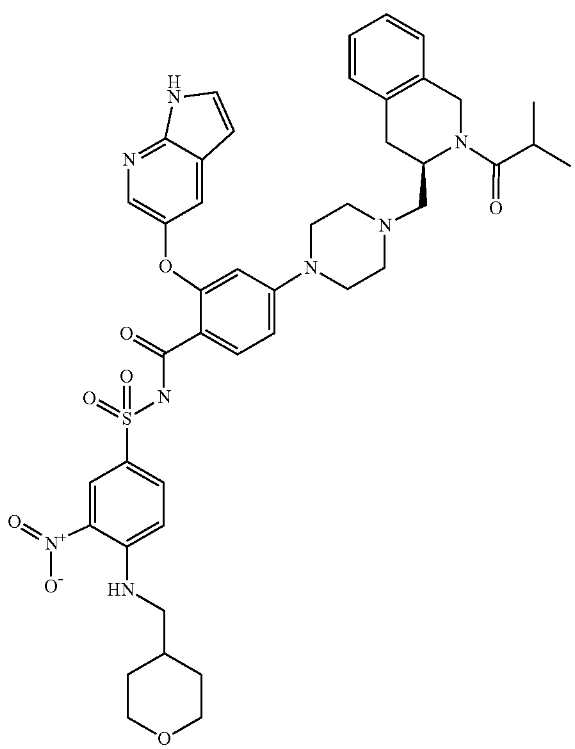 | 4-[4-[[(3R)-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 38 | 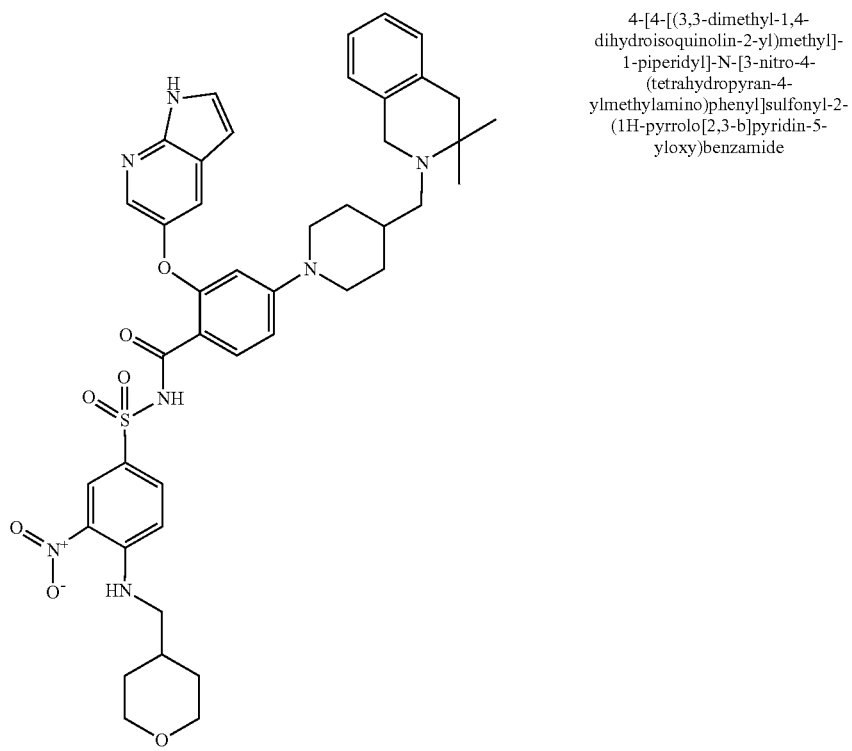 | 4-[4-[(3,3-dimethyl-1,4-dihydroisoquinolin-2-yl)methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 39 | 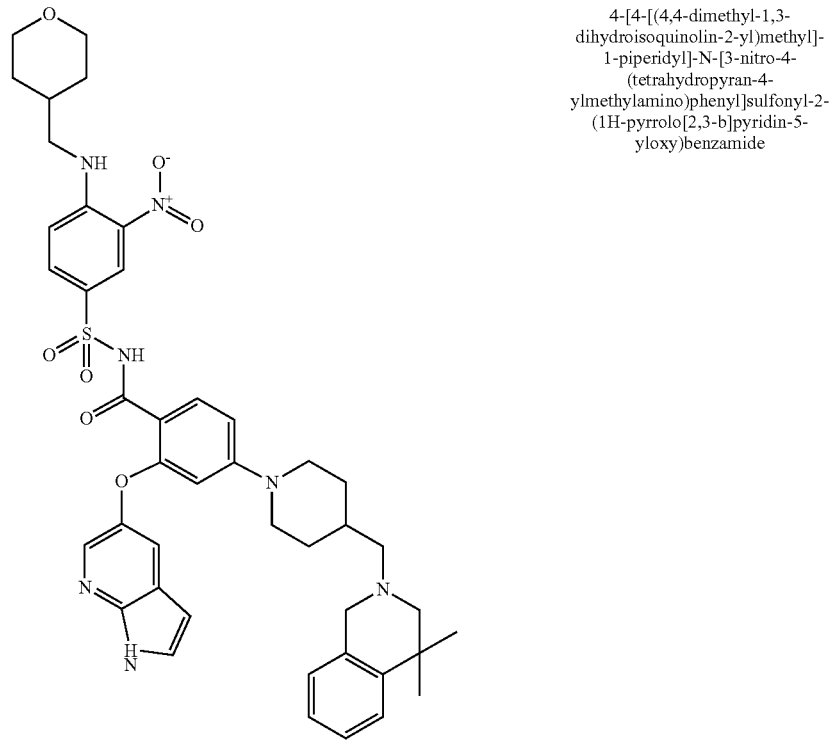 | 4-[4-[(4,4-dimethyl-1,3-dihydroisoquinolin-2-yl)methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 40 | 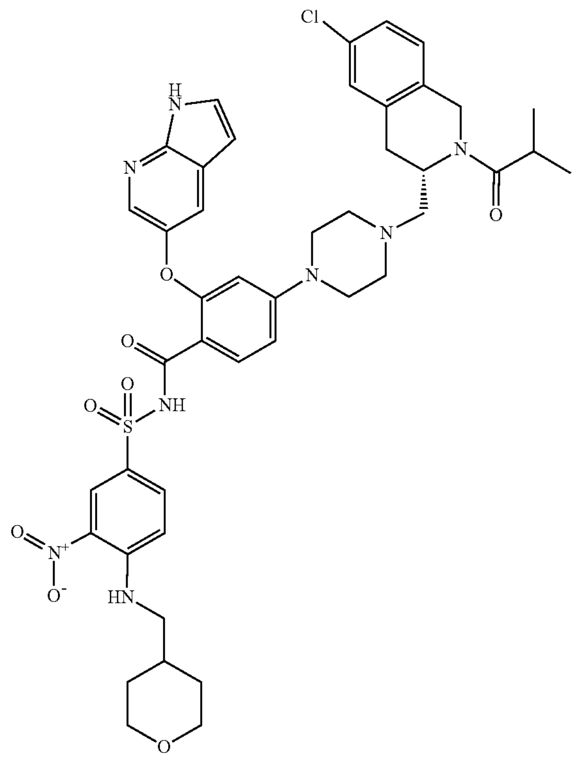 | 4-[4-[[(3S)-6-chloro-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 41 | 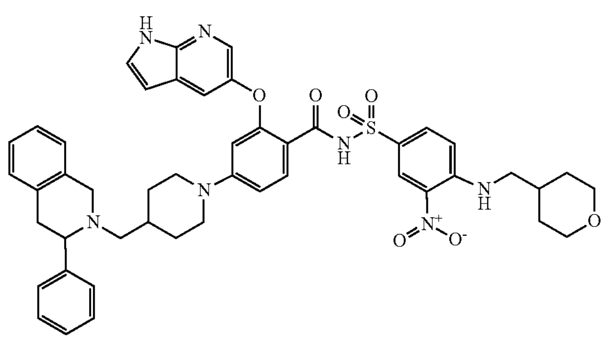 | N-[3-nitro-4-(tetrahydropyran-4-ylmethylamino)phenyl]sulfonyl-4-[4-[(3-phenyl-3,4-dihydro-1H-isoquinolin-2-yl)methyl]-1-piperidyl]-2-(1H-pyrrolo[2,3-b]pyridin-5-yloxy)benzamide |
| 42 | 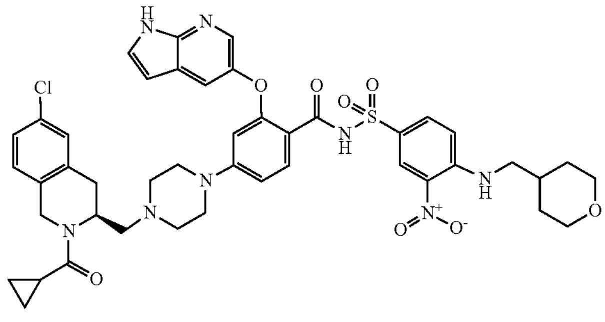 [SMILES: O=C(NS(=O)(=O)c1ccc(NCC2CCOCC2)c([N+](=O)[O-])c1)c1ccc(N2CCN(C[C@@H]3Cc4cc(Cl)ccc4CN3C(=O)C3CC3)CC2)cc1Oc1cnc2[nH]ccc2c1] | 4-[4-[[(3S)-6-chloro-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 43 | 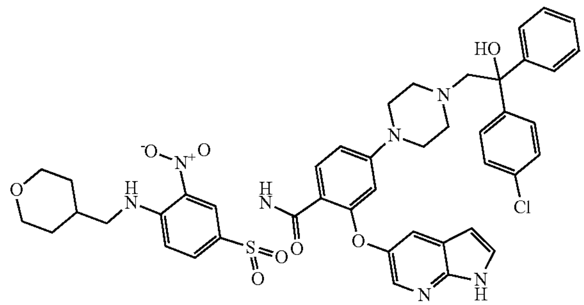 | 4-[4-[2-(4-chlorophenyl)-2-hydroxy-2-phenyl-ethyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 44 | 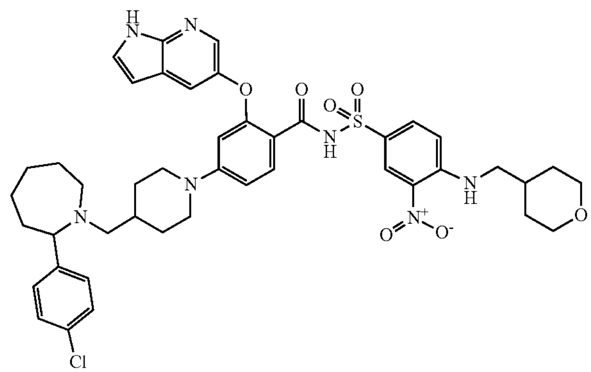 [SMILES: O=C(NS(=O)(=O)c1ccc(NCC2CCOCC2)c([N+](=O)[O-])c1)c1ccc(N2CCC(CN3CCCCCC3c3ccc(Cl)cc3)CC2)cc1Oc1cnc2[nH]ccc2c1] | 4-[4-[[2-(4-chlorophenyl)azepan-1-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 45 | 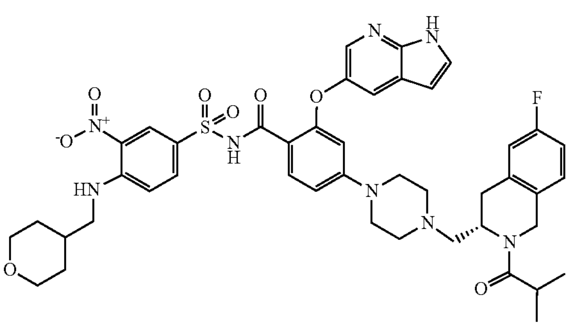 | 4-[4-[[(3S)-6-fluoro-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 46 | 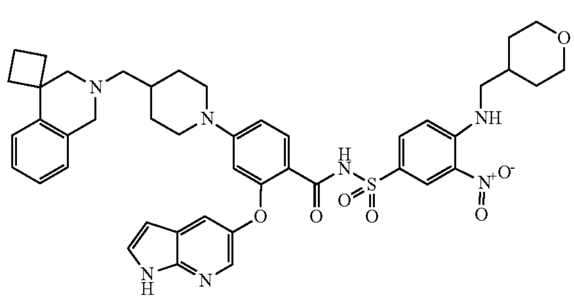 | N-[3-nitro-4-(tetrahydropyran-4-ylmethylamino)phenyl]sulfonyl-2-(1H-pyrrolo[2,3-b]pyridin-5-yloxy)-4-[4-(spiro[1,3-dihydroisoquinoline-4,1'-cyclobutane]-2-ylmethyl)-1-piperidyl]benzamide |

-continued

| Compound No | Structure | Name |
|---|---|---|
| 47 | 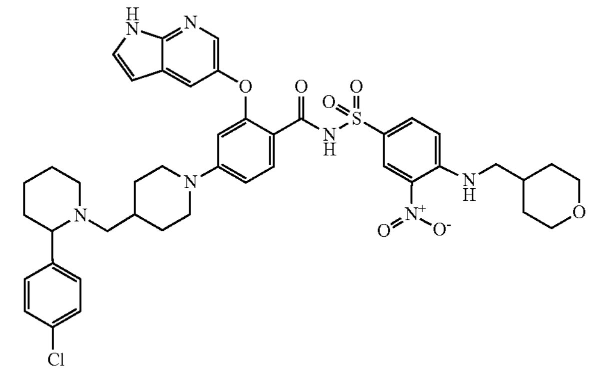 [SMILES: O=C(NS(=O)(=O)c1ccc(NCC2CCOCC2)c([N+](=O)[O-])c1)c1ccc(N2CCC(CN3CCCCC3c3ccc(Cl)cc3)CC2)cc1Oc1cnc2[nH]ccc2c1] | 4-[4-[[2-(4-chlorophenyl)-1-piperidyl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 48 | 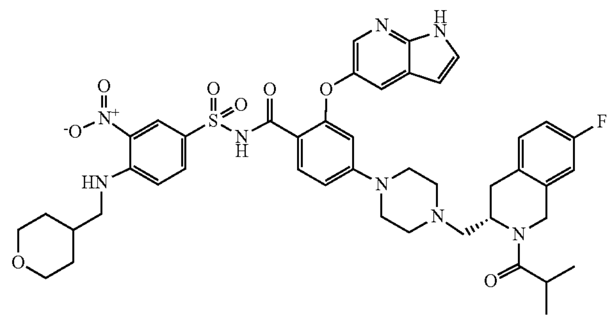 | 4-[4-[[(3S)-7-fluoro-2-(2-methyl propanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 49 | 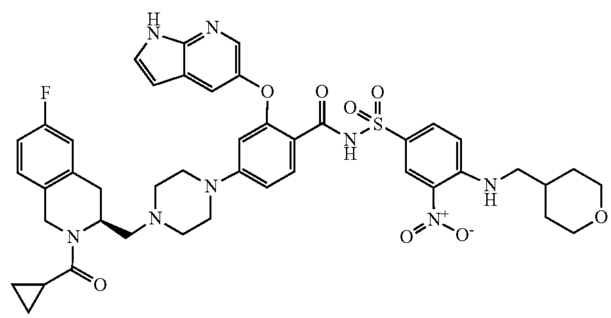 [SMILES: O=C(NS(=O)(=O)c1ccc(NCC2CCOCC2)c([N+](=O)[O-])c1)c1ccc(N2CCN(C[C@@H]3Cc4cc(F)ccc4CN3C(=O)C3CC3)CC2)cc1Oc1cnc2[nH]ccc2c1] | 4-[4-[[(3S)-2-(cyclopropanecarbonyl)-6-fluoro-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 50 | 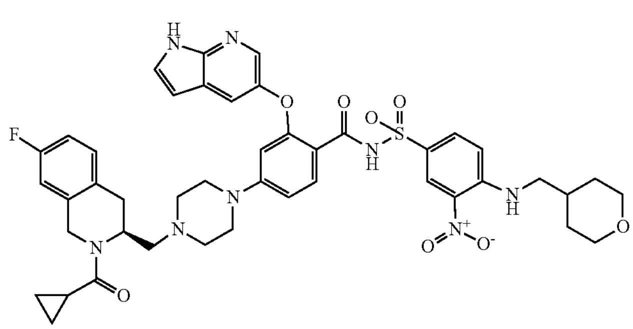 | 4-[4-[[(3S)-2-(cyclopropanecarbonyl)-7-fluoro-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 51 | 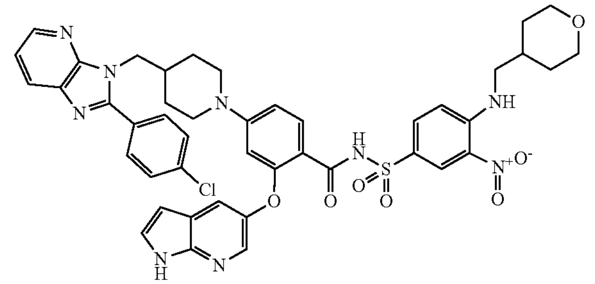 | 4-[4-[[2-(4-chlorophenyl)imidazo[4,5-b]pyridin-3-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 52 | 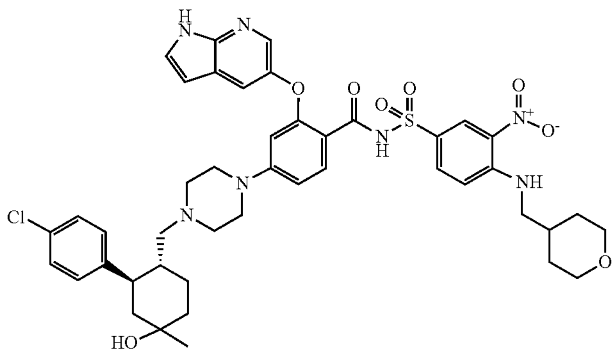 [SMILES: CC1(O)CC[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@H](c2ccc(Cl)cc2)C1] | 4-[4-[[(1R,2R)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 53 | 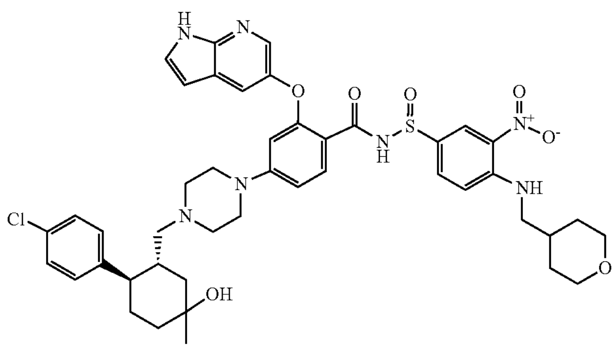 [SMILES: CC1(O)CC[C@@H](c2ccc(Cl)cc2)[C@H](CN2CCN(c3ccc(C(=O)NS(=O)c4ccc(NCC5CCOCC5)c([N+](=O)[O-])c4)c(Oc4cnc5[nH]ccc5c4)c3)CC2)C1] | 4-[4-[[(1R,2R)-2-(4-chlorophenyl)-5-hydroxy-5-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 54 | 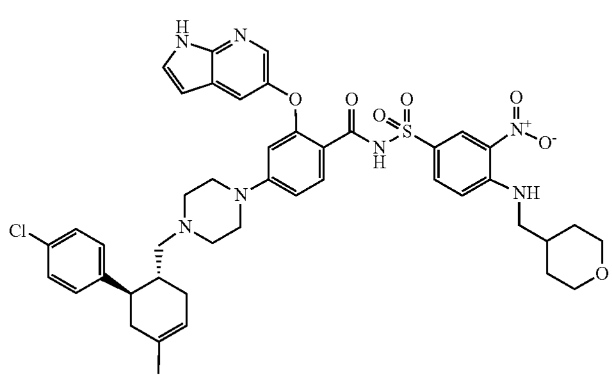 [SMILES: CC1=CC[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@H](c2ccc(Cl)cc2)C1] | 4-[4-[[(1R,6R)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 55 | 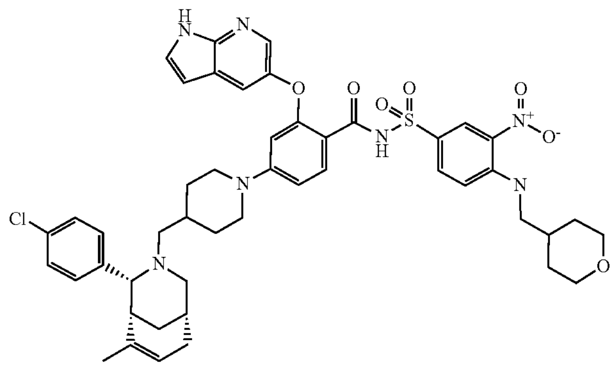 | 4-[4-[[(1R,4R, 5R)-4-(4-chlorophenyl)-6-methyl-3-azabicyclo[3.3.1]non-6-en-3-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 56 | 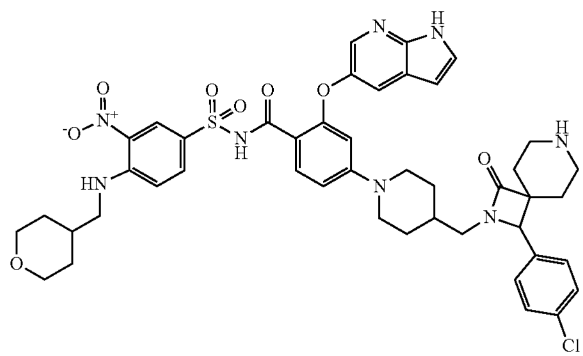 | 4-[4-[[1-(4-chlorophenyl)-3-oxo-2,7-diazaspiro[3.5]nonan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 57 | 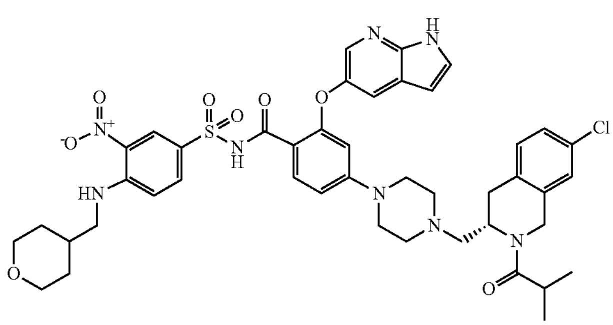 | 4-[4-[[(3S)-7-chloro-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 58 | 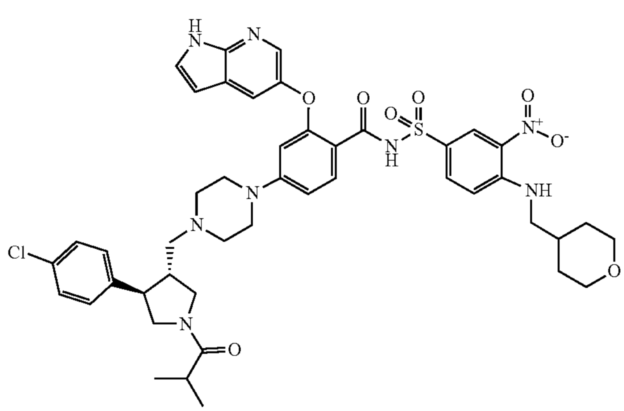 [SMILES: CC(C)C(=O)N1C[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@H](c2ccc(Cl)cc2)C1] | 4-[4-[[(3R,4R)-4-(4-chlorophenyl)-1-(2-methylpropanoyl)pyrrolidin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 59 | 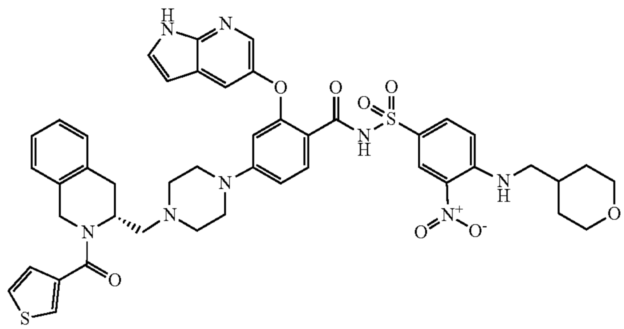 [SMILES: O=C(NS(=O)(=O)c1ccc(NCC2CCOCC2)c([N+](=O)[O-])c1)c1ccc(N2CCN(C[C@H]3Cc4ccccc4CN3C(=O)c3ccsc3)CC2)cc1Oc1cnc2[nH]ccc2c1] | N-[3-nitro-4-(tetrahydropyran-4-ylmethylamino)phenyl]sulfonyl-2-(1H-pyrrolo[2,3-b]pyridin-5-yloxy)-4-[4-[[(3R)-2-(thiophene-3-carbonyl)-3,4-dihydro-1H-isoquinolin-3-yl]methyl]piperazin-1-yl]benzamide |
| 60 | 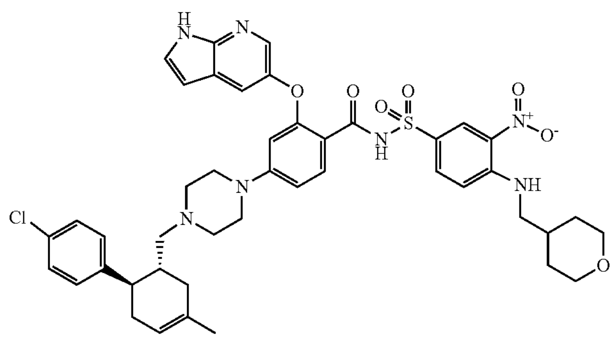 [SMILES: CC1=CC[C@@H](c2ccc(Cl)cc2)[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 4-[4-[[(1R,6R)-6-(4-chlorophenyl)-3-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 61 | 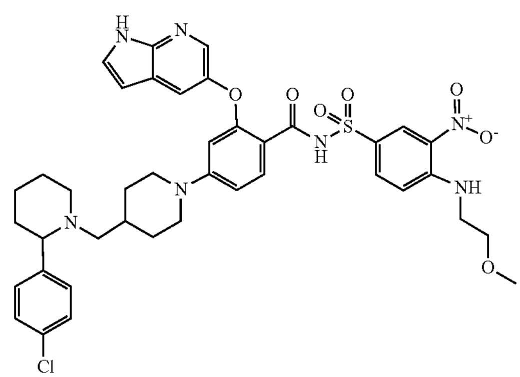 [SMILES: COCCNc1ccc(S(=O)(=O)NC(=O)c2ccc(N3CCC(CN4CCCCC4c4ccc(Cl)cc4)CC3)cc2Oc2cnc3[nH]ccc3c2)cc1[N+](=O)[O-]] | 4-[4-[[2-(4-chlorophenyl)-1-piperidyl]methyl]-1-piperidyl]-N-[4-(2-methoxyethylamino)-3-nitrophenyl]sulfonyl-2-(1H-pyrrolo[2,3-b]pyridin-5-yloxy)benzamide |
| 62 | 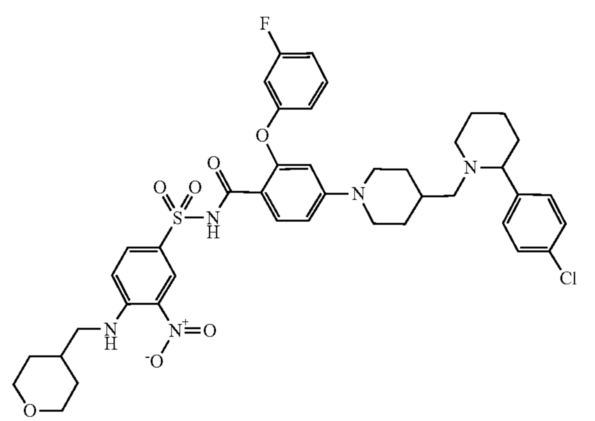 | 4-[4-[[2-(4-chlorophenyl)-1-piperidyl]methyl]-1-piperidyl]-2-(3-fluorophenoxy)-N-[3-nitro-4-(tetrahydropyran-4-ylmethylamino)phenyl]sulfonyl-benzamide |

| Compound No | Structure | Name |
|---|---|---|
| 63 | 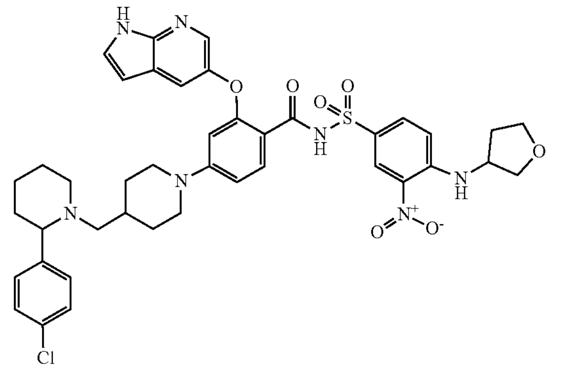 [SMILES: O=C(NS(=O)(=O)c1ccc(NC2CCOC2)c([N+](=O)[O-])c1)c1ccc(N2CCC(CN3CCCCC3c3ccc(Cl)cc3)CC2)cc1Oc1cnc2[nH]ccc2c1] | 4-[4-[[2-(4-chlorophenyl)-1-piperidyl]methyl]-1-piperidyl]-N-[3-nitro-4-(tetrahydrofuran-3-ylamino)phenyl]sulfonyl-2-(1H-pyrrolo[2,3-b]pyridin-5-yloxy)benzamide |
| 64 | 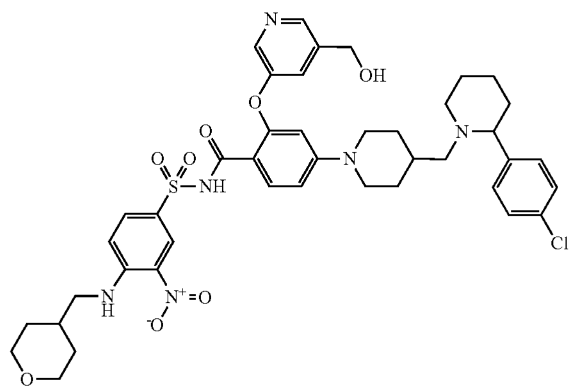 | 4-[4-[[2-(4-chlorophenyl)-1-piperidyl]methyl]-1-piperidyl]-2-[[5-(hydroxymethyl)-3-pyridyl]oxy]-N-[3-nitro-4-(tetrahydropyran-4-ylmethylamino)phenyl]sulfonyl-benzamide |
| 65 | 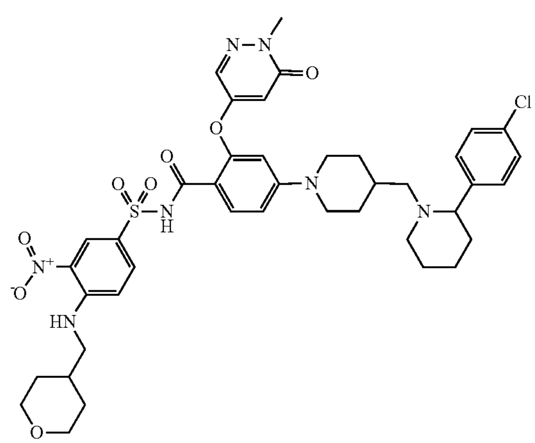 | 4-[4-[[2-(4-chlorophenyl)-1-piperidyl]methyl]-1-piperidyl]-2-(1-methyl-6-oxo-pyridazin-4-yl)oxy-N-[3-nitro-4-(tetrahydropyran-4-ylmethylamino)phenyl]sulfonyl-benzamide |
| 66 | 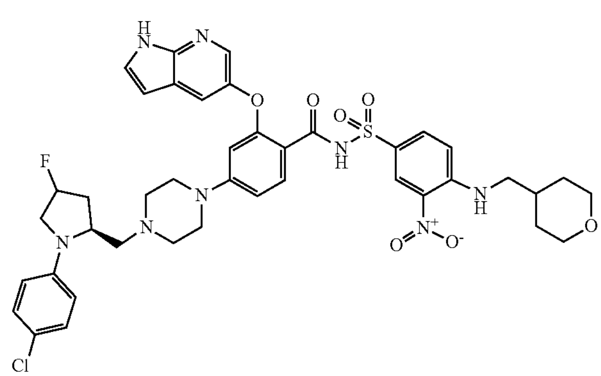 [SMILES: O=C(NS(=O)(=O)c1ccc(NCC2CCOCC2)c([N+](=O)[O-])c1)c1ccc(N2CCN(C[C@@H]3CC(F)CN3c3ccc(Cl)cc3)CC2)cc1Oc1cnc2[nH]ccc2c1] | 4-[4-[[(2S)-1-(4-chlorophenyl)-4-fluoro-pyrrolidin-2-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 67 | 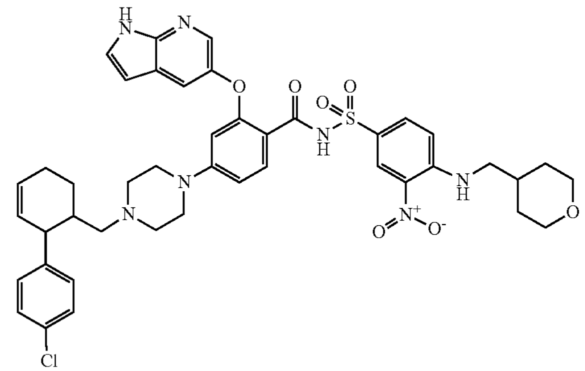 [SMILES: O=C(NS(=O)(=O)c1ccc(NCC2CCOCC2)c([N+](=O)[O-])c1)c1ccc(N2CCN(CC3CCC=CC3c3ccc(Cl)cc3)CC2)cc1Oc1cnc2[nH]ccc2c1] | 4-[4-[[2-(4-chlorophenyl)cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 68 | 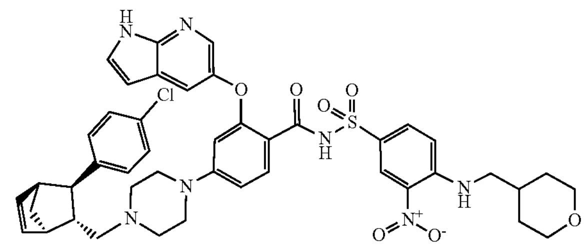 [SMILES: O=C(NS(=O)(=O)c1ccc(NCC2CCOCC2)c([N+](=O)[O-])c1)c1ccc(N2CCN(C[C@H]3[C@H](c4ccc(Cl)cc4)[C@@H]4C=C[C@H]3C4)CC2)cc1Oc1cnc2[nH]ccc2c1] | 4-[4-[[(1R,2R,3R,4S)-3-(4-chlorophenyl)-2-bicyclo[2.2.1]hept-5-enyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 69 | 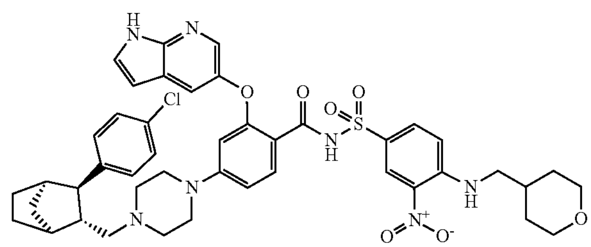 [SMILES: O=C(NS(=O)(=O)c1ccc(NCC2CCOCC2)c([N+](=O)[O-])c1)c1ccc(N2CCN(C[C@@H]3[C@H]4CC[C@H](C4)[C@H]3c3ccc(Cl)cc3)CC2)cc1Oc1cnc2[nH]ccc2c1] | 4-[4-[(2S)-2-[(1S,3R)-3-[(4-chlorophenyl)methyl]cyclopentyl]-propyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 70 | 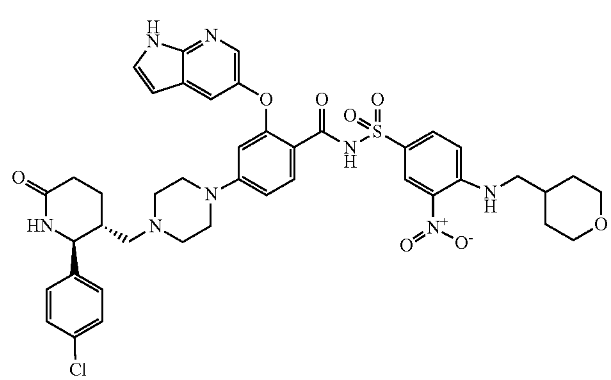 [SMILES: O=C1CC[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)N1] | 4-[4-[[(2S,3R)-2-(4-chlorophenyl)-6-oxo-3-piperidyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 71 | 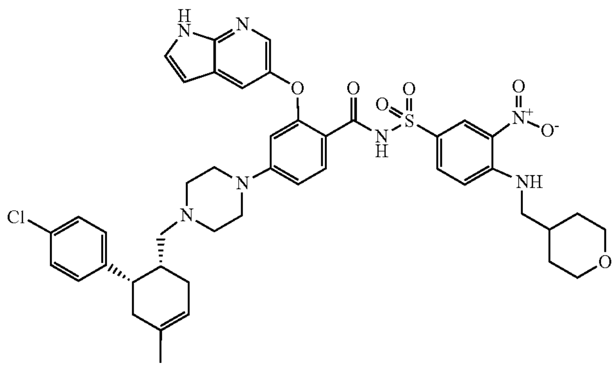 [SMILES: CC1=CC[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(1R,6S)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 72 | 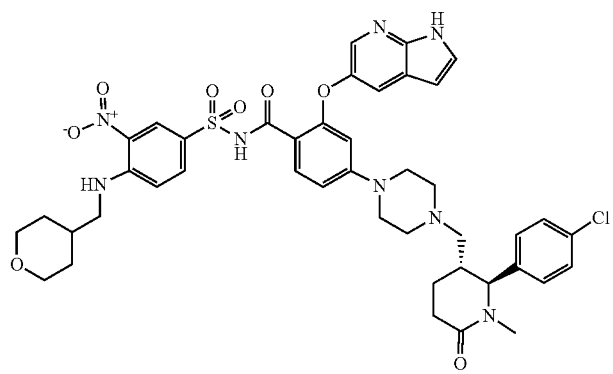 | 4-[4-[[(2S,3R)-2-(4-chlorophenyl)-1-methyl-6-oxo-3-piperidyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 73 | 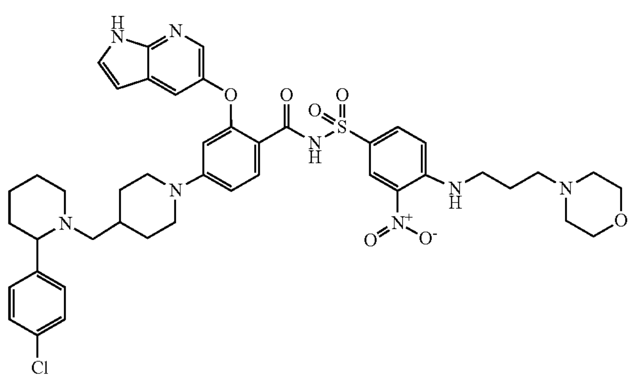 [SMILES: O=C(NS(=O)(=O)c1ccc(NCCCN2CCOCC2)c([N+](=O)[O-])c1)c1ccc(N2CCC(CN3CCCCC3c3ccc(Cl)cc3)CC2)cc1Oc1cnc2[nH]ccc2c1] | 4-[4-[[2-(4-chlorophenyl)-1-piperidyl]methyl]-1-piperidyl]-N[4-(3-morpholinopropylamino)-3-nitro-phenyl]sulfonyl-2-(1H-pyrrolo[2,3-b]pyridin-5-yloxy)benzamide |
| 74 | 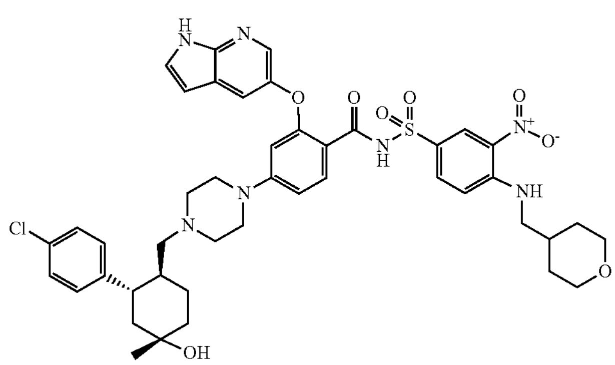 [SMILES: C[C@]1(O)CC[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(1S,2S,4S)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 75 | 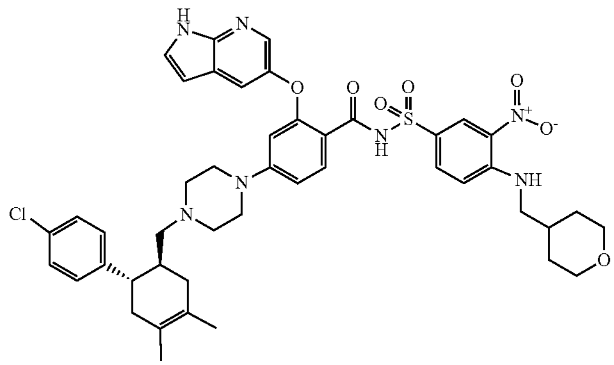 [SMILES: CC1=C(C)C[C@H](c2ccc(Cl)cc2)[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 4-[4-[[(1S,6S)-6-(4-chlorophenyl)-3,4-dimethyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 76 | 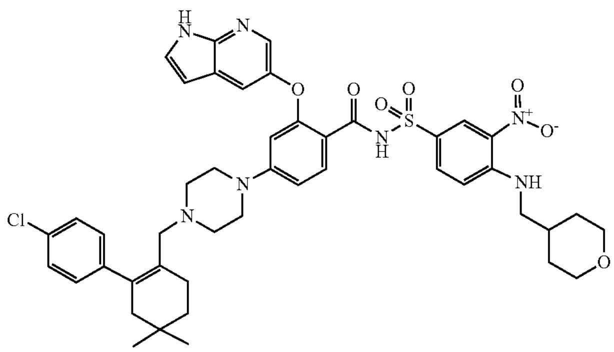 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] | 4-[4-[[2-(4-chlorophenyl)-4,4-dimethyl-cyclohexen-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 77 | 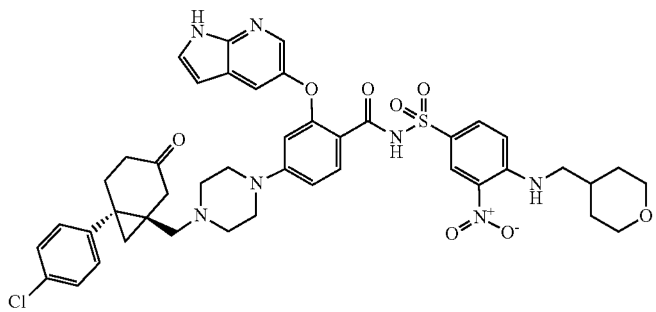 [SMILES: O=C1CC[C@]2(c3ccc(Cl)cc3)C[C@@]2(CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 4-[4-[[(1R,6R)-6-(4-chlorophenyl)-3-oxo-norcaran-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 78 | 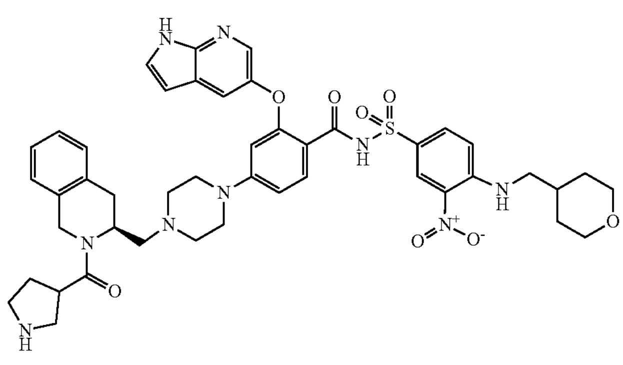 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)C3CCNC3)CC2)cc1Oc1cnc2[nH]ccc2c1] | N-[3-nitro-4-(tetrahydropyran-4-ylmethylamino)phenyl]sulfonyl-4-[4-[[(3S)-2-(pyrrolidine-3-carbonyl)-3,4-dihydro-1H-isoquinolin-3-yl]methyl]piperazin-1-yl]-2-(1H-pyrrolo[2,3-b]pyridin-5-yloxy)benzamide |

| Compound No | Structure | Name |
|---|---|---|
| 79 | 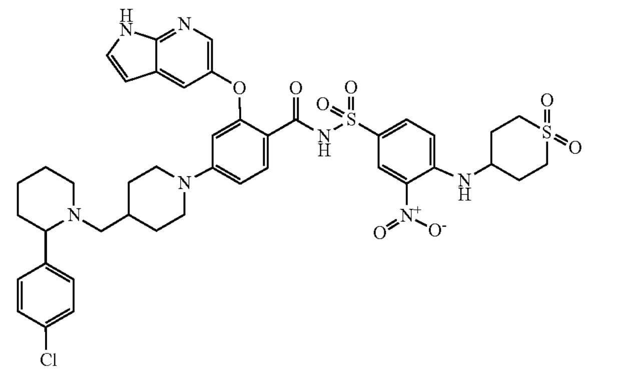 [SMILES: O=C(NS(=O)(=O)c1ccc(NC2CCS(=O)(=O)CC2)c([N+](=O)[O-])c1)c1ccc(N2CCC(CN3CCCCC3c3ccc(Cl)cc3)CC2)cc1Oc1cnc2[nH]ccc2c1] | 4-[4-[[2-(4-chlorophenyl)-1-piperidyl]methyl]-1-piperidyl]-N-[4-[(1,1-dioxothian-4-yl)amino]-3-nitro-phenyl]sulfonyl-2-(1H-pyrrolo[2,3-b]pyridin-5-yloxy)benzamide |
| 80 | 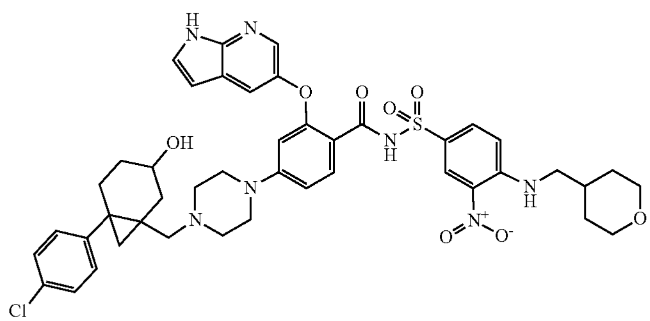 [SMILES: O=C(NS(=O)(=O)c1ccc(NCC2CCOCC2)c([N+](=O)[O-])c1)c1ccc(N2CCN(CC34CC(O)CCC3(c3ccc(Cl)cc3)C4)CC2)cc1Oc1cnc2[nH]ccc2c1] | 4-[4-[[6-(4-chlorophenyl)-3-hydroxy-norcaran-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 81 | | 4-[4-[[(2S)-1-(4-chlorophenyl)-4,4-difluoro-pyrrolidin-2-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide | and pharmaceutically acceptable salts, isomers, solvates, prodrugs, or tautomers thereof.

In some embodiments, the compound is a pharmaceutically acceptable salt. In some embodiments, the compound is a hydrochloride salt.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of BCL-2 proteins. In one embodiment, the compounds of the present invention are inhibitors of BCL-2 proteins. In another embodiment, the BCL-2 proteins is Isoform 1. In another embodiment, the BCL-2 proteins is Isoform 2.

In some embodiments, the compounds of Formula I are selective inhibitors of BCL-2 proteins.

In some embodiments, the compounds of Formula I are dual inhibitors of BCL-2/BCL-xL proteins.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-lnterscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes A-F which comprise different sequences of assembling intermediates or compounds of Formulae I and I'. Starting materials are either commercially available or made by known procedures in the reported literature or as illustrated below.

Scheme A

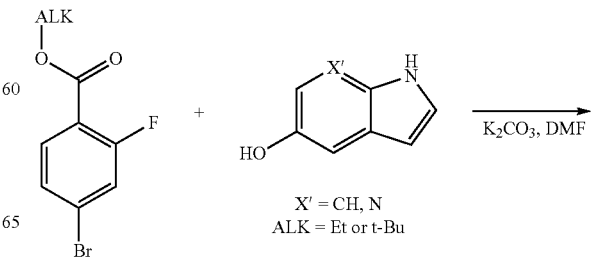

X' = CH, N
ALK = Et or t-Bu

101
-continued
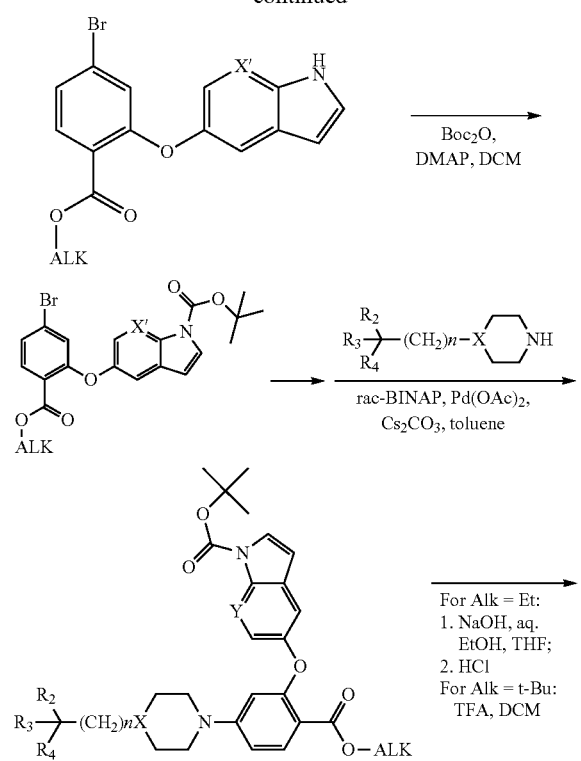
102
Scheme C
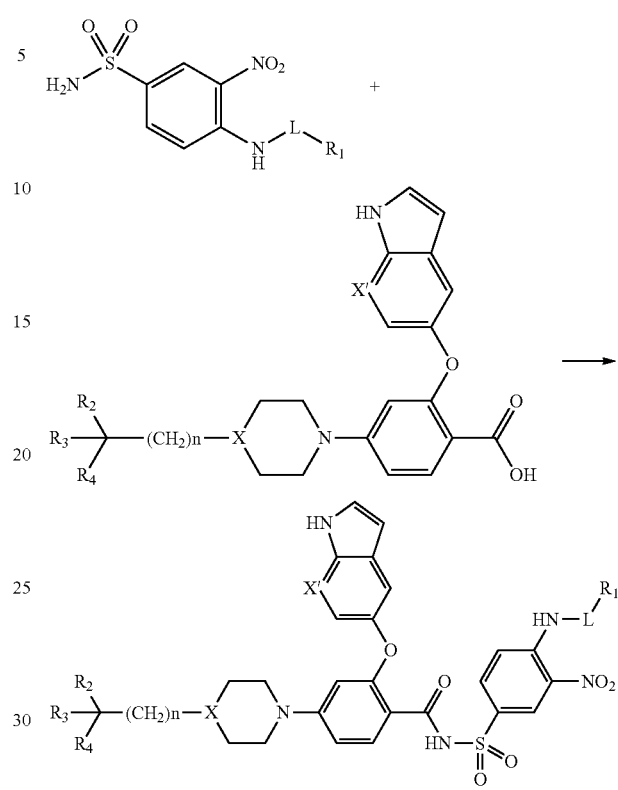
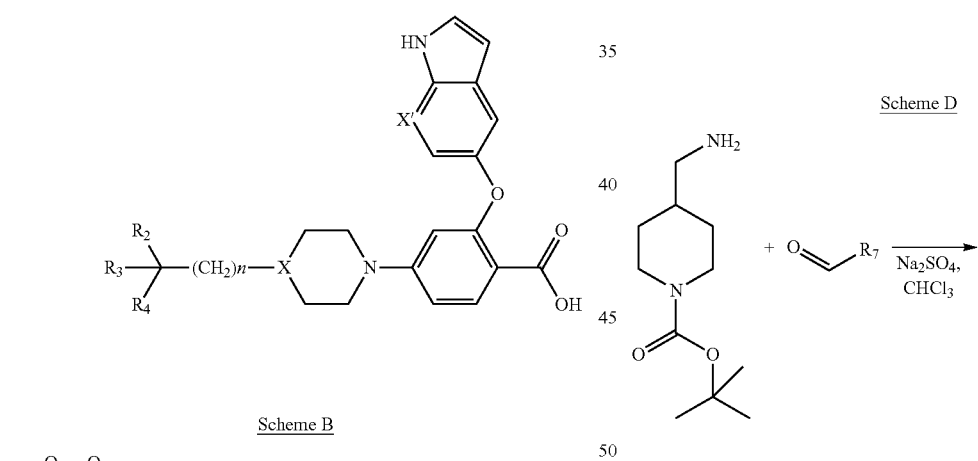
Scheme B
Scheme D
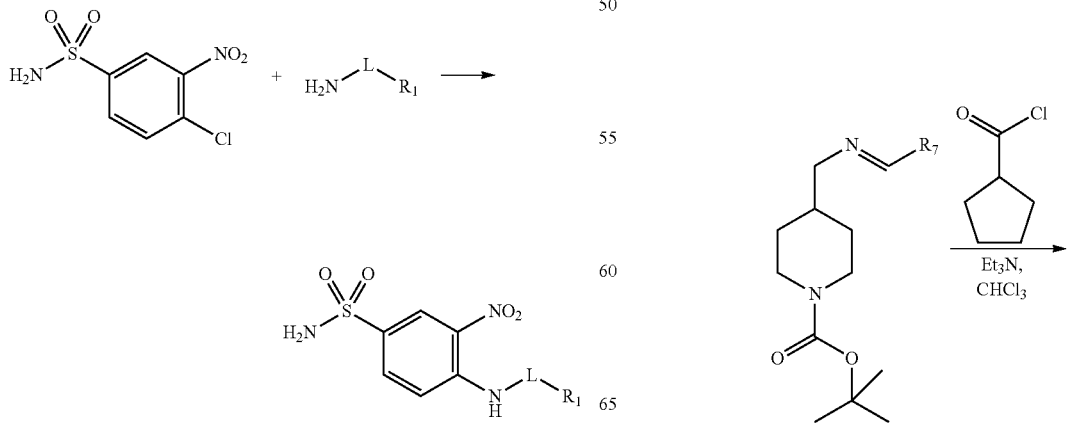

103
-continued
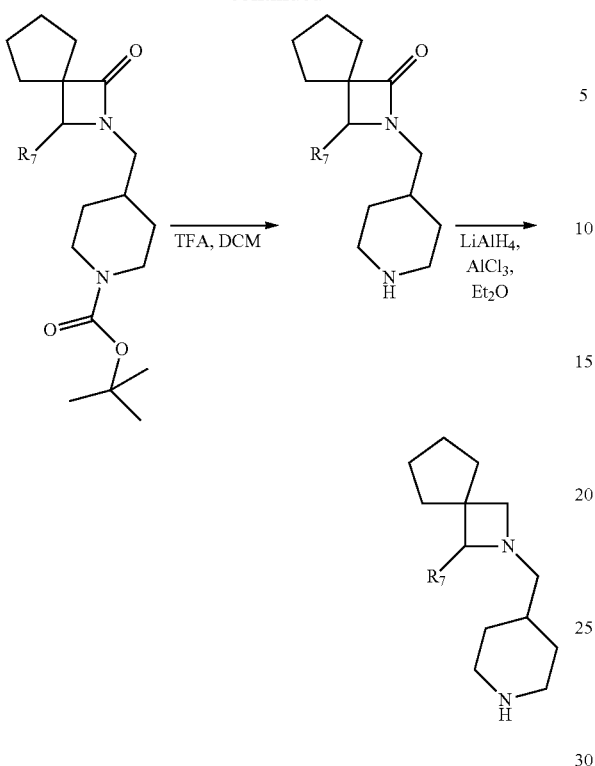
104
-continued
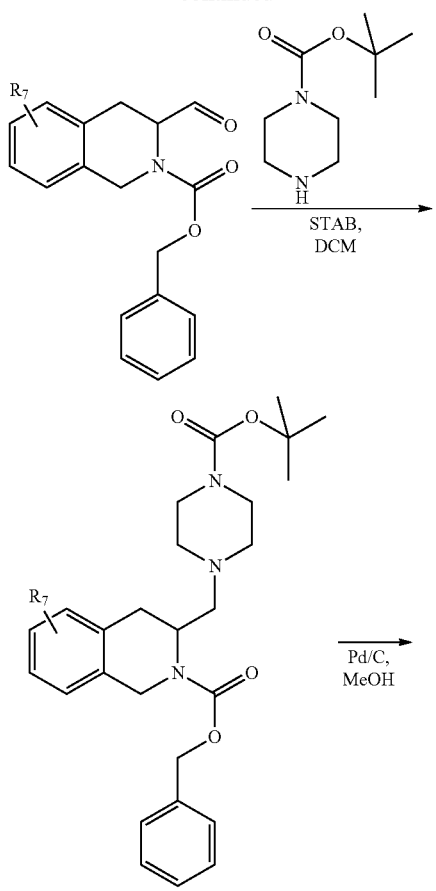
Scheme E
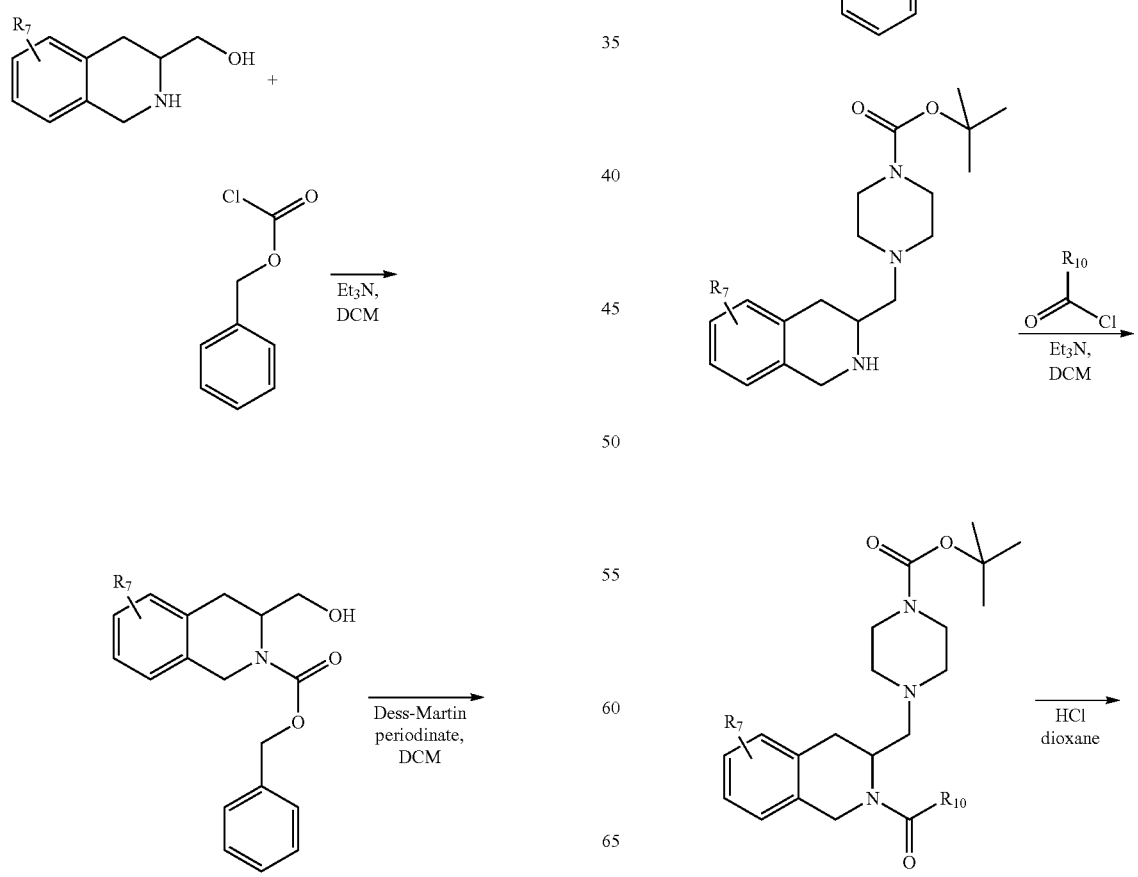

105
-continued

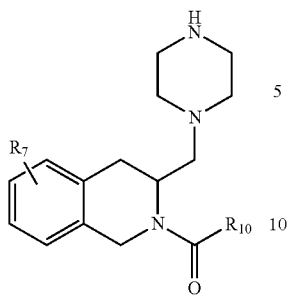

Scheme F

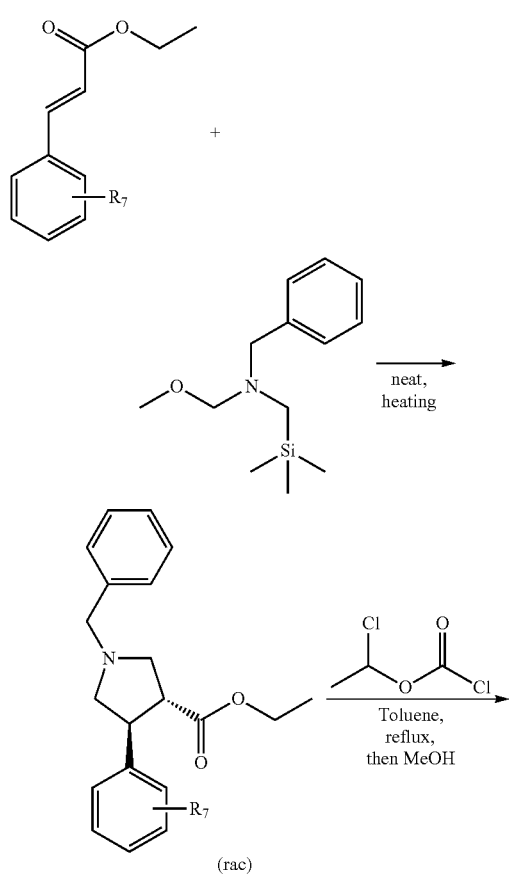

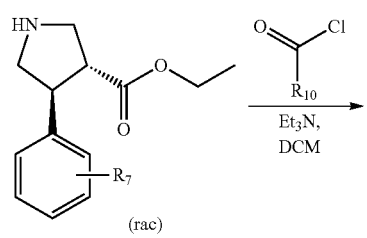

106
-continued

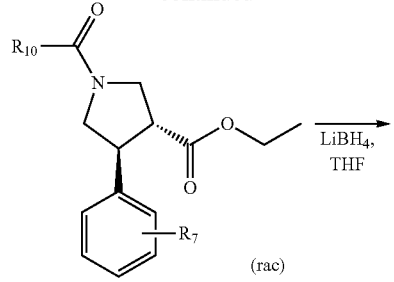

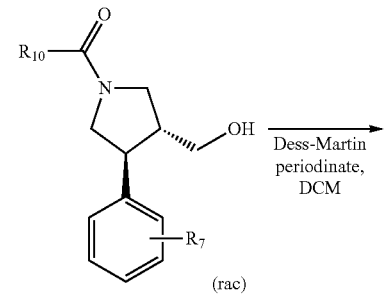

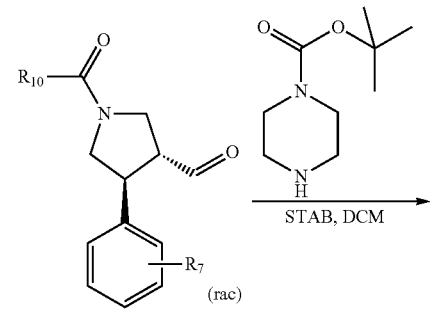

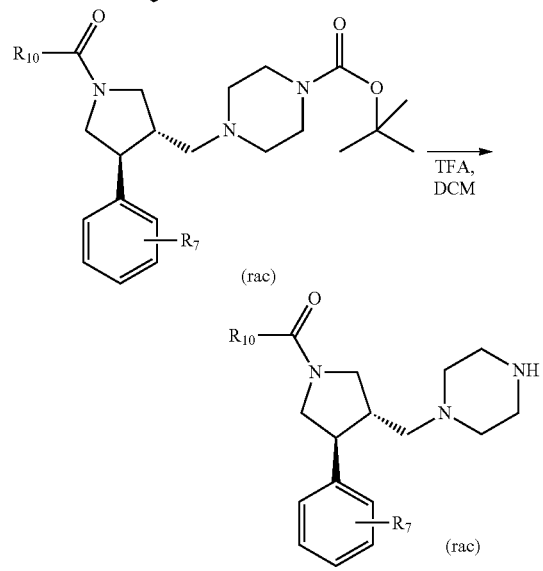

Methods of Using the Disclosed Compounds

Another aspect of the invention relates to a method of treating a disease or disorder associated with modulation of BCL-2 proteins. The method comprises administering to a patient in need of a treatment for diseases or disorders associated with modulation of BCL-2 proteins an effective amount the compositions and compounds of Formula (I).

In another aspect, the present invention is directed to a method of inhibiting BCL-2 proteins. The method involves administering to a patient in need thereof an effective amount of a compound of Formula (I).

Another aspect of the present invention relates to a method of treating, preventing, inhibiting or eliminating a disease or disorder in a patient associated with the inhibition of BCL-2 proteins, the method comprising administering to a patient in need thereof an effective amount of a compound of Formula (I). In one embodiment, the disease may be, but not limited to, cancer and metastasis.

The present invention also relates to the use of an inhibitor of BCL-2 proteins for the preparation of a medicament used in the treatment, prevention, inhibition or elimination of a disease or condition mediated by BCL-2 proteins, wherein the medicament comprises a compound of Formula (I).

In another aspect, the present invention relates to a method for the manufacture of a medicament for treating, preventing, inhibiting, or eliminating a disease or condition mediated by BCL-2 proteins, wherein the medicament comprises a compound of Formula (I).

Another aspect of the present invention relates to a compound of Formula (I) for use in the manufacture of a medicament for treating a disease associated with inhibiting BCL-2 proteins.

In another aspect, the present invention relates to the use of a compound of Formula (I) in the treatment of a disease associated with inhibiting BCL-2 proteins.

Another aspect of the invention relates to a method of treating cancer. The method comprises administering to a patient in need thereof an effective amount of a compound of Formula (I).

Another aspect of the invention relates to a method of treating or preventing cancer. The method comprises administering to a patient in need thereof an effective amount of a compound of Formula (I).

In one embodiment, the present invention relates to the use of an inhibitor of BCL-2 proteins for the preparation of a medicament used in treatment, prevention, inhibition or elimination of a disease or disorder associated with cancer.

In another embodiment, the present invention relates to a compound of Formula (I) or a pharmaceutical composition comprising a compound of the present invention and a pharmaceutically acceptable carrier used for the treatment of cancers including, but not limited to, bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL) and chronic lymphocytic leukemia/small lymphocytic lymphoma (CLL/SLL).

In another embodiment, the present invention relates to a compound of Formula (I) or a pharmaceutical composition comprising a compound of the present invention and a pharmaceutically acceptable carrier used for the treatment of cancers including, but not limited to, marginal zone lymphoma (MZL), follicular lymphoma (FL), diffuse large B-cell lymphoma (DLBCL) and chronic lymphocytic leukemia/small lymphocytic lymphoma (CLL/SLL).

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of BCL-2 proteins including, cancer or cell proliferative disorder, comprising administering to a patient suffering from at least one of said diseases or disorder a compound of Formula (I).

One therapeutic use of the compounds or compositions of the present invention which inhibit BCL-2 proteins is to provide treatment to patients or subjects suffering from a cancer or cell proliferative disorder.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant. In some embodiments, the pharmaceutical composition can further comprise an additional pharmaceutically active agent.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations used in the following examples and elsewhere herein are:

AcCl acetyl chloride
atm atmosphere
br broad
anh. anhydrous
aq. aqueous
BuLi butyl lithium
DCM dichloromethane (i.e. $CH_2C_{12}$)
DIAD diisopropyl azodiformate
DIPEA N,N-diisopropylethylamine
DMAc N,N-dimethyl acetamide
DMAP N,N-dimethylpyridin-4-amine
DME 1,2-Dimethoxyethane
DMEDA N,N'-Dimethylethylenediamine
DMF N,N-dimethyl formamide
DMSO dimethyl sulfoxide
EDCI 1-(3-Dimethylaminopropyl)-3-ethylcarbodiimide
ESI electrospray ionization
Et-I iodoethane
EtOAc ethyl acetate
EtOH ethanol
FA formic acid
h hour(s)
Hal halogen
HATU [bis(dimethylamino)methylene]-1H-1,2,3-triazolo[4,5-b]pyridinium 3-oxide hexafluorophosphate
HPLC high pressure (or performance) liquid chromatography
t-BuOK potassium tert-butoxide
LCMS liquid chromatography mass spectrometry
LHMDS Lithium bis(trimethylsilyl)amide
m multiplet
M molar
MeCN acetonitrile
2-MeTHF 2-methyl tetrahydrofuran
MeOH methanol
MHz megahertz
min minutes
MS molecular sieves
MsCl methanesulfonyl chloride
n-BuLi butyl lithium
NBS N-bromosuccinimide
NMR nuclear magnetic resonance
ppm parts per million
quant. quantitative
rac racemic mixture
rt room temperature
RT retention time
sat. saturated
STAB sodium triacetoxyborohydride TBAB tetrabutylammonium bromide
TBTU O-(Benzotriazol-1-yl)-N,N,N',N'-tetramethyluronium tetrafluoroborate
t-BuOH tert-butanol
TFA trifluoroacetic acid
THF tetrahydrofuran
TLC thin layer chromatography Purity and identity of all synthesized compounds was confirmed by LC-MS analysis performed on Shimadzu Analytical 10 Avp equipped with PE SCIEX API 165 mass, Sedex 75 ELSD, and Shimadzu UV (254 and 215) detectors. Separation was achieved with $C_{18}$ column 100×4.6 mm, 5.0 μm, pore size 100 Å, water-acetonitrile+0.1% trifluoroacetic acid, gradient 5 to 87% for 10 min.

Preparative HPLC purification was carried out on Shimadzu instrument equipped with SPD-10 Avp detector and FRC-10A fraction collector. Separation was achieved with a column YMC-Pack ODS-AQ 250×20 mml, S-10 μm, 12 nm, gradient solution A-solution B (A: 1000 mL water-226 μL trifluoroacetic acid; B: 1000 mL acetonitrile-226 μL trifluoroacetic acid).

3-Nitro-4-[(tetrahydro-2H-pyran-4-ylmethyl)amino]benzenesulfonamide and tert-butyl 4-bromo-2-(1H-pyrrolo[2,3-b]pyridin-5-yloxy)benzoate were synthesized according to reported procedure (US2014/275540).

Synthesis of Intermediates

Preparation 1: tert-butyl 5-(5-bromo-2-(ethoxycarbonyl)phenoxy)-1H-indole-1-carboxylate Step 1: Synthesis of ethyl 4-bromo-2-(1H-indol-5-yloxy)benzoate A mixture of ethyl 4-bromo-2-fluorobenzoate (8.0 g, 32 mmol), 1H-indol-5-ol (5.17 g, 0.038 mol) and $K_2CO_3$ (6.71 g, 48 mmol), and DMF (100 mL) was stirred at 80° C. overnight, cooled to ambient temperature, diluted with water (100 mL) and extracted twice with EtOAc. Combined organic layers were dried over $Na_2SO_4$ and concentrated under reduced temperature. The residue was purified by silica flash chromatography eluting with a mixture (5→50%) EtOAc and DCM to afford 9.4 g (81%) of the title compound.

Step 2: Synthesis of tert-butyl 5-[5-bromo-2-(ethoxycarbonyl)phenoxy]-1H-indole-1-carboxylate A mixture of ethyl 4-bromo-2-(1H-indol-5-yloxy)benzoate obtained at Step 1 (9.4 g, 26 mmol), $Boc_2O$ (6.83 g, 31.2 mmol), DMAP (3.82 g, 31.2 mmol), and DCM (100 ml) was stirred overnight at ambient temperature, washed twice with water, and concentrated under reduced pressure. The residue was purified by silica flash chromatography eluting with a mixture (5→20%) EtOAc to afford 11.0 g (91%) of the title compound.

Preparation 2: tert-Butyl 5-[5-bromo-2-(tert-butoxycarbonyl)phenoxy]-1H-pyrrolo[2,3-b]pyridine-1-carboxylate

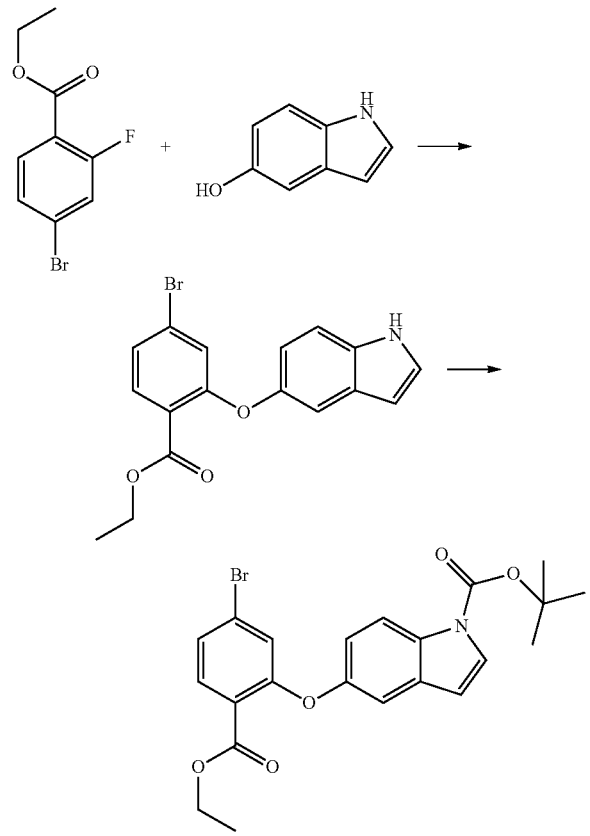

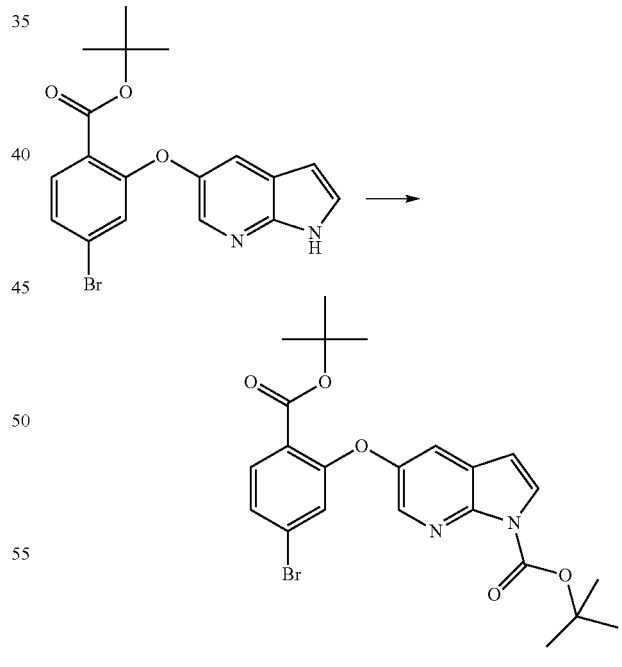

A mixture of tert-butyl 4-bromo-2-(1H-pyrrolo[2,3-b]pyridin-5-yloxy)benzoate (4.5 g, 11.6 mmol), $Boc_2O$ (2.65 g. 12 mmol), DMAP (67 mg, 0.55 mmol), and DCM (100 mL) was stirred overnight at ambient temperature, washed with water, dried over $Na_2SO_4$, and concentrated under reduced pressure to afford crude product that was used for the next step without further purification.

Preparation 3: 3-(4-chlorophenyl)-2-(piperidin-4-ylmethyl)-2-azaspiro[3.4]octan-1-one

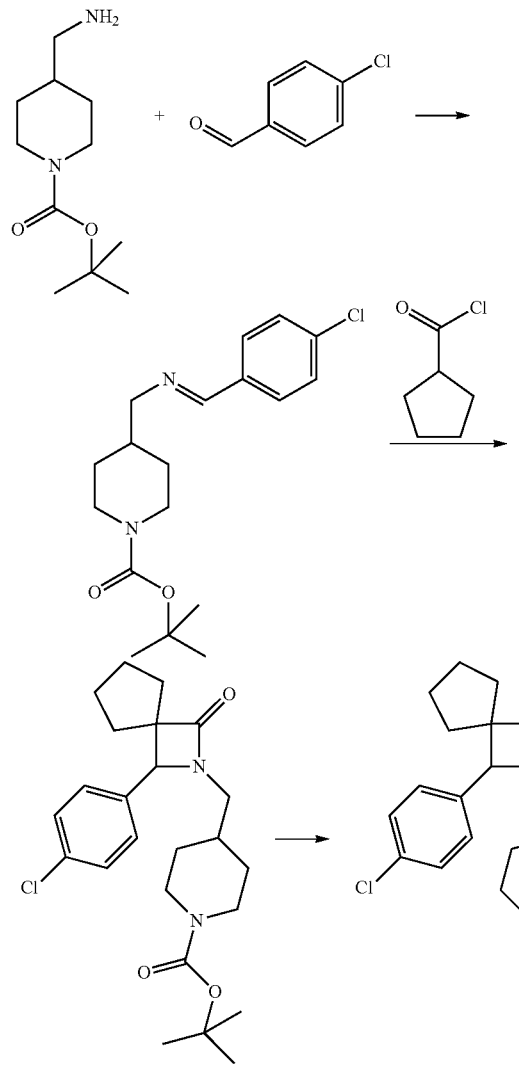

Step 1: Synthesis of tert-butyl 4-({[(1E)-(4-chlorophenyl)methylidene]amino}methyl)piperidine-1-carboxylate A mixture of 4-chlorobenzaldehyde (5.7 g, 41 mmol), tert-butyl 4-(aminomethyl)piperidine-1-carboxylate (8.7 g, 41 mmol), anh. $Na_2SO_4$ (15.3 g, 123 mmol), and $CHCl_3$ (100 mL) was stirred at ambient temperature overnight. Solid was filtered off and washed with $CHCl_3$, and the combined filtrate was concentrated under reduced pressure to afford crude product that was used in the next step without further purification.

Step 2: Synthesis of tert-Butyl 4-[1-(4-chlorophenyl)-3-oxo-2-azaspiro[3.4]oct-2-yl]methyltetrahydro-1(2H)-pyridinecarboxylate A solution of cyclopentanecarbonyl chloride (2.19 g, 16.5 mmol) in $CHCl_3$ (20 mL) was added dropwise to a stirred boiling solution of the crude product obtained at Step 1 and $Et_3N$ (6.9 mL, 49 mmol) in $CHCl_3$ (60 mL) over a period of 1 h. The reaction mixture was stirred at reflux overnight, cooled to ambient temperature, and quenched with a 5 mL of MeOH, and then with 5% aq. solution of citric acid (80 mL). The organic layer was separated, and the aqueous layer was extracted with $CHCl_3$. The combined organic layers were dried over $Na_2SO_4$ and concentrated under reduced pressure. The residue was purified by silica flash chromatography eluting with a mixture (2→10%) EtOAc and hexane to afford 3.3 g (46%) of the title compound.

Step 3: Synthesis of 3-(4-chlorophenyl)-2-(4-piperidylmethyl)-2-azaspiro[3.4]octan-1-one TFA (10 mL) was added portion wise to a stirred solution of the compound obtained at Step 2 (3.3 g, 7 mmol) in DCM (30 mL). The resultant mixture was stirred overnight at ambient temperature and then concentrated under reduced pressure. The residue was partitioned between water (50 mL) and $Et_2O$ (60 mL). The organic layer was discarded, and the aqueous layer was washed twice with $Et_2O$, basified with 50% NaOH to pH 12, and extracted twice with $CHCl_3$. Combined organic layers were dried over $Na_2SO_4$ and evaporated under reduced pressure to provide 2.5 g (98%) of the title compound that was used for the next step without additional purification.

Preparation 4: 3-phenyl-2-(piperidin-4-ylmethyl)-2-azaspiro[3.4]octan-1-one

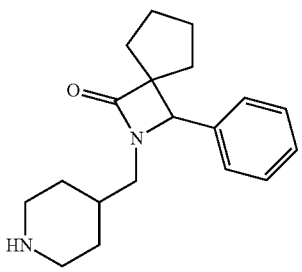 [SMILES: O=C1N(CC2CCNCC2)C(c2ccccc2)C12CCCC2]

The procedure was as in the process of Preparation 3 using benzaldehyde instead of 4-chlorobenzaldehyde as a starting material.

Preparation 5: 3-(4-chloro-2-methylphenyl)-2-(piperidin-4-ylmethyl)-2-azaspiro[3.4]octan-1-one

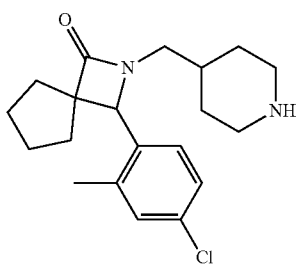 [SMILES: Cc1cc(Cl)ccc1C1N(CC2CCNCC2)C(=O)C12CCCC2]

The procedure was as in the process of Preparation 3, using 4-chloro-2-methylbenzaldehyde instead of 4-chlorobenzaldehyde as a starting material.

115

Preparation 6: 3-(5-chloropyridin-3-yl)-2-(piperidin-4-ylmethyl)-2-azaspiro[3.4]octan-1-one

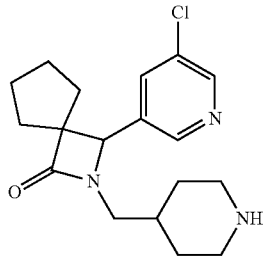 [SMILES: O=C1N(CC2CCNCC2)C(c2cncc(Cl)c2)C12CCCC2]

The procedure was as in the process of Preparation 3, using 5-chloropyridine-3-carbaldehyde instead of 4-chlorobenzaldehyde as a starting material.

Preparation 7: 3-[3-(benzyloxy)phenyl]-2-(piperidin-4-ylmethyl)-2-azaspiro[3.4]octan-1-one

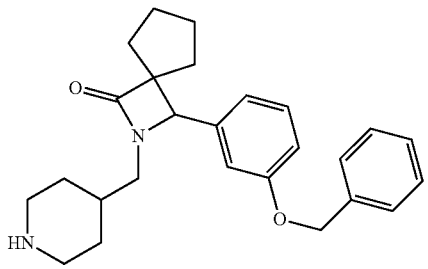 [SMILES: O=C1N(CC2CCNCC2)C(c2cccc(OCc3ccccc3)c2)C12CCCC2]

The procedure was as in the process of Preparation 3, using 3-benzyloxybenzaldehyde instead of 4-chlorobenzaldehyde as a starting material.

Preparation 8: 4-(4-{[1-(4-chlorophenyl)-3-oxo-2-azaspiro[3.4]oct-2-yl]methyl}piperidin-1-yl)-2-(1H-indol-5-yloxy)benzoic acid

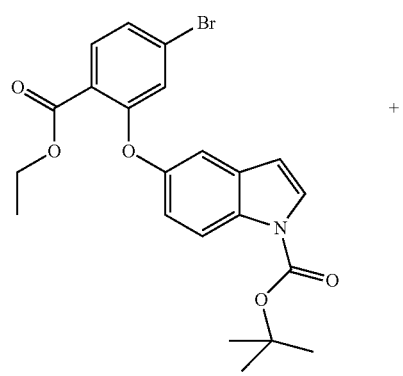

+

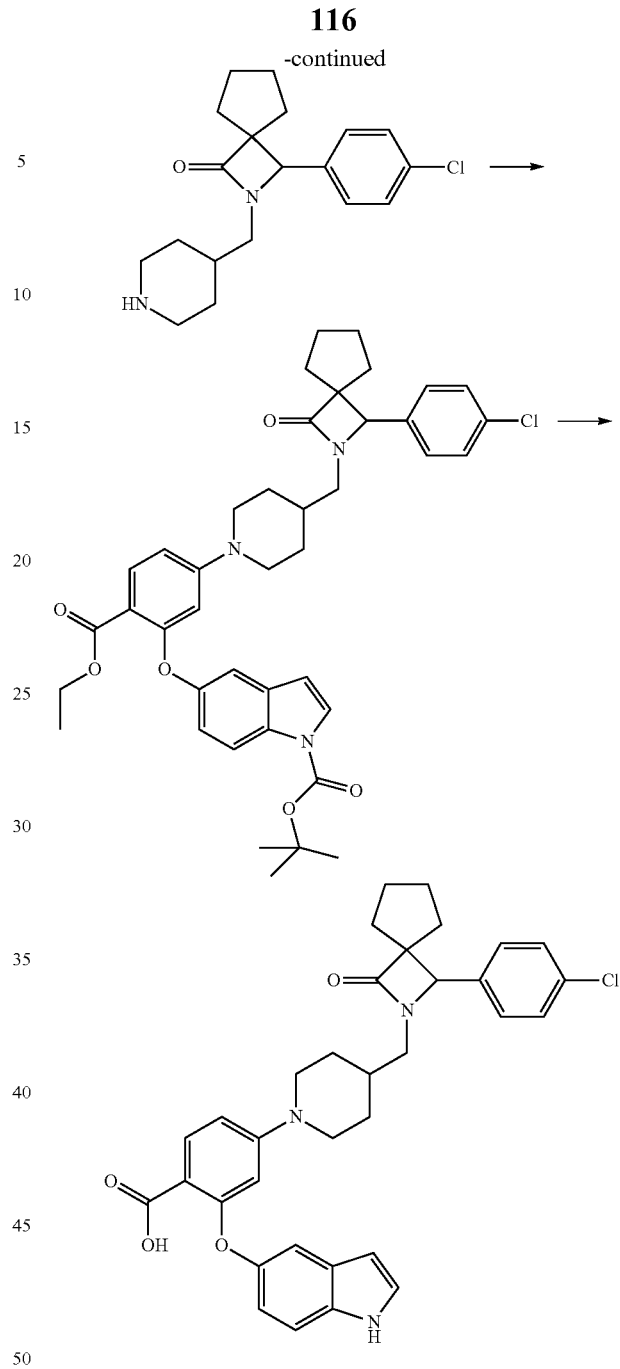

Step 1: Synthesis of tert-butyl 5-[5-(4-{[1-(4-chlorophenyl)-3-oxo-2-azaspiro[3.4]oct-2-yl]methyl}piperidin-1-yl)-2-(ethoxycarbonyl)phenoxy]-1H-indole-1-carboxylate A mixture of tert-butyl 5-[5-bromo-2-(ethoxycarbonyl)phenoxy]-1H-indole-1-carboxylate (See Preparation 1) (1.1 g, 2.4 mmol), 3-(4-chlorophenyl)-2-(piperidin-4-ylmethyl)-2-azaspiro[3.4]octan-1-one (See Preparation 3) (0.8 g, 2.4 mmol), palladium diacetate (0.054 g, 0.24 mmol), (±)-2,2'-bis(diphenylphosphino)-1,1'-binaphthalene (0.22 g, 0.36 mmol), and cesium carbonate (0.97 g, 3 mmol) in toluene (20 mL) was heated under nitrogen at 60° C. for 20 h, cooled to ambient temperature, and concentrated under reduced pressure. The residue was dissolved in DCM (30 mL), the obtained solution was filtered through Celite pad, and filtrate was washed with water, and then with brine. The organic layer was dried over Na$_2$SO$_4$ and concentrated under reduced pressure. The residue was subjected to silica flash chromatography eluting with a mixture of EtOAc (10→30%) and hexane to afford 0.6 g (35%) of the title compound.

Step 2: Synthesis of 4-(4-[1-(4-chlorophenyl)-3-oxo-2-azaspiro[3.4]oct-2-yl]methylpiperidino)-2-(1H-indol-5-yloxy)benzoic acid A mixture of the compound obtained at Step 1 (0.4 g, 0.56 mmol), NaOH (0.045 g, 1.1 mmol), THE (2 mL), EtOH (2 mL), and H$_2$O (2 mL) was stirred at 50° C. for 20 h, cooled to ambient temperature, and acidified with aq. HCl. The precipitate that formed was filtered off, washed twice with water, dried, and purified by prep. HPLC to afford 0.02 g (6%) of the title compound.

Preparation 9: 4-(4-{[1-(4-chlorophenyl)-3-oxo-2-azaspiro[3.4]oct-2-yl]methyl}piperidin-1-yl)-2-(1H-pyrrolo[2,3-b]pyridin-5-yloxy)benzoic acid

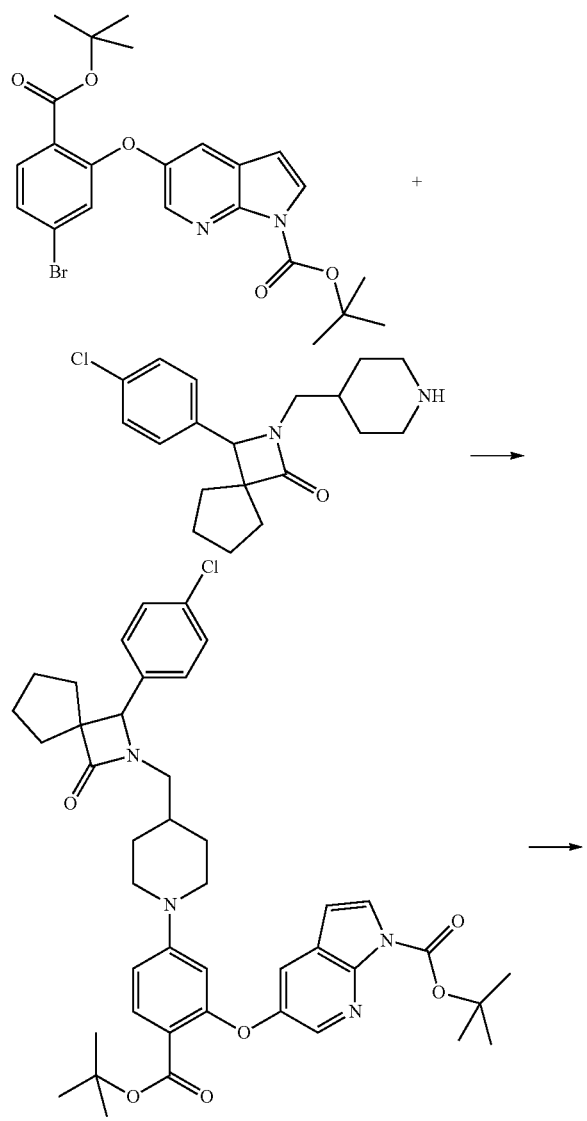

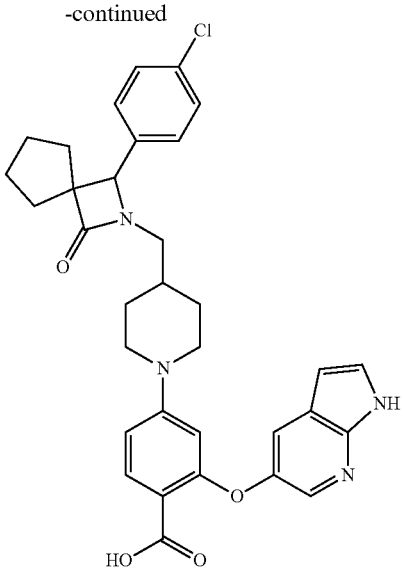

Step 1: Synthesis of tert-Butyl 5-[2-(tert-butoxycarbonyl)-5-(4-{[1-(4-chlorophenyl)-3-oxo-2-azaspiro[3.4]oct-2-yl]methyl}piperidin-1l-yl)phenoxy]-1H-pyrrolo[2,3-b]pyridine-1-carboxylate A mixture of tert-Butyl 5-[5-bromo-2-(tert-butoxycarbonyl)phenoxy]-1H-pyrrolo[2,3-b]pyridine-1-carboxylate (see Preparation 2) (0.22 g, 0.451 mmol), 3-(4-chlorophenyl)-2-(piperidin-4-ylmethyl)-2-azaspiro[3.4]octan-1-one (see Preparation 3) (0.15 g, 0.21 mmol), palladium diacetate (0.003 g, 0.013 mmol), (±)-2,2'-bis(diphenylphosphino)-1,1'-binaphthalene (0.016 g, 0.026 mmol), cesium carbonate (0.735 g, 2.25 mmol), and toluene (25 mL) was stirred and heated under nitrogen at 80° C. for 12 h, cooled to ambient temperature, and concentrated under reduced pressure. The residue was dissolved in EtOAc (25 mL), the obtained solution was filtered through Celite pad, and the filtrate was washed with water and then with brine. The organic layer was dried over Na$_2$SO$_4$ and concentrated under reduced pressure. The residue was subjected to silica flash chromatography eluting with a mixture of EtOAc (20→50%) and hexane to afford 0.157 g (47%) of the title compound.

Step 2: Synthesis of 4-(4-{[1-(4-chlorophenyl)-3-oxo-2-azaspiro[3.4]oct-2-yl]methyl}piperidin-1-yl)-2-(1H-pyrrolo[2,3-b]pyridin-5-yloxy)benzoic acid CF$_3$COOH (3 mL) was added to a stirred solution of compound obtained at Step 1 in DCM (15 mL), the mixture was stirred at room temperature for 12 h, then volatiles were removed under reduced pressure, the residue was partitioned between DCM (20 mL) and saturated aqueous solution of NaHCO$_3$ (20 mL). The organic layer was separated, and the aqueous layer extracted with DCM. Combined organic layers were dried over Na$_2$SO$_4$ and concentrated under reduced pressure to provide 0.124 g (100%) of the title compound that was used for the next step without further purification.

Preparation 10: 4-{4-[(1-oxo-3-phenyl-2-azaspiro[3.4]oct-2-yl)methyl]piperidin-1-yl}-2-(H-pyrrolo[2,3-b]pyridin-5-yloxy)benzoic acid

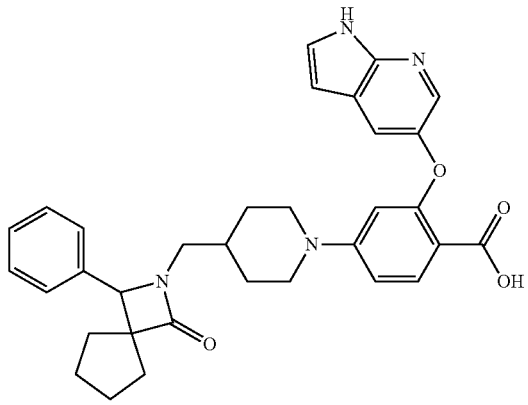 [SMILES: O=C(O)c1ccc(N2CCC(CN3C(=O)C4(CCCC4)C3c3ccccc3)CC2)cc1Oc1cnc2[nH]ccc2c1]

The procedure was as in the process of Preparation 9 using 3-phenyl-2-(piperidin-4-ylmethyl)-2-azaspiro[3.4]octan-1-one (See Preparation 4) instead of 3-(4-chlorophenyl)-2-(piperidin-4-ylmethyl)-2-azaspiro[3.4]octan-1-one as a starting material.

Preparation 11: 4-(4-{[1-(4-chloro-2-methylphenyl)-3-oxo-2-azaspiro[3.4]oct-2-yl]methyl}piperidin-1-yl)-2-(1H-pyrrolo[2,3-b]pyridin-5-yloxy)benzoic acid

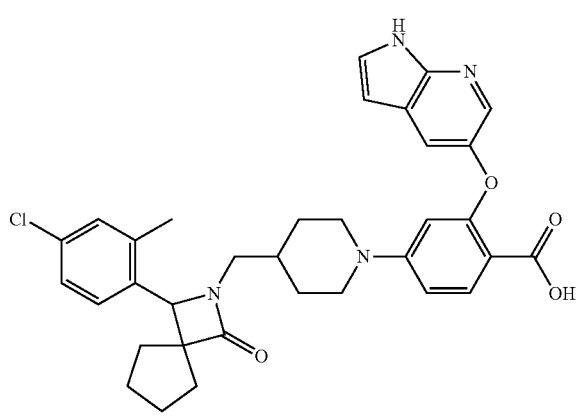 [SMILES: Cc1cc(Cl)ccc1C1N(CC2CCN(c3ccc(C(=O)O)c(Oc4cnc5[nH]ccc5c4)c3)CC2)C(=O)C12CCCC2]

The procedure was as in the process of Preparation 9 using 3-(4-chloro-2-methylphenyl)-2-(piperidin-4-ylmethyl)-2-azaspiro[3.4]octan-1-one (See Preparation 5) instead of 3-(4-chlorophenyl)-2-(piperidin-4-ylmethyl)-2-azaspiro[3.4]octan-1-one as a starting material.

Preparation 12: 4-(4-{[1-(5-chloropyridin-3-yl)-3-oxo-2-azaspiro[3.4]oct-2-yl]methyl}piperidin-1-yl)-2-(1H-pyrrolo[2,3-b]pyridin-5-yloxy)benzoic acid

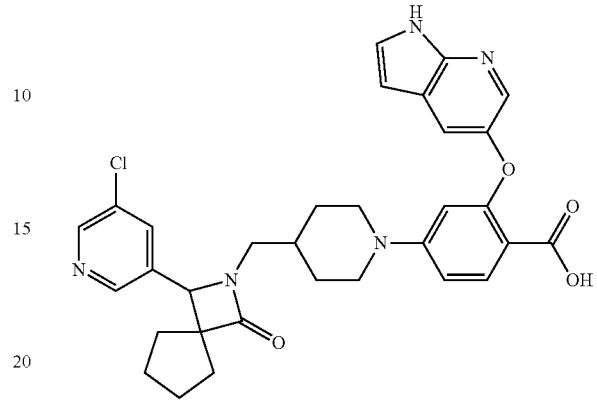

The procedure was as in the process of Preparation 9 using 3-(5-chloropyridin-3-yl)-2-(piperidin-4-ylmethyl)-2-azaspiro[3.4]octan-1-one (See Preparation 6) instead of 3-(4-chlorophenyl)-2-(piperidin-4-ylmethyl)-2-azaspiro[3.4]octan-1-one as a starting material.

Preparation 13: 4-[4-({1-[3-(benzyloxy)phenyl]-3-oxo-2-azaspiro[3.4]oct-2-yl}methyl)piperidin-1-yl]-2-(1H-indol-5-yloxy)benzoic acid

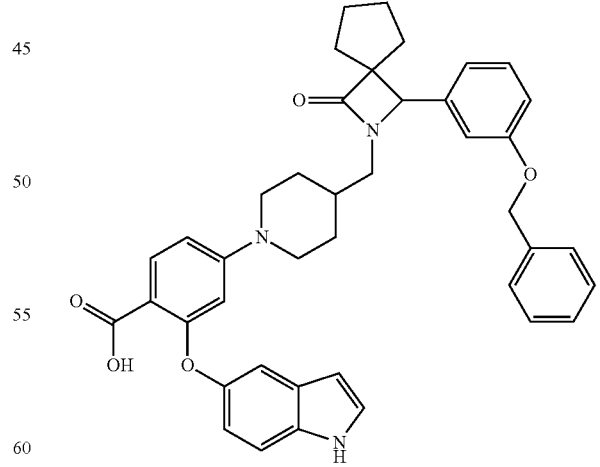

The procedure was as in the process of Preparation 8 using 3-[3-(benzyloxy)phenyl]-2-(piperidin-4-ylmethyl)-2-azaspiro[3.4]octan-1-one (See Preparation 7) instead of 3-(4-chlorophenyl)-2-(piperidin-4-ylmethyl)-2-azaspiro[3.4]octan-1-one as a starting material.

Preparation 14: 2-(1H-pyrrolo[2,3-b]pyridin-5-yloxy)-4-(4-((1-phenyl-2-azaspiro[3.4]octan-2-yl)methyl)piperidin-1-yl)benzoic acid

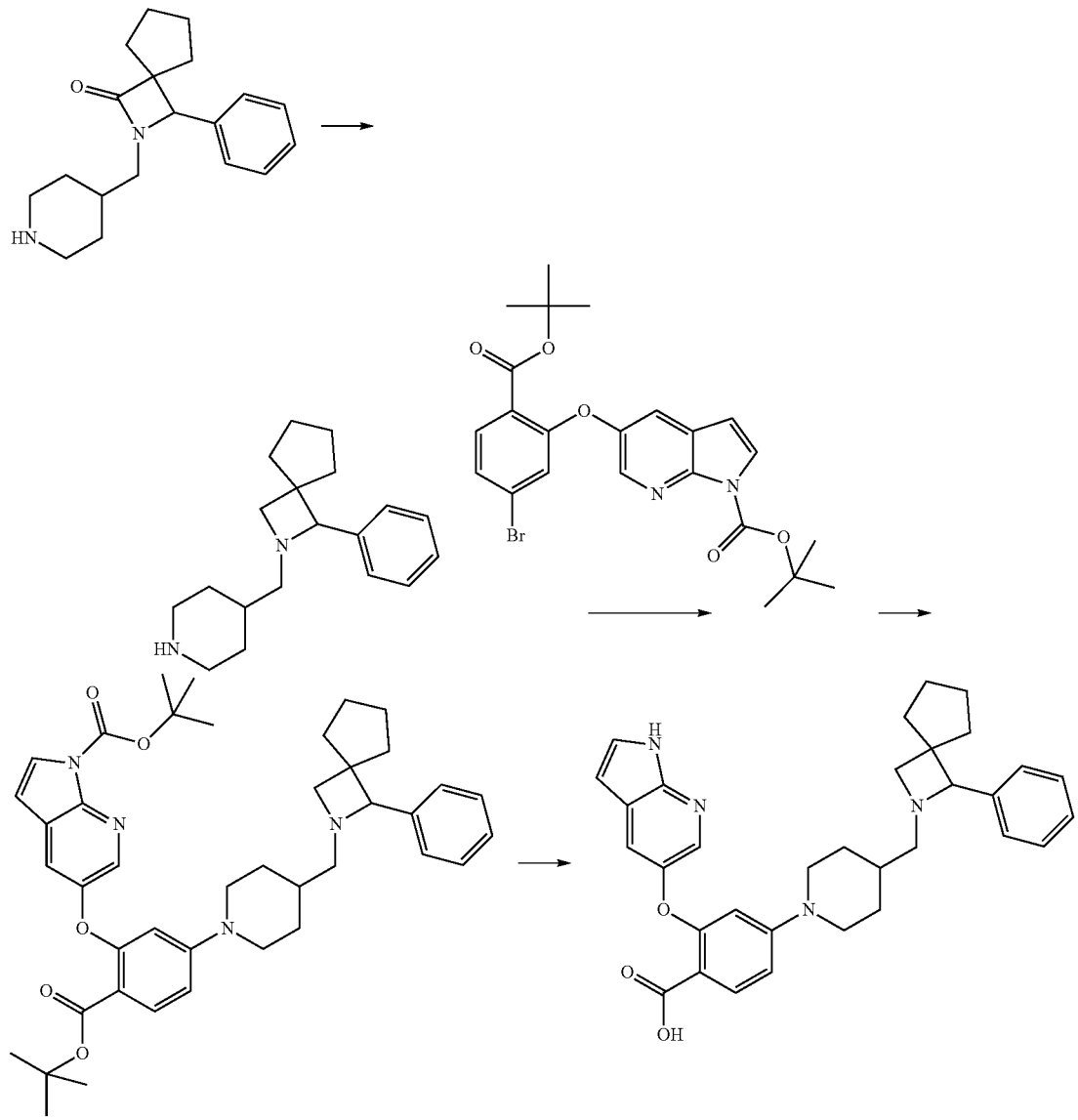

Step 1: Synthesis of 1-phenyl-2-(piperidin-4-ylmethyl)-2-azaspiro[3.4]octane

A solution of AlCl$_3$ (2.8 g, 21 mmol) in Et$_2$O (30 mL) was added dropwise to a stirred suspension of LiAlH$_4$ (0.8 g, 21 mmol) in Et$_2$O (20 mL) under argon atmosphere. The resultant mixture was stirred and heated under reflux for 1 h, and subsequently cooled down to ambient temperature. A solution of 3-phenyl-2-(piperidin-4-ylmethyl)-2-azaspiro[3.4]octan-1-one (See Preparation 4) (2 g, 7 mmol) in DCM was added dropwise. The reaction mixture was stirred overnight at ambient temperature, then 10% aq. solution of NaOH (20 mL) was added dropwise. Layers were separated, organic layer was washed with brine, dried over Na$_2$SO$_4$, and concentrated under reduced pressure to afford 1.2 g (60%) of the title compound that was used for the next step without additional purification.

Step 2: Synthesis of tert-butyl 5-(2-(tert-butoxycarbonyl)-5-(4-((1-phenyl-2-azaspiro[3.4]octan-2-yl)methyl)piperidin-1-yl)phenoxy)-1H-pyrrolo[2,3-b]pyridine-1-carboxylate A mixture of the compound obtained at the Step 1 (1.2 g, 4 mmol), tert-butyl 5-[5-bromo-2-(tert-butoxycarbonyl)phenoxy]-1H-pyrrolo[2,3-b]pyridine-1-carboxylate (See Preparation 2) (1.9 g, 4 mmol), palladium diacetate (0.009 g, 0.04 mmol), (±)-2,2'-bis(diphenylphosphino)-1,1'-binaphthalene (0.62 g, 0.08 mmol), Cs$_2$CO$_3$, (2.6 g, 8 mmol), and toluene (30 mL) was stirred and heated at 80° C. under nitrogen for 20 h, subsequently cooled down to ambient temperature, and concentrated under reduced pressure. The residue was partitioned between water (50 mL) and DCM (50 mL), the organic layer was separated, washed with water, brine, dried over Na$_2$SO$_4$, and concentrated under reduced pressure. The residue was subjected to silica flash chromatography eluting with a mixture of (20→50%) of EtOAc and hexane to afford 0.8 g (29%) of the title compound.

Step 3: Synthesis of 2-(1H-pyrrolo[2,3-b]pyridin-5-yloxy)-4-(4-((1-phenyl-2-azaspiro[3.4]octan-2-yl)methyl)piperidin-1-yl)benzoic acid TFA (2 ml) was added portion wise to a stirred solution of tert-butyl 5-(2-(tert-butoxycarbonyl)-5-{4-[(1-phenyl-2-azaspiro[3.4]oct-2-yl)methyl]piperidin-1-yl}phenoxy)-1H-pyrrolo[2,3-b]pyridine-1-carboxylate (0.8 g, 1 mmol) in DCM (15 mL). The mixture was stirred at ambient temperature for 12 h, then volatiles were removed under reduced pressure. The residue was dissolved in Et$_2$O (20 mL), and 6M solution of HCl in dioxane (5 mL) was added. The formed precipitate was filtered off, washed with Et$_2$O (20 mL), and dried to afford 0.5 g (93%) of the title compound.

Preparation 15: 4-(3-chloro-4-methylphenylamino)-3-nitrobenzenesulfonamide

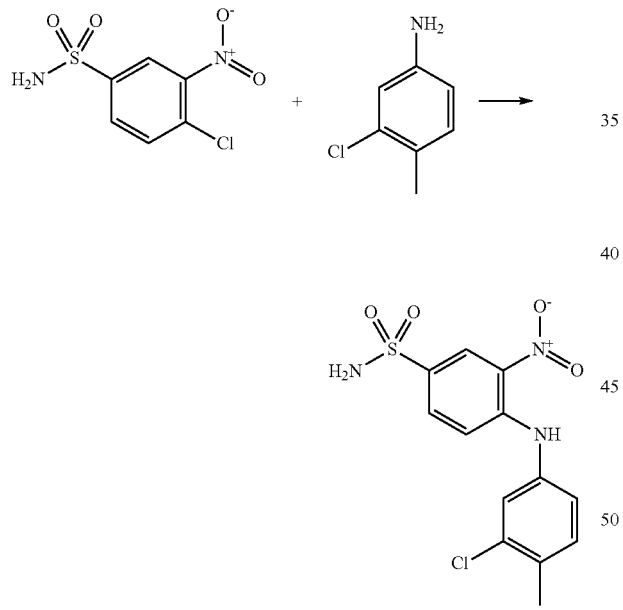

A mixture of 4-chloro-3-nitro-1-benzenesulfonamide (1.52 g, 6.4 mmol) and 3-chloro-4-methylaniline (4.54 g, 32 mmol) was stirred at 90° C. overnight, subsequently cooled down to ambient temperature, and subjected to silica flash chromatography eluting with a mixture of (5→50%) EtOAc and DCM to afford 0.85 g (39%) of the title compound. A neat mixture of the compounds was stirred at 90° C. overnight.

3-Nitro-4-[(tetrahydro-2H-pyran-4-ylmethyl)amino]benzenesulfonamide and tert-butyl 4-bromo-2-(1H-pyrrolo[2,3-b]pyridin-5-yloxy)benzoate were synthesized according to reported procedure (US2014/275540).

Preparation 16: tert-Butyl 4-[(3S)-1,2,3,4-tetrahydroisoquinolin-3-ylmethyl]piperazine-1-carboxylate

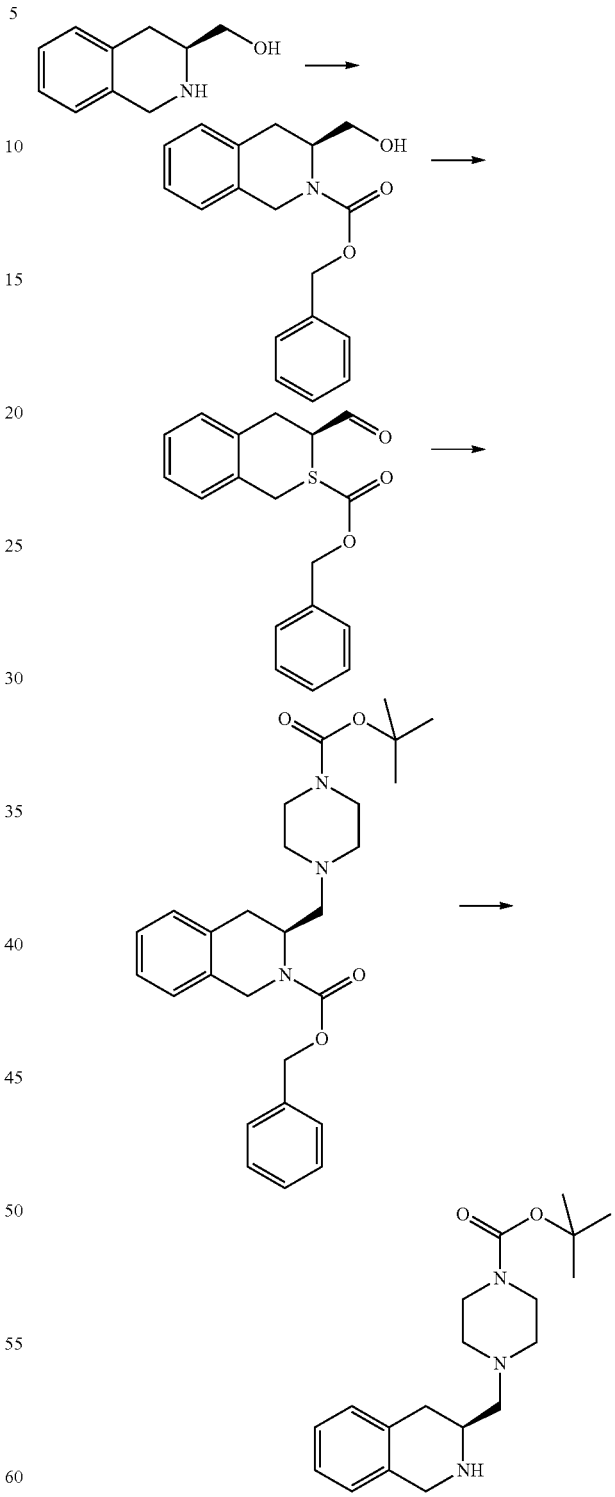

Step 1: Synthesis of benzyl (3S)-3-(hydroxymethyl)-3,4-dihydroisoquinoline-2(1H)-carboxylate Cbz-Cl (11.6 g, 68 mmol) was added dropwise to a stirred solution of solution of (3S)-1,2,3,4-tetrahydroisoquinolin-3- ylmethanol (10.1 g, 62 mmol) and Et₃N (12.5 g, 123 mmol) in DCM (150 mL) maintaining internal temperature below −10° C. The mixture was allowed to warm to ambient temperature and stirred overnight. A saturated aqueous solution of NaHCO₃ (100 mL) was added to reaction mixture. The organic layer was separated, and the aqueous layer was extracted with DCM (3×100 mL). The combined organic layers were washed with brine, dried over anhydrous MgSO₄, and concentrated under reduced pressure. The residue was purified by silica chromatography eluting with a CH₂Cl₂ to afford 12.6 g (68.5%) of the title compound.

Step 2: Synthesis of benzyl (3S)-3-formyl-3,4-dihydroisoquinoline-2(1H)-carboxylate A solution of Dess-Martin periodinate (28.7 g, 64 mmol) in DCM (200 mL) was added dropwise to a stirred solution of the alcohol obtained at Step 1 (12.6 g, 42 mmol) in DCM (150 mL) maintaining an internal temperature below 0° C. The reaction mixture was allowed to warm to ambient temperature, stirred overnight at ambient temperature, then quenched with a saturated aqueous solution of a mixture of NaHCO₃ and Na₂S₂O₃ (1:1, 100 mL) and stirred additionally for 10 min. The organic layer was separated, dried over MgSO₄, filtered, and concentrated under reduced pressure. The resulting residue was purified by silica flash chromatography eluting with a mixture of EtOAc (0→20%) and hexane to afford 5.1 g (41%) of the title compound.

Step 3: Synthesis of benzyl (3S)-3-{[4-(tert-butoxycarbonyl)piperazin-1-yl]methyl}-3,4-dihydroisoquinoline-2(1H)-carboxylate A mixture of aldehyde obtained at the step 2 (5.1 g, 17 mmol), N-Boc-piperazine (3.86 g, 21 mmol), sodium triacetoxyborohydride (11 g, 51 mmol), and DCM (75 mL) was stirred at ambient temperature overnight. A saturated aqueous solution of NH₄Cl (100 mL) was added, the organic layer was separated, and the aqueous layer was extracted with DCM (3×100 mL). The combined organic layers were dried over anhydrous MgSO₄ and concentrated. The crude product was purified by silica flash chromatography eluting with a mixture of EtOAc (0→20%) and DCM to afford 5.8 g (72%) of the title compound.

Step 4: Synthesis of tert-Butyl 4-[(3S)-1,2,3,4-tetrahydroisoquinolin-3-ylmethyl]piperazine-1-carboxylate A mixture of the compound obtained at Step 3 (5.8 g, 12.5 mmol), 10% palladium on charcoal (0.6 g), and methanol (100 mL) was vigorously stirred under H₂ atmosphere overnight, filtered through a Celite pad, and filtrate was evaporated to dryness to afford 4.1 g (99%) of the title compound that was used for the next step without purification.

Preparation 17: tert-Butyl 4-[(3R)-1,2,3,4-tetrahydroisoquinolin-3-ylmethyl]piperazine-1-carboxylate

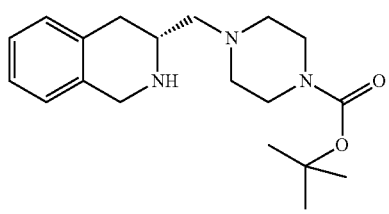 [SMILES: CC(C)(C)OC(=O)N1CCN(C[C@H]2Cc3ccccc3CN2)CC1]

The procedure was as in the process of Preparation 16 using (3R)-1,2,3,4-tetrahydroisoquinolin-3-ylmethanol instead of (3S)-1,2,3,4-tetrahydroisoquinolin-3-ylmethanol.

Preparation 18: (3S)-3-(piperazin-1-ylmethyl)-2-(thiophen-2-ylcarbonyl)-1,2,3,4-tetrahydroisoquinoline

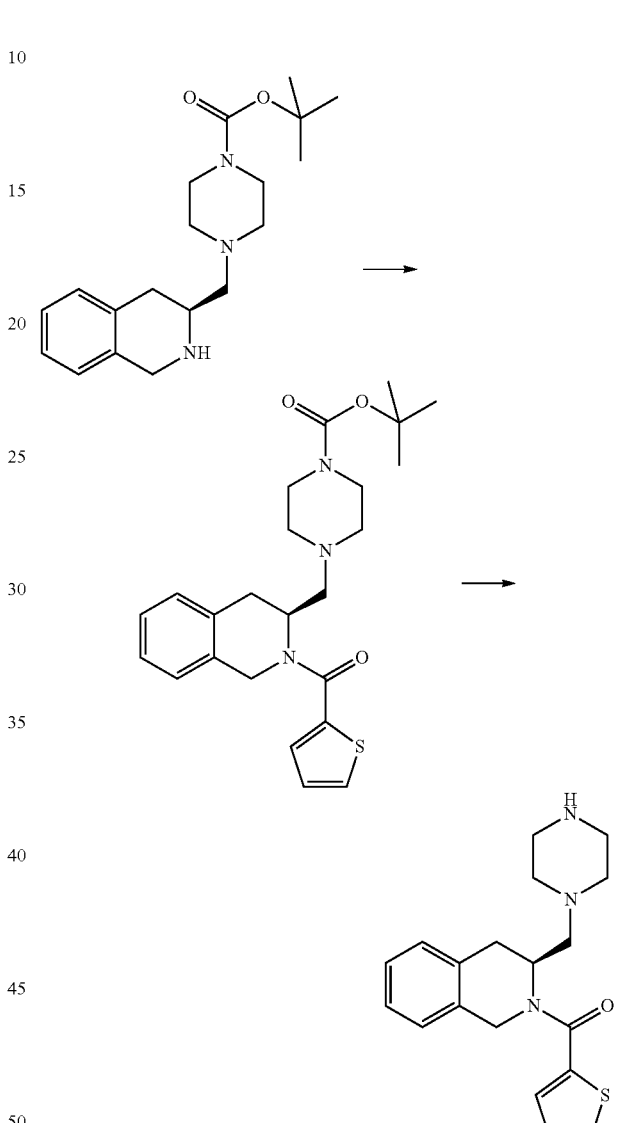

Step 1: Synthesis of tert-Butyl 4-{[(3S)-2-(thiophen-2-ylcarbonyl)-1,2,3,4-tetrahydroisoquinolin-3-yl]methyl}piperazine-1-carboxylate Thiophene-2-carbonyl chloride (0.1 g, 0.68 mmol) was added to a stirred solution of tert-butyl 4-[(3S)-1,2,3,4-tetrahydroisoquinolin-3-ylmethyl]piperazine-1-carboxylate (See preparation 16) (0.2 g, 0.6 mmol) and Et₃N (0.1 g, 1 mmol) in DCM (10 mL) maintaining internal temperature below 10° C. The mixture was allowed to warm to ambient temperature and stirred overnight. A saturated aqueous solution of NaHCO₃ (10 mL) was added to the reaction mixture portion wise. The organic layer was separated, and the aqueous layer was extracted with DCM (3×5 mL). The combined organic layers were washed with brine, dried over anhydrous MgSO₄, and concentrated under reduced pressure. The residue was treated with ether, the formed precipitate was filtered off, washed with ether, and dried to afford 0.14 g (53%) of the title compound.

Step 2: Synthesis of (3S)-3-(piperazin-1-ylmethyl)-2-(thiophen-2-ylcarbonyl)-1,2,3,4-tetrahydroisoquinoline A 3M solution of HCl in dioxane (1.76 mL, 3.2 mmol) was added to a stirred solution of the compound prepared at Step 1 (0.14 g, 0.32 mmol) in DCM (2 mL). The resultant mixture was stirred overnight at ambient temperature and then diluted with ether (10 ml). The formed precipitate was filtered off, washed with ether, dried, and dissolved in water. The obtained solution was basified with 50% NaOH to pH 12 and extracted twice with DCM. Combined organic layers were dried over Na₂SO₄ and evaporated under reduced pressure to provide 86 mg (79%) of the title compound that was used for the next step without additional purification.

Preparation 19: (3S)-2-(2-methylpropanoyl)-3-(piperazin-1-ylmethyl)-1,2,3,4-tetrahydroisoquinoline

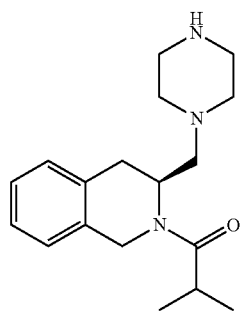 [SMILES: CC(C)C(=O)N1Cc2ccccc2C[C@H]1CN1CCNCC1]

The procedure was as in the process of Preparation 18 using 2-methylpropanoyl chloride instead of thiophene-2-carbonyl chloride.

Preparation 20: (S)-cyclopropyl(3-(piperazin-1-ylmethyl)-3,4-dihydroisoquinolin-2(1H)-yl)methanone

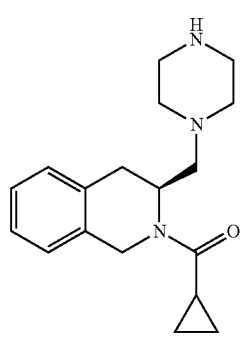 [SMILES: O=C(C1CC1)N1Cc2ccccc2C[C@H]1CN1CCNCC1]

The procedure was as in the process of Preparation 18 using cyclopropanecarbonyl chloride instead of thiophene-2-carbonyl chloride.

Preparation 21: 2-(1H-pyrrolo[2,3-b]pyridin-5-yloxy)-4-(4-{[(3S)-2-(thiophen-2-ylcarbonyl)-1,2,3,4-tetrahydroisoquinolin-3-yl]methyl}piperazin-1-yl)benzoic acid

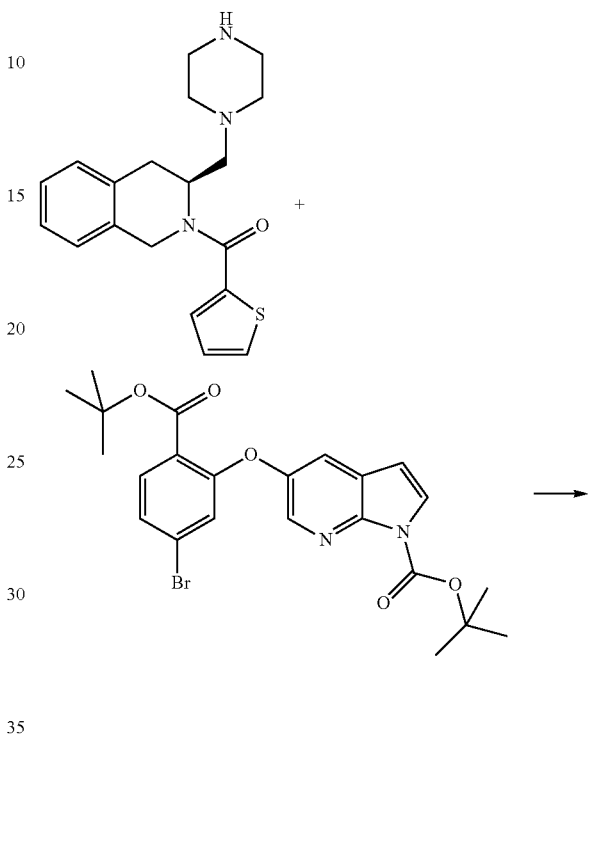

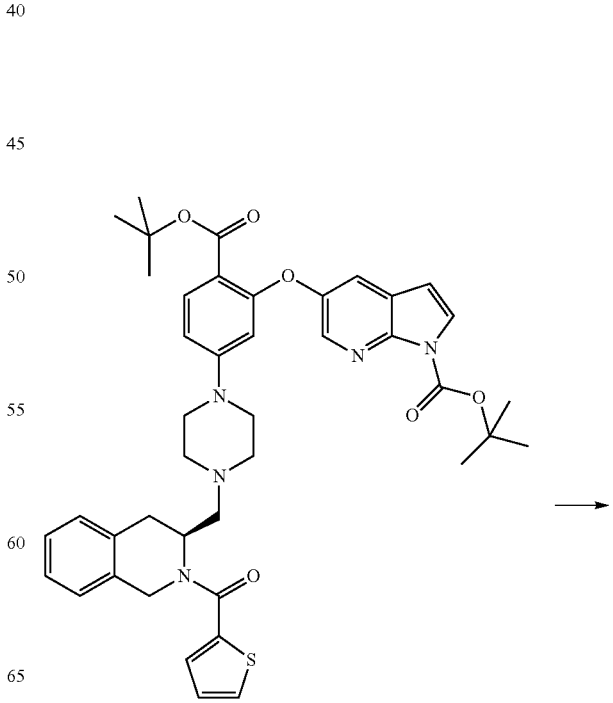

-continued

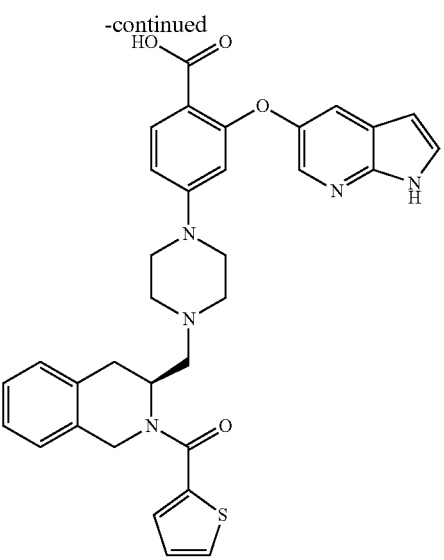

Step 1: Synthesis of tert-butyl 5-[2-(tert-butoxycarbonyl)-5-(4-{[(3S)-2-(thiophen-2-ylcarbonyl)-1,2,3,4-tetrahydroisoquinolin-3-yl]methyl}piperazin-1-yl)phenoxy]-1H-pyrrolo[2,3-b]pyridine-1-carboxylate A mixture of tert-butyl 5-[5-bromo-2-(ethoxycarbonyl)phenoxy]-1H-indole-1-carboxylate (See Preparation 2) (0.123 g, 0.25 mmol), (3S)-3-(piperazin-1-ylmethyl)-2-(2-thienylcarbonyl)-1,2,3,4-tetrahydroisoquinoline (See Preparation 18) (0.086 g, 0.25 mmol), Pd(OCOCH$_3$)$_2$ (5.6 mg, 0.025 mmol), 2,2'-bis(diphenylphosphino)-1,1'-binaphthalene (15 mg, 0.025 mmol), Cs$_2$CO$_3$ (105 mg, 0.32 mmol) and toluene (2 mL) was heated under Argon at 80° C. for 20 h, cooled to ambient temperature, and concentrated under reduced pressure. The residue was dissolved in DCM (30 mL), and the obtained solution was filtered through a Celite pad. The filtrate was washed with water, and then with brine. The organic layer was dried over Na$_2$SO$_4$ and concentrated under reduced pressure. The residue was subjected to silica flash chromatography eluting with a mixture of EtOAc (5→50%) and DCM to afford 0.1 g (53%) of the title compound.

Step 2: Synthesis of 2-(1H-pyrrolo[2,3-b]pyridin-5-yloxy)-4-(4-{[(3S)-2-(thiophen-2-ylcarbonyl)-1,2,3,4-tetrahydroisoquinolin-3-yl]methyl}piperazin-1-yl)benzoic acid CF$_3$COOH (0.24 g, 2 mmol) was added to a stirred solution of tert-butyl 5-[2-(tert-butoxycarbonyl)-5-(4-{[(3S)-2-(thiophen-2-ylcarbonyl)-1,2,3,4-tetrahydroisoquinolin-3-yl]methyl}piperazin-1-yl)phenoxy]-1H-pyrrolo[2,3-b]pyridine-1-carboxylate (0.1 g, (0.13 mmol) in DCM (1 mL). The mixture was stirred at room temperature for 12 h, then volatiles were removed under reduced pressure. The residue was treated with ether, the formed precipitate was filtered off, washed with ether, and dried to afford 0.85 mg (92%) of the title compound as trifluoro acetic salt that was used for the next step without further purification.

Preparation 22: 4-(4-{[(3S)-2-(2-methylpropanoyl)-1,2,3,4-tetrahydroisoquinolin-3-yl]methyl}piperazin-1-yl)-2-(1H-pyrrolo[2,3-b]pyridin-5-yloxy)benzoic acid

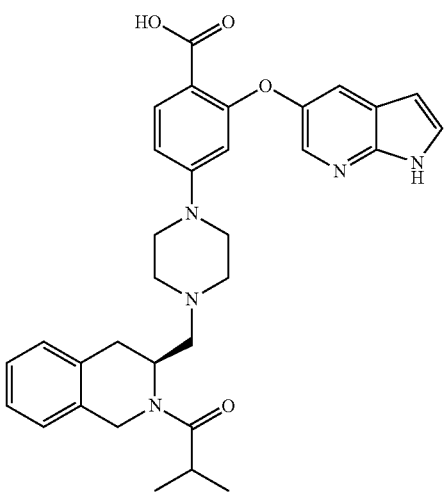 [SMILES: CC(C)C(=O)N1Cc2ccccc2C[C@H]1CN1CCN(c2ccc(C(=O)O)c(Oc3cnc4[nH]ccc4c3)c2)CC1]

The procedure was as in the process of Preparation 21 using (3S)-2-(2-methylpropanoyl)-3-(piperazin-1-ylmethyl)-1,2,3,4-tetrahydroisoquinoline (See Preparation 19) instead of (3S)-3-(piperazin-1-ylmethyl)-2-(2-thienylcarbonyl)-1,2,3,4-tetrahydroisoquinoline.

Preparation 23: 4-(4-{[(3S)-2-(cyclopropylcarbonyl)-1,2,3,4-tetrahydroisoquinolin-3-yl]methyl}piperazin-1-yl)-2-(1H-pyrrolo[2,3-b]pyridin-5-yloxy)benzoic acid

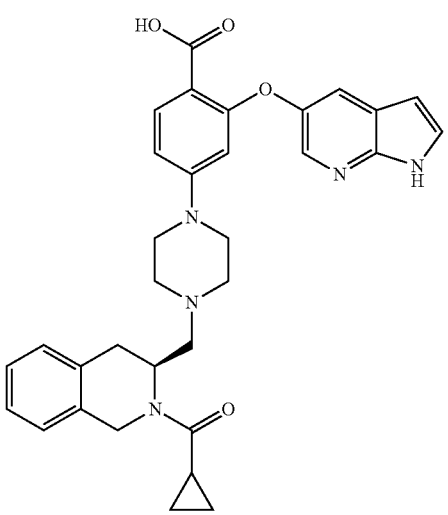 [SMILES: O=C(O)c1ccc(N2CCN(C[C@@H]3Cc4ccccc4CN3C(=O)C3CC3)CC2)cc1Oc1cnc2[nH]ccc2c1]

The procedure was as in the process of Preparation 21 using (3S)-2-(2-methylpropanoyl)-3-(piperazin-1-ylmethyl)-1,2,3,4-tetrahydroisoquinoline (See Preparation 20) instead of (3S)-3-(piperazin-1-ylmethyl)-2-(2-thienylcarbonyl)-1,2,3,4-tetrahydroisoquinoline.

Preparation 24: (3R)-3-(piperazin-1-ylmethyl)-2-(thiophen-2-ylcarbonyl)-1,2,3,4-tetrahydroisoquinoline

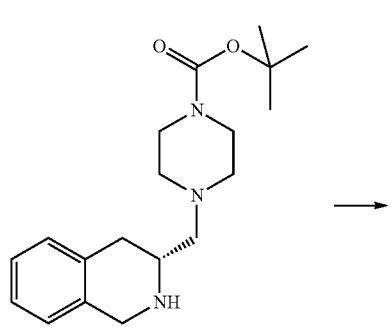

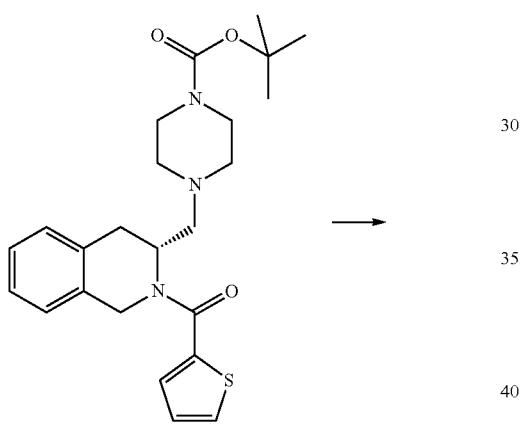

The procedure was as in the process of Preparation 18 using tert-Butyl 4-[(3R)-1,2,3,4-tetrahydroisoquinolin-3-ylmethyl]piperazine-1-carboxylate (See Preparation 17) instead of tert-butyl 4-[(3S)-1,2,3,4-tetrahydroisoquinolin-3-ylmethyl]piperazine-1-carboxylate.

Preparation 25: (3R)-2-(2-methylpropanoyl)-3-(piperazin-1-ylmethyl)-1,2,3,4-tetrahydroisoquinoline

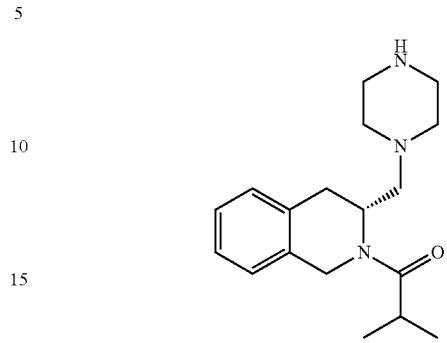

The procedure was as in the process of Preparation 24 using 2-methylpropanoyl chloride instead of thiophene-2-carbonyl chloride.

Preparation 26: ((3R)-2-(cyclopropylcarbonyl)-3-(piperazin-1-ylmethyl)-1,2,3,4-tetrahydroisoquinoline

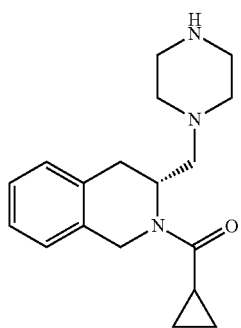 [SMILES: O=C(C1CC1)N1Cc2ccccc2C[C@@H]1CN1CCNCC1]

The procedure was as in the process of Preparation 24 using cyclopropanecarbonyl chloride instead of thiophene-2-carbonyl chloride.

Preparation 27: 2-(1H-pyrrolo[2,3-b]pyridin-5-yloxy)-4-(4-{[(3R)-2-(thiophen-2-ylcarbonyl)-1,2,3,4-tetrahydroisoquinolin-3-yl]methyl}piperazin-1-yl)benzoic acid

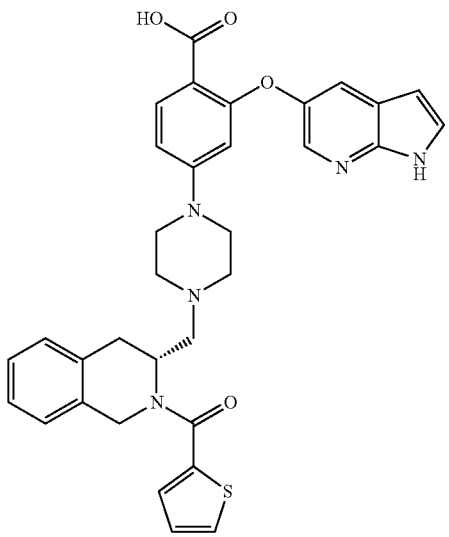 [SMILES: O=C(O)c1ccc(N2CCN(C[C@H]3Cc4ccccc4CN3C(=O)c3cccs3)CC2)cc1Oc1cnc2[nH]ccc2c1]

The procedure was as in the process of Preparation 21 using (3R)-3-(piperazin-1-ylmethyl)-2-(thiophen-2-ylcarbonyl)-1,2,3,4-tetrahydroisoquinoline (See Preparation 25) instead of (3S)-3-(piperazin-1-ylmethyl)-2-(thiophen-2-ylcarbonyl)-1,2,3,4-tetrahydroisoquinoline.

Preparation 28: 4-(4-{[(3R)-2-(2-methylpropanoyl)-1,2,3,4-tetrahydroisoquinolin-3-yl]methyl}piperazin-1-yl)-2-(1H-pyrrolo[2,3-b]pyridin-5-yloxy)benzoic acid

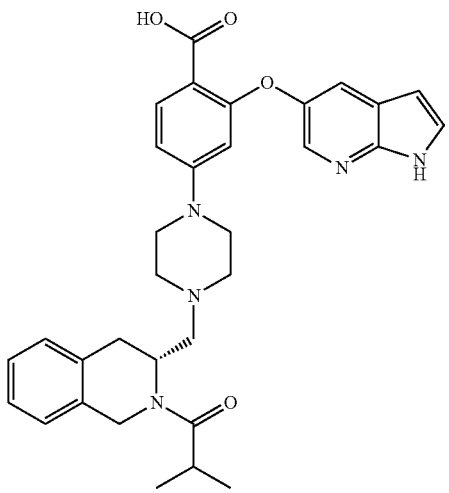 [SMILES: CC(C)C(=O)N1Cc2ccccc2C[C@@H]1CN1CCN(c2ccc(C(=O)O)c(Oc3cnc4[nH]ccc4c3)c2)CC1]

The procedure was as in the process of Preparation 27 using (3R)-2-(2-methylpropanoyl)-3-(piperazin-1-ylmethyl)-1,2,3,4-tetrahydroisoquinoline (See Preparation 25) instead of (3R)-3-(piperazin-1-ylmethyl)-2-(thiophen-2-ylcarbonyl)-1,2,3,4-tetrahydroisoquinoline.

Preparation 29: 4-(4-{[(3R)-2-(cyclopropylcarbonyl)-1,2,3,4-tetrahydroisoquinolin-3-yl]methyl}piperazin-1-yl)-2-(1H-pyrrolo[2,3-b]pyridin-5-yloxy)benzoic acid

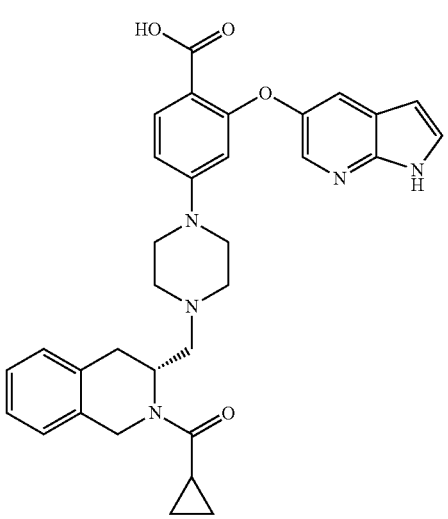 [SMILES: O=C(O)c1ccc(N2CCN(C[C@H]3Cc4ccccc4CN3C(=O)C3CC3)CC2)cc1Oc1cnc2[nH]ccc2c1]

The procedure was as in the process of Preparation 27 using ((3R)-2-(cyclopropylcarbonyl)-3-(piperazin-1-ylmethyl)-1,2,3,4-tetrahydroisoquinoline (See Preparation 26) instead of (3R)-3-(piperazin-1-ylmethyl)-2-(thiophen-2-ylcarbonyl)-1,2,3,4-tetrahydroisoquinoline.

Example 1: 4-[4-[[1-(4-chlorophenyl)-3-oxo-2-azaspiro[3.4]octan-2-yl]methyl]-1-piperidyl]-2-(1H-indol-5-yloxy)-N-[3-nitro-4-(tetrahydropyran-4-ylmethylamino)phenyl]sulfonyl-benzamide (Compound 10)

-continued

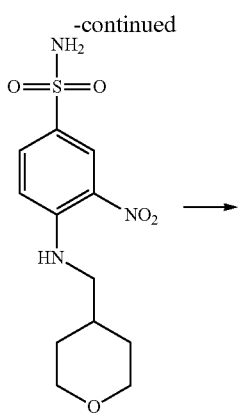

Example 2: 4-[4-[[1-(4-chlorophenyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide (Compound 1)

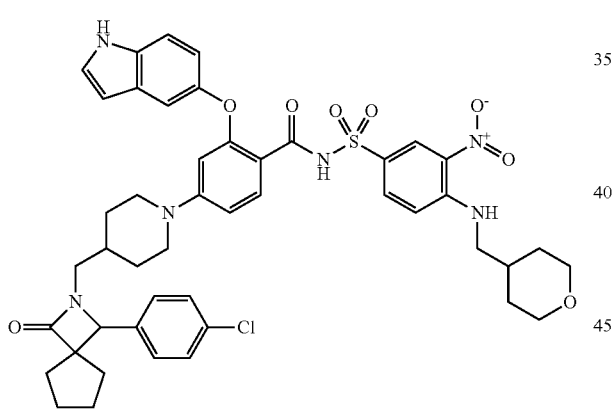

A mixture of 4-(4-{[1-(4-chlorophenyl)-3-oxo-2-azaspiro[3.4]oct-2-yl]methyl}piperidin-1-yl)-2-(1H-indol-5-yloxy)benzoic acid (See Preparation 8) (0.02 g, 0.034 mmol), 3-nitro-4-[(tetrahydro-2H-pyran-4-ylmethyl)amino]benzenesulfonamide (0.01 g, 0.034 mmol), EDCI (0.007 g, 0.037 mmol), DMAP (0.004 g, 0.037 mmol) and DCM (1 mL) was stirred at ambient temperature for 20 h and partitioned between water (2 mL) and DCM (2 mL). The organic layer was separated, dried over Na$_2$SO$_4$, and concentrated under reduced pressure. The residue was subjected to HPLC to afford 0.012 g (40%) of the title compound.

A mixture of 4-(4-{[1-(4-chlorophenyl)-3-oxo-2-azaspiro[3.4]oct-2-yl]methyl}piperidin-1-yl)-2-(1H-pyrrolo[2,3-b]pyridin-5-yloxy)benzoic acid (See Preparation 9) (0.124 g, 0.21 mmol), 3-nitro-4-[(tetrahydro-2H-pyran-4-ylmethyl)amino]benzenesulfonamide (0.067 g, 0.21 mmol), EDCI (0.122 g, 0.63 mmol), DMAP (0.052 g, 0.42 mmol), Et$_3$N (0.3 ml, 2.1 mmol), and DCM (15 mL) was stirred at ambient temperature for 12 h, washed with water, the organic layer was dried over Na$_2$SO$_4$, and concentrated under reduced pressure. The residue was subjected to HPLC purification to provide 0.023 g (12%) of the title compound.

Example 3: N-[3-nitro-4-(tetrahydropyran-4-ylmethylamino)phenyl]sulfonyl-4-[4-[(3-oxo-1-phenyl-2-azaspiro[3.4]octan-2-yl)methyl]-1-piperidyl]-2-(1H-pyrrolo[2,3-b]pyridin-5-yloxy)benzamide (Compound 2)

Example 4: 4-[4-[[1-(4-chloro-2-methyl-phenyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide (Compound 3)

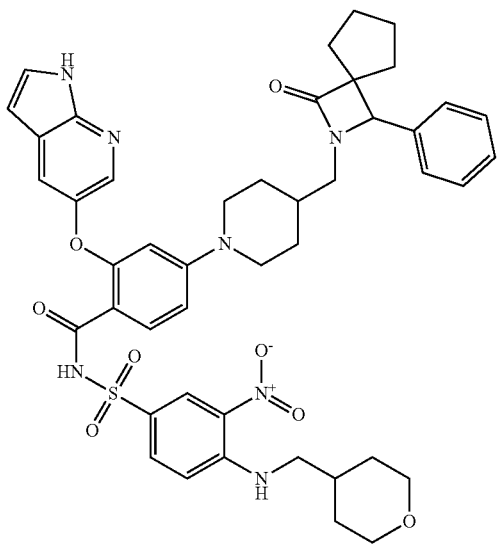 [SMILES: O=C(NS(=O)(=O)c1ccc(NCC2CCOCC2)c([N+](=O)[O-])c1)c1ccc(N2CCC(CN3C(=O)C4(CCCC4)C3c3ccccc3)CC2)cc1Oc1cnc2[nH]ccc2c1]

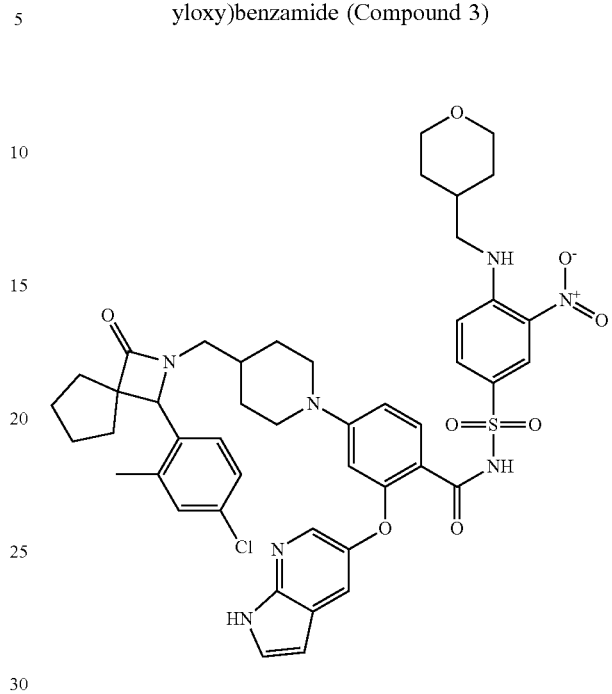

The procedure was as in the process of Example 2 using 4-(4-{[1-(4-chloro-2-methylphenyl)-3-oxo-2-azaspiro[3.4]oct-2-yl]methyl}piperidin-1-yl)-2-(1H-pyrrolo[2,3-b]pyridin-5-yloxy)benzoic acid (See Preparation 11) instead of 4-(4-{[1-(4-chlorophenyl)-3-oxo-2-azaspiro[3.4]oct-2-yl]methyl}piperidin-1-yl)-2-(1H-pyrrolo[2,3-b]pyridin-5-yloxy)benzoic acid.

The procedure was as in the process of Example 2 using 4-{4-[(1-oxo-3-phenyl-2-azaspiro[3.4]oct-2-yl)methyl]piperidin-1-yl}-2-(1H-pyrrolo[2,3-b]pyridin-5-yloxy)benzoic acid (See Preparation 10) instead of 4-(4-{[1-(4-chlorophenyl)-3-oxo-2-azaspiro[3.4]oct-2-yl]methyl}piperidin-1-yl)-2-(1H-pyrrolo[2,3-b]pyridin-5-yloxy)benzoic acid.

Example 5: 4-[4-[[1-(5-chloro-3-pyridyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide (Compound 9)

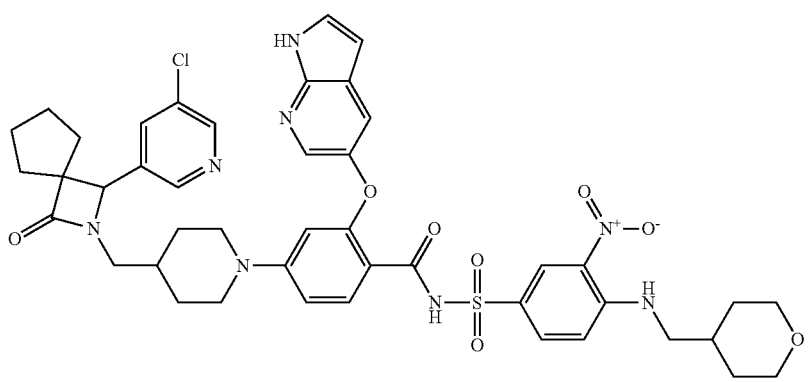 [SMILES: O=C(NS(=O)(=O)c1ccc(NCC2CCOCC2)c([N+](=O)[O-])c1)c1ccc(N2CCC(CN3C(=O)C4(CCCC4)C3c3cncc(Cl)c3)CC2)cc1Oc1cnc2[nH]ccc2c1]

The procedure was as in the process of Example 2 using 4-(4-{[1-(5-chloropyridin-3-yl)-3-oxo-2-azaspiro[3.4]oct-2-yl]methyl}piperidin-1-yl)-2-(1H-pyrrolo[2,3-b]pyridin-5-yloxy)benzoic acid (See Preparation 12) instead of 4-(4-{[1-(4-chlorophenyl)-3-oxo-2-azaspiro[3.4]oct-2-yl]methyl}piperidin-1-yl)-2-(1H-pyrrolo[2,3-b]pyridin-5-yloxy)benzoic acid.

Example 6: N-(4-anilino-3-nitro-phenyl)sulfonyl-4-(4-benzhydrylpiperazin-1-yl)-2-(1H-indol-5-yloxy)benzamide (Compound 26)

Example 7: N-[3-nitro-4-(tetrahydropyran-4-ylmethylamino)phenyl]sulfonyl-4-[4-[(3-phenyl-2-azaspiro[3.4]octan-2-yl)methyl]-1-piperidyl]-2-(1H-pyrrolo[2,3-b]pyridin-5-yloxy)benzamide (Compound 27)

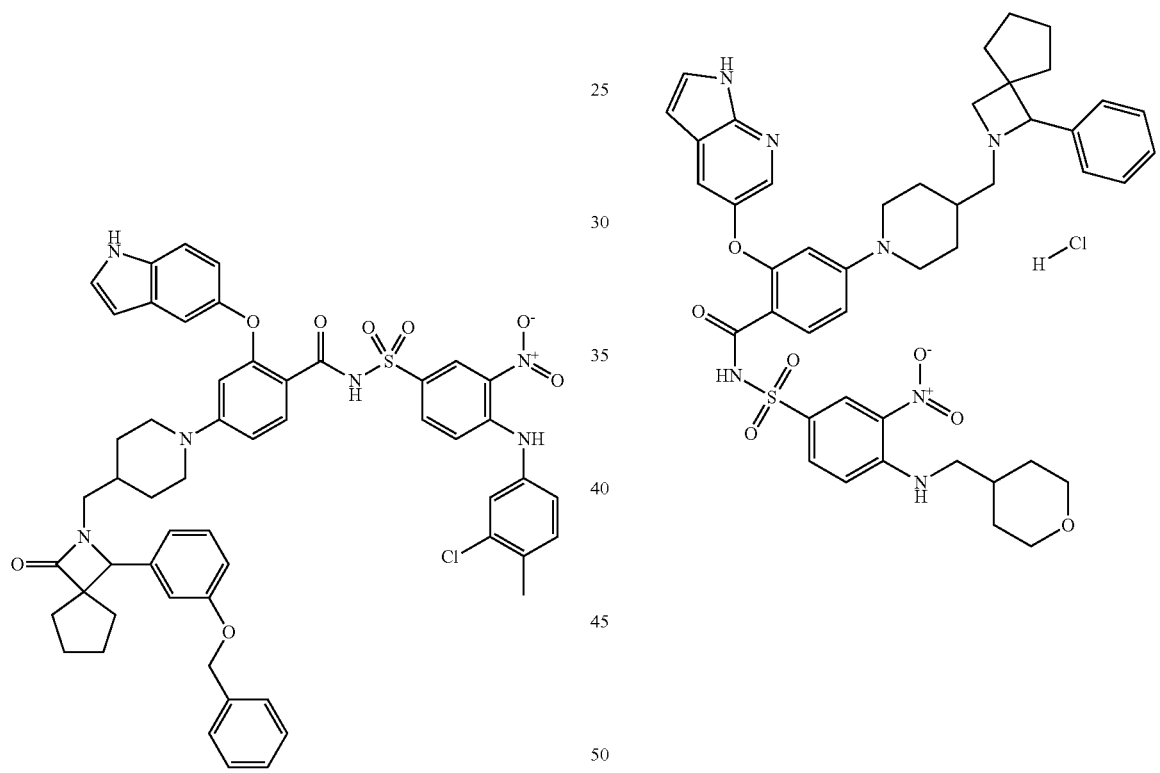

The procedure was as in the process of Example 2 using 4-[4-({1-[3-(benzyloxy)phenyl]-3-oxo-2-azaspiro[3.4]oct-2-yl}methyl)piperidin-1-yl]-2-(1H-indol-5-yloxy)benzoic acid (See Preparation 13) instead of 4-(4-{[1-(4-chlorophenyl)-3-oxo-2-azaspiro[3.4]oct-2-yl]methyl}piperidin-1-yl)-2-(1H-pyrrolo[2,3-b]pyridin-5-yloxy)benzoic acid and 4-(3-chloro-4-methylphenylamino)-3-nitrobenzenesulfonamide (See Preparation 15) instead of 3-nitro-4-[(tetrahydro-2H-pyran-4-ylmethyl)amino]benzenesulfonamide.

The procedure was as in the process of Example 2 using 2-(1H-pyrrolo[2,3-b]pyridin-5-yloxy)-4-(4-((1-phenyl-2-azaspiro[3.4]octan-2-yl)methyl)piperidin-1-yl)benzoic acid (See Preparation 14) instead of 4-(4-{[1-(4-chlorophenyl)-3-oxo-2-azaspiro[3.4]oct-2-yl]methyl}piperidin-1-yl)-2-(1H-pyrrolo[2,3-b]pyridin-5-yloxy)benzoic acid. Thus, obtained free base was converted to hydrochloride by treatment of its solution in acetonitrile with an excess of 6M solution of HCl in dioxane followed by removal of volatiles under reduced pressure and washing of the residue with $Et_{2O}$.

Example 8. N-[3-nitro-4-(tetrahydropyran-4-ylmethylamino)phenyl]sulfonyl-2-(1H-pyrrolo[2,3-b]pyridin-5-yloxy)-4-[4-[[2-(thiophene-2-carbonyl)-3,4-dihydro-1H-isoquinolin-3-yl]methyl]piperazin-1-yl]benzamide (Compound 6)

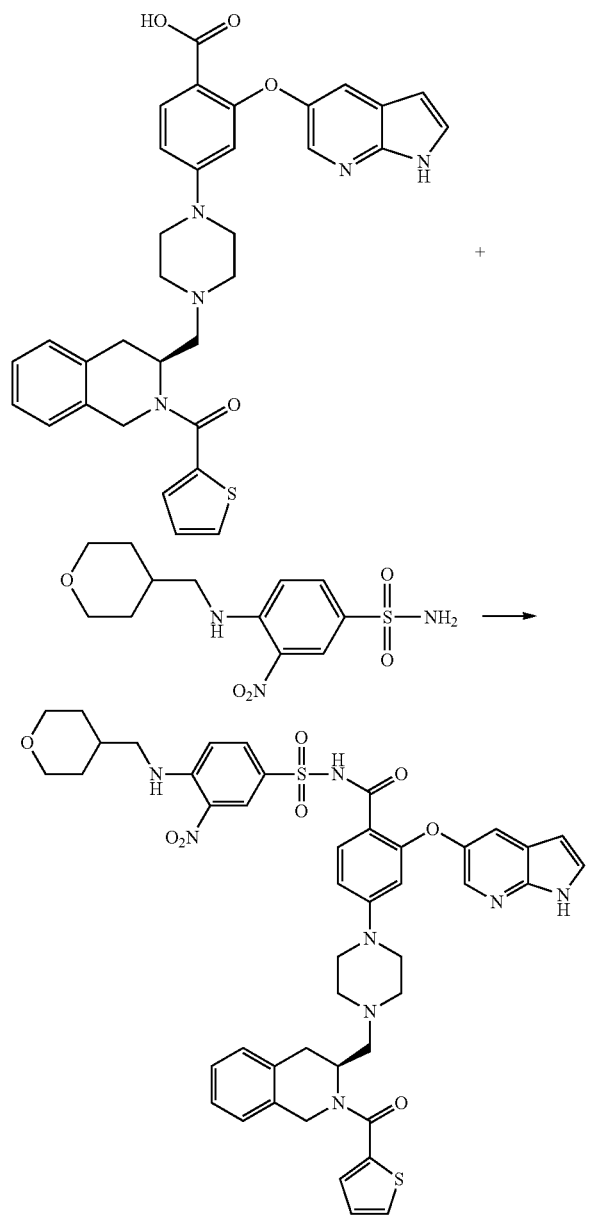

A mixture of 2-(1H-pyrrolo[2,3-b]pyridin-5-yloxy)-4-(4-{[(3S)-2-(thiophen-2-ylcarbonyl)-1,2,3,4-tetrahydroisoquinolin-3-yl]methyl}piperazin-1-yl)benzoic acid (See Preparation 21) (0.85 g, 0.12 mmol), 3-nitro-4-[(tetrahydro-2H-pyran-4-ylmethyl)amino]benzenesulfonamide (45 mg, 0.0143 mmol), EDCI (35 mg, 0.18 mmol), DMAP (0.29 g, 0.24 mmol), Et$_3$N (0.24 g, 0.24 mmol), and DCM (10 mL) was stirred at ambient temperature for 20 h and then partitioned between water (2 mL) and DCM (4 mL). The organic layer was separated, dried over Na$_2$SO$_4$, and concentrated under reduced pressure. The residue was purified by silica flash-chromatography eluting with a mixture of methanol (1→5%) and DCM to afford 40 mg (37%) of the title compound.

Example 9. 4-[4-[[2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide (Compound 8)

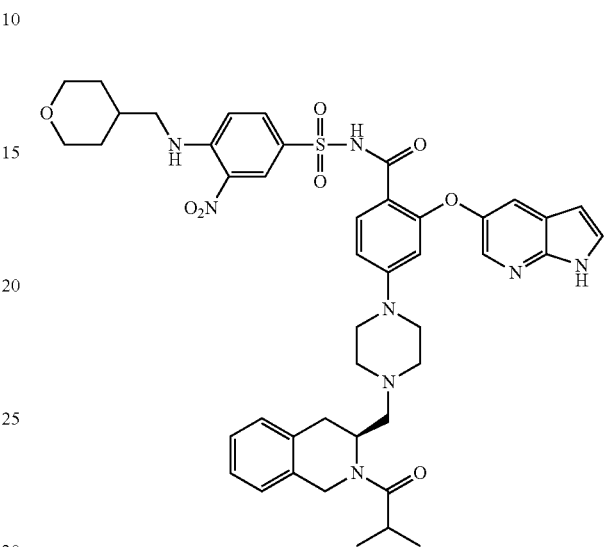

The procedure was as in the process of Example 8 using 4-(4-{[(3S)-2-(2-methylpropanoyl)-1,2,3,4-tetrahydroisoquinolin-3-yl]methyl}piperazin-1-yl)-2-(1H-pyrrolo[2,3-b]pyridin-5-yloxy)benzoic acid (See Preparation 22) instead of 2-(1H-pyrrolo[2,3-b]pyridin-5-yloxy)-4-(4-{[(3S)-2-(thiophen-2-ylcarbonyl)-1,2,3,4-tetrahydroisoquinolin-3-yl]methyl}piperazin-1-yl)benzoic acid.

Example 10. 4-[4-[[(3S)-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide (Compound 5)

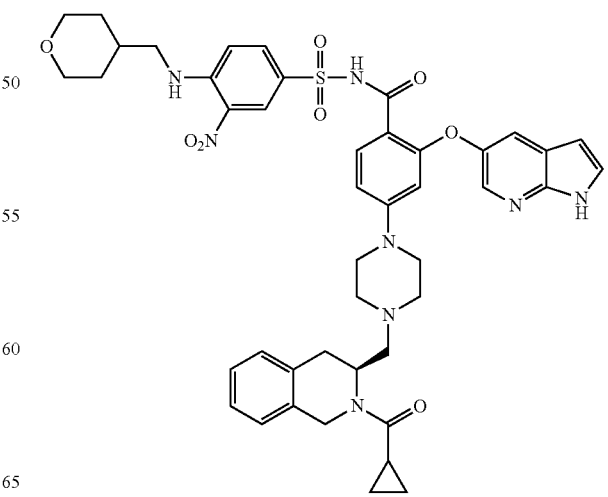

The procedure was as in the process of Example 8 using 4-(4-{[(3S)-2-(cyclopropylcarbonyl)-1,2,3,4-tetrahydroisoquinolin-3-yl]methyl}piperazin-1-yl)-2-(1H-pyrrolo[2,3-b]pyridin-5-yloxy)benzoic acid (See Preparation 23) instead of 2-(1H-pyrrolo[2,3-b]pyridin-5-yloxy)-4-(4-{[(3S)-2-(thiophen-2-ylcarbonyl)-1,2,3,4-tetrahydroisoquinolin-3-yl]methyl}piperazin-1-yl)benzoic acid.

Example 11. N-[3-nitro-4-(tetrahydropyran-4-ylmethylamino)phenyl]sulfonyl-2-(1H-pyrrolo[2,3-b]pyridin-5-yloxy)-4-[[(3R)-2-(thiophene-2-carbonyl)-3,4-dihydro-1H-isoquinolin-3-yl]methyl]piperazin-1-yl]benzamide (Compound 34)

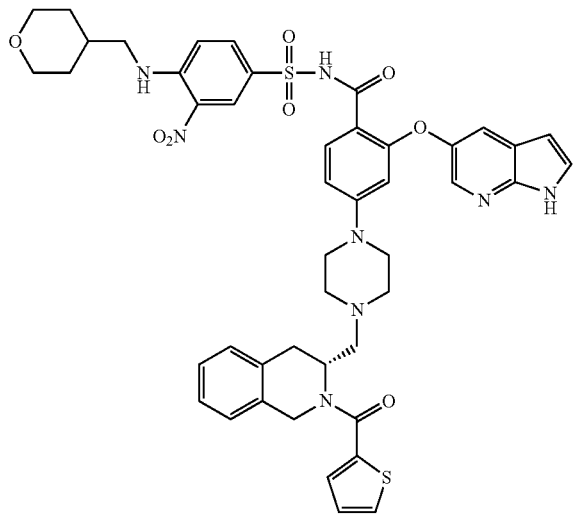 [SMILES: O=C(NS(=O)(=O)c1ccc(NCC2CCOCC2)c([N+](=O)[O-])c1)c1ccc(N2CCN(C[C@H]3Cc4ccccc4CN3C(=O)c3cccs3)CC2)cc1Oc1cnc2[nH]ccc2c1]

The procedure was as in the process of Example 8 using 2-(1H-pyrrolo[2,3-b]pyridin-5-yloxy)-4-(4-{[(3R)-2-(thiophen-2-ylcarbonyl)-1,2,3,4-tetrahydroisoquinolin-3-yl]methyl}piperazin-1-yl)benzoic acid (See Preparation 27) instead of 2-(1H-pyrrolo[2,3-b]pyridin-5-yloxy)-4-(4-{[(3S)-2-(thiophen-2-ylcarbonyl)-1,2,3,4-tetrahydroisoquinolin-3-yl]methyl}piperazin-1-yl)benzoic acid.

Example 12. 4-[4-[[(3R)-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide (Compound 33)

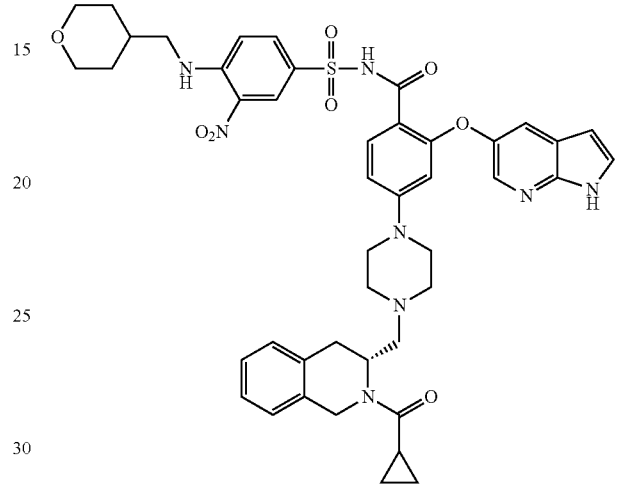

The procedure was as in the process of Example 8 using 4-(4-{[(3R)-2-(cyclopropylcarbonyl)-1,2,3,4-tetrahydroisoquinolin-3-yl]methyl}piperazin-1-yl)-2-(1H-pyrrolo[2,3-b]pyridin-5-yloxy)benzoic acid (See Preparation 29) instead of 2-(1H-pyrrolo[2,3-b]pyridin-5-yloxy)-4-(4-{[(3S)-2-(thiophen-2-ylcarbonyl)-1,2,3,4-tetrahydroisoquinolin-3-yl]methyl}piperazin-1-yl)benzoic acid.

TABLE 1

Analytical data.

| Cmpd No. | Example | Name | MW | RT, min | MS (ESI) [M + H]+ calcltd | MS (ESI) [M + H]+ exp | Purity, % 220 nm | Purity, % 254 nm |
|---|---|---|---|---|---|---|---|---|
| 10 | 1 | 4-(4-{[1-(4-chlorophenyl)-3-oxo-2-azaspiro[3.4]oct-2-yl]methyl}piperidin-1-yl)-2-(1H-indol-5-yloxy)-N-({3-nitro-4-[(tetrahydro-2H-pyran-4-ylmethyl)amino]phenyl}sulfonyl)benzamide | 881.5 | 9.19 | 882 | 882 | 94 | N/A |
| 1 | 2 | 4-(4-{[1-(4-chlorophenyl)-3-oxo-2-azaspiro[3.4]oct-2-yl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 882.4 | 8.89 | 883 | 883 | 100 | 97 |
| 2 | 3 | N-({3-nitro-4-[(tetrahydro-2H-pyran-4-ylmethyl)amino]phenyl}sulfonyl)-4-{4-[(1-oxo- | 848.0 | 8.13 | 848 | 848 | 100 | N/A |

TABLE 1-continued

Analytical data.

| Cmpd No. | Example | Name | MW | RT, min | MS (ESI) [M + H]+ calcltd | MS (ESI) [M + H]+ exp | Purity, % 220 nm | Purity, % 254 nm |
|---|---|---|---|---|---|---|---|---|
| 3 | 4 | 3-phenyl-2-azaspiro[3.4]oct-2-yl)methyl]piperidin-1-yl}-2-(1H-pyrrolo[2,3-b]pyridin-5-yloxy)benzamide 4-(4-{[1-(4-chloro-2-methylphenyl)-3-oxo-2-azaspiro[3.4]oct-2-yl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 896.5 | 9.19 | 896 | 896 | 98 | 98 |
| 9 | 5 | 4-(4-{[1-(5-chloropyridin-3-yl)-3-oxo-2-azaspiro[3.4]oct-2-yl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 883.4 | 7.92 | 883 | 883 | 97 | 96 |
| 32 | 6 | 4-[4-({1-[3-(benzyloxy)phenyl]-3-oxo-2-azaspiro[3.4]oct-2-yl}methyl)piperidin-1-yl]-N-({4-[(3-chloro-4-methylphenyl)amino]-3-nitrophenyl}sulfonyl)-2-(1H-indol-5-yloxy)benzamide | 979.6 | 8.81 | 979 | 979 | 95 | 99 |
| 27 | 7 | N-({3-nitro-4-[(tetrahydro-2H-pyran-4-ylmethyl)amino]phenyl}sulfonyl)-4-{4-[(1-phenyl-2-azasprio[3.4]oct-2-yl)methyl]piperidin-1-yl}-2-(1H-pyrrolo[2,3-b]pyridin-5-yloxy)benzamide hydrochloride | 834.0 | 6.83 | 834 | 834 | 100 | 95 |
| 6 | 8 | N-({3-nitro-4-[(tetrahydro-2H-pyran-4-ylmethyl)amino]phenyl}sulfonyl)-2-(1H-pyrrolo[2,3-b]pyridin-5-yloxy)-4-(4-{[(3S)-2-(thiophen-2-ylcarbonyl)-1,2,3,4-tetrahydroisoquinolin-3-yl]methyl}piperazin-1-yl)benzamide | 891.0 | 5.92 | 891 | 891 | 97 | 98 |
| 8 | 9 | 4-(4-{[(3S)-2-(2-methylpropanoyl)-1,2,3,4-tetrahydroisoquinolin-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 851.0 | 5.58 | 851 | 851 | 97 | 99 |

TABLE 1-continued

Analytical data.

| Cmpd No. | Example | Name | MW | RT, min | MS (ESI) [M + H]+ calcltd | MS (ESI) [M + H]+ exp | Purity, % 220 nm | Purity, % 254 nm |
|---|---|---|---|---|---|---|---|---|
| 5 | 10 | 4-(4-{[(3S)-2-(cyclopropylcarbonyl)-1,2,3,4-tetrahydroisoquinolin-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 849.0 | 5.73 | 849 | 849 | 99 | 99 |
| 34 | 11 | N-({3-nitro-4-[(tetrahydro-2H-pyran-4-ylmethyl)amino]phenyl}sulfonyl)-2-(1H-pyrrolo[2,3-b]pyridin-5-yloxy)-4-(4-{[(3R)-2-(thiophen-2-ylcarbonyl)-1,2,3,4-tetrahydroisoquinolin-3-yl]methyl}piperazin-1-yl)benzamide | 891.0 | 5.90 | 891 | 891 | 99 | 99 |
| 33 | 12 | 4-(4-{[(3R)-2-(cyclopropylcarbonyl)-1,2,3,4-tetrahydroisoquinolin-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 849.0 | 5.72 | 849 | 849 | 96 | 97 |

Using procedures describe above directly or with slightly modification or procedures know in the Art were prepared further compounds, presented in the Table 2 below.

TABLE 2

Further Compounds of the Disclosure

| Cmpd No. | Structure | ¹H-NMR |
|---|---|---|
| 16 | 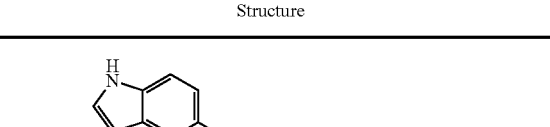 | ¹H NMR (400 MHz, DMSO-$d_6$), δ: 11.24 (s, 1H), 11.15 (s, 1H), 8.62 (t, J = 5.0 Hz, 1H), 8.58 (d, J = 2.3 Hz, 1H), 7.78 (d, J = 9.4 Hz, 1H), 7.53 (d, J = 8.8 Hz, 1H), 7.39 (m, 6H), 7.11 (m, 6H), 6.86 (dd, J = 8.9, 2.1 Hz, 1H), 6.67 (d, J = 9.0 Hz, 1H), 6.37 (s, 1H), 6.18 (s, 1H), 4.35 (s, 1H), 3.85 (d, J = 11.3 Hz, 2H), 3.27 (m, 4H), 3.11 (s, 4H), 2.30 (s, 4H), 1.88 (s, 1H), 1.61 (d, J = 13.1 Hz, 2H), 1.27 (m, 2H) |

TABLE 2-continued

Further Compounds of the Disclosure

| Cmpd No. | Structure | ¹H-NMR |
|---|---|---|
| 32 | 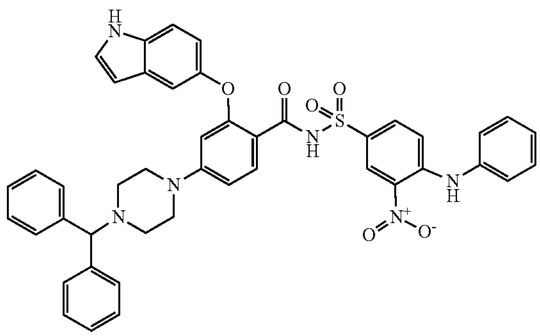 [SMILES: O=C(NS(=O)(=O)c1ccc(Nc2ccccc2)c([N+](=O)[O-])c1)c1ccc(N2CCN(C(c3ccccc3)c3ccccc3)CC2)cc1Oc1ccc2[nH]ccc2c1] | ¹H NMR (400 MHz, DMSO-$d_6$), δ: 11.30 (s, 1H), 11.11 (s, 1H), 9.90 (s, 1H), 8.63 (d, J = 2.3 Hz, 1H), 7.74 (dd, J = 9.1, 2.1 Hz, 1H), 7.50 (m, 3H), 7.40 (d, J = 7.7 Hz, 4H), 7.35 (m, 3H), 7.30 (t, J = 2.8 Hz, 1H), 7.26 (t, J = 7.5 Hz, 4H), 7.14 (m, 3H), 7.00 (d, J = 9.2 Hz, 1H), 6.85 (dd, J = 8.7, 2.3 Hz, 1H), 6.68 (d, J = 9.0 Hz, 1H), 6.35 (s, 1H), 6.19 (s, 1H), 5.75 (s, 1H), 4.27 (s, 1H), 3.12 (s, 4H), 2.32 (s, 4H) |
| 35 | 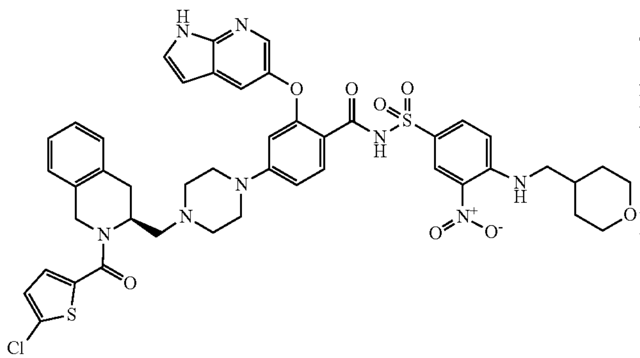 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)c3ccc(Cl)s3)CC2)cc1Oc1cnc2[nH]ccc2c1] | ¹H NMR (400 MHz, DMSO-$d_6$), δ: 11.62 (s, 1H), 11.50 (s, 1H), 8.50 (s, 2H), 8.00 (s, 1H), 7.73 (d, J = 9.1 Hz, 1H), 7.52 (d, J = 8.8 Hz, 1H), 7.45 (m, 3H), 7.17 (q, J = 7.8, 6.6 Hz, 5H), 7.01 (s, 1H), 6.69 (dd, J = 9.1, 2.3 Hz, 1H), 6.36 (dd, J = 3.5, 1.9 Hz, 1H), 6.23 (d, J = 2.2 Hz, 1H), 4.66 (m, 3H), 3.84 (m, 2H), 3.26 (m, 4H), 3.01 (s, 4H), 2.75 (m, 1H), 2.20 (m, 6H), 1.88 (m, 1H), 1.61 (d, J = 13.0 Hz, 2H), 1.26 (m, 3H) |
| 36 | 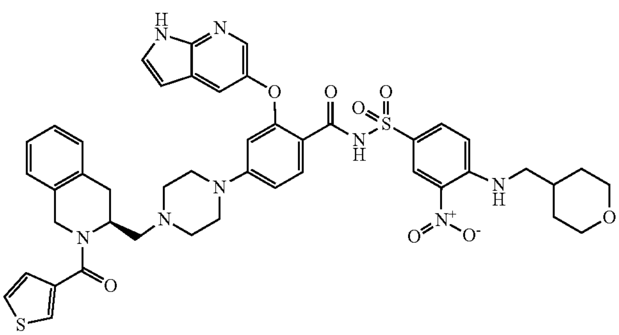 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)c3ccsc3)CC2)cc1Oc1cnc2[nH]ccc2c1] | ¹H NMR (400 MHz, DMSO-$d_6$), δ: 11.66 (s, 1H), 11.49 (s, 1H), 8.56 (m, 2H), 8.03 (s, 1H), 7.78 (m, 2H), 7.58 (s, 1H), 7.50 (m, 3H), 7.19 (m, 6H), 6.70 (d, J = 9.0 Hz, 1H), 6.38 (dd, J = 3.5, 1.9 Hz, 1H), 6.23 (s, 1H), 5.07 (s, 1H), 4.38 (m, 2H), 3.85 (m, 2H), 3.26 (m, 2H), 3.02 (m, 6H), 2.69 (m, 1H), 2.37 (m, 2H), 2.16 (m, 3H), 1.88 (m, 1H), 1.61 (m, 2H), 1.26 (m, 4H) |
| 37 | 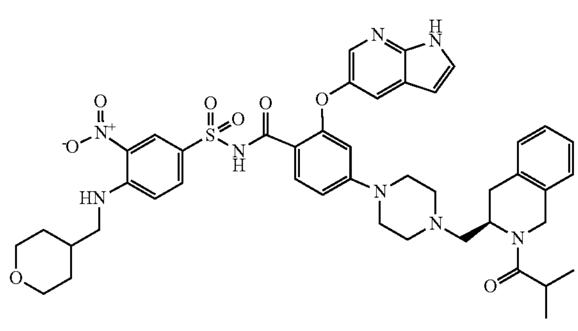 | ¹H NMR (400 MHz, DMSO-$d_6$), δ: 11.57 (m, 2H), 8.46 (s, 2H), 7.97 (s, 1H), 7.68 (d, J = 9.0 Hz, 1H), 7.55 (d, J = 8.7 Hz, 1H), 7.44 (m, 1H), 7.38 (s, 1H), 7.15 (m, 4H), 6.93 (d, J = 8.6 Hz, 1H), 6.68 (d, J = 9.0 Hz, 1H), 6.33 (m, 1H), 6.26 (m, 1H), 5.01 (m, 1H), 4.84 (d, J = 16.9 Hz, 1H), 4.37 (d, J = 16.6 Hz, 1H), 3.85 (m, 2H), 3.27 (m, 4H), 2.96 (m, 6H), 2.68 (d, J = 15.7 Hz, 1H), 2.28 (m, 4H), 1.87 (m, 1H), 1.61 (m, 2H), 1.25 (m, 4H), 0.99 (m, 6H) |

TABLE 2-continued

Further Compounds of the Disclosure

| Cmpd No. | Structure | ¹H-NMR |
|---|---|---|
| 38 | 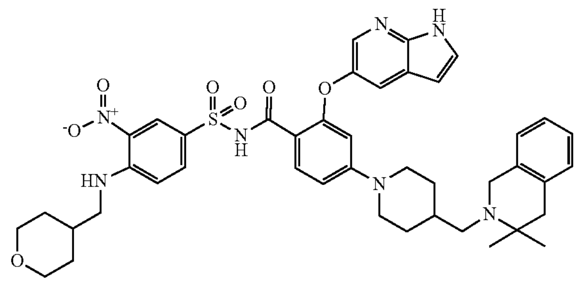 | ¹H NMR (400 MHz, DMSO-d$_6$), δ: 11.66 (m, 2H), 8.54 (m, 2H), 8.04 (d, J = 2.5 Hz, 1H), 7.78 (d, J = 9.2 Hz, 1H), 7.51 (m, 3H), 7.08 (m, 5H), 6.72 (d, J = 9.1 Hz, 1H), 6.37 (d, J = 3.0 Hz, 1H), 6.23 (s, 1H), 3.84 (m, 2H), 3.67 (m, 3H), 3.51 (m, 1H), 2.73 (m, 3H), 1.68 (m, 8H), 1.18 (m, 15H) |
| 39 | 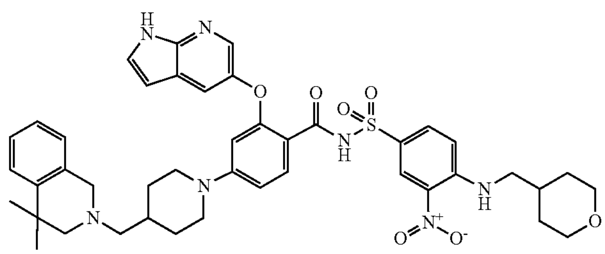 [SMILES: CC1(C)CN(CC2CCN(c3ccc(C(=O)NS(=O)(=O)c4ccc(NCC5CCOCC5)c([N+](=O)[O-])c4)c(Oc4cnc5[nH]ccc5c4)c3)CC2)Cc2ccccc21] | ¹H NMR (400 MHz, DMSO-d$_6$), δ: 11.68 (s, 1H), 11.38 (s, 1H), 8.58 (m, 2H), 8.06 (d, J = 2.6 Hz, 1H), 7.81 (dd, J = 9.2, 2.3 Hz, 1H), 7.52 (m, 3H), 7.31 (d, J =7.8 Hz, 1H), 7.09 (m, 3H), 6.98 (d, J = 7.6 Hz, 1H), 6.72 (dd, J = 9.1, 2.4 Hz, 1H), 6.39 (dd, J = 3.4, 1.9 Hz, 1H), 6.21 (d, J = 2.3 Hz, 1H), 3.85 (m, 2H), 3.66 (m, 2H), 3.50 (s, 2H), 3.26 (m, 3H), 2.74 (t, J = 12.4 Hz, 2H), 2.31 (m, 4H), 1.87 (m, 2H), 1.73 (d, J = 13.1 Hz, 2H), 1.62 (m, 2H), 1.24 (m, 8H), 1.09 (m, 3H) |
| 40 | 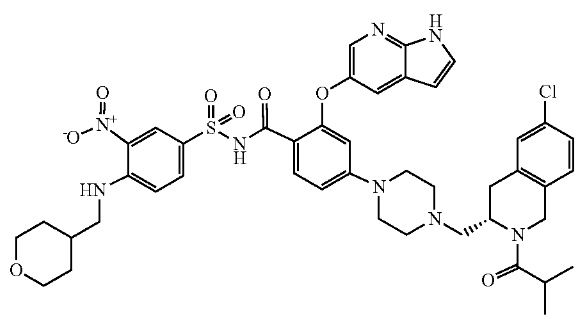 | ¹H NMR (400 MHz, DMSO-d$_6$), δ: 11.67 (m, 2H), 8.59 (m, 2H), 8.04 (d, J = 2.8 Hz, 1H), 7.80 (dd, 7 = 9.1, 2.4 Hz, 1H), 7.52 (m, 3H), 7.26 (m, 3H), 7.11 (d,J =9.3 Hz, 1H), 6.78 (s, 1H), 6.38 (m, 2H), 5.18 (m, 1H), 4.90 (d, J = 17.0 Hz, 1H), 4.50 (m, 1H), 3.85 (m, 2H), 3.28 (m, 7H), 2.98 (m, 8H), 2.72 (m, 1H), 1.89 (m, 1H), 1.61 (d, J = 12.9 Hz, 2H), 1.26 (m, 2H), 1.00 (m, 7H) |
| 57 | 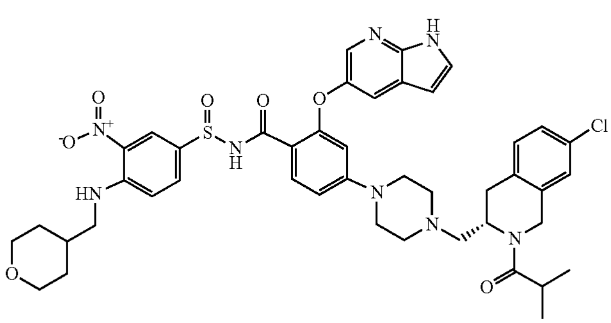 | ¹H NMR (400 MHz, DMSO-d$_6$), δ: 11.67 (s, 1H), 11.47 (s, 1H), 8.57 (m, 2H), 8.04 (m, 1H), 7.80 (dd, J = 9.2, 2.4 Hz, 1H), 7.52 (m, 3H), 7.29 (m, 1H), 7.16 (m, 3H), 6.72 (m, 1H), 6.38 (dt, J = 3.5, 2.1 Hz, 1H), 6.23 (dd,J = 8.0, 2.3 Hz, 1H), 5.00 (m, 1H), 4.88 (d, J = 17.2 Hz, 1H), 4.34 (d, J = 17.0 Hz, 1H), 3.85 (m, 2H), 3.29 (m, 3H), 2.92 (m, 8H), 2.27 (m, 6H), 1.89 (m, 1H), 1.61 (d, J = 12.9 Hz, 2H), 1.27 (m, 2H), 0.98 (m, 6H) |

US 11,834,450 B2

TABLE 2-continued

Further Compounds of the Disclosure

| Cmpd No. | Structure | ¹H-NMR |
|---|---|---|
| 61 | 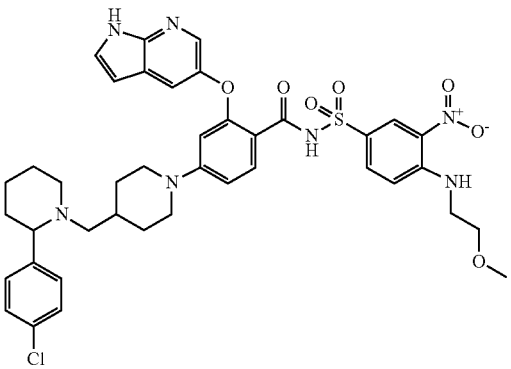 [SMILES: COCCNc1ccc(S(=O)(=O)NC(=O)c2ccc(N3CCC(CN4CCCCC4c4ccc(Cl)cc4)CC3)cc2Oc2cnc3[nH]ccc3c2)cc1[N+](=O)[O-]] | ¹H NMR (400 MHz, DMSO-$d_6$), δ: 11.68 (s, 1H), 11.38 (s, 1H), 8.55 (m, 2H), 8.03 (d, J = 2.6 Hz, 1H), 7.80 (d, J = 9.3 Hz, 1H), 7.50 (m, 3H), 7.30 (m, 4H), 7.09 (d, J = 9.2 Hz, 1H), 6.64 (dd, J = 9.1, 2.4 Hz, 1H), 6.39 (dd, J = 3.5, 1.9 Hz, 1H), 6.13 (d, J = 2.4 Hz, 1H), 3.57 (m, 7H), 3.08 (m, 2H), 2.63 (m, 2H), 1.18-2.06 (m, 14H), 0.72 (s, 2H) |
| 62 | 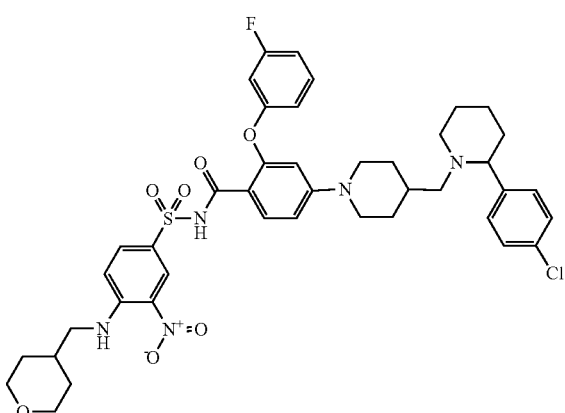 | ¹H NMR (400 MHz, DMSO-$d_6$), δ: 11.63 (s, 1H), 8.60 (s, 1H), 8.43 (s, 1H), 7.72 (d, J = 9.3 Hz, 1H), 7.48 (d, J = 8.8 Hz, 1H), 7.32 (s, 4H), 7.20 (q, J = 7.9 Hz, 1H), 7.11 (d, J = 9.3 Hz, 1H), 6.74 (m, 2H), 6.54 (m, 2H), 6.42 (s, 1H), 3.86 (dd, J = 11.0, 4.2 Hz, 2H), 3.69 (t, J = 13.1 Hz, 2H), 3.27 (m, 4H), 3.05 (m, 2H), 2.71 (m, 2H), 1.46 (m, 17H), 0.81 (m, 2H) |
| 63 | 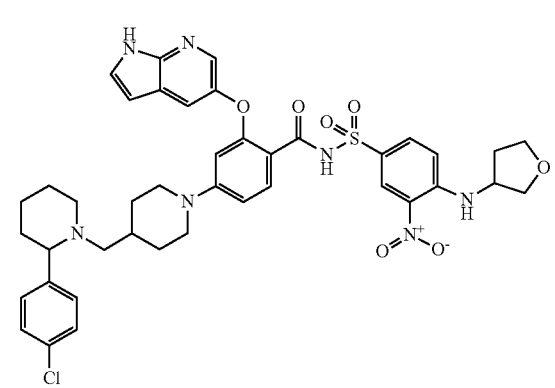 [SMILES: O=C(NS(=O)(=O)c1ccc(NC2CCOC2)c([N+](=O)[O-])c1)c1ccc(N2CCC(CN3CCCCC3c3ccc(Cl)cc3)CC2)cc1Oc1cnc2[nH]ccc2c1] | ¹H NMR (400 MHz, DMSO-$d_6$), δ: 11.67 (s, 1H), 11.42 (s, 1H), 8.55 (s, 1H), 8.28 (d, J = 6.7 Hz, 1H), 8.02 (d, J = 2.5 Hz, 1H), 7.83 (d, J = 9.0 Hz, 1H), 7.48 (m, 3H), 7.30 (m, 4H), 7.09 (d, J = 9.3 Hz, 1H), 6.65 (d, J = 8.9 Hz, 1H), 6.38 (s, 1H), 6.14 (s, 1H), 4.35 (s, 1H), 3.90 (m, 2H), 3.73 (m, 2H), 3.54 (m, 2H), 3.02 (m, 2H), 2.63 (m, 2H), 2.33 (m, 2H), 1.19-2.14 (m, 12H), 0.73 (s, 2H) |
| 64 | 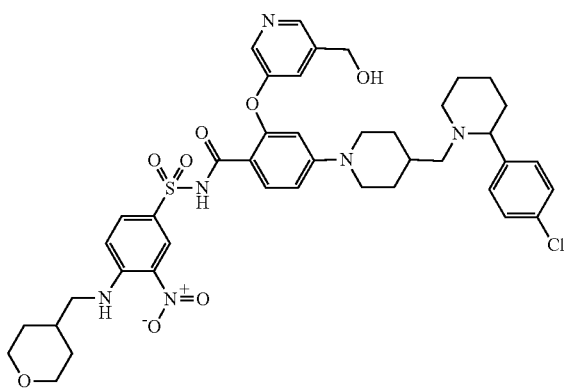 | ¹H NMR (400 MHz, DMSO-$d_6$), δ: 11.67 (s, 1H), 8.61 (s, 1H), 8.45 (m, 1H), 8.10 (s, 1H), 8.03 (d, J = 2.4 Hz, 1H), 7.73 (m, 1H), 7.50 (d, J = 8.8 Hz, 1H), 7.33 (s, 4H), 7.13 (d, J = 9.3 Hz, 1H), 7.04 (s, 1H), 6.74 (dd, J = 9.1, 2.4 Hz, 1H), 6.41 (d, J = 2.4 Hz, 1H), 5.28 (t, J = 5.6 Hz, 1H), 4.40 (d, J = 5.4 Hz, 2H), 3.86 (m, 2H), 3.71 (m, 2H), 3.32 (m, 4H), 3.06 (m, 2H), 2.70 (m, 2H), 1.10-2.09 (m, 17H), 0.79 (m, 2H) |

TABLE 2-continued

Further Compounds of the Disclosure

| Cmpd No. | Structure | ¹H-NMR |
|---|---|---|
| 65 | 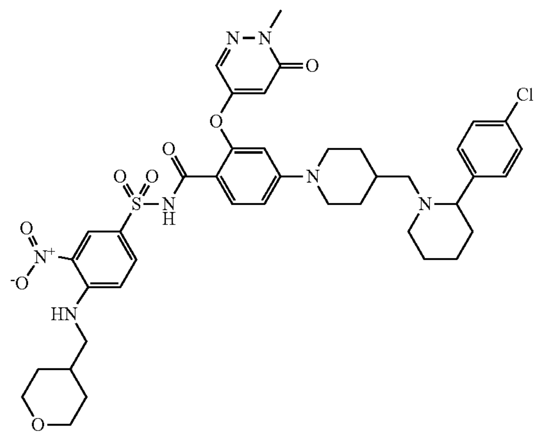 | ¹H NMR (400 MHz, DMSO-d$_6$), δ: 11.97 (s, 1H), 8.55 (s, 1H), 8.45 (s, 1H), 7.73 (m, 2H), 7.58 (d, J = 8.8 Hz, 1H), 7.34 (s, 4H), 7.11 (d, J = 9.1 Hz, 1H), 6.80 (dd, J = 9.0, 2.4 Hz, 1H), 6.59 (s, 1H), 5.44 (s, 1H), 3.86 (m, 2H), 3.75 (s, 2H), 3.50 (s, 3H), 3.30 (s, 4H), 3.08 (m, 2H), 2.72 (m, 2H), 0,99-2,10 (m, 17H), 0.83 (m, 2H) |
| 66 | 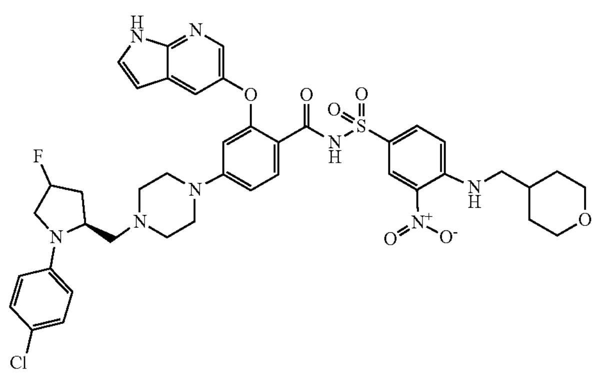 | ¹H NMR (400 MHz, DMSO-d$_6$), δ: 11.67 (s, 1H), 11.42 (s, 1H), 8.58 (m, 2H), 8.05 (d, J = 2.6 Hz, 1H), 7.82 (dd, J = 9.2, 2.4 Hz, 1H), 7.53 (m, 3H), 7.14 (m, 3H), 6.72 (m, 1H), 6.61 (d, J = 9.0 Hz, 2H), 6.40 (dd, J = 3.3, 1.9 Hz, 1H), 6.22 (d, J = 2.3 Hz, 1H), 5.39 (m, 1H), 4.08 (m, 1H), 3.85 (m, 2H), 3.52 (m, 2H), 3.30 (m, 6H), 3.12 (s, 4H), 2.35 (m, 6H), 1.90 (m, 1H), 1.62 (d,J = 13.1 Hz, 2H), 1.27 (tt, J = 12.5, 6.1Hz, 2H) |
| 67 | 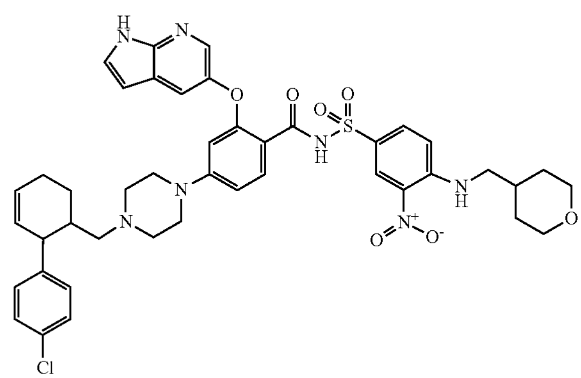 [SMILES: O=C(NS(=O)(=O)c1ccc(NCC2CCOCC2)c([N+](=O)[O-])c1)c1ccc(N2CCN(CC3CCC=CC3c3ccc(Cl)cc3)CC2)cc1Oc1cnc2[nH]ccc2c1] | ¹H NMR (400 MHz, DMSO-d$_6$), δ: 11.69 (s, 2H), 9.15(s, 1H), 8.61 (t, J = 6.0 Hz, 1H), 8.56 (t, J = 1.8 Hz, 1H), 8.04 (m, 1H), 7.80 (dd, J = 9.3, 2.3 Hz, 1H), 7.54 (m, 2H), 7.51 (m, 1H), 7.38 (m, 2H), 7.22 (m, 2H), 7.12 (d, J = 9.4 Hz, 1H), 6.79 (m, 1H), 6.38 (m, 1H), 6.32 (m, 1H), 5.90 (m, 1H), 5.60 (m, 1H), 3.85 (m, 4H), 3.48 (m, 2H), 3.28 (m, 4H), 3.08 (m, 6H), 2.13 (m, 2H), 1.82 (m, 2H), 1.61 (d, J = 12.9 Hz, 2H), 1.22 (m, 4H) |
| 68 | 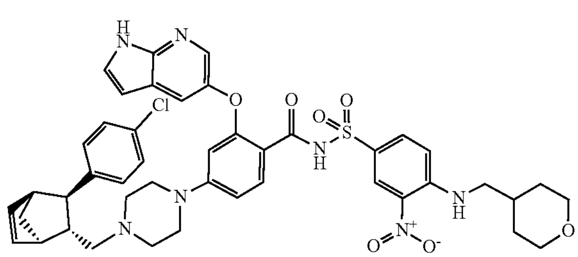 [SMILES: O=C(NS(=O)(=O)c1ccc(NCC2CCOCC2)c([N+](=O)[O-])c1)c1ccc(N2CCN(C[C@H]3[C@H](c4ccc(Cl)cc4)[C@@H]4C=C[C@H]3C4)CC2)cc1Oc1cnc2[nH]ccc2c1] | ¹H NMR (400 MHz, DMSO-d$_6$), δ: 11.71 (s, 1H), 11.67 (s, 1H), 10.52 (s, 1H), 8.60 (t, J = 5.6 Hz, 1H), 8.56 (d, J = 2.3 Hz, 1H), 8.05 (d, J = 2.6Hz, 1H), 7.81 (dd, J = 9.3, 2.2 Hz, 1H), 7.55 (m, 2H), 7.51 (m, 2H), 7.36 (q, J = 8.4 Hz, 1H), 7.27 (d, J = 8.4 Hz, 2H), 7.21 (m, 2H), 7.12 (d, J = 9.4 Hz, 1H), 6.78 (d, J = 9.1 Hz, 1H), 6.38 (m, 3H), 5.84 (m, 1H), 3.81 (m, 6H), 3.28 (m, 8H), 3.03 (m, 3H), 1.92 (m, 1H), 1.62 (m, 3H), 1.23 (m, 3H) |

TABLE 2-continued

Further Compounds of the Disclosure

| Cmpd No. | Structure | ¹H-NMR |
|---|---|---|
| 69 | 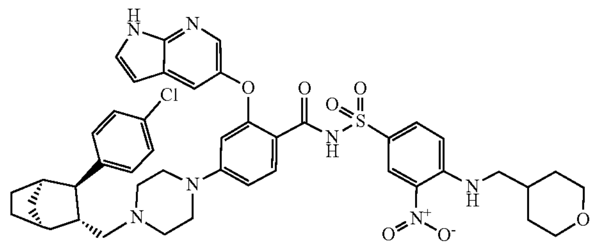 [SMILES: O=C(NS(=O)(=O)c1ccc(NCC2CCOCC2)c([N+](=O)[O-])c1)c1ccc(N2CCN(C[C@@H]3C[C@H]4CC[C@H](C4)[C@H]3c3ccc(Cl)cc3)CC2)cc1Oc1cnc2[nH]ccc2c1] | ¹H NMR (400 MHz, DMSO-d₆), δ: 11.69 (m, 1H), 10.40 (s, 1H), 8.58 (m, 2H), 8.05 (s, 1H), 7.81 (m, 1H), 7.54 (m, 2H), 7.31 (m, 5H), 7.12 (d, J = 9.9 Hz, 1H), 6.78 (d, J = 9.3 Hz, 1H), 6.39 (s, 1H), 6.34 (d, 7 = 2.3 Hz, 1H), 3.85 (m, 4H), 3.25 (m, 12H), 2.25 (m, 3H), 1.91 (m, 1H), 1.61 (m, 4H), 1.28 (m, 7H) |
| 70 | 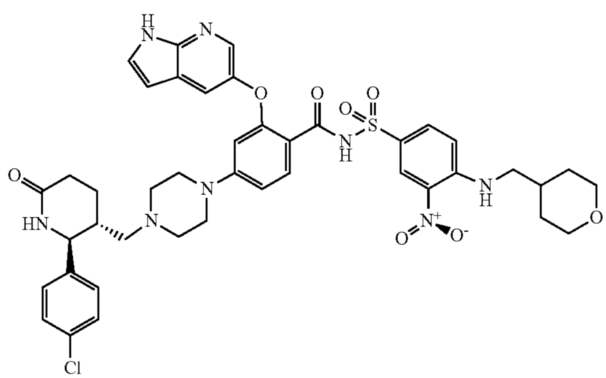 | ¹H NMR (400 MHz, DMSO-d₆), δ: 11.68 (s, 1H), 11.41 (s, 1H), 8.57 (m, 2H), 8.04 (d, J = 2.7 Hz, 1H), 7.80 (m, 1H), 7.62 (s, 1H), 7.51 (m, 3H), 7.38 (d, J = 8.2 Hz, 2H), 7.26 (d, J = 8.3 Hz, 2H), 7.11 (d, J = 9.3 Hz, 1H), 6.69 (m, 1H), 6.39 (m, 1H), 6.20 (s, 1H), 4.24 (m, 1H), 3.84 (m, 2H), 3.26 (s, 4H), 3.06 (s, 4H), 2.25 (m, 8H), 1.85 (m, 3H), 1.61 (m, 2H), 1.44 (m, 1H), 1.25 (m, 2H) |
| 71 | 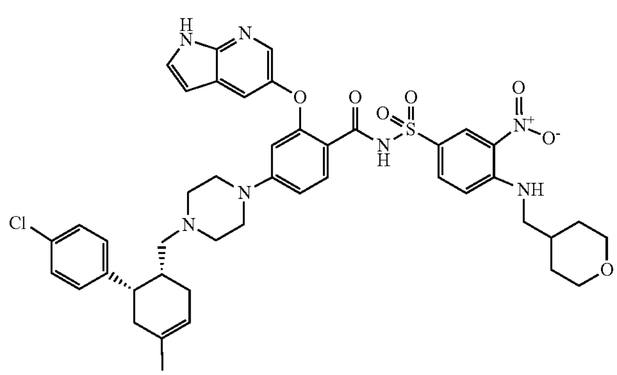 [SMILES: CC1=CC[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | ¹H NMR (400 MHz, DMSO-d₆), δ: 11.68 (s, 1H), 11.31 (s, 1H), 8.57 (m, 2H), 8.03 (s, 1H), 7.78 (d, J = 9.1 Hz, 1H), 7.50 (m, 3H), 7.25 (m, 4H), 7.09 (d, J = 9.4 Hz, 1H), 6.69 (d, J = 9.6 Hz, 1H), 6.38 (s, 1H), 6.19 (s, 1H), 5.40 (s, 1H), 3.84 (m, 2H), 3.32 (s, 4H), 3.07 (s, 4H), 2.04 (m, 11H), 1.61 (m, 6H), 1.25 (m, 3H) |
| 72 | 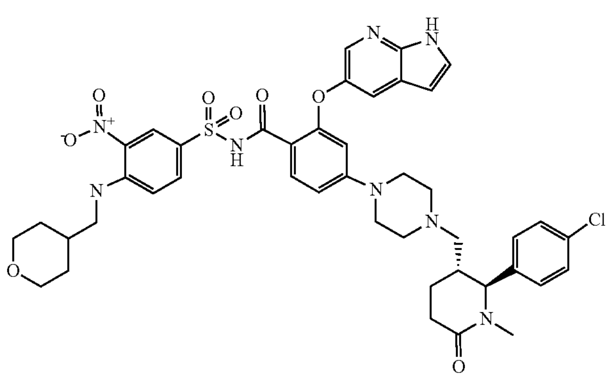 | ¹H NMR (400 MHz, DMSO-d₆), δ: 11.69 (s, 1H), 11.42 (s, 1H), 8.58 (m, 2H), 8.05 (d, J = 2.6 Hz, 1H), 7.81 (d, J = 8.7 Hz, 1H), 7.53 (m, 3H), 7.42 (d, J = 8.0 Hz, 2H), 7.19 (d, J = 8.0 Hz, 2H), 7.12 (d, J = 9.4 Hz, 1H), 6.72 (d, J = 9.1 Hz, 1H), 6.39 (d, J = 3.1 Hz, 1H), 6.21 (s, 1H), 4.37 (m, 1H), 3.84 (m, 2H), 3.10 (s, 5H), 2.56 (s, 3H), 2.33 (m, 9H), 1.93 (m, 3H), 1.72 (s, 1H), 1.61 (m, 2H), 1.47 (m, 1H), 1.26 (m, 3H) |

TABLE 2-continued

Further Compounds of the Disclosure

| Cmpd No. | Structure | $^1$H-NMR |
|---|---|---|
| 73 | 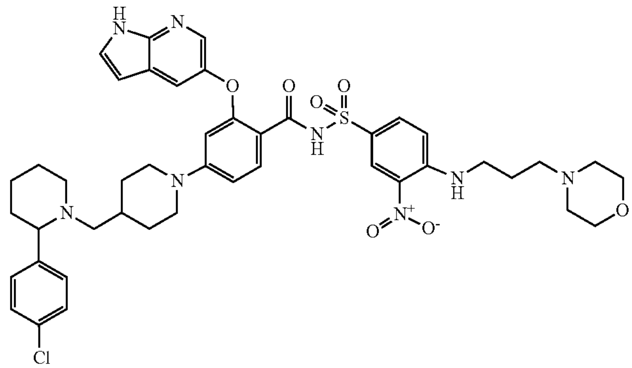 [SMILES: O=C(NS(=O)(=O)c1ccc(NCCCN2CCOCC2)c([N+](=O)[O-])c1)c1ccc(N2CCC(CN3CCCCC3c3ccc(Cl)cc3)CC2)cc1Oc1cnc2[nH]ccc2c1] | $^1$H NMR (400 MHz, DMSO-$d_6$), δ: 11.67 (s, 1H), 8.75 (s, 1H), 8.54 (d, J = 2.3 Hz, 1H), 8.02 (d, J = 2.6 Hz, 1H), 7.79 (dd, J = 8.9, 2.0 Hz, 1H), 7.49 (m, 3H), 7.30 (m, 4H), 7.04 (d, J = 9.4 Hz, 1H), 6.64 (dd, 9.1, 2.1 Hz, 1H), 6.38 (d, J = 2.8 Hz, 1H), 6.13 (d, J = 2.2 Hz, 1H), 3.61 (m, 7H), 3.43 (m, 3H), 2.98 (m, 2H), 2.64 (m, 2H), 2.45 (s, 4H), 1.17-2,03 (m, 15H), 0.73 (m, 2H) |
| 74 | 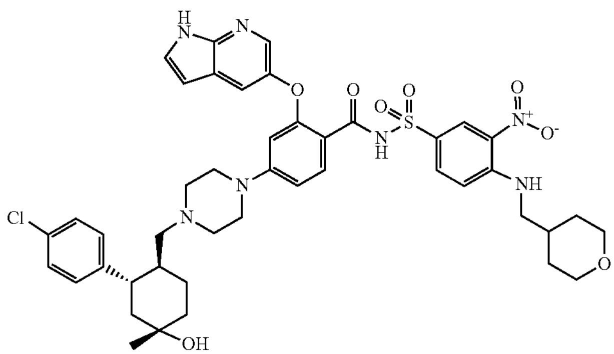 [SMILES: C[C@]1(O)CC[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | $^1$H NMR (400 MHz, DMSO-$d_6$), δ: 11.66 (m, 2H), 9.01 (s, 1H), 8.58 (m, 2H), 8.03 (d, J = 2.6 Hz, 1H), 7.80 (dd, J = 9.5, 2.3 Hz, 1H), 7.52 (m, 3H), 7.34 (d, J = 8.1 Hz, 2H), 7.23 (d, J = 8.1 Hz, 2H), 7.11 (d, J = 9.3 Hz, 1H), 6.74 (d, J = 8.9 Hz, 1H), 6.38 (dd, J = 3.5, 1.9 Hz, 1H), 6.29 (d, J = 2.3 Hz, 1H), 3.85 (m, 2H), 3.69 (m, 2H), 3.49 (m, 1H), 3.28 (m, 5H), 2.97 (m, 4H), 2.67 (m, 2H), 1.95 (m, 3H), 1.58 (m, 6H), 1.21 (m, 6H) |
| 75 | 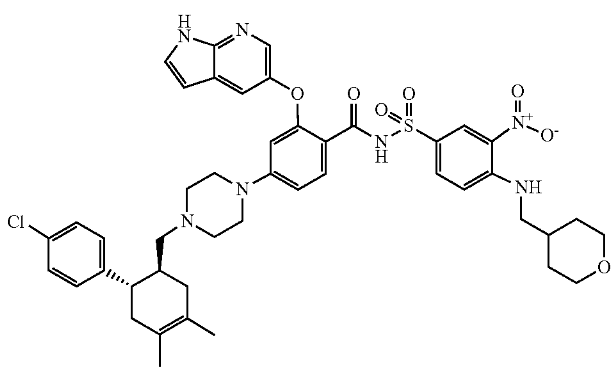 [SMILES: CC1=C(C)C[C@H](c2ccc(Cl)cc2)[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | $^1$H NMR (400 MHz, DMSO-$d_6$), δ: 11.67 (s, 1H), 11.39 (s, 1H), 8.56 (m, 2H), 8.03 (d, J = 2.6 Hz, 1H), 7.78 (dd, J = 9.2, 2.3 Hz, 1H), 7.50 (m, 3H), 7.29 (d, J = 8.1 Hz, 2H), 7.20 (d, J = 8.2 Hz, 2H), 7.08 (d, J = 9.3 Hz, 1H), 6.68 (dd, J = 9.0, 2.3 Hz, 1H), 6.38 (m, 1H), 6.19 (d, J = 2.3 Hz, 1H), 3.85 (m, 2H), 3.30 (m, 2H), 3.06 (s, 4H), 2.38 (m, 2H), 1,67-2,24 (m, 13H), 1.58 (m, 8H), 1.23 (m, 2H) |
| 78 | 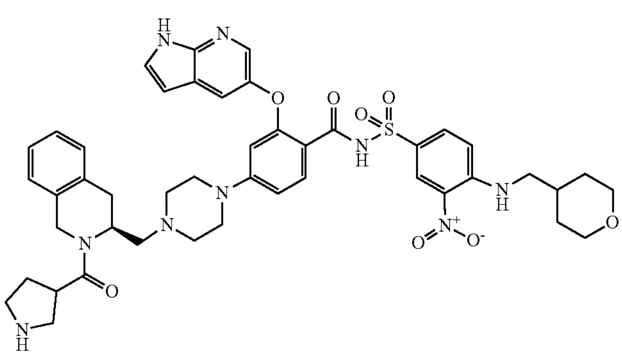 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)C3CCNC3)CC2)cc1Oc1cnc2[nH]ccc2c1] | $^1$H NMR (400 MHz, DMSO-$d_6$), δ: 11.71 (m, 2H), 11.15 (m, 1H), 9.12 (m, 2H), 8.59 (m, 2H), 8.05 (d, J = 2.6 Hz, 1H), 7.79 (dd, J = 9.3, 2.4 Hz, 1H), 7.52 (m, 3H), 7.19 (m, 5H), 6.80 (dd, J = 9.1, 2.2 Hz, 1H), 6.39 (m, 2H), 5.31 (s, 1H), 4.87 (m, 2H), 3.78 (m, 6H), 3.30 (m, 17H), 2.72 (m, 1H), 2.25 (m, 1H), 1.90 (d, J = 8.1 Hz, 1H), 1.61 (m, 2H), 1.26 (m, 2H) |

TABLE 2-continued

Further Compounds of the Disclosure

| Cmpd No. | Structure | ¹H-NMR |
|---|---|---|
| 79 | 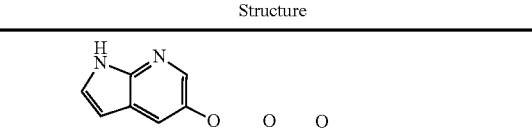 | ¹H NMR (400 MHz, DMSO-$d_6$), δ: 11.66 (s, 1H), 11.43 (s, 1H), 8.54 (s, 1H), 8.24 (m, 1H), 8.02 (d, J = 2.7 Hz, 1H), 7.85 (d, J = 8.9 Hz, 1H), 7.49 (m, 3H), 7.29 (m, 6H), 6.64 (m, 1H), 6.38 (s, 1H), 6.14 (s, 1H), 4.07 (m, 1H), 3.53 (m, 3H), 3.16 (m, 4H), 2.64 (m, 2H), 2.20 (m, 4H), 1.11-2.04 (m, 10H), 0.72 (m, 4H) |

Example 13. Primary PPI Inhibition Assays

BCL-2 TR-FRET Assay (BPS Bioscience, #50222) Assay Condition: The following assay concentrations and times were used: 3 ng BCL-2, 5 ul of 1:100 anti-His Tb-labeled donor, 5 ul of 1:100 Dye-labeled acceptor, 5 ul of 1:40 BCL-2 Peptide Ligand, and 2 ul of test compound, with 60 min incubation time. The results of the assay were read using a Clariostar (BMG Labtech) plate reader with the following parameters: TR FRET, 340 ex/620 and 665 em; 60 µsec Delay; and 500 µsec integration.

BCL-XL TR-FRET Assay (BPS Bioscience, #50223) Assay Condition: The following assay concentrations and times were used: 10.5 ng BCL-XL, 5 ul of 1:100 anti-His Tb-labeled donor, 5 ul of 1:100 Dye-labeled acceptor, 5 ul of 1:80 BCL-XL Peptide Ligand, and 2 ul of test compound, with 60 min incubation time. The results of the assay were read using a Clariostar (BMG Labtech) plate reader with the following parameters: TR FRET, 340 ex/620 and 665 em; 60 µsec Delay; and 500 µsec integration.

MCL-1 TR-FRET Assay (BPS Bioscience, #79506) Assay Condition: The following assay concentrations and times were used: 10 ng MCL-1, 5 ul of 1:200 anti-His Tb-labeled donor, 5ul of 1:200 Dye-labeled acceptor, 5 ul of 1:10 MCL-1 Peptide Ligand, and 2 ul of test compound, with 60 min incubation time. The results of the assay were read using a Clariostar (BMG Labtech) plate reader with the following parameters: TR FRET, 340 ex/620 and 665 em; 60 µsec Delay; and 500 µsec integration.

Table A assigns a code for potency for BCL-2 TR-FRET Assay: A, B, C, or D. According to the code, A represents an $IC_{50}$ value ≤5 nM; B represents $IC_{50}$>5 nM and ≤10 nM; C represents $IC_{50}$>10 nM and ≤50 nM D represents $IC_{50}$>50 nM.

Table A assigns a code for potency for BCL-XL TR-FRET Assay: A, B, or C. According to the code, A represents $IC_{50}$ value ≤2,000 nM; B represents $IC_{50}$ values >2,000 nM and ≤4,000 nM; C represents $IC_{50}$ values >4,000 nM.

TABLE A

Primary PPI inhibition

| Compound No. | BCL2 | BCLxL |
|---|---|---|
| 1 | C | C |
| 2 | D | C |
| 3 | C | B |
| 4 | D | C |
| 5 | C | A |
| 6 | D | A |
| 7 | C | C |
| 8 | D | A |
| 9 | D | B |
| 10 | D | N/A |
| 11 | D | C |
| 12 | D | C |
| 13 | D | C |
| 14 | D | N/A |
| 15 | D | C |
| 16 | D | C |
| 17 | D | C |
| 19 | D | C |
| 20 | D | C |
| 22 | D | C |
| 27 | D | B |
| 28 | A | A |
| 33 | C | C |
| 34 | C | B |
| 35 | D | C |
| 36 | D | C |
| 37 | D | C |
| 38 | D | C |
| 39 | D | C |
| 40 | D | C |
| 41 | D | C |
| 43 | D | C |
| 44 | D | C |
| 45 | D | c |
| 46 | D | C |
| 47 | C | C |
| 48 | D | C |
| 49 | C | C |
| 50 | D | C |
| 51 | C | C |
| 52 | B | A |
| 54 | C | B |
| 55 | D | C |
| 56 | C | B |
| 57 | D | C |
| 58 | C | C |
| 59 | C | B |

TABLE A-continued

Primary PPI inhibition

| Compound No. | BCL2 | BCLxL |
|---|---|---|
| 60 | D | C |
| 61 | D | A |
| 62 | D | A |
| 63 | D | B |
| 64 | D | C |
| 65 | D | C |
| 66 | D | C |
| 67 | C | N/A |
| 68 | D | C |
| 69 | D | C |
| 70 | D | C |
| 71 | C | C |
| 72 | D | A |
| 73 | C | B |
| 74 | C | B |
| 75 | D | A |
| 76 | B | A |
| 77 | D | C |
| 78 | B | B |
| 79 | D | C |
| 80 | D | A |

Example 14. Cell Viability Assays (Cell Lines HEK293, RS4-11, MOLT-4)

Assay Condition: Used culture medium for HEK293-DMEM (PanEco, Cat #C420), for the rest of the cell lines—culture medium RPMI-1640 (PanEco, Cat #C363).

Assay Procedure: Compounds were prepared as 200× stocks with serial dilution in 100% DMSO with a final concentration of 1×. Dispersed 40 µl in 384-well plates at a concentration of 2000 cells per well for HEK293 and at a concentration of 4000 cells per well for the rest of the cell lines using a robotic station Biomek (Beckman). Before adding compounds, the cells were incubated at 37° C. (HEK293 were incubated for a day before adding compounds).

A dilution plate was prepared by pouring 78 µl of the appropriate culture medium using a robotic station Biomek (Beckman). Sequentially, using a robotic station, 2 µl of substances were taken and added to 78 µl of culture medium (dilution of compounds 40×). Took from there 10 µl and added to the plates to the cells (dilution of compounds 5×). The plates were incubated for 3 days at a temperature 37° C. After 3 days, 10 µl of CellTiter-Glo (Promega) was added to the cells and the luminescence was measured.

Table B assigns a code for potency for RS4-11 Assay: A, B, or C. According to the code, A represents an $CC_{50}$ value ≤0.1 µM; B represents $CC_{50}>0.1$ µM and ≤0.2 µM; C represents $CC_{50}>0.2$ µM.

Table B assigns a code for potency for MOLT-4 Assay: A, B, or C. According to the code, A represents an $CC_{50}$ value ≤2 µM; B represents $CC_{50}>2$ µM and ≤10 µM; C represents $CC_{50}>10$ µM.

Table B assigns a code for potency for BTEK293 Assay: A, B, or C. According to the code, A represents an $CC_{50}$ value ≤10 µM; B represents $CC_{50}>10$ µM and ≤25 µM; C represents $CC_{50}>25$ µM.

TABLE B

Cellular models efficacy and cytotoxicity.

| Compound No. | RS4-11 | MOLT-4 | HEK293 |
|---|---|---|---|
| 1 | C | B | C |
| 2 | C | C | C |
| 3 | C | B | C |
| 4 | C | B | C |
| 5 | C | B | C |
| 6 | C | B | C |
| 7 | C | B | C |
| 8 | C | B | C |
| 9 | C | B | C |
| 10 | C | C | A |
| 11 | C | B | C |
| 12 | C | C | C |
| 13 | C | A | A |
| 16 | C | C | C |
| 17 | C | C | C |
| 19 | C | C | C |
| 20 | C | B | C |
| 22 | C | B | C |
| 27 | C | B | C |
| 28 | B | B | C |
| 30 | C | B | C |
| 31 | B | B | B |
| 33 | C | B | C |
| 35 | C | B | C |
| 36 | C | B | B |
| 39 | C | B | C |
| 40 | C | B | B |
| 41 | C | B | C |
| 42 | C | B | C |
| 43 | C | B | C |
| 44 | C | B | C |
| 45 | C | C | C |
| 46 | C | B | C |
| 47 | C | B | B |
| 48 | C | C | C |
| 49 | C | B | C |
| 50 | C | C | C |
| 51 | C | B | C |
| 52 | A | B | B |
| 53 | C | C | C |
| 54 | B | B | B |
| 55 | C | B | C |
| 56 | C | C | C |
| 57 | C | B | B |
| 58 | C | B | C |
| 59 | C | B | C |
| 61 | B | B | C |
| 62 | C | B | B |
| 63 | C | B | C |
| 64 | C | C | B |
| 65 | C | C | B |
| 66 | c | B | B |
| 68 | C | B | B |
| 69 | C | B | n/d |
| 70 | C | C | B |
| 72 | C | C | C |
| 73 | C | B | B |
| 74 | C | B | B |
| 75 | C | B | C |
| 77 | C | B | B |
| 78 | C | C | C |
| 79 | C | B | C |
| 80 | C | C | B |
| 81 | C | B | B |

Example 15. Cas-3/7 Activation

Assay Principle: The Caspase-Glo 3/7 Assay is homogeneous, luminescent assay that measures caspase-3 and -7 activities. The assay provides a luminogenic caspase-3/7 substrate, which contains the tetrapeptide sequence DEVD, in a reagent optimized for caspase activity.

Assay Procedure: Incubate RS4-11 cells with varying concentrations of test compounds for 3.5 h in a humidified incubator at 37° C. and 5% $CO_2$ and 30 min at r.t. Add 15 µl Caspase-Glo reagent to each well and incubate the plate for 30 min at r.t. Read on ClarioStar Plus instrument.

Materials: Promega Caspase-Glo (Promega, #8212); Frozen RS4-11 cells; 384-well white plate (Corning, #3570).

Instrumentation: ClarioStar Plus; Biomek FX for liquid handling (Beckman Coulter).

Table C assigns a code for potency for Cas-3/7 Assay: A, B, or C. According to the code, A represents an $EC_{50}$ value ≤0.1 µM; B represents $EC_{50}$>0.1 µM and 0.25 µM; C represents $EC_{50}$>0.25 µM.

TABLE C

Caspase-3/7 activation.

| Compound No. | Cas-3/7 |
| --- | --- |
| 2 | C |
| 3 | C |
| 4 | C |
| 5 | C |
| 6 | C |
| 7 | C |
| 8 | C |
| 9 | C |
| 11 | C |
| 13 | C |
| 20 | C |
| 22 | C |
| 28 | B |
| 30 | C |
| 31 | B |
| 33 | C |
| 35 | C |
| 36 | C |
| 37 | C |
| 38 | C |
| 39 | C |
| 40 | C |

TABLE C-continued

Caspase-3/7 activation.

| Compound No. | Cas-3/7 |
| --- | --- |
| 41 | C |
| 42 | C |
| 43 | C |
| 44 | C |
| 45 | C |
| 46 | C |
| 47 | C |
| 48 | C |
| 49 | C |
| 50 | C |
| 51 | C |
| 52 | A |
| 53 | C |
| 54 | B |
| 55 | C |
| 56 | C |
| 57 | C |
| 58 | C |
| 59 | C |
| 61 | C |
| 63 | C |
| 67 | C |
| 72 | C |
| 75 | C |
| 78 | C |
| 79 | C |
| 80 | C |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound selected from:

| Compound No | Structure | Name |
| --- | --- | --- |
| 1 | 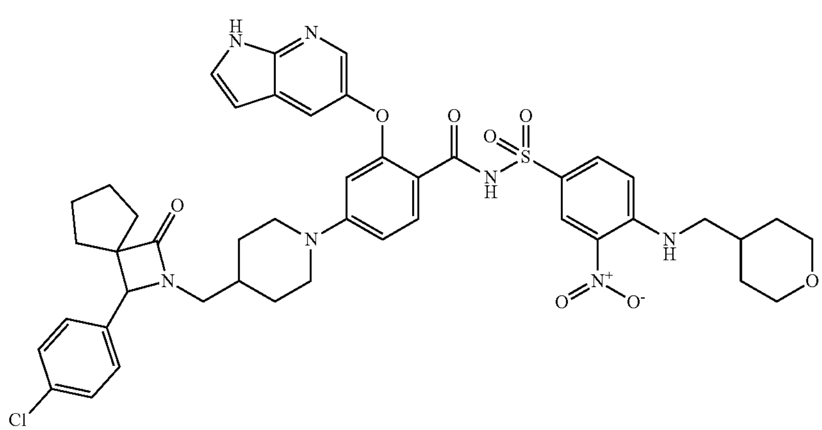 [SMILES: O=C(NS(=O)(=O)c1ccc(NCC2CCOCC2)c([N+](=O)[O-])c1)c1ccc(N2CCC(CN3C(=O)C4(CCCC4)C3c3ccc(Cl)cc3)CC2)cc1Oc1cnc2[nH]ccc2c1] | 4-[4-[[1-(4-chlorophenyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
| --- | --- | --- |
| 2 | 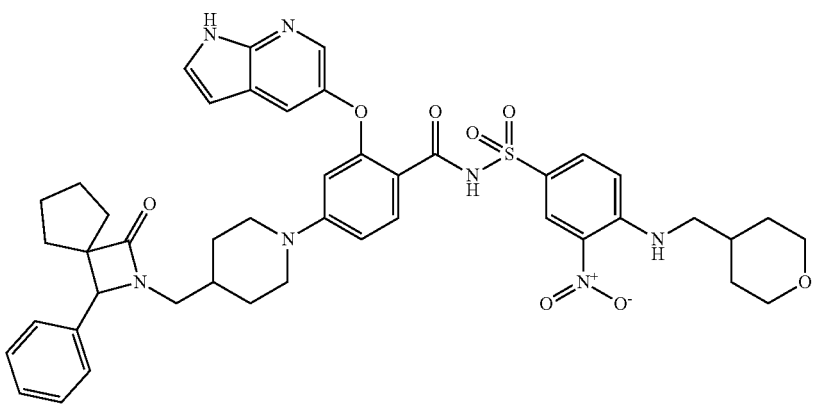 [SMILES: O=C(NS(=O)(=O)c1ccc(NCC2CCOCC2)c([N+](=O)[O-])c1)c1ccc(N2CCC(CN3C(=O)C4(CCCC4)C3c3ccccc3)CC2)cc1Oc1cnc2[nH]ccc2c1] | N-[3-nitro-4-(tetrahydropyran-4-ylmethylamino)phenyl]sulfonyl-4-[4-[(3-oxo-1-phenyl-2-azaspiro[3.4]octan-2-yl)methyl]-1-piperidyl]-2-(1H-pyrrolo[2,3-b]pyridin-5-yloxy)benzamide |
| 3 | 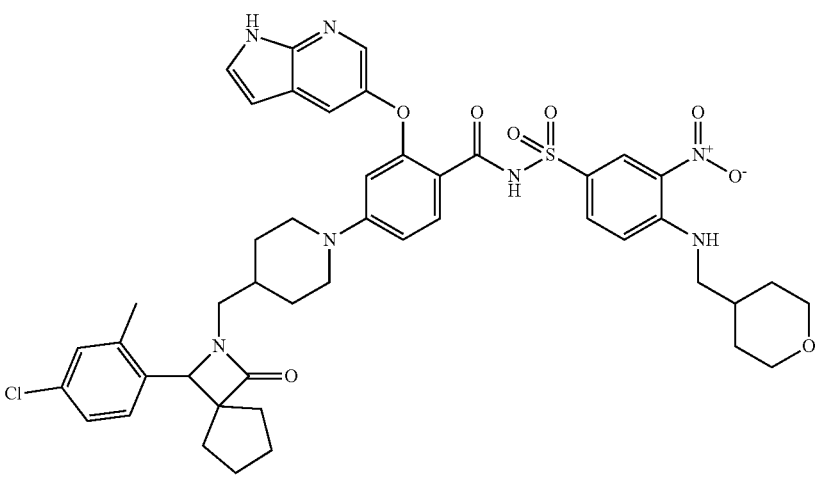 [SMILES: Cc1cc(Cl)ccc1C1N(CC2CCN(c3ccc(C(=O)NS(=O)(=O)c4ccc(NCC5CCOCC5)c([N+](=O)[O-])c4)c(Oc4cnc5[nH]ccc5c4)c3)CC2)C(=O)C12CCCC2] | 4-[4-[[1-(4-chloro-2-methyl-phenyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 5 | 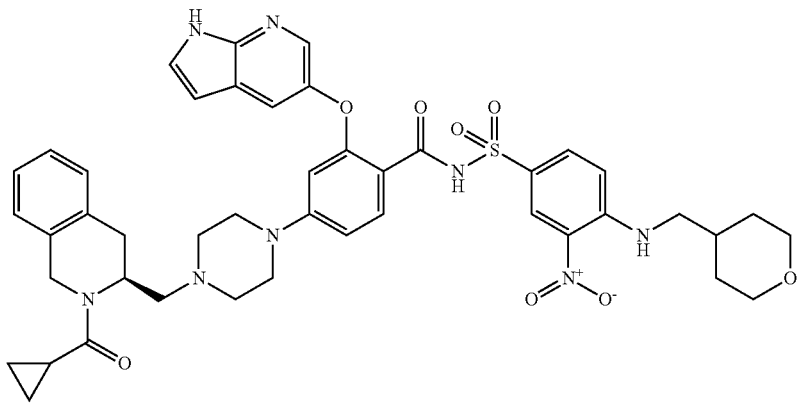 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)C3CC3)CC2)cc1Oc1cnc2[nH]ccc2c1] | 4-[4-[[(3S)-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 6 | 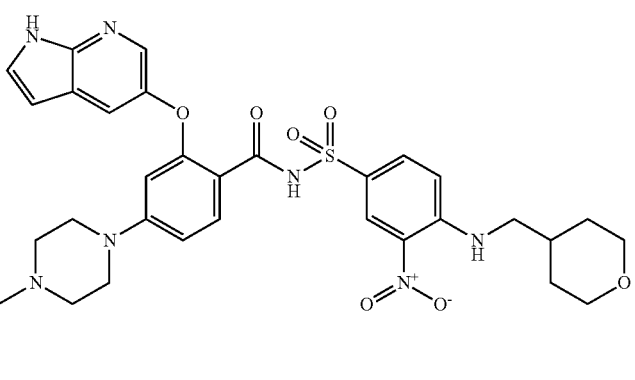 | N-[3-nitro-4-(tetrahydropyran-4-ylmethylamino)phenyl]sulfonyl-2-(1H-pyrrolo[2,3-b]pyridin-5-yloxy)-4-[4-[[2-(thiophene-2-carbonyl)-3,4-dihydro-1H-isoquinolin-3-yl]methyl]piperazin-1-yl]benzamide |
| 8 | 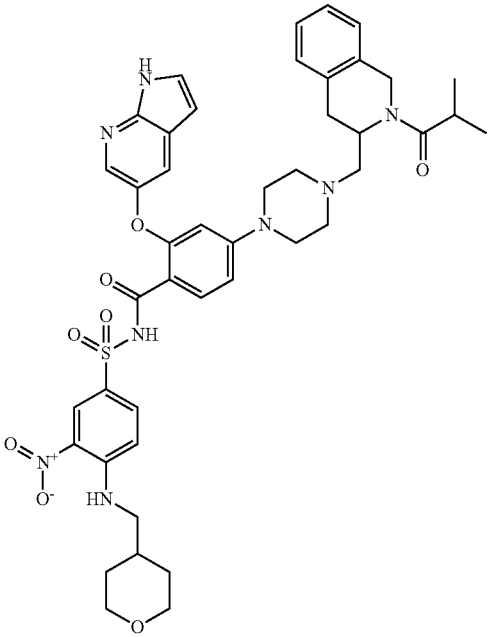 [SMILES: CC(C)C(=O)N1Cc2ccccc2CC1CN1CCN(c2ccc(C(=O)NS(=O)(=O)c3ccc(NCC4CCOCC4)c([N+](=O)[O-])c3)c(Oc3cnc4[nH]ccc4c3)c2)CC1] | 4-[4-[[2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 9 | 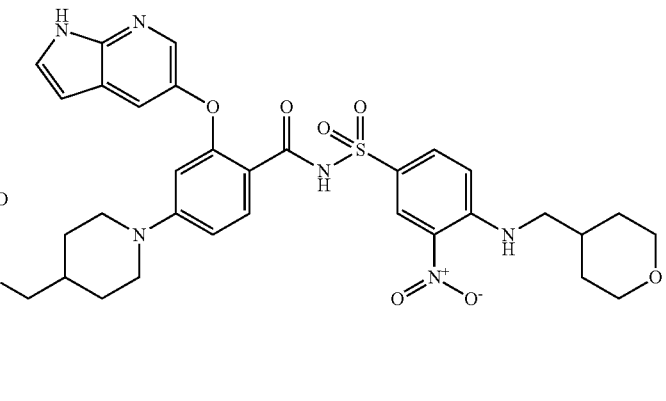 | 4-[4-[[1-(5-chloro-3-pyridyl)-3-oxo-2-azaspiro[3.4]octan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 10 | 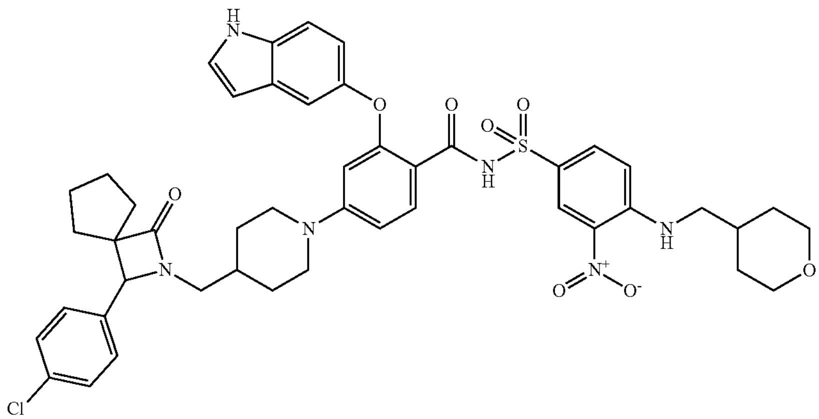 | 4-[4-[[1-(4-chlorophenyl)-3-oxo-2-azaspiro[3.4]octan-2-yl]methyl]-1-piperidyl]-2-(1H-indol-5-yloxy)-N-[3-nitro-4-(tetrahydropyran-4-ylmethylamino)phenyl]sulfonyl-benzamide |
| 20 | 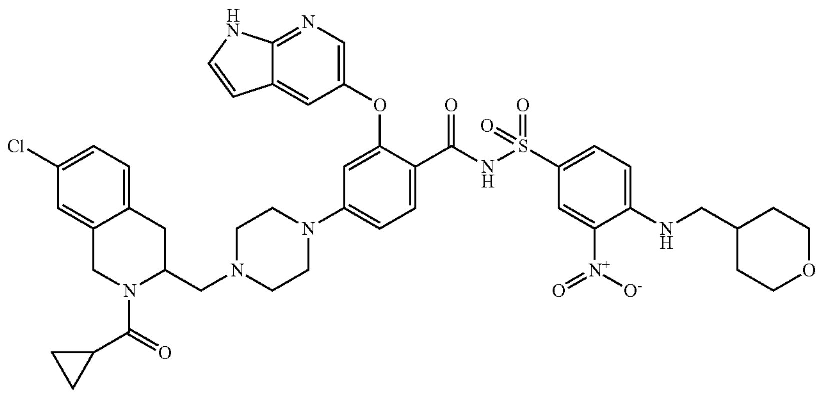 [SMILES: O=C(NS(=O)(=O)c1ccc(NCC2CCOCC2)c([N+](=O)[O-])c1)c1ccc(N2CCN(CC3Cc4ccc(Cl)cc4CN3C(=O)C3CC3)CC2)cc1Oc1cnc2[nH]ccc2c1] | 4-[4-[[7-chloro-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 21 | 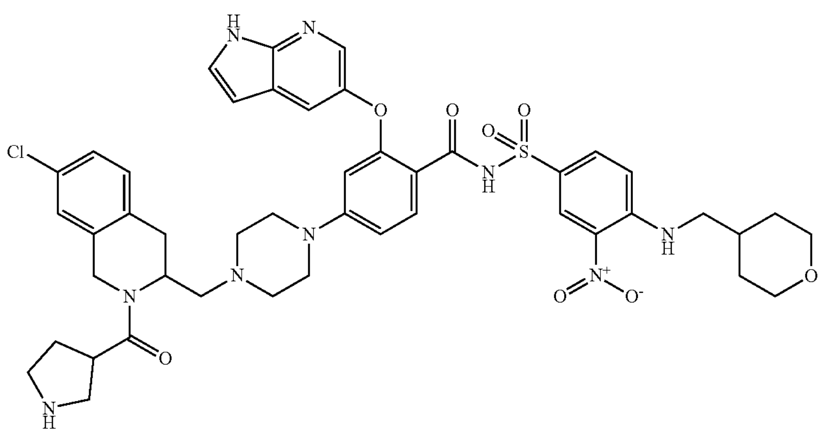 [SMILES: O=C(NS(=O)(=O)c1ccc(NCC2CCOCC2)c([N+](=O)[O-])c1)c1ccc(N2CCN(CC3Cc4ccc(Cl)cc4CN3C(=O)C3CCNC3)CC2)cc1Oc1cnc2[nH]ccc2c1] | 4-[4-[[7-chloro-2-(pyrrolidine-3-carbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 22 | 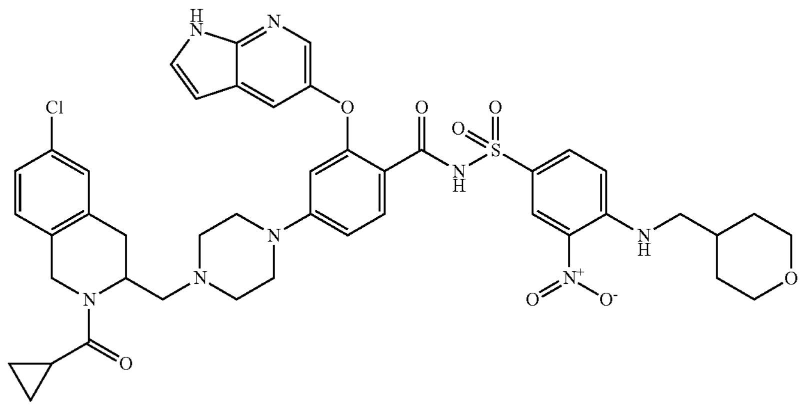 [SMILES: O=C(NS(=O)(=O)c1ccc(NCC2CCOCC2)c([N+](=O)[O-])c1)c1ccc(N2CCN(CC3Cc4cc(Cl)ccc4CN3C(=O)C3CC3)CC2)cc1Oc1cnc2[nH]ccc2c1] | 4-[4-[[6-chloro-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 23 | 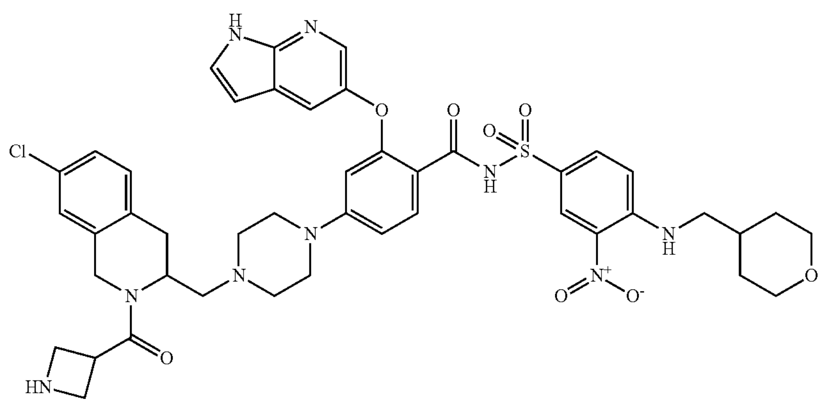 [SMILES: O=C(NS(=O)(=O)c1ccc(NCC2CCOCC2)c([N+](=O)[O-])c1)c1ccc(N2CCN(CC3Cc4ccc(Cl)cc4CN3C(=O)C3CNC3)CC2)cc1Oc1cnc2[nH]ccc2c1] | 4-[4-[[2-(azetidine-3-carbonyl)-7-chloro-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 24 | 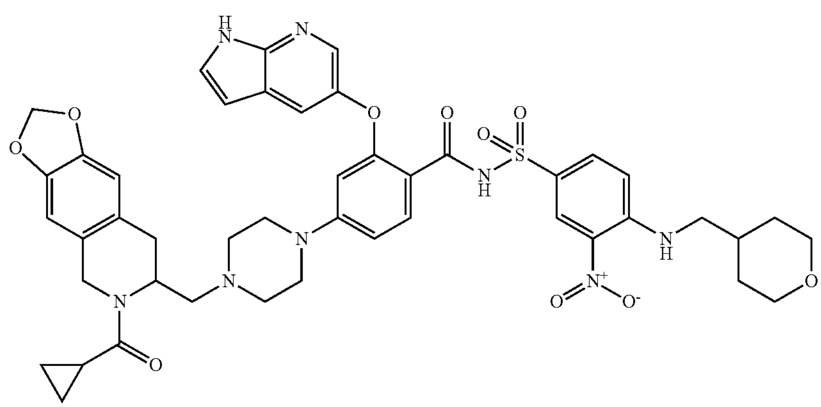 [SMILES: O=C(NS(=O)(=O)c1ccc(NCC2CCOCC2)c([N+](=O)[O-])c1)c1ccc(N2CCN(CC3Cc4cc5c(cc4CN3C(=O)C3CC3)OCO5)CC2)cc1Oc1cnc2[nH]ccc2c1] | 4-[4-[[6-(cyclopropanecarbonyl)-7,8-dihydro-5H-[1,3]dioxolo[4,5-g]isoquinolin-7-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 25 | 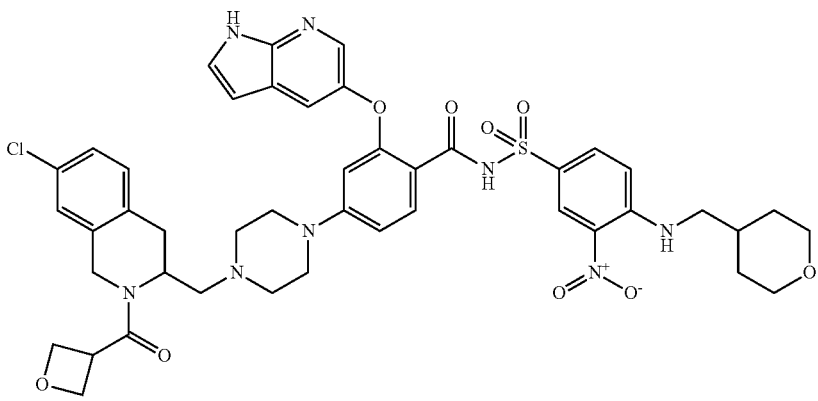 [SMILES: O=C(NS(=O)(=O)c1ccc(NCC2CCOCC2)c([N+](=O)[O-])c1)c1ccc(N2CCN(CC3Cc4ccc(Cl)cc4CN3C(=O)C3COC3)CC2)cc1Oc1cnc2[nH]ccc2c1] | 4-[4-[[7-chloro-2-(oxetane-3-carbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benazmide |
| 26 | 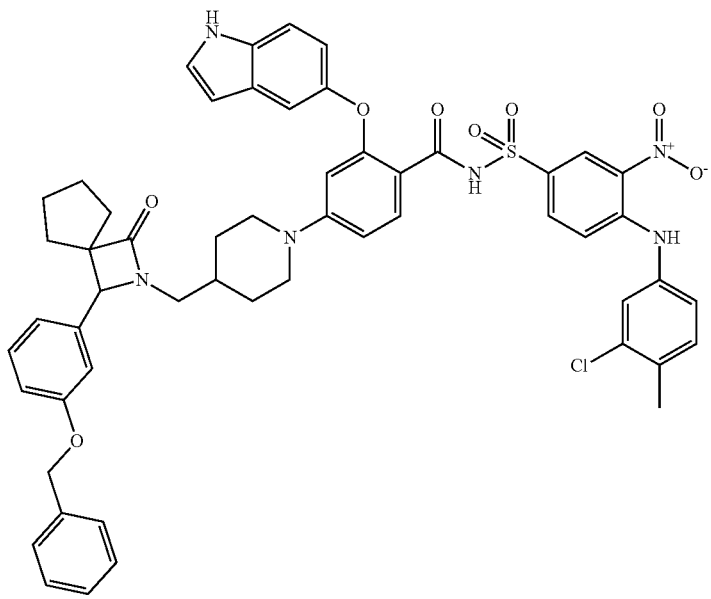 [SMILES: Cc1ccc(Nc2ccc(S(=O)(=O)NC(=O)c3ccc(N4CCC(CN5C(=O)C6(CCCC6)C5c5cccc(OCc6ccccc6)c5)CC4)cc3Oc3ccc4[nH]ccc4c3)cc2[N+](=O)[O-])cc1Cl] | 4-[4-[[1-(3-[[1-(3-benzyloxyphenyl)-3-oxo-2-azaspiro[3.4]octan-2-yl]methyl]-1-piperidyl]-N-[4-(3-chloro-4-methyl-anilino)-3-nitro-phenyl]sulfonyl-2-(1H-indol-5-yloxy)benzamide |
| 27 | 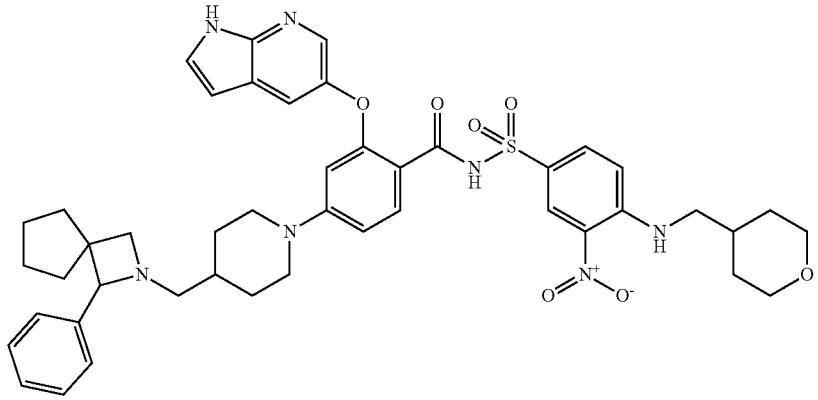 [SMILES: O=C(NS(=O)(=O)c1ccc(NCC2CCOCC2)c([N+](=O)[O-])c1)c1ccc(N2CCC(CN3CC4(CCCC4)C3c3ccccc3)CC2)cc1Oc1cnc2[nH]ccc2c1] | N-[3-nitro-4-(tetrahydropyran-4-ylmethylamino)phenyl]sulfonyl-4-[4-[(3-phenyl-2-azaspiro[3.4]octan-2-yl)methyl]-1-piperidyl]-2-(1H-pyrrolo[2,3-b]pyridin-5-yloxy)benzamide |

| Compound No | Structure | Name |
|---|---|---|
| 33 | 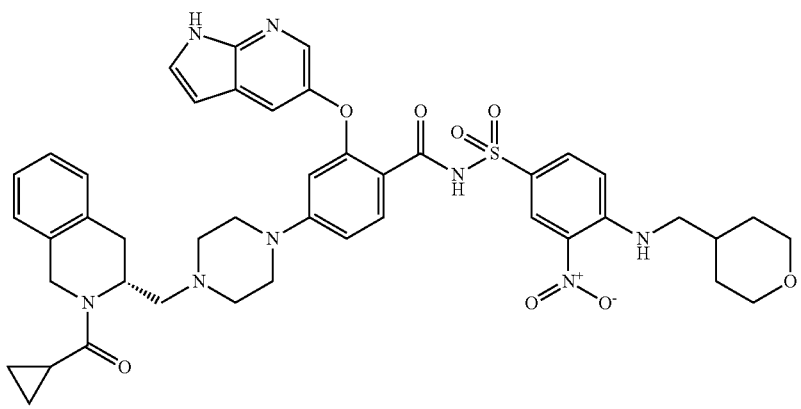 [SMILES: O=C(NS(=O)(=O)c1ccc(NCC2CCOCC2)c([N+](=O)[O-])c1)c1ccc(N2CCN(C[C@H]3Cc4ccccc4CN3C(=O)C3CC3)CC2)cc1Oc1cnc2[nH]ccc2c1] | 4-[4-[[(3R)-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 34 | 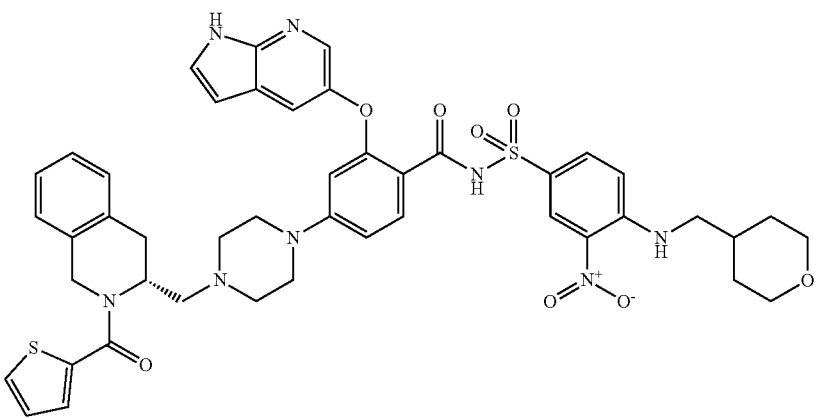 [SMILES: O=C(NS(=O)(=O)c1ccc(NCC2CCOCC2)c([N+](=O)[O-])c1)c1ccc(N2CCN(C[C@H]3Cc4ccccc4CN3C(=O)c3cccs3)CC2)cc1Oc1cnc2[nH]ccc2c1] | N-[3-nitro-4-(tetrahydropyran-4-ylmethylamino)phenyl]sulfonyl-2-(1H-pyrrolo[2,3-b]pyridin-5-yloxy)-4-[4-[[(3R)-2-(thiophene-2-carbonyl)-3,4-dihydro-1H-isoquinolin-3-yl]methyl]piperazin-1-yl]benzamide |
| 35 | 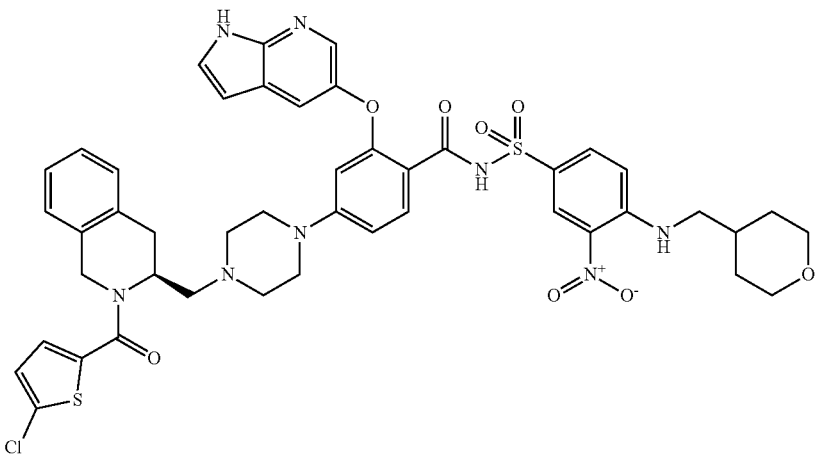 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)c3ccc(Cl)s3)CC2)cc1Oc1cnc2[nH]ccc2c1] | 4-[4-[[(3S)-2-(5-chlorothiophene-2-carbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 36 | 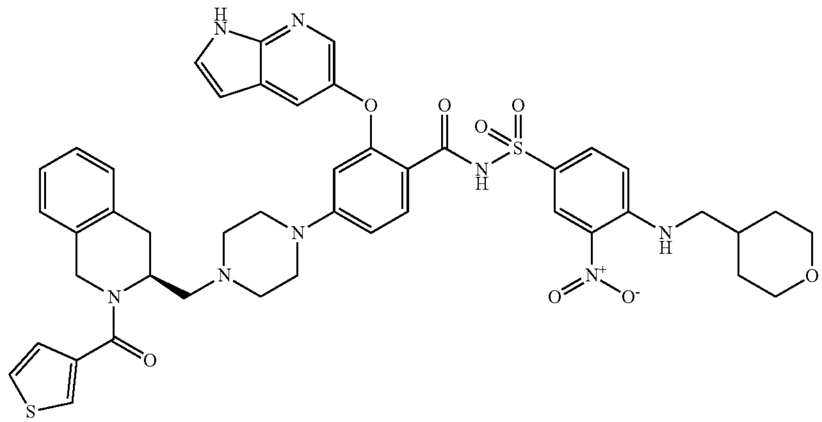 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)c3ccsc3)CC2)cc1Oc1cnc2[nH]ccc2c1] | N-[3-nitro-4-(tetrahydropyran-4-ylmethylamino)phenyl]sulfonyl-2-(1H-pyrrolo[2,3-b]pyridin-5-yloxy)-4-[4-[[(3S)-2-(thiophene-3-carbonyl)-3,4-dihydro-1H-isoquinolin-3-yl]methyl]piperazin-1-yl]benzamide |
| 37 | 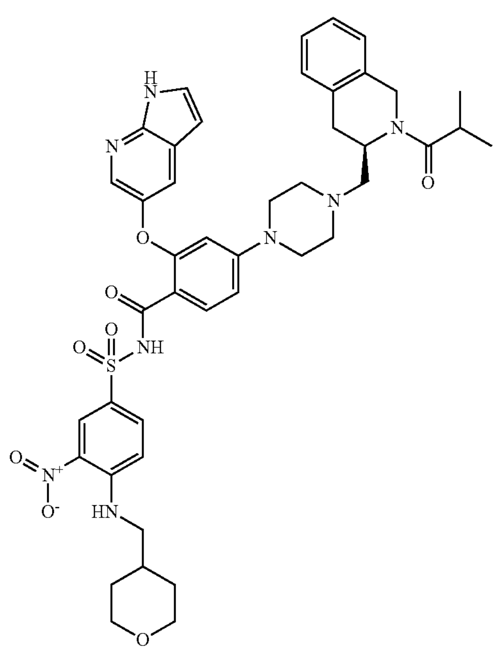 [SMILES: CC(C)C(=O)N1Cc2ccccc2C[C@@H]1CN1CCN(c2ccc(C(=O)NS(=O)(=O)c3ccc(NCC4CCOCC4)c([N+](=O)[O-])c3)c(Oc3cnc4[nH]ccc4c3)c2)CC1] | 4-[4-[[(3R)-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 38 | 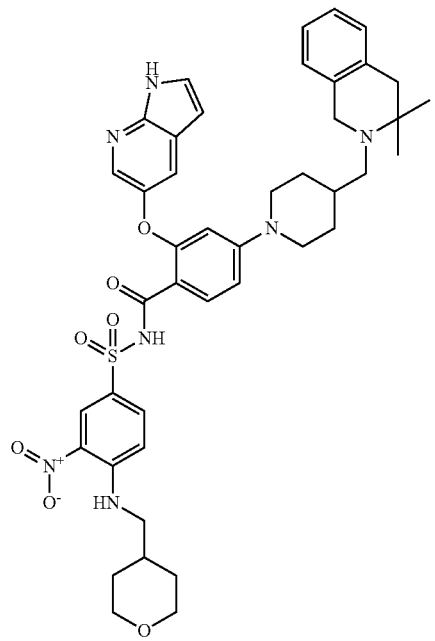 [SMILES: CC1(C)Cc2ccccc2CN1CC1CCN(c2ccc(C(=O)NS(=O)(=O)c3ccc(NCC4CCOCC4)c([N+](=O)[O-])c3)c(Oc3cnc4[nH]ccc4c3)c2)CC1] | 4-[4-[(3,3-dimethyl-1,4-dihydroisoquinolin-2-yl)methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 39 | 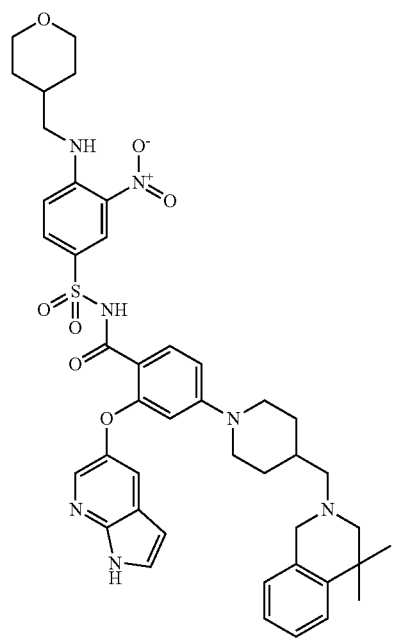 [SMILES: CC1(C)CN(CC2CCN(c3ccc(C(=O)NS(=O)(=O)c4ccc(NCC5CCOCC5)c([N+](=O)[O-])c4)c(Oc4cnc5[nH]ccc5c4)c3)CC2)Cc2ccccc21] | 4-[4-[(4,4-dimethyl-1,3-dihydroisoquinolin-2-yl)methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 40 | 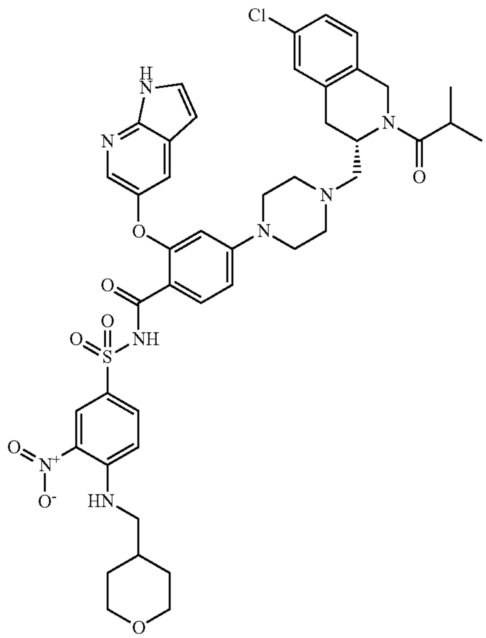 [SMILES: CC(C)C(=O)N1Cc2ccc(Cl)cc2C[C@H]1CN1CCN(c2ccc(C(=O)NS(=O)(=O)c3ccc(NCC4CCOCC4)c([N+](=O)[O-])c3)c(Oc3cnc4[nH]ccc4c3)c2)CC1] | 4-[4-[[(3S)-6-chloro-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 41 | 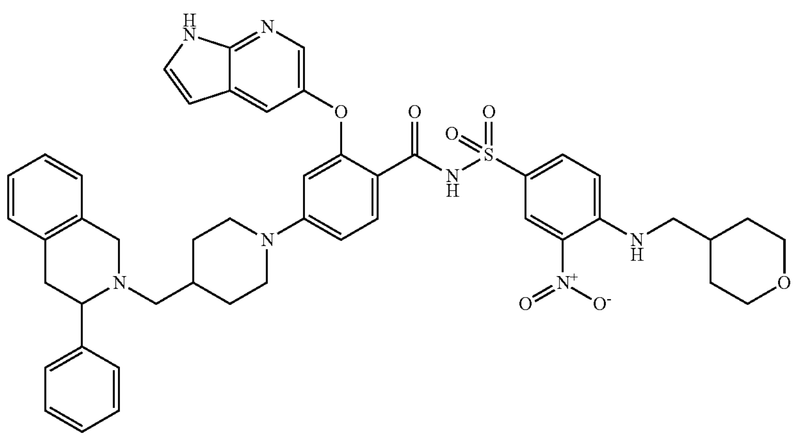 [SMILES: O=C(NS(=O)(=O)c1ccc(NCC2CCOCC2)c([N+](=O)[O-])c1)c1ccc(N2CCC(CN3Cc4ccccc4CC3c3ccccc3)CC2)cc1Oc1cnc2[nH]ccc2c1] | N-[3-nitro-4-(tetrahydropyran-4-ylmethylamino)phenyl]sulfonyl-4-[4-[(3-phenyl-3,4-dihydro-1H-isoquinolin-2-yl)methyl]-1-piperidyl]-2-(1H-pyrrolo[2,3-b]pyridin-5-yloxy)benzamide |
| 42 | 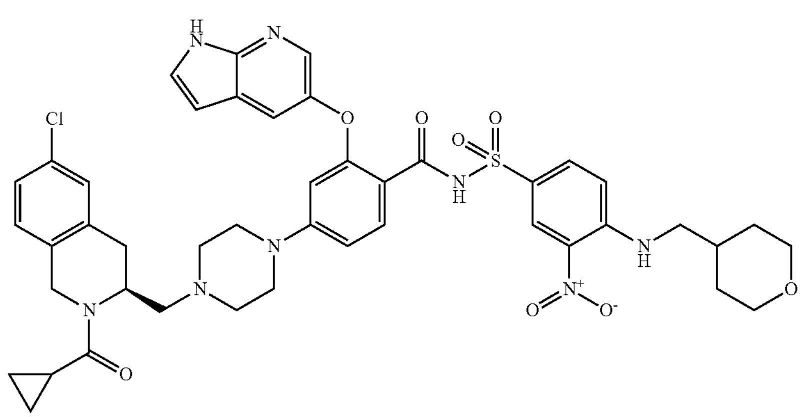 | 4-[4-[[(3S)-6-chloro-2-(cyclopropanecarbonyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 45 | 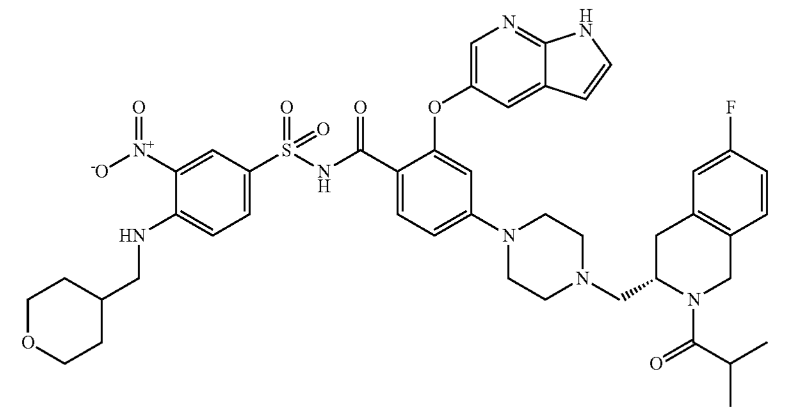 [SMILES: CC(C)C(=O)N1Cc2ccc(F)cc2C[C@H]1CN1CCN(c2ccc(C(=O)NS(=O)(=O)c3ccc(NCC4CCOCC4)c([N+](=O)[O-])c3)c(Oc3cnc4[nH]ccc4c3)c2)CC1] | 4-[4-[[(3S)-6-fluoro-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 46 | 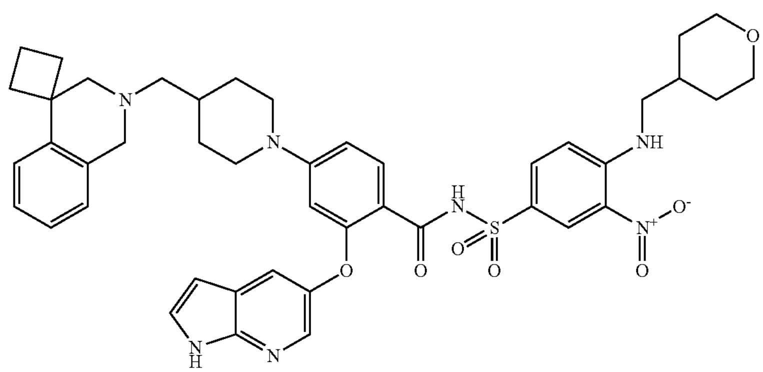 [SMILES: O=C(NS(=O)(=O)c1ccc(NCC2CCOCC2)c([N+](=O)[O-])c1)c1ccc(N2CCC(CN3Cc4ccccc4C4(CCC4)C3)CC2)cc1Oc1cnc2[nH]ccc2c1] | N-[3-nitro-4-(tetrahydropyran-4-ylmethylamino)phenyl]sulfonyl-2-(1H-pyrrolo[2,3-b]pyridin-5-yloxy)-4-[4-(spiro[1,3-dihydroisoquinoline-4,1'-cyclobutane]-2-ylmethyl)-1-piperidyl]benzamide |
| 48 | 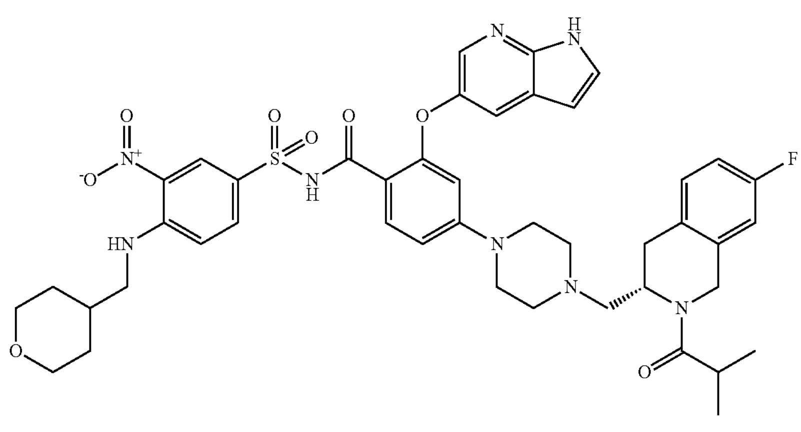 [SMILES: CC(C)C(=O)N1Cc2cc(F)ccc2C[C@H]1CN1CCN(c2ccc(C(=O)NS(=O)(=O)c3ccc(NCC4CCOCC4)c([N+](=O)[O-])c3)c(Oc3cnc4[nH]ccc4c3)c2)CC1] | 4-[4-[[(3S)-7-fluoro-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

| Compound No | Structure | Name |
|---|---|---|
| 49 | 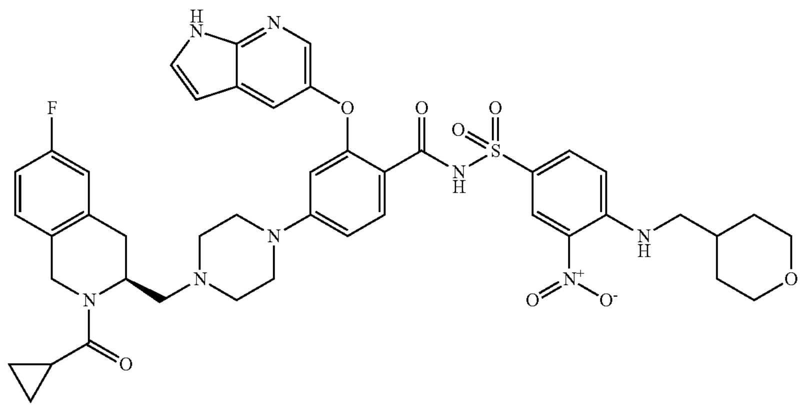 [SMILES: O=C(NS(=O)(=O)c1ccc(NCC2CCOCC2)c([N+](=O)[O-])c1)c1ccc(N2CCN(C[C@@H]3Cc4cc(F)ccc4CN3C(=O)C3CC3)CC2)cc1Oc1cnc2[nH]ccc2c1] | 4-[4-[[(3S)-2-(cyclopropanecarbonyl)-6-fluoro-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 50 | 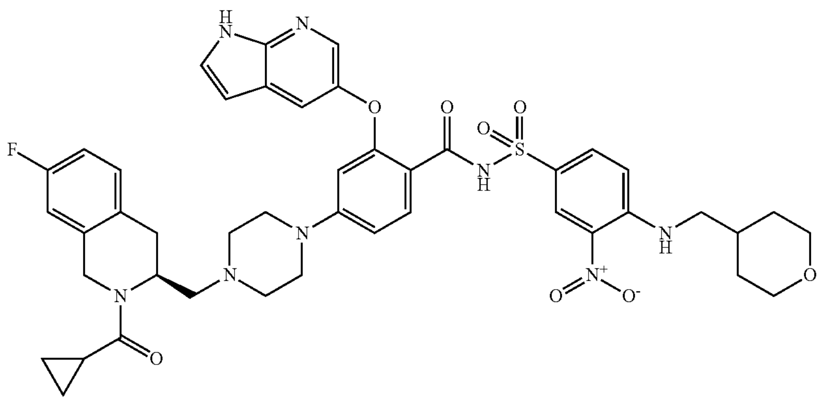 [SMILES: O=C(NS(=O)(=O)c1ccc(NCC2CCOCC2)c([N+](=O)[O-])c1)c1ccc(N2CCN(C[C@@H]3Cc4ccc(F)cc4CN3C(=O)C3CC3)CC2)cc1Oc1cnc2[nH]ccc2c1] | 4-[4-[[(3S)-2-(cyclopropanecarbonyl)-7-fluoro-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 55 | 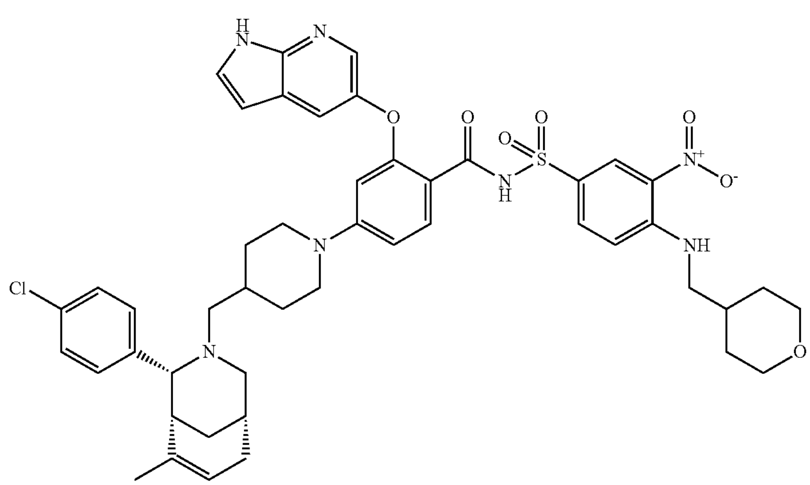 [SMILES: CC1=CC[C@@H]2C[C@H]1[C@H](c1ccc(Cl)cc1)N(CC1CCN(c3ccc(C(=O)NS(=O)(=O)c4ccc(NCC5CCOCC5)c([N+](=O)[O-])c4)c(Oc4cnc5[nH]ccc5c4)c3)CC1)C2] | 4-[4-[[(1R,4R,5R)-4-(4-chlorophenyl)-6-methyl-3-azabicyclo[3.3.1]non-6-en-3-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 56 | 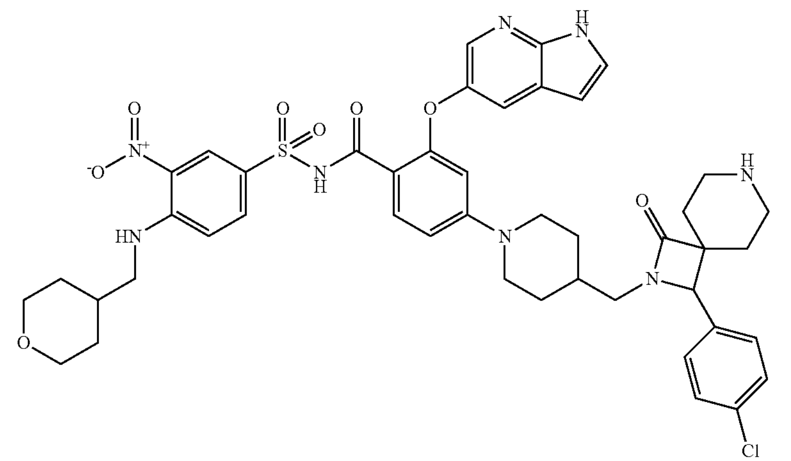 [SMILES: O=C(NS(=O)(=O)c1ccc(NCC2CCOCC2)c([N+](=O)[O-])c1)c1ccc(N2CCC(CN3C(=O)C4(CCNCC4)C3c3ccc(Cl)cc3)CC2)cc1Oc1cnc2[nH]ccc2c1] | 4-[4-[[1-(4-chlorophenyl)-3-oxo-2,7-diazaspiro[3.5]nonan-2-yl]methyl]-1-piperidyl]-N-[3-nitro-4-(tetrahydropyran-4-ylmethylamino)phenyl]sulfonyl-2-(1H-pyrrolo[2,3-b]pyridin-5-yloxy)benzamide |
| 57 | 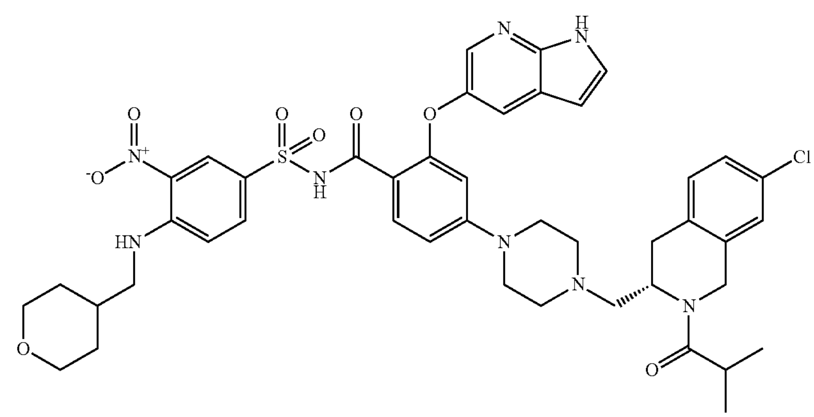 [SMILES: CC(C)C(=O)N1Cc2cc(Cl)ccc2C[C@H]1CN1CCN(c2ccc(C(=O)NS(=O)(=O)c3ccc(NCC4CCOCC4)c([N+](=O)[O-])c3)c(Oc3cnc4[nH]ccc4c3)c2)CC1] | 4-[4-[[(3S)-7-chloro-2-(2-methylpropanoyl)-3,4-dihydro-1H-isoquinolin-3-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 59 | 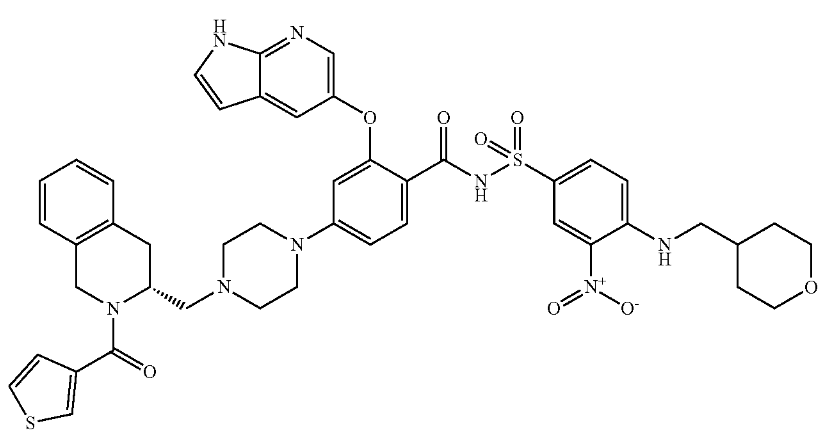 [SMILES: O=C(NS(=O)(=O)c1ccc(NCC2CCOCC2)c([N+](=O)[O-])c1)c1ccc(N2CCN(C[C@H]3Cc4ccccc4CN3C(=O)c3ccsc3)CC2)cc1Oc1cnc2[nH]ccc2c1] | N-[3-nitro-4-(tetrahydropyran-4-ylmethylamino)phenyl]sulfonyl-2-(1H-pyrrolo[2,3-b]pyridin-5-yloxy)-4-[4-[[(3R)-2-(thiophene-3-carbonyl)-3,4-dihydro-1H-isoquinolin-3-yl]methyl]piperazin-1-yl]benzamide |

-continued

| Compound No | Structure | Name |
|---|---|---|
| 74 | 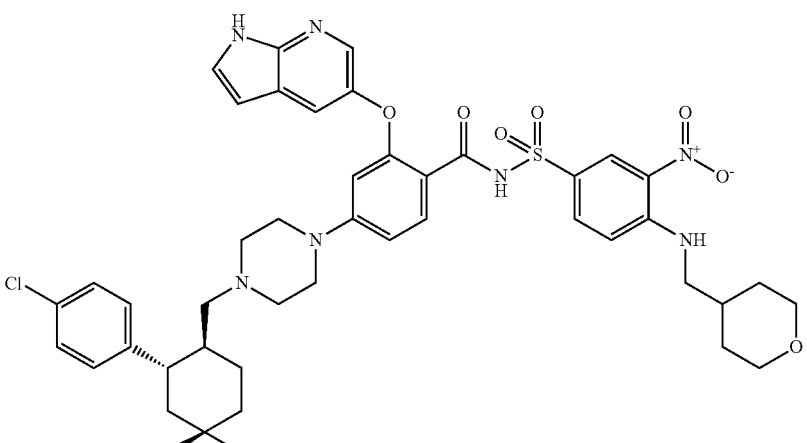 | 4-[4-[[(1S,2S,4S)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 75 | 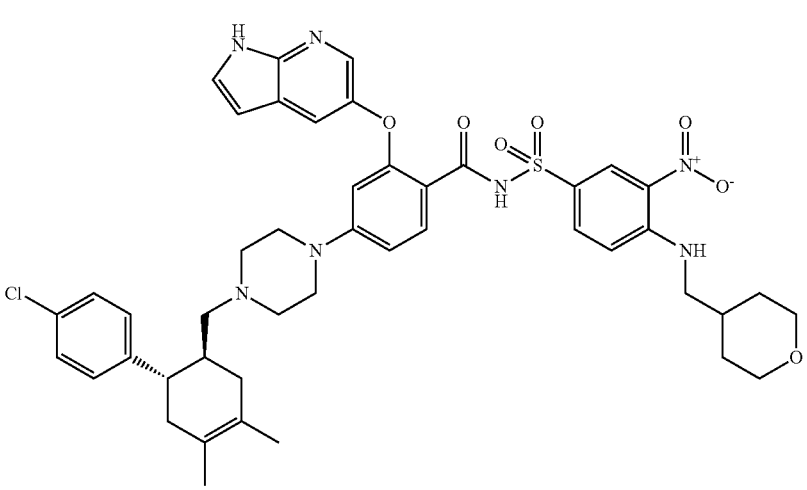 [SMILES: CC1=C(C)C[C@H](c2ccc(Cl)cc2)[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 4-[4-[[(1S,6S)-6-(4-chlorophenyl)-3,4-dimethyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 78 | 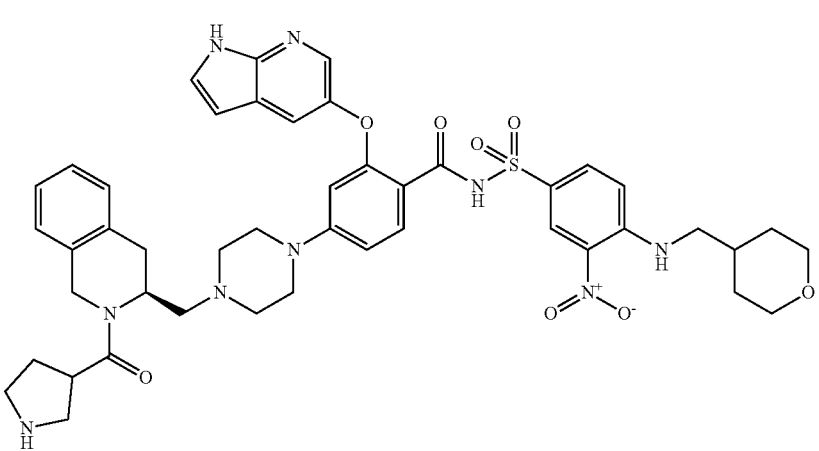 [SMILES: O=C(NS(=O)(=O)c1ccc(NCC2CCOCC2)c([N+](=O)[O-])c1)c1ccc(N2CCN(C[C@@H]3Cc4ccccc4CN3C(=O)C3CCNC3)CC2)cc1Oc1cnc2[nH]ccc2c1] | N-[3-nitro-4-(tetrahydropyran-4-ylmethylamino)phenyl]sulfonyl-4-[4-[[(3S)-2-(pyrrolidine-3-carbonyl)-3,4-dihydro-1H-isoquinolin-3-yl]methyl]piperazin-1-yl]-2-(1H-pyrrolo[2,3-b]pyridin-5-yloxy)benzamide | or a pharmaceutically acceptable salt, isomer, solvate, prodrug, or tautomer thereof.

2. A pharmaceutical composition comprising a compound or a pharmaceutically acceptable salt, prodrug, solvate, hydrate, isomer, or tautomer thereof of claim 1, and a pharmaceutically acceptable carrier.

3. The pharmaceutical composition of claim 2, further comprising an additional pharmaceutically active agent.

4. A method of inhibiting BCL-2, comprising administering to a subject in need of a treatment for cancer a compound of claim 1.

5. A method of treating a disease or disorder associated with the inhibition of BCL-2, comprising administering to a subject in need of a treatment for cancer a compound of claim 1.

6. A method of treating cancer, comprising administering to a subject in need of a treatment for cancer a compound of claim 1.

7. The method of claim 6, wherein the cancer is selected from bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL) and chronic lymphocytic leukemia/small lymphocytic lymphoma (CLL/SLL).

8. The method of claim 4, wherein the BCL-2 protein is Isoform 1 or Isoform 2.

9. The method of claim 5, wherein the BCL-2 protein is Isoform 1 or Isoform 2.

* * * * *